(12) United States Patent
Kurokawa et al.

(10) Patent No.: US 11,875,837 B2
(45) Date of Patent: Jan. 16, 2024

(54) SEMICONDUCTOR DEVICE AND ELECTRONIC DEVICE

(71) Applicant: SEMICONDUCTOR ENERGY LABORATORY CO., LTD., Atsugi (JP)

(72) Inventors: Yoshiyuki Kurokawa, Kanagawa (JP); Munehiro Kozuma, Kanagawa (JP); Takeshi Aoki, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 202 days.

(21) Appl. No.: 17/617,969

(22) PCT Filed: Jun. 8, 2020

(86) PCT No.: PCT/IB2020/055352
§ 371 (c)(1),
(2) Date: Dec. 10, 2021

(87) PCT Pub. No.: WO2020/254909
PCT Pub. Date: Dec. 24, 2020

(65) Prior Publication Data
US 2022/0254401 A1  Aug. 11, 2022

(30) Foreign Application Priority Data

Jun. 21, 2019 (JP) .................. 2019-115347
Jul. 26, 2019 (JP) .................. 2019-137473
(Continued)

(51) Int. Cl.
*G11C 11/405* (2006.01)
*G01N 33/00* (2006.01)
(Continued)

(52) U.S. Cl.
CPC ........ *G11C 11/405* (2013.01); *G01N 33/0001* (2013.01); *G01V 3/02* (2013.01);
(Continued)

(58) Field of Classification Search
CPC ... G11C 11/405; G11C 5/025; G11C 11/4074; G11C 11/4091; G11C 11/4096;
(Continued)

(56) References Cited

U.S. PATENT DOCUMENTS 3,727,196 A * 4/1973 McKenny ............. G11C 11/405
257/E27.084
9,716,852 B2  7/2017 Kurokawa
(Continued)

FOREIGN PATENT DOCUMENTS

JP    10-078406 A    3/1998
JP    2016-219011 A  12/2016
(Continued)

OTHER PUBLICATIONS

International Search Report (Application No. PCT/IB2020/055352) dated Sep. 1, 2020.
(Continued)

*Primary Examiner* — Fernando Hidalgo
(74) *Attorney, Agent, or Firm* — Fish & Richardson P.C.

(57) ABSTRACT

A semiconductor device resistant to a high temperature with low power consumption is provided. The semiconductor device includes a first and a second circuit, a first and a second cell, and a first and a second wiring. The first cell includes a first transistor, and the second cell includes a second transistor. The first and the second transistor operate in a subthreshold region. The first cell is electrically connected to the first circuit through the first wiring, the first cell is electrically connected to the second circuit through the second wiring, and the second cell is electrically connected
(Continued)

to the second circuit through the second wiring. The first cell sets a current flowing through the first transistor to a first current and the second cell sets a current flowing through the second transistor to a second current. At this time, a potential corresponding to the second current is input from the second wiring to the first cell. Then, a third current flows from the second circuit to change a potential of the second wiring, whereby the first cell outputs a fourth current corresponding to the amount of the potential change and the first current.

20 Claims, 49 Drawing Sheets

(30) Foreign Application Priority Data

| Sep. 9, 2019 | (JP) | 2019-163598 |
| Nov. 1, 2019 | (JP) | 2019-200140 |
| Nov. 22, 2019 | (JP) | 2019-211005 |
| Dec. 6, 2019 | (JP) | 2019-221167 |

(51) Int. Cl.

| G01V 3/02 | (2006.01) |
| H01L 27/12 | (2006.01) |
| H01L 29/786 | (2006.01) |
| H10B 12/00 | (2023.01) |

(52) U.S. Cl.
CPC ........ *H01L 27/124* (2013.01); *H01L 27/1225* (2013.01); *H01L 27/1255* (2013.01); *H01L 29/7869* (2013.01); *H01L 29/78648* (2013.01); *H10B 12/00* (2023.02)

(58) Field of Classification Search
CPC .. G11C 11/4097; G01N 33/0001; G01V 3/02; H01L 27/1225; H01L 27/124; H01L 27/1255; H01L 29/78648; H01L 29/7869; H01L 29/78696; H01L 29/786; H01L 27/105; H10B 12/00; H10B 41/70; G06G 7/60; G06N 3/063

USPC ........................................................ 365/149

See application file for complete search history.

(56) References Cited

U.S. PATENT DOCUMENTS

| 9,773,832 | B2 | 9/2017 | Kurokawa | |
| 9,851,942 | B2 | 12/2017 | Kurokawa | |
| 10,141,069 | B2 | 11/2018 | Ikeda et al. | |
| 10,319,743 | B2 | 6/2019 | Kurokawa | |
| 10,699,794 | B2 | 6/2020 | Ikeda et al. | |
| 11,004,528 | B2 | 5/2021 | Ikeda et al. | |
| 11,037,525 | B2 | 6/2021 | Shiokawa et al. | |
| 2016/0293643 | A1 | 10/2016 | Kim et al. | |
| 2016/0343452 | A1 | 11/2016 | Ikeda et al. | |
| 2017/0117283 | A1* | 4/2017 | Matsuzaki | G11C 16/0433 |
| 2017/0317085 | A1 | 11/2017 | Kurokawa | |
| 2018/0004881 | A1 | 1/2018 | Li et al. | |
| 2018/0005588 | A1 | 1/2018 | Kurokawa | |
| 2018/0102365 | A1* | 4/2018 | Van Houdt | G11C 11/405 |
| 2019/0164620 | A1 | 5/2019 | Ikeda et al. | |
| 2019/0206474 | A1* | 7/2019 | Van Houdt | G11C 11/2257 |
| 2019/0371802 | A1* | 12/2019 | Morris | G11C 11/2275 |
| 2020/0043548 | A1* | 2/2020 | Ishizu | G11C 16/28 |
| 2020/0091156 | A1* | 3/2020 | Sharma | H01L 27/1225 |
| 2021/0264998 | A1 | 8/2021 | Ikeda et al. | |

FOREIGN PATENT DOCUMENTS

| JP | 2017-130195 A | 7/2017 |
| JP | 2019-046374 A | 3/2019 |
| JP | 2019-047006 A | 3/2019 |

OTHER PUBLICATIONS

Written Opinion (Application No. PCT/IB2020/055352) dated Sep. 1, 2020.

Guo.X et al., "Fast, Energy-Efficient, Robust, and Reproducible Mixed-Signal Neuromorphic Classifier Based on Embedded NOR Flash Memory Technology", IEDM 17: Technical Digest of International Electron Devices Meeting, Dec. 2, 2017, pp. 151-154.

* cited by examiner

100

FIG. 38A
| Amorphous | Intermediate state<br>New crystalline phase<br>Crystalline | Crystal |
|---|---|---|
| • completely amorphous | • CAAC<br>• nc<br>• CAC<br>excluding single crystal and poly crystal | • single crystal<br>• poly crystal |
FIG. 38B
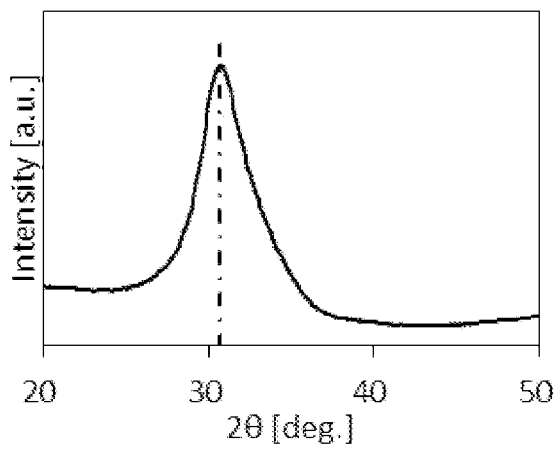
FIG. 38C
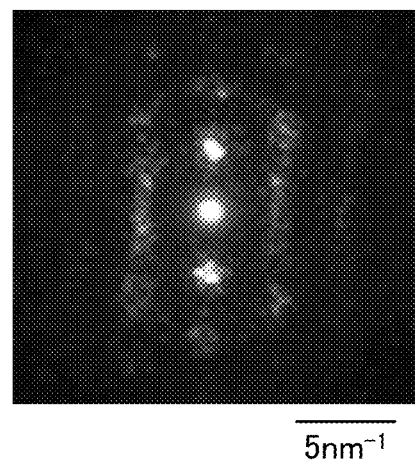

6900

6140

6150

SEMICONDUCTOR DEVICE AND ELECTRONIC DEVICE

CROSS REFERENCE TO RELATED APPLICATIONS

This application is a U.S. National Phase Application under 35 U.S.C. § 371 of International Application PCT/IB2020/055352, filed on Jun. 8, 2020, which is incorporated by reference and claims the benefit of foreign priority applications filed in Japan on Jun. 21, 2019, as Application No. 2019-115347, on Jul. 26, 2019, as Application No. 2019-137473, on Sep. 9, 2019, as Application No. 2019-163598, on Nov. 1, 2019, as Application No. 2019-200140, on Nov. 22, 2019, as Application No. 2019-211005, and on Dec. 6, 2019, as Application No. 2019-221167.

TECHNICAL FIELD

One embodiment of the present invention relates to a semiconductor device and an electronic device.

Note that one embodiment of the present invention is not limited to the above technical field. The technical field of the invention disclosed in this specification and the like relates to an object, a driving method, or a manufacturing method. Alternatively, one embodiment of the present invention relates to a process, a machine, manufacture, or a composition of matter. Therefore, specific examples of the technical field of one embodiment of the present invention disclosed in this specification include a semiconductor device, a display device, a liquid crystal display device, a light-emitting device, a power storage device, an imaging device, a memory device, a signal processing device, a sensor, a processor, an electronic device, a system, a driving method thereof, a manufacturing method thereof, and a testing method thereof.

BACKGROUND ART

Integrated circuits that imitate the mechanism of the human brain are currently under active development. The integrated circuits incorporate electronic circuits as the brain mechanism and include circuits corresponding to "neurons" and "synapses" of the human brain. Such integrated circuits may therefore be called "neuromorphic", "brain-morphic", or "brain-inspired" circuits. The integrated circuits have a non-von Neumann architecture and are expected to be able to perform parallel processing with extremely low power consumption as compared with a von Neumann architecture, in which power consumption increases with increasing processing speed.

An information processing model that imitates a biological neural network including "neurons" and "synapses" is called an artificial neural network (ANN). By using an artificial neural network, inference with an accuracy as high as or higher than that of a human can be carried out. In an artificial neural network, the main arithmetic operation is the weighted sum operation of outputs from neurons, i.e., the product-sum operation.

Non-Patent Document 1 proposes a product-sum operation circuit including a nonvolatile memory element. Each memory element of the product-sum operation circuit outputs a current corresponding to a product of data corresponding to a multiplier stored in each memory and input data corresponding to a multiplicand by using an operation in the subthreshold region of a transistor including silicon in its channel formation region. With the sum of currents output from the memory elements in each column, data corresponding to a product-sum operation can be obtained. The product-sum operation circuit includes memory elements, and does not need to read and write data from and to an external memory when it carries out multiplication and addition. This can decrease the number of data transfer for reading and writing data and the like, and thus the power consumption can be expected to be reduced.

REFERENCE

Non-Patent Document

[Non-Patent Document 1]
X. Guo et al., "Fast, Energy-Efficient, Robust, and Reproducible Mixed-Signal Neuromorphic Classifier Based on Embedded NOR Flash Memory Technology" IEDM2017, pp. 151-154.

SUMMARY OF THE INVENTION

Problems to be Solved by the Invention

Transistor characteristics and a field-effect mobility of a transistor including silicon in its channel formation region and the like easily change due to a change in temperature. In particular, when a product-sum operation circuit or the like is formed as an integrated circuit, the product-sum operation circuit operates to yield heat and the temperature of the integrated circuit rises, which makes characteristics of the transistors included in the integrated circuit change; thus, a normal arithmetic operation cannot be carried out in some cases.

When a digital circuit carries out a product-sum operation, a digital multiplication circuit carries out multiplication of multiplier digital data (multiplier data) and multiplicand digital data (multiplicand data). The digital data yielded by the multiplication (product data) are added in a digital addition circuit to yield digital data (product-sum data) resulted from the product-sum operation. The digital multiplication circuit and the digital addition circuit preferably have a specification which allows a multi-bit arithmetic operation. This requires a large digital multiplication circuit and a large digital addition circuit, whereby the circuit area may expand and the power consumption may increase.

An arithmetic circuit which carries out a neural network arithmetic operation and a sensor are combined, whereby electronic devices and the like can recognize various information in some cases. For example, an optical sensor (e.g., photodiode) as a sensor is combined with the arithmetic circuit, whereby image data obtained through the optical sensor can be used for a pattern recognition such as face recognition, image recognition, and the like. For example, a sound sensor as a sensor is combined with the arithmetic circuit, whereby a sound data obtained through the sound sensor can be used for sensing and the like such as voiceprint recognition and abnormal sound sensing. As described above, an optical sensor and the arithmetic circuit are combined to form an electronic device, a system, or the like corresponding to human "vision" in some cases. In addition, a sound sensor and the arithmetic circuit are combined to form an electronic device, a system, or the like corresponding to human "hearing" in some cases.

Almost all odor sensors like a gas detector detect only specific odor components. Odor components in the air include, for example, bacteria, virus, bio-aerosols, and dangerous/harmful substances; it is difficult for one odor sensor to detect and classify these odor components. This is because over 400,000 kinds of molecules are related to make an odor and one odor consists of a combination of hundreds or thousands of molecules; to identify one odor, a combination of these molecules (e.g., kind and ratio) must be detected precisely. To precisely identify an odor in the air with one odor sensor, detector elements need to be provided to detect a lot of odor molecules, which makes the odor sensor large in some cases.

An element including a sensing film is proposed as a detector element for odor components, for example. The sensing film contracts or expands when it adsorbs odor molecules. The sensing film is formed on a strain gauge and the contraction or expansion as strain can be converted into an electric signal when the sensing film adsorbs odor molecules; the sensing film formed on the strain gauge can be used as a detector element of an odor sensor for odor molecules. However, the electric signal is weak, so that the detector element requires, for example, an amplification circuit and an analog-digital converter circuit; this makes a peripheral circuit of the detector element large in some cases. That is why an odor sensor is difficult to be made small and the power consumption thereof is difficult to reduce.

An industrial manipulator (also referred to as a robot arm) is equipped with a tactile sensor and the like. To hold an object certainly with a manipulator, it is necessary to control the direction of force, the scale of force, the area in contact, and the like as well as to control point contacts between the hand portion of the manipulator and the object. When a doctor performs palpation, it is necessary to identify a subtle difference of the hardness or size of lumps. For these usages, a tactile sensor which can precisely detect a pressure distribution in a plane is required.

The tactile sensor includes, for example, densely arranged pressure sensors capable of detecting point pressures. The pressure sensor including a strain gauge is proposed. Like an odor sensor, the pressure sensor converts the contraction and expansion of the strain gauge caused by pressure into an electric signal and outputs the electric signal. The electric signal is weak, so that the detector element requires, for example, an amplification circuit and an analog-digital circuit; this makes a peripheral circuit of the detector element large in some cases. That is why a tactile sensor is difficult to be made small and the power consumption thereof is difficult to reduce.

To evaluate the tastes of foods, drinks, medicines, and the like (in this specification and the like, these are referred to as materials for evaluation) objectively, a taste-evaluating device including a taste sensor has been developed. The taste sensor includes, for example, a detector electrode with a lipid film in which lipids are dissolved in polyvinyl chloride and a reference electrode. On the detector electrode, a taste component of a material for evaluation is adsorbed, which causes a potential difference between the detector electrode and the reference electrode. Taste sensors corresponding to factors to determine taste such as the five basic tastes, i.e., sweetness, bitterness, sourness, savoriness, and saltiness, and spiciness, astringency, and the like which stimulate algesia are used to detect the potential difference in each taste sensor. The taste sensor can output an electric signal corresponding to the potential difference; the potential difference and the electric signal are analyzed, whereby the difference of taste can be determined.

It is difficult for one taste sensor to quantitatively evaluate taste components in, for example, sweetness since taste components of sweetness include various components such as sucrose, glucose, fructose, oligosaccharide, xylitol, sorbitol, and synthetic sweetener. In other words, a plurality of taste sensors is required just to determine sweetness. For bitterness, sourness, savoriness, and saltiness as well, a plurality of taste sensors is required in accordance with the kind of taste components.

The electric signal output from the taste sensor is weak as in the odor sensor and the pressure sensor, so that an amplification circuit and an analog-digital circuit are required, for example. That is why a device including a taste sensor is difficult to be made small and the power consumption thereof is difficult to reduce.

Spiciness, astringency, and the like, which stimulate algesia, are not tastes to be sensed with taste nerves but in this specification and the like, sensors determining spiciness, astringency, and the like are called taste sensors for convenience.

An object of one embodiment of the present invention is to provide a semiconductor device capable of performing a product-sum operation. Another object of one embodiment of the present invention is to provide a semiconductor device with low power consumption. Another object of one embodiment of the present invention is to provide a semiconductor device with reduced circuit area. Another object of one embodiment of the present invention is to provide a semiconductor device whose operation capability is inhibited from being reduced due to heat.

Another object of one embodiment of the present invention is to provide a novel semiconductor device and the like. Another object of one embodiment of the present invention is to provide an electronic device including the semiconductor device.

An object of one embodiment of the present invention is to provide an odor sensor capable of detecting various odor molecules. An object of one embodiment of the present invention is to provide an odor sensor with low power consumption. An object of one embodiment of the present invention is to provide an odor sensor with reduced circuit area.

An object of one embodiment of the present invention is to provide a pressure sensor capable of detecting pressure distributions in various planes. An object of one embodiment of the present invention is to provide a pressure sensor with low power consumption. An object of one embodiment of the present invention is to provide a pressure sensor with reduced circuit area.

An object of one embodiment of the present invention is to provide a taste sensor capable of evaluating a taste of a substance including a plurality of taste components. An object of one embodiment of the present invention is to provide a taste sensor with low power consumption. Another object of one embodiment of the present invention is to provide a taste sensor with reduced circuit area.

Note that the objects of one embodiment of the present invention are not limited to the objects listed above. The objects listed above do not preclude the existence of other objects. Note that the other objects are objects that are not described in this section and are described below. The objects that are not described in this section are derived from the description of the specification, the drawings, and the like and can be extracted as appropriate from the description by those skilled in the art. Note that one embodiment of the present invention is to achieve at least one of the objects listed above and the other objects. Note that one embodiment of the present invention does not necessarily achieve all the objects listed above and the other objects.

Means for Solving the Problems (1)
One embodiment of the present invention is a semiconductor device, including a first circuit, a second circuit, a first cell, a second cell, a first wiring, and a second wiring. The first cell includes a first transistor. The second cell includes a second transistor. The first cell is electrically connected to the first circuit through the first wiring. The first cell is electrically connected to the second circuit through the second wiring. The second cell is electrically connected to the second circuit through the second wiring. The first circuit has a function of making a first current flow from the first circuit to the first cell through the first wiring. The second circuit has a function of making a second current flow from the second circuit to the second cell through the second wiring and a function of supplying a first potential corresponding to the second current from the second circuit to each of the first cell and the second cell through the second wiring. The first cell has a function of setting a current flowing between a first terminal and a second terminal of the first transistor to the first current. The second cell has a function of setting a current flowing between a first terminal and a second terminal of the second transistor to the second current. The second circuit has a function of changing the second current flowing in the second wiring to a third current to change the first potential supplied to each of the first cell and the second cell to a second potential. The first cell has a function of changing the first current flowing between the first terminal and the second terminal of the first transistor to a fourth current corresponding to a difference between the first potential and the second potential. An amount of each of the first current and the fourth current is an amount of current flowing when the first transistor operates in a subthreshold region. An amount of each of the second current and the third current is an amount of current flowing when the second transistor operates in a subthreshold region.

(2)
In the above (1), one embodiment of the present invention may have a structure in which each of the first transistor and the second transistor includes a metal oxide in a channel formation region.

(3)
One embodiment of the present invention is a semiconductor device, including a first circuit, a second circuit, a first cell, a second cell, a first wiring, and a second wiring. The first cell comprises a first transistor, a third transistor, and a first capacitor. The second cell comprises a second transistor, a fourth transistor, and a second capacitor. The first circuit is electrically connected to the first wiring. The second circuit is electrically connected to the second wiring. A first terminal of the third transistor is electrically connected to a first terminal of the first transistor and the first wiring. A second terminal of the third transistor is electrically connected to a gate of the first transistor and a first terminal of the first capacitor. A second terminal of the first capacitor is electrically connected to the second wiring. A first terminal of the fourth transistor is electrically connected to a first terminal of the second transistor and the second wiring. A second terminal of the fourth transistor is electrically connected to a gate of the second transistor and a first terminal of the second capacitor. A second terminal of the second capacitor is electrically connected to the second wiring. The first circuit has a function of making a first current flow from the first circuit to the first terminal of the first transistor through the first wiring. The second circuit has a function of making a second current flow from the second circuit to the first terminal of the second transistor through the second wiring and a function of supplying a first potential corresponding to the second current from the second circuit to each of the second terminal of the first capacitor and the second terminal of the second capacitor through the second wiring. The first cell has a function of setting the first current flowing between the first terminal and a second terminal of the first transistor. The second cell has a function of setting the second current flowing between the first terminal and a second terminal of the second transistor. The second circuit has a function of changing the second current flowing in the second wiring to a third current to change the first potential supplied to each of the second terminal of the first capacitor and the second terminal of the second capacitor to a second potential. The first cell has a function of changing the first current flowing between the first terminal and the second terminal of the first transistor to a fourth current corresponding to a difference between the first potential and the second potential. An amount of each of the first current and the fourth current is an amount of current flowing when the first transistor operates in a subthreshold region. An amount of each of the second current and the third current is an amount of current flowing when the second transistor operates in a subthreshold region.

(4)
In the above (3), one embodiment of the present invention may have a structure in which each of the first transistor to the fourth transistor includes a metal oxide in a channel formation region.

(5)
In one of the above (1) to (4), one embodiment of the present invention may have a structure in which the first circuit includes a fifth transistor and a sixth transistor. It is preferable that the sixth transistor includes a first gate and a second gate, a first terminal of the fifth transistor is electrically connected to the first wiring, and a second terminal of the fifth transistor is electrically connected to a first terminal of the sixth transistor, the first gate of the sixth transistor, and the second gate of the sixth transistor.

(6)
In the above (5), one embodiment of the present invention may have a structure in which each of the fifth transistor and the sixth transistor includes a metal oxide in a channel formation region.

(7)
In one of the above (1) to (4), one embodiment of the present invention is preferably has a structure in which the second circuit includes a seventh transistor and an eighth transistor, the eighth transistor includes a third gate and a fourth gate, a first terminal of the seventh transistor is electrically connected to the second wiring, and a second terminal of the seventh transistor is electrically connected to a first terminal of the eighth transistor, the third gate of the eighth transistor, and the fourth gate of the eighth transistor.

(8)
In the above (7), one embodiment of the present invention may have a structure in which each of the seventh transistor and the eighth transistor includes a metal oxide in a channel formation region.

(9)
In one of the above (1) to (6), one embodiment of the present invention may have a structure in which the second circuit includes an optical sensor. The optical sensor is electrically connected to the second wiring. The optical sensor has a function of performing first sensing to make the second current flow from the optical sensor to the second wiring, and a function of performing second sensing to change an amount of the second current to an amount of the third current.

(10)

In one of the above (1) to (6), one embodiment of the present invention may have a structure in which the second circuit includes a sensor. The sensor is electrically connected to the second wiring. Especially, the sensor has a function of detecting an odor component, and a function of making the second current flow from the sensor to the second wiring when the odor component is not detected and changing an amount of the second current to an amount of the third current when the odor component is detected.

(11)

In one of the above (1) to (6), one embodiment of the present invention may have a structure in which the second circuit includes a sensor. The sensor is electrically connected to the second wiring. Especially, the sensor has a function of detecting a contact of an object, and a function of making the second current flow from the sensor to the second wiring when the contact of the object is not detected and changing an amount of the second current to an amount of the third current when the contact by the object is detected.

(12)

In one of the above (1) to (6), one embodiment of the present invention may have a structure in which the second circuit includes a sensor. The sensor is electrically connected to the second wiring. Especially, the sensor has a function of detecting a taste component, and a function of making the second current flow from the sensor to the second wiring when the taste component is not detected and changing an amount of the second current to an amount of the third current when the taste component is detected.

(13)

One embodiment of the present invention is an electronic device including the semiconductor device according to any one of the above (1) to (12) and a housing. The semiconductor device has a function of performing a product-sum operation.

Note that in this specification and the like, a semiconductor device refers to a device that utilizes semiconductor characteristics, and means a circuit including a semiconductor element (a transistor, a diode, a photodiode, or the like), a device including the circuit, and the like. The semiconductor device also means all devices that can function by utilizing semiconductor characteristics. For example, an integrated circuit, a chip including an integrated circuit, and an electronic component including a chip in a package are examples of the semiconductor device. Moreover, a memory device, a display device, a light-emitting device, a lighting device, an electronic device, and the like themselves are semiconductor devices, or include semiconductor devices in some cases.

In the case where there is a description "X and Y are connected" in this specification and the like, the case where X and Y are electrically connected, the case where X and Y are functionally connected, and the case where X and Y are directly connected are regarded as being disclosed in this specification and the like. Accordingly, without being limited to a predetermined connection relation, for example, a connection relation shown in drawings or texts, a connection relation other than one shown in drawings or texts is regarded as being disclosed in the drawings or the texts.

Each of X and Y denotes an object (e.g., a device, an element, a circuit, a wiring, an electrode, a terminal, a conductive film, or a layer).

For example, in the case where X and Y are electrically connected, one or more elements that allow(s) electrical connection between X and Y (e.g., a switch, a transistor, a capacitor, an inductor, a resistor, a diode, a display device, a light-emitting device, and a load) can be connected between X and Y. Note that a switch has a function of being controlled to be turned on or off That is, the switch has a function of being in a conduction state (on state) or a non-conduction state (off state) to control whether a current flows or not.

For example, in the case where X and Y are functionally connected, one or more circuits that allow(s) functional connection between X and Y (e.g., a logic circuit (an inverter, a NAND circuit, a NOR circuit, or the like); a signal converter circuit (a digital-analog converter circuit, an analog-digital converter circuit, a gamma correction circuit, or the like); a potential level converter circuit (a power supply circuit (a step-up circuit, a step-down circuit, or the like), a level shifter circuit for changing the potential level of a signal, or the like); a voltage source; a current source; a switching circuit; an amplifier circuit (a circuit that can increase signal amplitude, the amount of current, or the like, an operational amplifier, a differential amplifier circuit, a source follower circuit, a buffer circuit, or the like); a signal generation circuit; a memory circuit; or a control circuit) can be connected between X and Y. For example, even when another circuit is interposed between X and Y, X and Y are functionally connected when a signal output from X is transmitted to Y.

Note that an explicit description, X and Y are electrically connected, includes the case where X and Y are electrically connected (i.e., the case where X and Y are connected with another element or another circuit interposed therebetween) and the case where X and Y are directly connected (i.e., the case where X and Y are connected without another element or another circuit interposed therebetween).

It can be expressed as, for example, "X, Y, a source (or a first terminal or the like) of a transistor, and a drain (or a second terminal or the like) of the transistor are electrically connected to each other, and X, the source (or the first terminal or the like) of the transistor, the drain (or the second terminal or the like) of the transistor, and Y are electrically connected to each other in this order". Alternatively, it can be expressed as "a source (or a first terminal or the like) of a transistor is electrically connected to X; a drain (or a second terminal or the like) of the transistor is electrically connected to Y; and X, the source (or the first terminal or the like) of the transistor, the drain (or the second terminal or the like) of the transistor, and Y are electrically connected to each other in this order". Alternatively, it can be expressed as "X is electrically connected to Y through a source (or a first terminal or the like) and a drain (or a second terminal or the like) of a transistor, and X, the source (or the first terminal or the like) of the transistor, the drain (or the second terminal or the like) of the transistor, and Y are provided in this connection order". When the connection order in a circuit structure is defined by an expression similar to the above examples, a source (or a first terminal or the like) and a drain (or a second terminal or the like) of a transistor can be distinguished from each other to specify the technical scope. Note that these expressions are examples and the expression is not limited to these expressions. Here, X and Y each denote an object (e.g., a device, an element, a circuit, a wiring, an electrode, a terminal, a conductive film, or a layer).

Even when independent components are electrically connected to each other in a circuit diagram, one component has functions of a plurality of components in some cases. For example, when part of a wiring also functions as an electrode, one conductive film has functions of both components: a function of the wiring and a function of the electrode. Thus, electrical connection in this specification includes, in its category, such a case where one conductive film has functions of a plurality of components.

In this specification and the like, a "resistor" can be, for example, a circuit element or a wiring having a resistance higher than 0Ω. Therefore, in this specification and the like, a "resistor" sometimes includes a wiring having a resistance value, a transistor in which a current flows between its source and drain, a diode, and a coil. Thus, the term "resistor" can be replaced with the terms "resistance", "load", and "a region having a resistance value", and the like; conversely, the terms "resistance", "load", and "a region having a resistance" can be replaced with the term "resistor" and the like. The resistance value can be, for example, preferably greater than or equal to 1 mΩ and less than or equal to 10Ω, further preferably greater than or equal to 5 mΩ and less than or equal to 5Ω, still further preferably greater than or equal to 10 mΩ and less than or equal to 1Ω. As another example, the resistance value may be greater than or equal to 1Ω and less than or equal to $1\times10^9$Ω.

In this specification and the like, a "capacitor" can be, for example, a circuit element having an electrostatic capacitance higher than 0 F, a region of a wiring having an electrostatic capacitance value, parasitic capacitance, or gate capacitance of a transistor. Therefore, in this specification and the like, a "capacitor" sometimes includes not only a circuit element that has a pair of electrodes and a dielectric between the electrodes, but also parasitic capacitance generated between wirings, gate capacitance generated between a gate and one of a source and a drain of a transistor, and the like. The terms "capacitor", "parasitic capacitance", "gate capacitance", and the like can be replaced with the term "capacitance" and the like; conversely, the term "capacitance" can be replaced with the terms "capacitor", "parasitic capacitance", "gate capacitance", and the like. The term "pair of electrodes" of "capacitor" can be replaced with "pair of conductors", "pair of conductive regions", "pair of regions", and the like. Note that the electrostatic capacitance value can be greater than or equal to 0.05 fF and less than or equal to 10 pF, for example. Alternatively, the electrostatic capacitance value may be greater than or equal to 1 pF and less than or equal to 10 μF, for example.

In this specification and the like, a transistor includes three terminals called a gate, a source, and a drain. The gate functions as a control terminal for controlling the conduction state of the transistor. Two terminals functioning as the source or the drain are input/output terminals of the transistor. One of the two input/output terminals serves as the source and the other serves as the drain on the basis of the conductivity type (n-channel type or p-channel type) of the transistor and the levels of potentials applied to the three terminals of the transistor. Thus, the terms "source" and "drain" can be replaced with each other in this specification and the like. In this specification and the like, expressions "one of a source and a drain" (or a first electrode or a first terminal) and "the other of the source and the drain" (or a second electrode or a second terminal) are used in description of the connection relation of a transistor. Depending on the transistor structure, a transistor may include a back gate in addition to the above three terminals. In that case, in this specification and the like, one of the gate and the back gate of the transistor may be referred to as a first gate and the other of the gate and the back gate of the transistor may be referred to as a second gate. Moreover, the terms "gate" and "back gate" can be replaced with each other in one transistor in some cases. In the case where a transistor includes three or more gates, the gates may be referred to as a first gate, a second gate, and a third gate, for example, in this specification and the like.

In this specification and the like, a node can be referred to as a terminal, a wiring, an electrode, a conductive layer, a conductor, an impurity region, or the like depending on the circuit structure, the device structure, or the like. Furthermore, a terminal, a wiring, or the like can be referred to as a node.

In this specification and the like, "voltage" and "potential" can be replaced with each other as appropriate. The "voltage" refers to a potential difference from a reference potential, and when the reference potential is a ground potential, for example, the "voltage" can be replaced with the "potential". Note that the ground potential does not necessarily mean 0 V. Moreover, potentials are relative values, and a potential supplied to a wiring, a potential applied to a circuit and the like, a potential output from a circuit and the like, for example, are changed with a change of the reference potential.

In this specification and the like, the term "high-level potential" or "low-level potential" does not mean a particular potential. For example, in the case where two wirings are both described as "functioning as a wiring for supplying a high-level potential", the levels of the high-level potentials that these wirings supply are not necessarily equal to each other. Similarly, in the case where two wirings are both described as "functioning as a wiring for supplying a low-level potential", the levels of the low-level potentials that these wirings supply are not necessarily equal to each other.

Note that "current" is a charge transfer (electrical conduction); for example, the description "electrical conduction of positively charged particles occurs" can be rephrased as "electrical conduction of negatively charged particles occurs in the opposite direction". Therefore, unless otherwise specified, "current" in this specification and the like refers to a charge transfer (electrical conduction) accompanied by carrier movement. Examples of a carrier here include an electron, a hole, an anion, a cation, and a complex ion, and the type of carrier differs between current flow systems (e.g., a semiconductor, a metal, an electrolyte solution, and a vacuum). The "direction of a current" in a wiring or the like refers to the direction in which a carrier with a positive charge moves, and the amount of current is expressed as a positive value. In other words, the direction in which a carrier with a negative charge moves is opposite to the direction of a current, and the amount of current is expressed as a negative value. Thus, in the case where the polarity of a current (or the direction of a current) is not specified in this specification and the like, the description "current flows from element A to element B" can be rephrased as "current flows from element B to element A", for example. The description "current is input to element A" can be rephrased as "current is output from element A", for example.

Ordinal numbers such as "first", "second", and "third" in this specification and the like are used to avoid confusion among components. Thus, the terms do not limit the number of components. In addition, the terms do not limit the order of components. In this specification and the like, for example, a "first" component in one embodiment can be referred to as a "second" component in other embodiments or the scope of claims. Furthermore, in this specification and the like, for example, a "first" component in one embodiment can be omitted in other embodiments or the scope of claims.

In this specification and the like, the terms for describing positioning, such as "over" or "above" and "under" or "below", are sometimes used for convenience to describe the positional relation between components with reference to drawings. The positional relation between components is changed as appropriate in accordance with a direction in which the components are described. Thus, the positional relation is not limited to the terms described in the specification and the like, and can be described with another term as appropriate depending on the situation. For example, the expression "an insulator positioned over (on) a top surface of a conductor" can be replaced with the expression "an insulator positioned under (on) a bottom surface of a conductor" when the direction of a drawing showing these components is rotated by 180°

Furthermore, the terms such as "over" or "above" and "under" or "below" do not necessarily mean that a component is placed directly over or directly under and in direct contact with another component. For example, the expression "electrode B over insulating layer A" does not necessarily mean that the electrode B is formed on and in direct contact with the insulating layer A, and does not exclude the case where another component is provided between the insulating layer A and the electrode B.

In this specification and the like, the terms "film", "layer", and the like can be interchanged with each other depending on the situation. For example, the term "conductive layer" can be changed into the term "conductive film" in some cases. Moreover, the term "insulating film" can be changed into the term "insulating layer" in some cases. Alternatively, the term "film", "layer", or the like is not used and can be interchanged with another term depending on the case or the situation. For example, the term "conductive layer" or "conductive film" can be changed into the term "conductor" in some cases. Furthermore, for example, the term "insulating layer" or "insulating film" can be changed into the term "insulator" in some cases.

In this specification and the like, the term such as an "electrode", a "wiring", or a "terminal" does not limit the function of a component. For example, an "electrode" is used as part of a "wiring" in some cases, and vice versa. Furthermore, the term "electrode" or "wiring" also includes the case where a plurality of "electrodes" or "wirings" are formed in an integrated manner, for example. For example, a "terminal" is used as part of a "wiring" or an "electrode" in some cases, and vice versa. Furthermore, the term "terminal" can also mean the case where a plurality of "electrodes", "wirings", "terminals", or the like is formed in an integrated manner. Therefore, for example, an "electrode" can be part of a "wiring" or a "terminal", and a "terminal" can be part of a "wiring" or an "electrode". Moreover, the terms "electrode", "wiring", "terminal", and the like are sometimes replaced with the term "region" depending on the case, for example.

In this specification and the like, the terms "wiring", "signal line", "power supply line", and the like can be interchanged with each other depending on the case or the situation. For example, the term "wiring" can be changed into the term "signal line" in some cases. As another example, the term "wiring" can be changed into the term "power supply line" in some cases. Conversely, the term "signal line", "power supply line", or the like can be changed into the term "wiring" in some cases. The term "power supply line" or the like can be changed into the term "signal line" or the like in some cases. Conversely, the term "signal line" or the like can be changed into the term "power supply line" or the like in some cases. The term "potential" that is applied to a wiring can be changed into the term "signal" or the like depending on the case or the situation. Conversely, the term "signal" or the like can be changed into the term "potential" in some cases.

In this specification and the like, an impurity in a semiconductor refers to an element other than a main component of a semiconductor layer, for example. For example, an element with a concentration of lower than 0.1 atomic % is an impurity. When an impurity is contained, for example, the density of defect states in a semiconductor may be increased, the carrier mobility may be decreased, or the crystallinity may be decreased. In the case where the semiconductor is an oxide semiconductor, examples of an impurity that changes characteristics of the semiconductor include Group 1 elements, Group 2 elements, Group 13 elements, Group 14 elements, Group 15 elements, and transition metals other than the main components; specific examples are hydrogen (including water), lithium, sodium, silicon, boron, phosphorus, carbon, and nitrogen. Specifically, when the semiconductor is a silicon layer, examples of an impurity that changes characteristics of the semiconductor include Group 1 elements, Group 2 elements, Group 13 elements, and Group 15 elements (except oxygen and hydrogen).

In this specification and the like, a switch is in a conduction state (on state) or a non-conduction state (off state) to determine whether a current flows or not. Alternatively, a switch has a function of selecting and changing a current path. For example, an electrical switch or a mechanical switch can be used. That is, a switch can be any element capable of controlling a current, and is not limited to a particular element.

Examples of an electrical switch include a transistor (e.g., a bipolar transistor and a MOS transistor), a diode (e.g., a PN diode, a PIN diode, a Schottky diode, a MIM (Metal Insulator Metal) diode, a MIS (Metal Insulator Semiconductor) diode, and a diode-connected transistor), and a logic circuit in which such elements are combined. Note that in the case of using a transistor as a switch, a "conduction state" of the transistor refers to a state where a source electrode and a drain electrode of the transistor can be regarded as being electrically short-circuited. Furthermore, a "non-conduction state" of the transistor refers to a state where the source electrode and the drain electrode of the transistor can be regarded as being electrically disconnected. Note that in the case where a transistor operates just as a switch, there is no particular limitation on the polarity (conductivity type) of the transistor.

An example of a mechanical switch is a switch formed using a MEMS (micro electro mechanical system) technology. Such a switch includes an electrode that can be moved mechanically, and operates by controlling conduction and non-conduction with movement of the electrode.

In this specification, "parallel" indicates a state where two straight lines are placed at an angle greater than or equal to −10° and less than or equal to 10°. Thus, the case where the angle is greater than or equal to −5° and less than or equal to 5° is also included. In addition, the term "approximately parallel" or "substantially parallel" indicates a state where two straight lines are placed at an angle greater than or equal to −30° and less than or equal to 30°. Moreover, "perpendicular" indicates a state where two straight lines are placed at an angle greater than or equal to 80° and less than or equal to 100°. Thus, the case where the angle is greater than or equal to 85° and less than or equal to 95° is also included. Furthermore, "approximately perpendicular" or "substantially perpendicular" indicates a state where two straight lines are placed at an angle greater than or equal to 60° and less than or equal to 120°.

Effect of the Invention

Another embodiment of the present invention can provide a semiconductor device capable of performing a product-sum operation. Alternatively, one embodiment of the present invention can provide a semiconductor device with low power consumption. Another embodiment of the present invention can provide a semiconductor device with reduced circuit area. Another embodiment of the present invention can provide a semiconductor device whose operation capability is inhibited from being decreased due to heat.

Another embodiment of the present invention can provide a novel semiconductor device and the like. Another embodiment of the present invention can provide an electronic device including the semiconductor device.

One embodiment of the present invention can provide an odor sensor capable of detecting various odor molecules. One embodiment of the present invention can provide an odor sensor with low power consumption. One embodiment of the present invention can provide an odor sensor with reduced circuit area.

One embodiment of the present invention can provide a pressure sensor capable of detecting various pressure distributions in various planes. One embodiment of the present invention can provide a pressure sensor with low power consumption. Another embodiment of the present invention can provide a pressure sensor with reduced circuit area.

One embodiment of the present invention can provide a taste sensor capable of evaluating a taste of a substance including a plurality of taste components. One embodiment of the present invention can provide a taste sensor with low power consumption. One embodiment of the present invention can provide a taste sensor with reduced circuit area.

Note that the effects of embodiments of the present invention are not limited to the effects listed above. The effects listed above do not preclude the existence of other effects. Note that the other effects are effects that are not described in this section and will be described below. The effects that are not described in this section are derived from the descriptions of the specification, the drawings, and the like and can be extracted from these descriptions by those skilled in the art. Note that one embodiment of the present invention has at least one of the effects listed above and the other effects. Accordingly, depending on the case, one embodiment of the present invention does not have the effects listed above in some cases.

BRIEF DESCRIPTION OF THE DRAWINGS

FIG. 21A to FIG. 21C are schematic diagrams showing a structure example of a hand portion included in a manipulator or the like.

FIG. 22A and FIG. 22B are schematic diagrams showing a structure example of a hand portion included in a manipulator or the like.

FIG. 38A is a table showing classifications of crystal structures of IGZO, FIG. 38B is a graph showing an XRD spectrum of crystalline IGZO, and FIG. 38C is an image showing a nanobeam electron diffraction pattern of crystalline IGZO.

MODE FOR CARRYING OUT THE INVENTION

Figure 1:
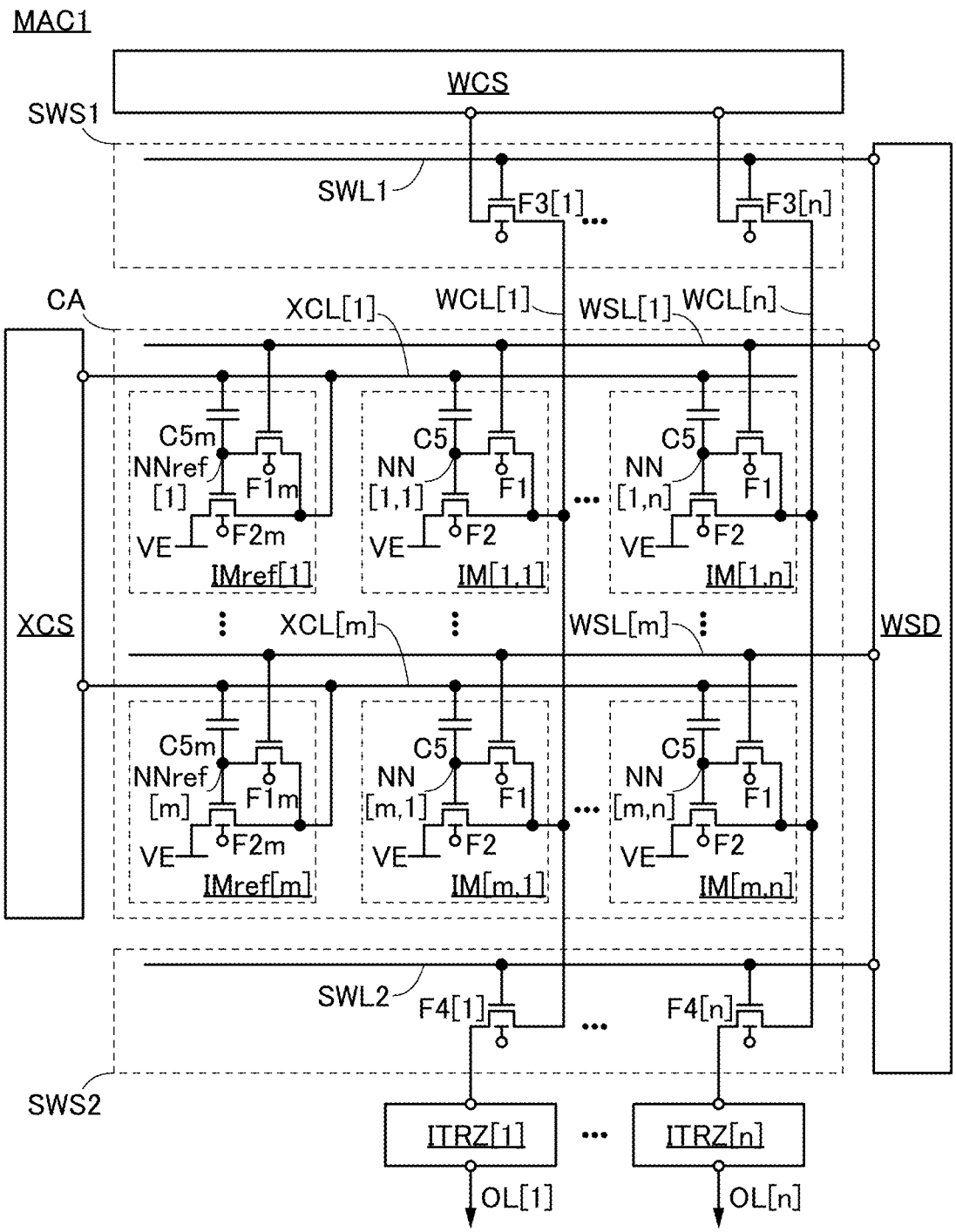
FIG. 1 is a block diagram showing a configuration example of a semiconductor device.

In an artificial neural network (hereinafter, referred to as a neural network), the connection strength between synapses can be changed when existing information is given to the neural network. The processing for determining a connection strength by providing a neural network with existing data in such a manner is called "learning" in some cases.

Furthermore, when a neural network in which "learning" has been performed (the connection strength has been determined) is provided with some type of information, new information can be output on the basis of the connection strength. The processing for outputting new information on the basis of provided information and the connection strength in a neural network in such a manner is called "inference" or "recognition" in some cases.

Examples of the model of a neural network include a Hopfield type and a hierarchical type. In particular, a neural network with a multilayer structure is called a "deep neural network" (DNN), and machine learning using a deep neural network is called "deep learning" in some cases.

In this specification and the like, a metal oxide is an oxide of metal in a broad sense. Metal oxides are classified into an oxide insulator, an oxide conductor (including a transparent oxide conductor), an oxide semiconductor (also simply referred to as an OS), and the like. For example, in the case where a metal oxide is used in an active layer of a transistor, the metal oxide is referred to as an oxide semiconductor in some cases. That is, when a metal oxide can form a channel formation region of a transistor that has at least one of an amplifying function, a rectifying function, and a switching function, the metal oxide can be referred to as a metal oxide semiconductor. In the case where an OS transistor is mentioned, the OS transistor can also be referred to as a transistor including a metal oxide or an oxide semiconductor.

Furthermore, in this specification and the like, a metal oxide containing nitrogen is also collectively referred to as a metal oxide in some cases. A metal oxide containing nitrogen may be referred to as a metal oxynitride.

In this specification and the like, one embodiment of the present invention can be constituted by appropriately combining a structure described in an embodiment with any of the structures described in the other embodiments. In addition, in the case where a plurality of structure examples is described in one embodiment, the structure examples can be combined as appropriate.

Note that a content (or part of the content) described in one embodiment can be applied to, combined with, or replaced with at least one of another content (or part of the content) in the embodiment and a content (or part of the content) described in one or a plurality of different embodiments.

Note that in each embodiment (or the example), a content described in the embodiment is a content described with reference to a variety of diagrams or a content described with text disclosed in the specification.

Note that by combining a diagram (or part thereof) described in one embodiment with at least one of another part of the diagram, a different diagram (or part thereof) described in the embodiment, and a diagram (or part thereof) described in one or a plurality of different embodiments, much more diagrams can be formed.

Embodiments described in this specification are described with reference to the drawings. Note that the embodiments can be implemented in many different modes, and it will be readily appreciated by those skilled in the art that modes and details can be changed in various ways without departing from the spirit and scope thereof. Therefore, the present invention should not be interpreted as being limited to the description in the embodiments. Note that in the structures of the invention in the embodiments, the same portions or portions having similar functions are denoted by the same reference numerals in different drawings, and repeated description thereof is omitted in some cases. In perspective views and the like, some components might not be illustrated for clarity of the drawings.

In this specification and the like, when a plurality of components are denoted with the same reference numerals, and in particular need to be distinguished from each other, an identification sign such as "_1", "[n]", or "[m,n]" is sometimes added to the reference numerals.

In the drawings in this specification, the size, the layer thickness, or the region is exaggerated for clarity in some cases. Therefore, they are not limited to the illustrated scale. The drawings are schematic views showing ideal examples, and embodiments of the present invention are not limited to shapes or values shown in the drawings. For example, variations in signal, voltage, or current due to noise, variations in signal, voltage, or current due to difference in timing, or the like can be included.

Embodiment 1

In this embodiment, an example of a circuit capable of performing a product-sum operation that is a semiconductor device of one embodiment of the present invention will be described.

<Configuration Example 1 of Arithmetic Circuit>

FIG. 1 shows a configuration example of an arithmetic circuit which performs a product-sum operation of positive or "0" first data and positive or "0" second data. An arithmetic circuit MAC1 illustrated in FIG. 1 is a circuit that performs product-sum operation of the first data corresponding to a potential stored in each cell and the input second data, and performs arithmetic operation of an activation function using the result of the product-sum operation. Note that the first data and the second data can be analog data or multilevel data (discrete data), for example.

The arithmetic circuit MAC1 includes a circuit WCS, a circuit XCS, a circuit WSD, a circuit SWS1, a circuit SWS2, a cell array CA, and a converter circuit ITRZ[1] to a converter circuit ITRZ[n].

The cell array CA includes a cell IM[1,1] to a cell IM[m,n] (here, m is an integer greater than or equal to 1 and n is an integer greater than or equal to 1) and a cell IMref[1] to a cell IMref[m]. The cell IM[1,1] to the cell IM[m,n] have a function of storing a potential corresponding to the current amount corresponding to the first data, and the cell IMref[1] to the cell IMref[m] have a function of supplying a potential corresponding to the second data required for performing a product-sum operation with the stored first data to the wiring XCL[1] to the wiring XCL[m], respectively.

In the cell array CA in FIG. 1, cells are arranged in a matrix of n+1 rows and m columns; however, the cell array CA may have a structure in which cells are arranged in a matrix of two or more rows and one or more columns.

The cell IM[1,1] to the cell IM[m,n] each include a transistor F1, a transistor F2, and a capacitor C5, and the cell IMref[1] to the cell IMref[m] each include a transistor F1$m$, a transistor F2$m$, and a capacitor C5$m$, for example.

In particular, the sizes of the transistors F1 (e.g., channel length, channel width, and structure of transistor) included in the cell IM[1,1] to the cell IM[m,n] are preferably equal to each other, and the sizes of the transistors F2 included in the cell IM[1,1] to the cell IM[m,n] are preferably equal to each other. The sizes of the transistors F1$m$ included in the cell IMref[1] to the cell IMref[m] are preferably equal to each other, and the sizes of the transistors F2$m$ included in the cell IMref[1] to the cell IMref[m] are preferably equal to each other. The size of the transistor F1 is preferably equal to that of the transistor F1$m$, and the size of the transistor F2 is preferably equal to that of the transistor F2$m$.

By making the transistors have the same size, each transistor can have almost the same electrical characteristics. By making the transistors F1 included in the cell IM[1,1] to the cell IM[m,n] have the same size and the transistors F2 included in the cell IM[1,1] to the cell IM[m,n] have the same size, each of the cell IM[1,1] to the cell IM[m,n] can exhibit almost the same performance in the same condition with each other. The same condition means, for example, input potentials to a source, a drain, and a gate of the transistor F1, input potentials to a source, a drain, and a gate of the transistor F2, and a voltage input to each of the cell IM[1,1] to the cell IM[m,n]. By making the transistors F1$m$ included in the cell IMref[1] to the cell IMref[m] have the same size and the transistors F2$m$ included in the cell IMref[1] to the cell IMref[m] have the same size, the cell IMref[1] to the cell IMref[m] can exhibit almost the same performance and yield almost the same results. In the case of the same condition, the cell IMref[1] to the cell IMref[m] can exhibit almost the same performance. The same condition means, for example, input potentials to a source, a drain, and a gate of the transistor F1$m$, input potentials to a source, a drain, and a gate of the transistor F2$m$, and a voltage input to each of the cell IMref[1] to the cell IMref[m].

Unless otherwise specified, the transistor F1 and the transistor F1$m$ in an on state may operate in a linear region in the end. In other words, the gate voltage, the source voltage, and the drain voltage of each of the above-described transistors may be within the range where the transistor operates in the linear region. However, one embodiment of the present invention is not limited thereto. For example, the transistor F1 and the transistor F1$m$ in an on state may operate in a saturation region or may operate both in a linear region and a saturation region.

Unless otherwise specified, the transistor F2 and the transistor F2$m$ may operate in a subthreshold region (i.e., a voltage between the gate and the source of the transistor F2 or the transistor F2$m$ may be lower than the threshold voltage, preferably a drain voltage exponentially increases with respect to the voltage between the gate and the source). In other words, the gate voltage, the source voltage, and the drain voltage of each of the above-described transistors may be within the range where the transistor operates in the subthreshold region. Thus, the transistors F2 and the transistor F2$m$ may operate so that an off-state current flows between the source and the drain.

Like the transistor F1 and/or the transistor F1$m$ is preferably an OS transistor, for example. In addition, it is further preferable that a channel formation region in each of the transistor F1 and/or the transistor F1$m$ be an oxide containing at least one of indium, gallium, and zinc. Instead of the oxide, the channel formation region may be an oxide containing at least one of indium, an element M (as the element M, one or more kinds selected from aluminum, gallium, yttrium, copper, vanadium, beryllium, boron, titanium, iron, nickel, germanium, zirconium, molybdenum, lanthanum, cerium, neodymium, hafnium, tantalum, tungsten, magnesium, and the like can be given for example), and zinc. It is further preferable that the transistor F1 and/or the transistor F1*m* have a structure of the transistor described in Embodiment 6, in particular.

With the use of an OS transistor as the transistor F1 and/or the transistor F1*m*, the leakage current of the transistor F1 and/or the transistor F1*m* can be suppressed, so that the power consumption of the arithmetic circuit can be reduced. Specifically, in the case where the transistor F1 and/or the transistor F1*m* are/is in the off state, the amount of leakage current from a retention node to a write word line can be extremely small and the frequency of refresh operation for the potential at the retention node can be reduced. By reducing the frequency of refresh operations, the power consumption of the arithmetic circuit can be reduced. By making a leakage current from the retention node to a wiring WCL or a wiring XCL extremely small, cells can store the potential of the retention node for a long time, so that the arithmetic operation accuracy of the arithmetic circuit can be high.

The use of an OS transistor also as the transistor F2 and/or the transistor F2*m* enables operation with a wide range of current in the subthreshold region, leading to a reduction in the current consumption. By using an OS transistor also as the transistor F2 and/or the transistor F2*m*, the transistor F2 and/or the transistor F2*m* can be manufactured concurrently with the transistor F1 and the transistor F1*m*, and thus the number of manufacturing steps of the arithmetic circuit can be decreased in some cases. The transistor F2 and/or the transistor F2*m* can be, other than an OS transistor, a transistor including silicon in its channel formation region (hereinafter referred to as a Si transistor). As the silicon, amorphous silicon (referred to as hydrogenated amorphous silicon in some cases), microcrystalline silicon, polycrystalline silicon, single crystal silicon, or the like can be used, for example.

When a semiconductor device or the like is highly integrated into a chip or the like, the chip may have heat when the circuit operates. This heat makes the temperature of a transistor rise to change the characteristics of the transistor and the field-effect mobility thereof may change or the operation frequency thereof may decrease. Since an OS transistor has a higher heat resistance than a Si transistor, the field-effect mobility is not likely to change and the operation frequency is not likely to decrease due to a change in temperature. Even when an OS transistor has a high temperature, it is likely to keep a property of the drain current increasing exponentially with respect to agate-source voltage. With the use of an OS transistor, even in a high temperature environment, an arithmetic operation, processing, or the like can be easily performed. To fabricate a semiconductor device highly resistant to heat due to operation, an OS transistor is preferably used as its transistor.

In each of the cell IM[1,1] to the cell IM[m,n], a first terminal of the transistor F1 is electrically connected to a gate of the transistor F2. A first terminal of the transistor F2 is electrically connected to a wiring VE. A first terminal of the capacitor C5 is electrically connected to the gate of the transistor F2.

In each of the cell IMref[1] to the cell IMref[m], a first terminal of the transistor F1*m* is electrically connected to a gate of the transistor F2*m*. A first terminal of the transistor F2*m* is electrically connected to the wiring VE. A first terminal of the capacitor C5*m* is electrically connected to the gate of the transistor F2*m*.

In each of the transistor F1, the transistor F2, the transistor F1*m*, and the transistor F2*m* in FIG. 1, the back gate is illustrated but the connection structure of the back gate is not illustrated; however, a target to which the back gate is electrically connected can be determined at the design stage. For example, in a transistor including a back gate, a gate and the back gate may be electrically connected to each other to increase the on-state current of the transistor. For example, a gate and a back gate of the transistor F1 can be electrically connected, and a gate and a back gate of the transistor F1*m* can be electrically connected. Alternatively, for example, in a transistor including a back gate, a wiring electrically to connect the back gate of the transistor to an external circuit or the like may be provided and a potential may be supplied to the back gate of the transistor with the external circuit or the like to change the threshold voltage of the transistor or to reduce the off-state current of the transistor.

The transistor F1 and the transistor F2 illustrated in FIG. 1 have back gates; however, the semiconductor device of one embodiment of the present invention is not limited thereto. For example, the transistor F1 and the transistor F2 illustrated in FIG. 1 may each be a transistor having a structure not including a back gate, that is, a single-gate structure. It is also possible that some transistors have a structure including a back gate and the other transistors have a structure not including a back gate.

The transistor F1 and the transistor F2 illustrated in FIG. 1 are n-channel transistors; however, the semiconductor device of one embodiment of the present invention is not limited thereto. For example, some or all of the transistors F1 and the transistors F2 may be replaced with p-channel transistors. When some or all of the transistors F1 and the transistors F2 are replaced with p-channel transistors, a voltage applied by a wiring, a potential of a node NN, a potential of a node NNref, and the like, which are described in this specification and the like, can be changed as appropriate for the sake of desired operations of the transistor F1 and the transistor F2.

The above-described examples of changes in the structure and the polarity of the transistor are not limited to the transistor F1 and the transistor F2. For example, the structures and the polarities of the transistor F1*m* and the transistor F2*m*, a transistor F3[1] to a transistor F3[*n*] and a transistor F4[1] to a transistor F4[*n*] which are described later, a transistor described in other parts of the specification, and a transistor illustrated in other drawings can be changed.

The wiring VE functions as a wiring for causing a current to flow between the first terminal and a second terminal of the transistor F2 of each of the cell IM[1,1], the cell IM[m,1], the cell IM[1,*n*], and the cell IM[m,n] and a wiring for causing a current to flow between the first terminal and a second terminal of the transistor F2*m* of each of the cell IMref[1] and the cell IMref[m]. The wiring VE functions as a wiring for supplying a constant voltage, for example. The constant voltage can be, for example, a low-level potential, a ground potential, or the like.

In the cell IM[1,1], a second terminal of the transistor F1 is electrically connected to a wiring WCL[1], and agate of the transistor F1 is electrically connected to a wiring WSL[1]. The second terminal of the transistor F2 is electrically connected to the wiring WCL[1], and a second terminal of the capacitor C5 is electrically connected to the wiring XCL[1]. In FIG. 1, in the cell IM[1,1], a connection portion of the first terminal of the transistor F1, the gate of the transistor F2, and the first terminal of the capacitor C5 is a node NN[1,1].

In the cell IM[m,1], the second terminal of the transistor F1 is electrically connected to the wiring WCL[1], and the gate of the transistor FT is electrically connected to a wiring WSL[m]. The second terminal of the transistor F2 is electrically connected to the wiring WCL[1], and the second terminal of the capacitor C5 is electrically connected to the wiring XCL[m]. In FIG. 1, in the cell IM[m,1], a connection portion of the first terminal of the transistor F1, the gate of the transistor F2, and the first terminal of the capacitor C5 is a node NN[m,1].

In the cell IM[1,$n$], the second terminal of the transistor F1 is electrically connected to a wiring WCL[n], and the gate of the transistor F1 is electrically connected to the wiring WSL[1]. The second terminal of the transistor F2 is electrically connected to the wiring WCL[n], and the second terminal of the capacitor C5 is electrically connected to the wiring XCL[1]. In FIG. 1, in the cell IM[1,$n$], a connection portion of the first terminal of the transistor F1, the gate of the transistor F2, and the first terminal of the capacitor C5 is a node NN[1,$n$].

In the cell IM[m,n], the second terminal of the transistor F1 is electrically connected to the wiring WCL[n], and the gate of the transistor F1 is electrically connected to the wiring WSL[m]. The second terminal of the transistor F2 is electrically connected to the wiring WCL[n], and the second terminal of the capacitor C5 is electrically connected to the wiring XCL[m]. In FIG. 1, in the cell IM[m,n], a connection portion of the first terminal of the transistor F1, the gate of the transistor F2, and the first terminal of the capacitor C5 is a node NN[m,n].

In the cell IMref[1], a second terminal of the transistor F1$m$ is electrically connected to the wiring XCL[1], and a gate of the transistor F1$m$ is electrically connected to the wiring WSL[1]. A second terminal of the transistor F2$m$ is electrically connected to the wiring XCL[1], and the second terminal of the capacitor C5 is electrically connected to the wiring XCL[1]. In FIG. 1, in the cell IMref[1], a connection portion of a first terminal of the transistor F1$m$, a gate of the transistor F2$m$, and the first terminal of the capacitor C5 is a node NNref[1].

In the cell IMref[m], the second terminal of the transistor F1$m$ is electrically connected to the wiring XCL[m], and the gate of the transistor F1$m$ is electrically connected to the wiring WSL[m]. A second terminal of the transistor F2$m$ is electrically connected to the wiring XCL[m], and the second terminal of the capacitor C5 is electrically connected to the wiring XCL[m]. In FIG. 1, in the cell IMref[m], a connection portion of the first terminal of the transistor F1$m$, the gate of the transistor F2$m$, and the first terminal of the capacitor C5 is a node NNref[m].

The node NN[1,1] to the node NN[m,n], and the node NNref[1] to the node NNref[m] function as retention nodes of cells.

In the case where the transistor F1 is turned on in the cell IM[1,1] to the cell IM[m,n], for example, the transistor F2 is a diode-connected transistor. When a constant voltage supplied by the wiring VE is a ground potential (GND), the transistor F1 is turned on, and a current with a current amount I flows from the wiring WCL to the second terminal of the transistor F2, the potential of the gate of the transistor F2 (node NN) is determined by the current amount I. Since the transistor F1 is in the on state, the potential of the second terminal of the transistor F2 is ideally equal to that of the gate of the transistor F2 (node NN). By turning off the transistor F1, the potential of the gate of the transistor F2 (node NN) is stored. Accordingly, the transistor F2 can make the current amount I, which is a current corresponding to the ground potential of the first terminal of the transistor F2 and the potential of the gate of the transistor F2 (node NN), flow between a source and a drain of the transistor F2. In this specification and the like, the operation is called "setting (programing) the amount of current flowing between the source and the drain of the transistor F2 in the cell IM to I".

For example, the circuit SWS1 includes the transistor F3[1] to the transistor F3[$n$]. A first terminal of the transistor F3[1] is electrically connected to the wiring WCL[1], a second terminal of the transistor F3[1] is electrically connected to the circuit WCS, and a gate of the transistor F3[1] is electrically connected to a wiring SWL1. A first terminal of the transistor F3[$n$] is electrically connected to the wiring WCL[n], a second terminal of the transistor F3[$n$] is electrically connected to the circuit WCS, and a gate of the transistor F3[$n$] is electrically connected to a wiring SWL1.

As each of the transistor F3[1] to the transistor F3[$n$], for example, a transistor which can be used as the transistor F1 and/or the transistor F2 can be used. It is particularly preferable to use an OS transistor as each of the transistor F3[1] to the transistor F3[$n$].

The circuit SWS1 functions as a circuit that switches the conduction state and the non-conduction state between the circuit WCS and each of the wiring WCL[1] to the wiring WCL[n].

For example, the circuit SWS2 includes the transistor F4[1] to the transistor F4[$n$]. A first terminal of the transistor F4[1] is electrically connected to the wiring WCL[1], a second terminal of the transistor F4[1] is electrically connected to an input terminal of the converter circuit ITRZ[1], and a gate of the transistor F4[1] is electrically connected to a wiring SWL2. A first terminal of the transistor F4[$n$] is electrically connected to the wiring WCL[n], a second terminal of the transistor F4[$n$] is electrically connected to an input terminal of the converter circuit ITRZ[n], and a gate of the transistor F4[$n$] is electrically connected to a wiring SWL2.

As each of the transistor F4[1] to the transistor F4[$n$], for example, a transistor which can be used as the transistor F1 and/or the transistor F2 can be used. It is particularly preferable to use an OS transistor as each of the transistor F4[1] to the transistor F4[$n$].

The circuit SWS2 has a function of switching the conduction state and the non-conduction state between the wiring WCL[1] and the converter circuit ITRZ[1] and between the wiring WCL[n] and the converter circuit ITRZ[n].

The circuit WCS has a function of supplying data that is to be stored in each memory cell included in the cell array CA.

The circuit XCS is electrically connected to the wiring XCL[1] to the wiring XCL[m]. The circuit XCS has a function of causing a current to flow with the current amount corresponding to reference data described later or a current corresponding to the second data to each of the cell IMref[1] to the cell IMref[m] included in the cell array CA.

The circuit WSD is electrically connected to the wiring WSL[1] to the wiring WSL[m]. The circuit WSD has a function of selecting a row of the cell array CA to which first data is written by supplying a predetermined signal to each of the wiring WSL[1] to the wiring WSL[m] when the first data is written to the cell IM[1,1] to the cell IM[m,n]. The wiring WSL[1] to the wiring WSL[m] function as write word lines.

For example, the circuit WSD is electrically connected to the wiring SWL1 and the wiring SWL2. The circuit WSD has a function of creating the conduction state or the non-conduction state between the circuit WCS and the cell array CA by supplying a predetermined signal to the wiring SWL1 and a function of creating the conduction state or the non-conduction state between the converter circuit ITRZ[1] to the converter circuit ITRZ[n] and the cell array CA by supplying a predetermined signal to the wiring SWL2.

The converter circuit ITRZ[1] to the converter circuit ITRZ[n] each include an input terminal and an output terminal, for example. For example, an output terminal of the converter circuit ITRZ[1] is electrically connected to a wiring OL[1], and an output terminal of the converter circuit ITRZ[n] is electrically connected to a wiring OL[n].

The converter circuit ITRZ[1] to the converter circuit ITRZ[n] each have a function of converting a current input to input terminals into a voltage according to the amount of the current and outputting the voltage from output terminals. Examples of the voltage can be an analog voltage, a digital voltage, and the like. The converter circuit ITRZ[1] to the converter circuit ITRZ[n] may each have an arithmetic circuit of a function system. In that case, for example, the arithmetic circuit may perform an arithmetic operation of a function using the converted voltage and outputs the results to the wiring OL[1] to the wiring OL[n].

In the case of performing an arithmetic operation of the hierarchical neural network, a sigmoid function, a tanh function, a softmax function, a ReLU function, a threshold function, or the like can be used as the above described function.

<<Circuit WCS, Circuit XCS>>

Specific examples of the circuit WCS and the circuit XCS are described.

Figure 2A:
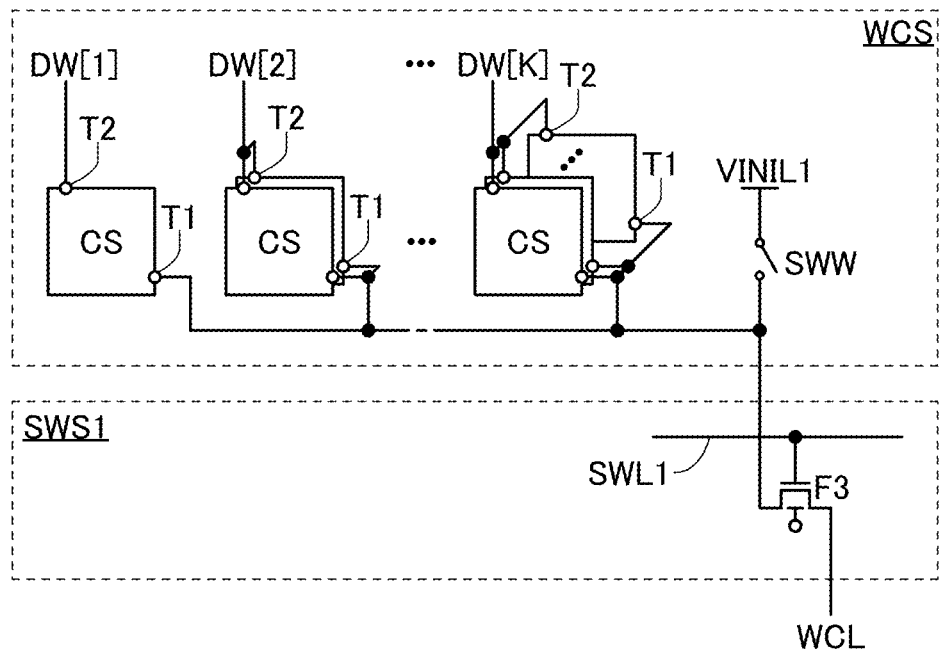
FIG. 2A to FIG. 2C are block diagrams each showing a configuration example of a circuit included in a semiconductor device.

First, the circuit WCS is described. FIG. 2A is a block diagram showing an example of the circuit WCS. In FIG. 2A, to show the electrical connection between the circuit WCS and its nearby circuits, the circuit SWS1, the transistor F3, the wiring SWL1, and the wiring WCL are illustrated. The transistor F3 is any one of the transistor F3[1] to the transistor F3[n] included in the arithmetic circuit MAC1 in FIG. 1, and the wiring WCL is any one of the wiring WCL[1] to the wiring WCL[n] included in the arithmetic circuit MAC1 in FIG. 1.

The circuit WCS illustrated in FIG. 2A includes a switch SWW, for example. A first terminal of the switch SWW is electrically connected to a second terminal of the transistor F3, and a second terminal of the switch SWW is electrically connected to a wiring VINIL1. The wiring VINIL1 functions as a wiring for supplying an initialization potential to the wiring WCL, and the initialization potential can be set to a ground potential (GND), a low-level potential, and a high-level potential. The switch SWW is turned on only when the initialization potential is supplied to the wiring WCL; otherwise, the switch is turned off.

As the switch SWW, an electrical switch such as an analog switch or a transistor can be used, for example. When a transistor is used as the switch SWW, for example, the transistor can have a structure similar to that of the transistor F1 and the transistor F2. A mechanical switch may be used other than the electrical switch.

The circuit WCS in FIG. 2A includes a plurality of current sources CS as an example. Specifically, the circuit WCS has a function of outputting K-bit first data ($2^K$ values) (K is an integer of 1 or more) as the current amount, and the circuit WCS includes $2^K-1$ current sources CS at that time. The circuit WCS includes one current source CS which outputs data corresponding to the first bit value as a current, two current sources CS which output data corresponding to the second bit value as a current, and $2^K-1$ current sources CS which output data corresponding to the K-th bit value as a current.

Each current source CS in FIG. 2A includes a terminal T1 and a terminal T2. The terminal T1 of each of the current sources CS is electrically connected to the second terminal of the transistor F3 included in the circuit SWS1. The terminal T2 of the one current source CS is electrically connected to a wiring DW[1], the terminals T2 of the two current sources CS are electrically connected to a wiring DW[2], and the terminals T2 of the $2^{K-1}$ current sources CS are electrically connected to a wiring DW[K].

The plurality of current sources CS included in the circuit WCS has a function of outputting the same constant currents $I_{Wut}$ from the terminals T1. In actuality, when the arithmetic circuit MAC1 is manufactured, the transistors in the current sources CS may have different electrical characteristics; this may yield errors. The errors of the constant currents $I_{Wut}$ output from the terminals T1 of the plurality of current sources CS are preferably within 10%, more preferably within 5%, and further preferably within 1%. In this embodiment, the description is made based on the assumption that there is no error in the constant currents $I_{Wut}$ output from the terminals T1 of the plurality of current sources CS included in the circuit WCS.

The wiring DW[1] to the wiring DW[K] which are electrically connected to the current sources CS function as wirings for sending control signals to make the current sources CS output the constant current $I_{Wut}$. Specifically, for example, when a high-level potential is supplied to the wiring DW[1], the current source CS electrically connected to the wiring DW[1] supplies $I_{Wut}$ as a constant current to the second terminal of the transistor F3, and when a low-level potential is supplied to the wiring DW[1], the current source CS electrically connected to the wiring DW[1] does not output $I_{Wut}$. For example, when a high-level potential is supplied to the wiring DW[2], the two current sources CS electrically connected to the wiring DW[2] supply the sum of $2I_{Wut}$ as a constant current to the second terminal of the transistor F3, and when a low-level potential is supplied to the wiring DW[2], the current sources CS electrically connected to the wiring DW[2] do not output the sum of $2I_{Wut}$. For example, when a high-level potential is supplied to the wiring DW[K], the $2^{K-1}$ current sources CS electrically connected to the wiring DW[K] supply the sum of $2^{K-1}I_{Wut}$ as a constant current to the second terminal of the transistor F3, and when a low-level potential is supplied to the wiring DW[K], the current sources CS electrically connected to the wiring DW[K] do not output the sum of $2^{K-1}I_{Wut}$.

The current flowing from the one current source CS electrically connected to the wiring DW[1] corresponds to the value of the first bit, the current flowing from the two current sources CS electrically connected to the wiring DW[2] corresponds to the value of the second bit, and the current amount flowing from the K current sources CS electrically connected to the wiring DW[K] corresponds to the value of the K-th bit. The circuit WCS with K of 2 is considered. For example, when the value of the first bit is "1" and the value of the second bit is "0", a high-level potential is supplied to the wiring DW[1], and a low-level potential is supplied to the wiring DW[2]. In this case, the constant current $I_{Wut}$ flows into the second terminal of the transistor F3 of the circuit SWS1 from the circuit WCS. For example, when the value of the first bit is "0" and value of the second bit is "1", a low-level potential is supplied to the wiring DW[1], and a high-level potential is supplied to the wiring DW[2]. In this case, the constant current $2I_{W_{ut}}$ flows from the circuit WCS to the second terminal of the transistor F3 of the circuit SWS1. For example, when the value of the first bit is "1" and the value of the second bit is "1", a high-level potential is supplied to the wiring DW[1] and the wiring DW[2]. In this case, the constant current $3I_{W_{ut}}$ flows from the circuit WCS to the second terminal of the transistor F3 of the circuit SWS1. For example, when the value of the first bit is "0" and the value of the second bit is "0", a low-level potential is supplied to the wiring DW[1] and the wiring DW[2]. In this case, the constant current does not flow from the circuit WCS into the second terminal of the transistor F3 of the circuit SWS1.

FIG. 2A shows the circuit WCS when K is an integer of 3 or more; when K is 1, the current sources CS electrically connected to the wiring DW[2] to the wiring DW[K] are not provided in the circuit WCS in FIG. 2A. When K is 2, the current sources CS electrically connected to the wiring DW[3] to the wiring DW[K] are not provided in the circuit WCS in FIG. 2A.

Next, a specific configuration example of the current source CS is described.

Figure 3A:
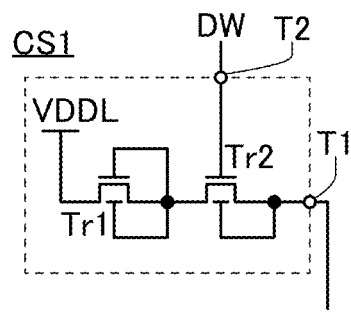
FIG. 3A to FIG. 3D are circuit diagrams each showing a configuration example of a circuit included in a semiconductor device.

A current source CS1 illustrated in FIG. 3A can be used as the current source CS included in the circuit WCS in FIG. 2A; the current source CS1 includes a transistor Tr1 and a transistor Tr2.

A first terminal of the transistor Tr1 is electrically connected to a wiring VDDL, and a second terminal of the transistor Tr1 is electrically connected to a gate of the transistor Tr1, a back gate of the transistor Tr1, and a first terminal of the transistor Tr2. A second terminal of the transistor Tr2 is electrically connected to the terminal T1, and a gate of the transistor Tr2 is electrically connected to the terminal T2. The terminal T2 is electrically connected to the wiring DW.

The wiring DW is any one of the wiring DW[1] to the wiring DW[n] in FIG. 2A.

The wiring VDDL functions as a wiring for supplying a constant voltage, for example. The constant voltage can be a high-level potential or the like, for example.

When a constant voltage supplied by the wiring VDDL is set at a high-level potential, a high-level potential is input to the first terminal of the transistor Tr1. The potential of the second terminal of the transistor Tr1 is lower than the high-level potential. At this time, the first terminal of the transistor Tr1 functions as a drain, and the second terminal of the transistor Tr1 functions as a source. Since the gate of the transistor Tr1 is electrically connected to the second terminal of the transistor Tr1, the gate-source voltage of the transistor Tr1 is 0 V. When the threshold voltage of the transistor Tr1 is within an appropriate range, a current in the current range of the subthreshold region (drain current) flows between the first terminal and the second terminal of the transistor Tr1. The amount of the current is preferably smaller than or equal to $1.0 \times 10^{-8}$ A, more preferably smaller than or equal to $1.0 \times 10^{-12}$ A, and further more preferably smaller than or equal to $1.0 \times 10^{-15}$ A when the transistor Tr1 is an OS transistor. For example, the current is preferably within a range in which the current exponentially increases with respect to a gate-source voltage. The transistor Tr1 functions as a current source to supply a current within a current range of the transistor Tr1 operating in the subthreshold region. The current corresponds to the above-described $I_{W_{ut}}$ or $I_{X_{ut}}$ described later.

The transistor Tr2 functions as a switching element. When the potential of the first terminal of the transistor Tr2 is higher than the potential of the second terminal of the transistor Tr2, the first terminal of the transistor Tr2 functions as a drain and the second terminal of the transistor Tr2 functions as a source. Since a back gate of the transistor Tr2 and the second terminal of the transistor Tr2 are electrically connected, a back gate-source voltage becomes 0 V. When the threshold voltage of the transistor Tr2 is within an appropriate range and a high-level potential is input to the gate of the transistor Tr2, the transistor Tr2 is turned on, and when a low-level potential is input to the gate of the transistor Tr2, the transistor Tr2 is turned off Specifically, when the transistor Tr2 is in the on state, a current within the current range of the subthreshold region flows from the second terminal of the transistor Tr1 to the terminal T1, and when the transistor Tr2 is in the off state, the current within the current range of the subthreshold region does not flow from the second terminal of the transistor Tr1 to the terminal T1.

Figure 3B:
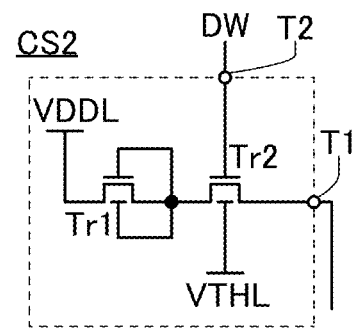

The circuit that can be used for the current source CS included in the circuit WCS in FIG. 2A is not limited to the current source CS1 in FIG. 3A. For example, in the current source CS1, the back gate of the transistor Tr2 and the second terminal of the transistor Tr2 are electrically connected, but the back gate of the transistor Tr2 may be electrically connected to another wiring. Such a configuration example is illustrated in FIG. 3B. In a current source CS2 illustrated in FIG. 3B, the back gate of the transistor Tr2 is electrically connected to a wiring VTHL. When the wiring VTHL of the current source CS2 is electrically connected to an external circuit or the like, the external circuit or the like supplies a predetermined potential to the wiring VTHL and the back gate of the transistor Tr2 can be supplied with the predetermined potential. This can change the threshold voltage of the transistor Tr2. The off-state current of the transistor Tr2 can be reduced by increasing the threshold voltage of the transistor Tr2.

Figure 3C:
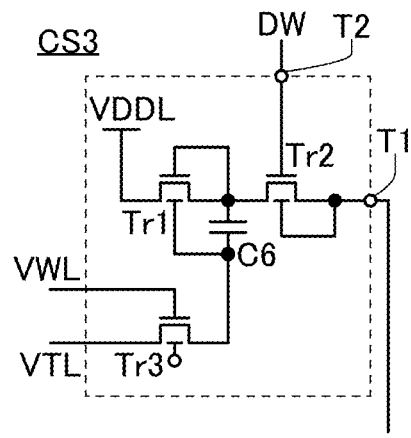

For example, in the current source CS1, the back gate of the transistor Tr1 and the second terminal of the transistor Tr1 are electrically connected; however, the voltage between the back gate and the second terminal of the transistor Tr2 can be stored with a capacitor. Such a configuration example is illustrated in FIG. 3C. A current source CS3 illustrated in FIG. 3C includes a transistor Tr3 and a capacitor C6 in addition to the transistor Tr1 and the transistor Tr2. The current source CS3 is different from the current source CS1 in that the second terminal of the transistor Tr1 and the back gate of the transistor Tr1 are electrically connected through the capacitor C6, and the back gate of the transistor Tr1 and a first terminal of the transistor Tr3 are electrically connected. In the current source CS3, a second terminal of the transistor Tr3 is electrically connected to a wiring VTL, and a gate of the transistor Tr3 is electrically connected to a wiring VWL. In the current source CS3, the wiring VWL is supplied with a high-level potential to turn the transistor Tr3 on, so that the wiring VTL and the back gate of the transistor Tr1 can be in the conduction state. In this case, a predetermined potential can be input to the back gate of the transistor Tr1 from the wiring VTL. By supplying a low-level potential to the wiring VWL to turn the transistor Tr3 off, a voltage between the second terminal of the transistor Tr1 and the back gate of the transistor Tr1 can be stored with the capacitor C6. The threshold voltage of the transistor Tr1 can be changed by setting the voltage supplied to the back gate of the transistor Tr1 with the wiring VTL, and the threshold voltage of the transistor Tr1 can be fixed with the transistor Tr3 and the capacitor C6.

Figure 3D:
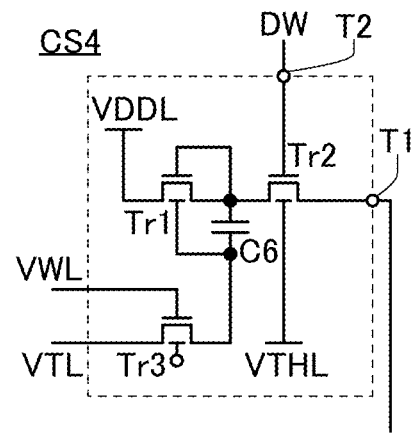

For example, a current source CS4 in FIG. 3D can be used as the current source CS included in the circuit WCS in FIG. 2A. In the current source CS4, the back gate of the transistor Tr2 is electrically connected not to the second terminal of the transistor Tr2 as in the current source CS3 in FIG. 3C but to the wiring VTHL. The current source CS4 can change the threshold voltage of the transistor Tr2 with the potential supplied by the wiring VTHL, as in the current source CS2 in FIG. 3B.

When a large current flows between the first terminal and the second terminal of the transistor Tr1 in the current source CS4, the on-state current of the transistor Tr2 needs to be increased to supply the current from the terminal T1 out of the current source CS4. In this case, in the current source CS4, the wiring VTHL is supplied with a high-level potential to decrease the threshold voltage of the transistor Tr2 and increase the on-state current of the transistor Tr2, whereby a large current flowing between the first terminal and the second terminal of the transistor Tr1 can be supplied from the terminal T1 out of the current source CS4.

By using the current source CS1 to the current source CS4 illustrated in FIG. 3A to FIG. 3D as the current sources CS included in the circuit WCS in FIG. 2A, the circuit WCS can output a current corresponding to the K-bit first data. The above-mentioned current amount can be the amount of current flowing between the first terminal and the second terminal of the transistor F1 that operates within the sub-threshold region.

Figure 2B:
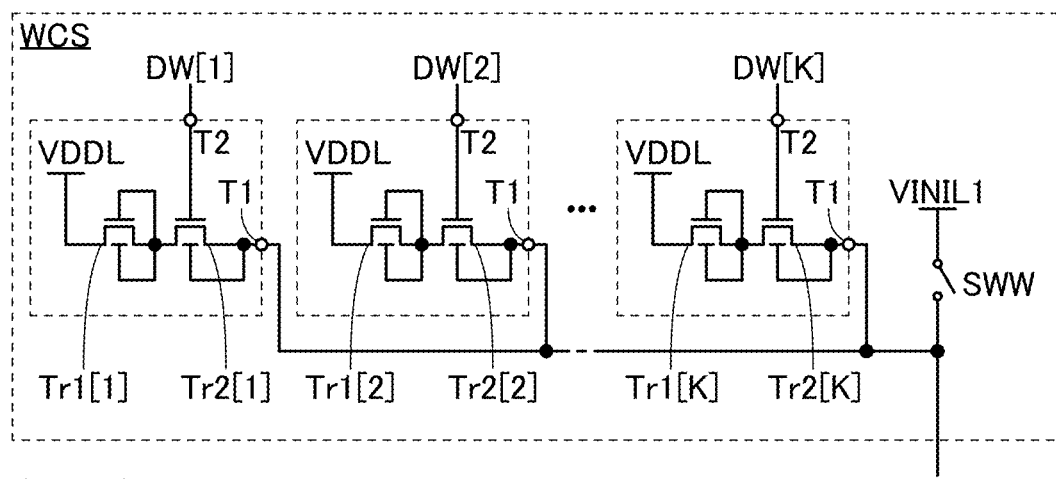

As the circuit WCS in FIG. 2A, a circuit WCS in FIG. 2B can be used. In the circuit WCS in FIG. 2B, one current source CS in FIG. 3A is connected to each of the wiring DW[1] to the wiring DW[K]. When the channel width of a transistor Tr1[1] is w[1], the channel width of a transistor Tr1[2] is w[2], and the channel width of a transistor Tr1[K] is w[K], the ratio of the channel widths is w[1]:w[2]:w[K] =1:2:$2^{K-1}$. Since a current flowing between a source and a drain of a transistor that operates in the subthreshold region is proportional to the channel width, the circuit WCS illustrated in FIG. 2B can output a current corresponding to the K-bit first data like the circuit WCS in FIG. 2A.

As the transistor Tr1 (including the transistor Tr1[1] to the transistor Tr2[K]), the transistor Tr2 (including the transistor Tr2[1] to the transistor Tr2[K]), and the transistor Tr3, a transistor which can be used as the transistor F1 and/or the transistor F2 can be used, for example. In particular, as the transistor Tr1 (including the transistor Tr1[1] to the transistor Tr2[K]), the transistor Tr2 (including the transistor Tr2[1] to the transistor Tr2[K]), and the transistor Tr3, OS transistors are preferably used.

Next, a specific example of the circuit XCS is described.

Figure 2C:
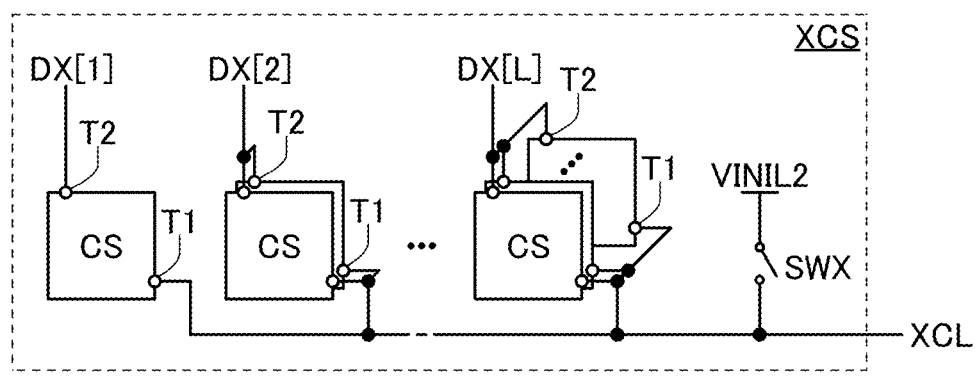

FIG. 2C is a block diagram showing an example of the circuit XCS. In FIG. 2C, to show the electrical connection between the circuit WCS and its nearby circuits, the wiring XCL is illustrated. The wiring XCL is any one of the wiring XCL [1] to the wiring XCL [m] included in the arithmetic circuit MAC1 in FIG. 1.

The circuit XCS illustrated in FIG. 2C includes a switch SWX, for example. A first terminal of the switch SWX is electrically connected to the wiring XCL and a plurality of current sources CS, and a second terminal of the switch SWX is electrically connected to a wiring VINIL2. The wiring VINIL2 functions as a wiring for supplying an initialization potential to the wiring XCL, and the initialization potential can be set to a ground potential (GND), a low-level potential, a high-level potential, or the like. The initialization potential supplied by the wiring VINIL2 can be the same as the potential supplied by the wiring VINIL1.

The switch SWX is turned on only when the initialization potential is supplied to the wiring XCL; otherwise, the switch is turned off.

As the switch SWX, a switch that can be used as the switch SWW can be used, for example.

The circuit XCS in FIG. 2C can have almost the same configuration as that of the circuit WCS in FIG. 3A. Specifically, the circuit XCS has a function of outputting reference data as the current amount, and a function of outputting L-bit second data ($2^L$ values) (L is an integer of 1 or more) as the current amount, and the circuit XCS includes $2^L-1$ current sources CS at that time. The circuit XCS includes one current source CS which outputs a current corresponding to data of the first bit value, two current sources CS which output a current corresponding to data of the second bit value, and $2^{L-1}$ current sources CS which output a current corresponding to data of the L-th bit value.

The reference data output by the circuit XCS as a current can be data in which the first bit value is "1" and the second and subsequent bit values are "0", for example.

In FIG. 2C, the terminal T2 of the one current source CS is electrically connected to the wiring DX[1], the terminals T2 of the two current sources CS are electrically connected to the wiring DX[2], and the terminals T2 of the $2^{L-1}$ current sources CS are electrically connected to the wiring DX[L].

The plurality of current sources CS included in the circuit XCS has a function of outputting the same constant currents $I_{Xut}$ from the terminals T1. The wiring DX[1] to the wiring DX[L] which are electrically connected to the current sources CS function as wirings for sending control signals to make the current sources CS output $I_{Xut}$. In other words, the circuit XCS has a function of supplying the current amount corresponding to the L-bit data sent from the wiring DX[1] to the wiring DX[L] to the wiring XCL.

Specifically, the circuit XCS with L of 2 is considered. For example, when the value of the first bit is "1" and the value of the second bit is "0", a high-level potential is supplied to the wiring DX[1], and a low-level potential is supplied to the wiring DX[2]. In this case, the constant current $I_{Xut}$ flows from the circuit XCS to the circuit XCL. For example, when the value of the first bit is "0" and the value of the second bit is "1", a low-level potential is supplied to the wiring DX[1], and a high-level potential is supplied to the wiring DX[2]. In this case, the constant current $2I_{Xut}$ flows from the circuit XCS to the wiring XCL. For example, when the value of the first bit is "1" and the value of the second bit is "1", a high-level potential is supplied to the wiring DX[1] and the wiring DX[2]. In this case, the constant current $3I_{Xut}$ flows from the circuit XCS to the wiring XCL. For example, when the value of the first bit is "0" and value of the second bit is "0", a low-level potential is supplied to the wiring DX[1] and the wiring DX[2]. In this case, the constant current does not flow from the circuit XCS to the wiring XCL. In this case, in this specification and the like, it is also said that the current amount 0 flows from the circuit XCS to the wiring XCL, in some cases. The current amount 0, $I_{Xut}$, $2I_{Wut}$, $3I_{Xut}$, or the like output from the circuit XCS can be the second data output from the circuit XCS; particularly, the current amount $I_{Xut}$ from the circuit XCS can be the reference data output from the circuit XCS.

When the transistors in the current sources CS included in the circuit XCS have different electrical characteristics and this yields errors, the errors of the constant currents $I_{Xut}$ output from the terminals T1 of the plurality of current sources CS are preferably within 10%, more preferably within 5%, and further preferably within 1%. In this embodiment, the description is made based on the assumption that there is no error in the constant currents $I_{Xut}$ output from the terminals T1 of the plurality of current sources CS included in the circuit XCS.

As the current source CS of the circuit XCS, any of the current source CS1 to the current source CS4 in FIG. 3A to FIG. 3D can be used as the current source CS of the circuit WCS. In that case, the wiring DW in FIG. 3A to FIG. 3D is replaced with the wiring DX. This allows the circuit XCS to make a current within the current range of the subthreshold region flow to the wiring XCL as the reference data or the L-bit second data.

As the circuit XCS in FIG. 2C, the circuit configuration similar to that of the circuit WCS illustrated in FIG. 2B can be used. In this case, the circuit WCS in FIG. 2B is replaced with the circuit XCS, the wiring DW[1] is replaced with the wiring DX[1], the wiring DW[2] is replaced with the wiring DX[2], the wiring DW[K] is replaced with the wiring DX[L], the switch SWW is replaced with the switch SWX, and the wiring VINIL1 is replaced with the wiring VINIL2.

<<Converter Circuit ITRZ[1] to Converter Circuit ITRZ[n]>>

A specific example of a circuit which can be used as the converter circuit ITRZ[1] to the converter circuit ITRZ[n] included in the arithmetic circuit MAC1 in FIG. 1 is described.

Figure 4A:
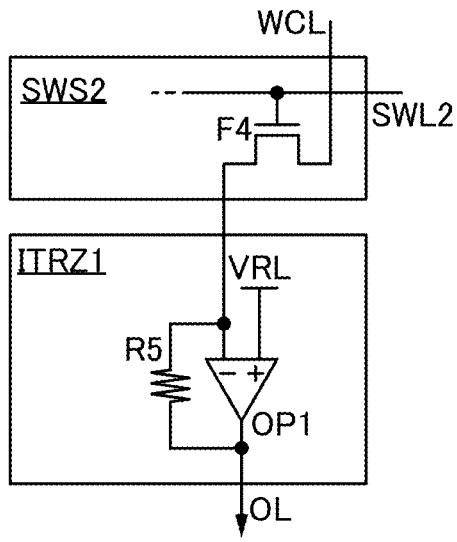
FIG. 4A to FIG. 4C are circuit diagrams each showing a configuration example of a circuit included in a semiconductor device.

The converter circuit ITRZ1 in FIG. 4A is an example of a circuit which can be used as the converter circuit ITRZ[1] to the converter circuit ITRZ[n] in FIG. 1. In FIG. 4A, to show the electrical connection between the converter circuit ITRZ1 and its nearby circuits, the circuit SWS2, the wiring WCL, the wiring SWL2, and the transistor F4 are illustrated. The wiring WCL is any one of the wiring WCL[1] to the wiring WCL[n] included in the arithmetic circuit MAC1 in FIG. 1, and the transistor F4 is any one of the transistor F4[1] to the transistor F4[n] included in the arithmetic circuit MAC1 in FIG. 1.

The converter circuit ITRZ1 in FIG. 4A is electrically connected to the wiring WCL through the transistor F4. The converter circuit ITRZ1 is electrically connected to the wiring OL. The converter circuit ITRZ1 has a function of converting the amount of current flowing from the converter circuit ITRZ1 to the wiring WCL, or the amount of current flowing from the wiring WCL to the converter circuit ITRZ1 into an analog voltage and outputting the analog voltage to the wiring OL. The converter circuit ITRZ1 includes a current-voltage converter circuit.

The converter circuit ITRZ1 in FIG. 4A includes a resistor R5 and an operational amplifier OP1, for example.

An inverting input terminal of the operational amplifier OP1 is electrically connected to a first terminal of the resistor R5 and a second terminal of the transistor F4. A non-inverting input terminal of the operational amplifier OP1 is electrically connected to a wiring VRL. An output terminal of the operational amplifier OP1 is electrically connected to a second terminal of the resistor R5 and the wiring OL.

The wiring VRL functions as a wiring for supplying a constant voltage, for example. The constant voltage can be a ground potential (GND), a low-level potential, or a high-level potential, for example.

The converter circuit ITRZ1 with the configuration in FIG. 4A can convert the amount of current flowing from the wiring WCL to the converter circuit ITRZ1 through the transistor F4 or the amount of current flowing from the converter circuit ITRZ1 to the wiring WCL through the transistor F4 into an analog voltage to output it to the wiring OL.

In particular, by setting the constant voltage supplied by the wiring VRL to a ground potential (GND), the inverting input terminal of the operational amplifier OP1 is virtually grounded, and the analog voltage output to the wiring OL can be a voltage with reference to the ground potential (GND).

Figure 4B:
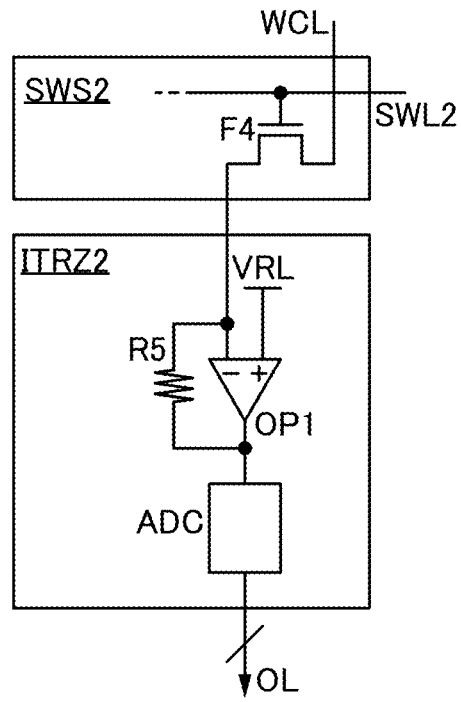

The converter circuit ITRZ1 in FIG. 4A outputs an analog voltage; however, a circuit configuration which can be used for the converter circuit ITRZ[1] to the converter circuit ITRZ[n] in FIG. 1 is not limited thereto. For example, the converter circuit ITRZ1 may include an analog-digital converter circuit ADC as illustrated in FIG. 4B. Specifically, in a converter circuit ITRZ2 in FIG. 4B, an input terminal of the analog-digital converter circuit ADC is electrically connected to an output terminal of the operational amplifier OP1 and the second terminal of the resistor R5, and the output terminal of the analog-digital converter circuit ADC is electrically connected to the wiring OL. With such a configuration, the converter circuit ITRZ2 in FIG. 4B can output a digital signal to the wiring OL.

Figure 4C:
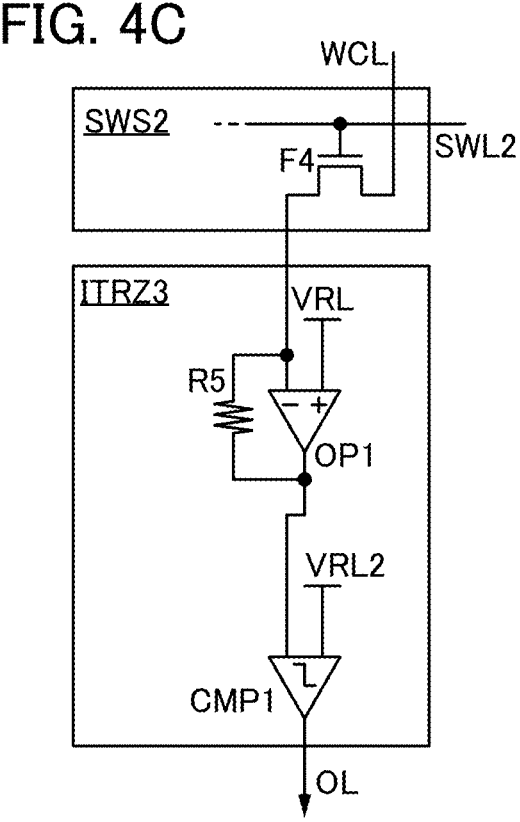

When the digital signal output to the wiring OL is 1 bit (binary) in the converter circuit ITRZ2, the converter circuit ITRZ2 may be replaced with a converter circuit ITRZ3 illustrated in FIG. 4C. The converter circuit ITRZ3 in FIG. 4C has a configuration in which the converter circuit ITRZ1 in FIG. 4A includes a comparator CMP1. Specifically, the converter circuit ITRZ3 has a configuration in which a first input terminal of the comparator CMP1 is electrically connected to the output terminal of the operational amplifier OP1 and the second terminal of the resistor R5, a second input terminal of the comparator CMP1 is electrically connected to a wiring VRL2, and an output terminal of the comparator CMP1 is electrically connected to the wiring OL. The wiring VRL2 functions as a wiring for supplying a potential compared to the potential of the first terminal of the comparator CMP1. With such a configuration, the converter circuit ITRZ3 in FIG. 4C can output a low-level potential or a high-level potential (a binary digital signal) to the wiring OL in accordance with the large-small relation between the voltage converted with the current-voltage converter circuit from the amount of current flowing between the source and the drain of the transistor F4 and the voltage supplied by the wiring VRL2.

The converter circuit ITRZ[1] to the converter circuit ITRZ[n] which can be used for the arithmetic circuit MAC1 in FIG. 1 are not limited to the converter circuit ITRZ1 to the converter circuit ITRZ3 illustrated in FIG. 4A to FIG. 4C. When the arithmetic circuit MAC1 is used for an arithmetic operation of the hierarchical neural network, for example, the converter circuit ITRZ1 to the converter circuit ITRZ3 preferably have arithmetic circuits of a function system. As an arithmetic circuit of a function system, an arithmetic circuit with a sigmoid function, a tanh function, a softmax function, a ReLU function, a threshold function, or the like can be used.

Figure 5:
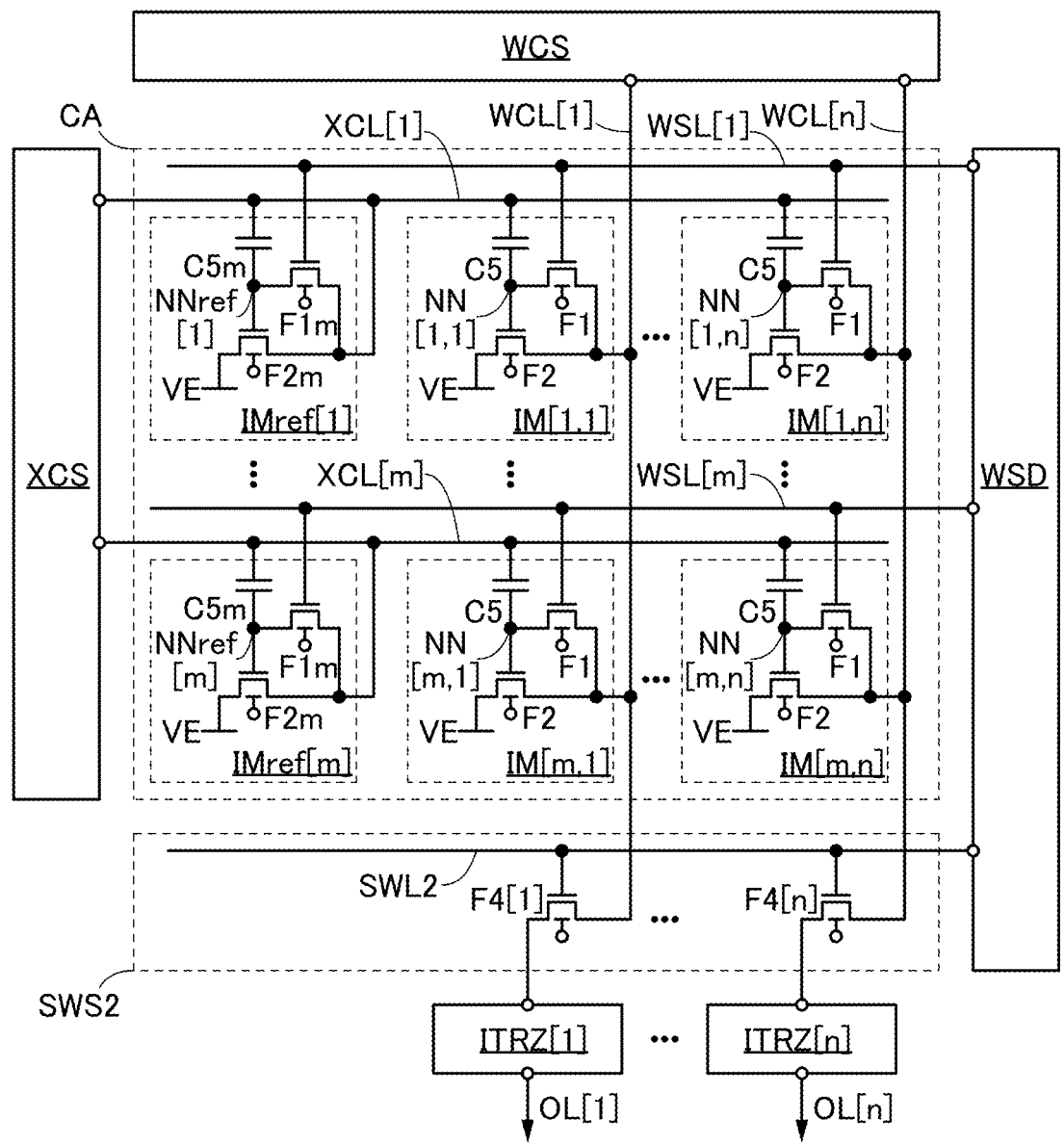
FIG. 5 is a block diagram showing a configuration example of a semiconductor device.

One embodiment of the present invention is not limited to the circuit configuration of the arithmetic circuit MAC1 described in this embodiment. The circuit configuration of the arithmetic circuit MAC1 can be changed depending on circumstances. For example, the arithmetic circuit MAC1 may be changed to a configuration without the circuit SWS1 like an arithmetic circuit MAC1A illustrated in FIG. 5. The arithmetic circuit MAC1 can stop a current flowing from the circuit WCS to the wiring WCL[1] to the wiring WCL[n] with the circuit SWS1; the arithmetic circuit MAC1A can stop a current flowing from the circuit WCS to the wiring WCL[1] to the wiring WCL[n] with the circuit WCS.

Specifically, when the circuit WCS in FIG. 2A is used as the circuit WCS included in the arithmetic circuit MAC1A and the current source CS1 in FIG. 3A is used as the current source CS, a low-level potential is input to the wiring DW[1] to the wiring DW[K] and the switch SWW is turned off By performing operations of the circuit WCS in this manner, a current flowing from the circuit WCS to the wiring WCL[1] to the wiring WCL[n] can be stopped. In this manner, a current flowing from the circuit WCS to the wiring WCL[1] to the wiring WCL[n] is stopped with the circuit WCS, whereby the arithmetic circuit MAC1A can be used instead of the arithmetic circuit MAC1 for an arithmetic operation.

<Operation Example 1 of Arithmetic Circuit>

Next, an operation example of the arithmetic circuit MAC1 is described.

Figure 6:
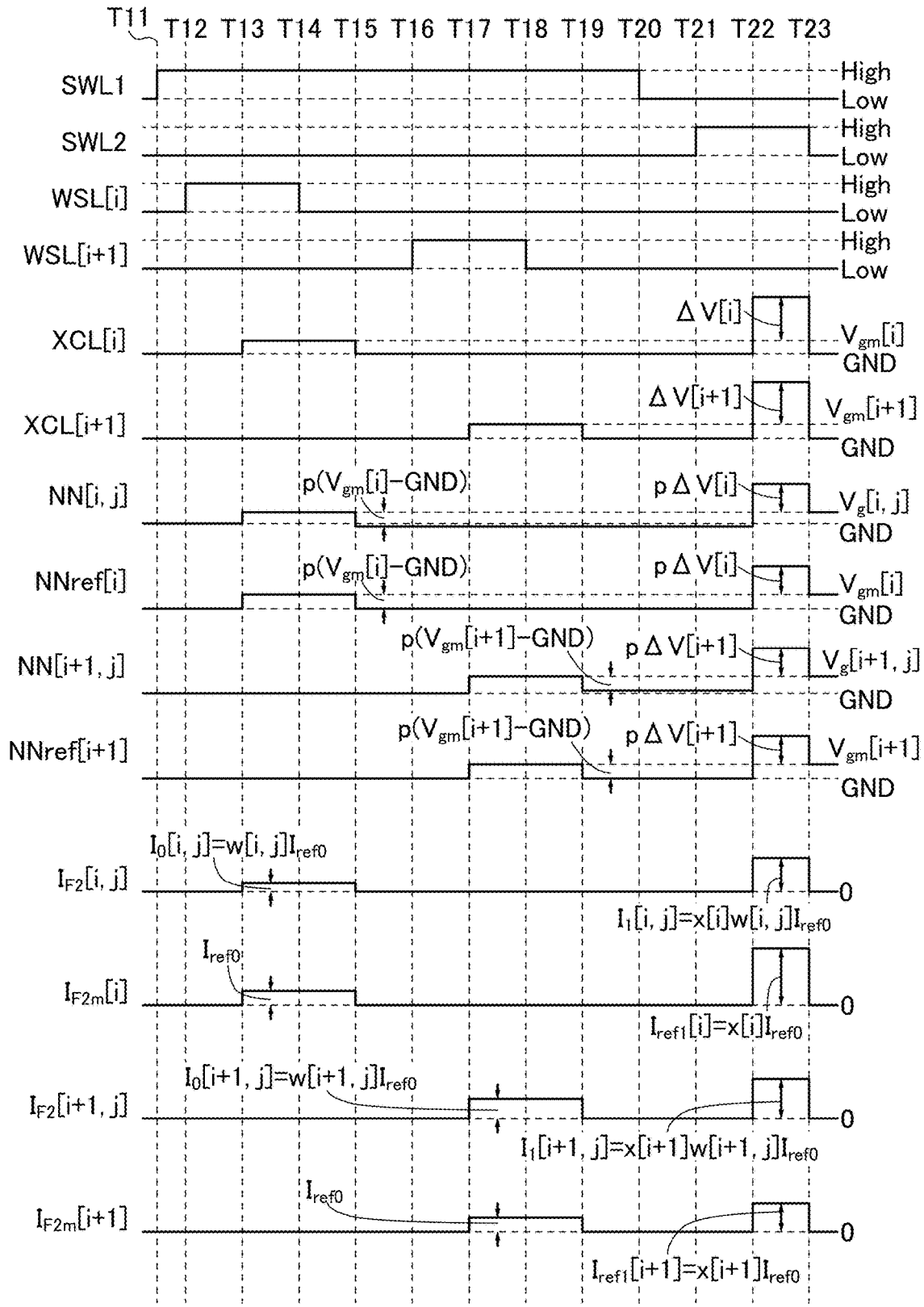
FIG. 6 is a timing chart showing an operation example of a semiconductor device.

FIG. 6 shows a timing chart of an operation example of the arithmetic circuit MAC1. The timing chart in FIG. 6 shows changes in the potentials of the wiring SWL1, the wiring SWL2, a wiring WSL[i] (i is an integer greater than or equal to 1 and less than or equal to m−1), a wiring WSL[i+1], a wiring XCL[i], a wiring XCL[i+1], a node NN[i,j] (j in an integer more than or equal to 1 and less than or equal to n−1), a node NN[i+1,j], a node NNref[i], and a node NNref[i+1] in the period from Time T11 to Time T23 and around the period. The timing chart in FIG. 6 also shows changes in the amount of current $I_{F2}[i,j]$ flowing between the first terminal and the second terminal of the transistor F2 included in the cell IM[i,j]; the amount of current $I_{F2m}[i]$ flowing between the first terminal and the second terminal of the transistor F2m included in the cell IMref[i]; the amount of current $I_{F2}[i+1,j]$ flowing between the first terminal and the second terminal of the transistor F2 included in the cell IM[i+1,j]; and the amount of current $I_{F2m}[i+1]$ flowing between the first terminal and the second terminal of the transistor F2m included in the cell IMref[i+1].

The circuit WCS in FIG. 2A is used as the circuit WCS of the arithmetic circuit MAC1, and the circuit XCS in FIG. 2C is used as the circuit XCS of the arithmetic circuit MAC1.

Note that in this operation example, the potential of the wiring VE is a ground potential GND. Before Time T11, each potential of the node NN[i,j], the node NN[i+1,j], the node NNref[i], and the node NNref[i+1] is the ground potential GND. Specifically, for example, the initialization potential of the wiring VINIL1 in FIG. 2A is set to the ground potential GND, and the switch SWW, the transistor F3, and each transistor F1 in the switch SWW, the transistor F3, the cell IM[i,j], and the cell IM[i+1,j] are turned on, whereby the potentials of the node NN[i,j] and the node NN[i+1,j] can be set to the ground potential GND. For example, the initialization potential of the wiring VINIL2 in FIG. 2C is set to the ground potential GND, and the switch SWX and each transistor F1m in the switch SWX, the cell IMref[i,j], and the cell IMref[i+1,j] are turned on, whereby the potentials of the node NNref[i,j] and the node NNref[i+1,j] can be set to the ground potential GND.

<<From Time T11 to Time T12>>

In the period from Time T11 to Time T12, a high-level potential (denoted with High in FIG. 6) is applied to the wiring SWL1, and a low-level potential (denoted with Low in FIG. 6) is applied to the wiring SWL2. Accordingly, the high-level potential is applied to each of the gates of the transistor F3[i] to the transistor F3[n] and the transistor F3[i] to the transistor F3[n] are turned on, and the low-level potential is applied to each of the gates of the transistor F4[i] to the transistor F4[n] and the transistor F4[i] to the transistor F4[n] are turned off.

In the period from Time T11 to Time T12, a low-level potential is applied to each of the wiring WSL[i] and the wiring WSL[i+1]. Accordingly, in the i-th row of the cell array CA, a low-level potential is applied to each of the gates of the transistors F1 included in a cell IM[i+1,1] to a cell IM[i+1,n] and the gate of the transistor F1m included in the cell IMref[i+1], and the transistors F1 and the transistor F1m are turned off. In addition, in the i+1-th row of the cell array CA, the low-level potential is applied to each of the gates of the transistors F1 included in a cell IM[i+1,1] to a cell IM[i+1,n] and the gate of the transistor F1m included in the cell IMref[i+1], and the transistors F1 and the transistor F1m are turned off.

In the period from Time T11 to Time T12, the ground potential GND is applied to the wiring XCL[i] and the wiring XCL[i+1]. Specifically, for example, when the wiring XCL illustrated in FIG. 2C is the wiring XCL[i] and the wiring XCL[i+1], the initialization potential of the wiring VINIL2 is set to the ground potential GND, and the switch SWX is turned on, the potential of the wiring XCL[i] and the wiring XCL[i+1] can be set to the ground potential GND.

In the period from Time T11 to Time T12, when the wiring WCL illustrated in FIG. 2A is the wiring WCL[1] to the wiring WCL[K], the first data is not input to the wiring DW[1] to the wiring DW[K]. When the wiring XCL in FIG. 2C is the wiring XCL[1] to the wiring XCL[K], the second data is not input to the wiring DX[1] to the wiring DX[L]. In this case, in the circuit WCS in FIG. 2A, a low-level potential is input to the wiring DW[1] to the wiring DW[K], and in the circuit XCS in FIG. 2C, a low-level potential is input to the wiring DX[1] to the wiring DX[L].

In the period from Time T11 to Time T12, a current does not flow through a wiring WCL[j], the wiring XCL[i], and the wiring XCL[i+1]. Therefore, $I_{F2}[i,j]$, $I_{F2m}[I]$, $I_{F2}[i+1,j]$, and $I_{F2m}[i+1]$ are each 0.

<<From Time T12 to Time T13>>

In the period from Time T12 to Time T13, a high-level potential is applied to the wiring WSL[i]. Accordingly, in the i-th row of the cell array CA, a high-level potential is applied to each of the gates of the transistors F1 included in the cell IM[i,1] to the cell IM[i,n] and the gate of the transistor F1m included in the cell IMref[i], and the transistors F1 and the transistor F1m are turned on. Furthermore, in the period from Time T12 to Time T13, a low-level potential is applied to each of the wiring WSL[1] to the wiring WSL[m] except the wiring WSL[i], and in the cell array CA, the transistors F1 included in the cell IM[1,1] to the cell IM[m,n] in the rows other than the i-th row and the transistors F1m included in the cell IMref[1] to the cell IMref[m] in the rows other than the i-th row are in the off state.

The ground potentials GND have been applied to the wiring XCL[1] to the wiring XCL[m] since before Time T12.

<<From Time T13 to Time T14>>

In the period from Time T13 to Time T14, the current amount $I_0[i,j]$ flows as the first data from the circuit WCS to the cell array CA through the transistor F3[j]. Specifically, when the wiring WCL illustrated in FIG. 2A is the wiring WCL[j], signals corresponding to the first data are input to the wiring DW[1] to the wiring DW[K], whereby the current $I_0[i,j]$ flows from the circuit WCS to the second terminal of the transistor F3[j]. When the value of the K bit signal input as the first data is $\alpha[i,j]$ ($\alpha[i,j]$ is an integer more than or equal to 0 and less than or equal to $2^K-1$), $I_0[i,j]$ is equal to $\alpha[i,j] \times I_{Wut}$.

When $\alpha[i,j]$ is 0, $I_0[i,j]$ is equal to 0; in a strict sense, a current does not flow from the circuit WCS to the cell array CA through the transistor F3[j], but in this specification and the like, it may be referred to as "the current with $I_0[i,j]=0$ flows" or the like.

Between Time T13 and Time T14, a conduction state is made between the wiring WCL[j] and the first terminal of the transistor F1 included in the cell IM[i,j] in the i-th row of the cell array CA, and a non-conduction state is made between the wiring WCL[j] and the first terminals of the transistors F1 included in a cell IM[1,j] to a cell IM[m,j] in the rows except the i-th row of the cell array CA; accordingly, the current amount $I_0[i,j]$ flows from the wiring WCL[j] to the cell IM[i,j].

When the transistor F1 included in the cell IM[i,j] is turned on, the transistor F2 included in the cell IM[i,j] has a diode-connected structure. Therefore, when a current flows from the wiring WCL[j] to the cell IM[i,j], the potentials of the gate of the transistor F2 and the second terminal of the transistor F2 are substantially equal to each other. The potential is determined by the amount of current flowing from the wiring WCL[j] to the cell IM[i,j], the potential of the first terminal of the transistor F2 (here, GND), and the like. In this operation example, the current of $I_0[i,j]$ flows from the wiring WCL[j] to the cell IM[i,j], whereby the potential of the gate of the transistor F2 (the node NN[i,j]) becomes $V_g[i,j]$. That is, a voltage between the gate and the source of the transistor F2 is $V_g[i,j]$–GND, and the current amount $I_0[i,j]$ is set for a current flowing between the first terminal and the second terminal of the transistor F2.

Here, the current amount $I_0[i,j]$ in the case where the threshold voltage of the transistor F2 is $V_{th}[i,j]$ and the transistor F2 operates in a subthreshold region can be expressed with the following formula.

[Formula 1]

$$I_0[i,j]=I_a \exp\{J(V_g[i,j]-V_{th}[i,j])\} \quad (1.1)$$

Note that $I_a$ is a drain current for the case where $V_g[i,j]$ is $V_{th}[i,j]$, and J is a coefficient of correction determined with the temperature, the device structure, and the like.

In the period from Time T13 to Time T14, a current with a current amount $I_{ref0}$ flows as the reference data from the circuit XCS to the wiring XCL[i]. Specifically, when the wiring XCL illustrated in FIG. 2C is the wiring XCL[i], a high-level potential is input to the wiring DX[1], a low-level potential is input to the wiring DX[2] to the wiring DX[K], and the current $I_{ref0}$ flows from the circuit XCS to the wiring XCL[i]. In other words, $I_{ref0}$ is equal to $I_{Xut}$.

Between Time T13 and Time T14, since a conduction state is made between the first terminal of the transistor F1m included in the cell IMref[i] and the wiring XCL[i], the current amount $I_{ref0}$ flows from the wiring XCL[i] to the cell IMref[i].

As in the cell IM[i,j], when the transistor F1m included in the cell IMref[i] is turned on, the transistor F2m included in the cell IMref[i] has a diode-connected structure. Therefore, when a current flows from the wiring XCL[i] to the cell IMref[i], the potentials of the gate of the transistor F2m and the second terminal of the transistor F2m are substantially equal to each other. The potential is determined with the amount of current flowing from the wiring XCL[i] to the cell IMref[i], the potential of the first terminal of the transistor F2m (here, GND), and the like. In this operation example, the current of $I_{ref0}$ flows from the wiring XCL[i] to the cell IMref[i], whereby the potential of the gate of the transistor F2 (the node NNref[i]) becomes $V_{gm}[i]$, and the potential of the wiring XCL[i] at this time is also $V_{gm}[i]$. That is, a voltage between the gate and the source of the transistor F2m is $V_{gm}[i]$–GND, and the current amount $I_{ref0}$ of a current flowing between the first terminal and the second terminal of the transistor F2m is set.

Here, the amount of the current $I_{ref0}$ in the case where the threshold voltage of the transistor F2m is $V_{thm}[i]$ and the transistor F2m operates in a subthreshold region can be expressed with the following formula. Note that the coefficient of correction J is the same as that of the transistor F2 included in the cell IM[i,j]. For example, the device structures, sizes (channel lengths or channel widths), or the like of the transistors are the same. In addition, although the coefficient of correction J of each transistor varies due to variation in manufacturing, the variation is suppressed so that the following arguments make sense with sufficient accuracy for practical use.

[Formula 2]

$$I_{ref0}=I_a \exp\{(V_{gm}[i]-V_{thm}[i])\} \quad (1.2)$$

Here, a coefficient of weight w[i,j] that is the first data is defined as follows.

[Formula 3]

$$w[i,j]=\exp\{J(V_g[i,j]-V_{th}[i,j]-V_{gm}[i]+V_{thm}[i])\} \quad (1.3)$$

Therefore, Formula (1.1) can be rewritten into the following formula.

[Formula 4]

$$I_0[i,j]=W[i,j]I_{ref0} \leftrightarrow \alpha[i,j]I_{Wut}=w[i,j]I_{Xut} \quad (1.4)$$

When the current $I_{Wut}$ output from the current source CS of the circuit WCS in FIG. 2A and the current $I_{Xut}$ output from the current source CS of the circuit XCS in FIG. 2C are equal, w[i,j] is equal to α[i,j]. That is, when $I_{Wut}$ and $I_{Xut}$ are equal, α[i,j] corresponds to the value of the first data; $I_{Wut}$ and $I_{Xut}$ are preferably equal.

<<From Time T14 to Time T15>>

In the period from Time T14 to Time T15, a low-level potential is applied to the wiring WSL[i]. Accordingly, in the i-th row of the cell array CA, a low-level potential is applied to each of the gates of the transistors F1 included in a cell IM[i,1] to a cell IM[i,n] and the gate of the transistor F1m included in the cell IMref[i], and the transistors F1 and the transistor F1m are turned off.

When the transistor F1 included in the cell IM[i,j] is turned off, $V_g[i,j]-V_{gm}[i]$, which is a difference between the potential of the gate of the transistor F2 (the node NN[i,j]) and the potential of the wiring XCL[i], is stored in the capacitor C5. When the transistor F1 included in the cell IMref[i] is turned off, 0, which is a difference between the potential of the gate of the transistor F2m (the node NNref[i]) and the potential of the wiring XCL[i], is stored in the capacitor C5m. In the operation from Time T13 to Time T14, the voltage stored in the capacitor C5m might be a voltage that is not 0 (e.g., Vas) depending on transistor characteristics of the transistor F1m and the transistor F2m and the like. In this case, the potential of the node NNref[i] is a potential obtained by adding Vas to the potential of the wiring XCL[i].

<<From Time T15 to Time T16>>

In the period from Time T15 to Time T16, GND is applied to the wiring XCL[i]. Specifically, for example, when the wiring XCL illustrated in FIG. 2C is the wiring XCL[i], the initialization potential of the wiring VINIL2 is set to the ground potential GND, and the switch SWX is turned on, the potential of the wiring XCL[i] can be set to the ground potential GND.

Thus, the potentials of the node NN[i,1] to the node NN[i,n] change because of capacitive coupling of the capacitors C5 included in the cell IM[i,1] to the cell IM[i,n] in the i-th row, and the potential of the node NNref[i] changes because of capacitive coupling of the capacitor C5m included in the cell IMref[i].

The amount of change in the potentials of the node NN[i,1] to the node NN[i,n] is a potential obtained by multiplying the amount of change in the potential of the wiring XCL[i] by the coefficient of capacitive coupling determined through the configurations of the cell IM[i,1] to the cell IM[i,n] included in the cell array CA. The coefficient of capacitive coupling is calculated using the capacitance of the capacitor C5, the gate capacitance of the transistor F2, the parasitic capacitance, and the like. When the coefficient of capacitive coupling due to the capacitor C5 is p in each of the cell IM[i,1] to the cell IM[i,n], the potential of the node NN[i,j] in the cell IM[i,j] decreases by $p(V_{gm}[i]-GND)$ from the potential of the period from Time T14 to Time T15.

Similarly, when the potential of the wiring XCL[i] changes, the potential of the node NNref[i] also changes because of capacitive coupling of the capacitor C5m included in the cell IMref[i]. The potential of the node NNref[i] of the cell IMref[i] in the case where the capacitive coupling coefficient due to the capacitor C5m is p like that due to the capacitor C5 decreases from the potential in the period from Time T14 to Time T15 by $p(V_{gm}[i]-GND)$. In the timing chart in FIG. 6, p is equal to 1, for example. The potential of the node NNref[i] is GND in the period from Time T15 to Time T16.

Accordingly, the potential of the node NN[i,j] of the cell IM[i,j] decreases, so that the transistor F2 is turned off; similarly, the potential of the node NNref[i] of the cell IMref[i] decreases, so that the transistor F2m is also turned off. Therefore, $I_{F2}[i,j]$ and $I_{F2m}[i]$ are each 0 in the period from Time T15 to Time T16.

<<From Time T16 to Time T17>>

In the period from Time T16 to Time T17, a high-level potential is applied to the wiring WSL[i+1]. Accordingly, in the i+1-th row of the cell array CA, a high-level potential is applied to each of the gates of the transistors F1 included in the cell IM[i+1,1] to the cell IM[i+1,n] and the gate of the transistor F1m included in the cell IMref[i+1], and the transistors F1 and the transistor F1m are turned on. Furthermore, in the period from Time T16 to Time T17, a low-level potential is applied to each of the wiring WSL[1] to the wiring WSL[m] except the wiring WSL[i+1], and in the cell array CA, the transistors F1 included in the cell IM[1,1] to the cell IM[m,n] in the rows other than the i+1-th row and the transistors F1m included in the cell IMref[1] to the cell IMref[m] in the rows other than the i+1-th row are in an off state.

The ground potential GND has been applied to the wiring XCL[1] to the wiring XCL[m]since the timing before Time T16.

<<From Time T17 to Time T18>>

In the period from Time T17 to Time T18, the current amount $I_0[i+1,j]$ flows as the first data from the circuit WCS to the cell array CA through the transistor F3[j]. Specifically, when the wiring WCL illustrated in FIG. 2A is the wiring WCL[j+1], signals corresponding to the first data are input to the wiring DW[1] to the wiring DW[K], whereby the current $I_0[i+1,j]$ flows from the wiring WCS to the second terminal of the transistor F3[j]. When the value of the K bit signal input as the first data is α[i+1,j] (α[i+1,j] is an integer more than or equal to 0 and less than or equal to $2^K-1$), $I_0[i+1,j]$ is equal to $α[i+1,j] \times I_{Wut}$.

When α[i+1,j] is 0, $I_0[i+1,j]$ is 0; in a strict sense, a current does not flow from the circuit WCS to the cell array CA through the transistor F3[j] but in this specification and the like, it may be referred to as "the current with $I_0[i+1,j]=0$ flows" or the like as in the case of $I_0[i,j]=0$.

At this time, a conduction state is made between the wiring WCL[j] and the first terminal of the transistor F1 included in the cell IM[i+1,j] in the i+1-th row of the cell array CA, and a non-conduction state is made between the wiring WCL[j] and the first terminals of the transistors F1 included in the cell IM[1,j] to the cell IM[m,j] in the rows except the i+1-th row of the cell array CA; accordingly, the current amount $I_0[i+1,j]$ flows from the wiring WCL[j] to the cell IM[i+1,j].

When the transistor F1 included in the cell IM[i+1,j] is turned on, the transistor F2 included in the cell IM[i+1,j] has a diode-connected structure. Therefore, when a current flows from the wiring WCL[j] to the cell IM[i+1,j], the potentials of the gate of the transistor F2 and the second terminal of the transistor F2 are substantially equal to each other. The potential is determined by the amount of current flowing from the wiring WCL[j] to the cell IM[i+1,j], the potential of the first terminal of the transistor F2 (here, GND), and the like. In this operation example, the current of $I_0[i+1,j]$ flows from the wiring WCL[j] to the cell IM[i+1,j], whereby the potential of the gate of the transistor F2 (the node NN[i+1,j]) becomes $V_g[i+1,j]$. That is, the voltage between the gate and the drain of the transistor F2 is $V_g[i+1,j]-GND$, and the current amount $I_0[i+1,j]$ as a current flowing between the first terminal and the second terminal of the transistor F2 is set.

Here, the current amount $I_0[i+1,j]$ in the case where the threshold voltage of the transistor F2 is $V_{th}[i+1,j]$ and the transistor F2 operates in a subthreshold region can be expressed by the following formula. Note that the coefficient of correction is J, which is the same as those of the transistor F2 included in the cell IM[i,j] and the transistor F2m included in the cell IMref[i].

[Formula 5]

$$I_0[i+1,j]=I_a \exp\{J(V_g[i+1,j]-V_{th}[i+1,j])\} \quad (1.5)$$

In the period from Time T17 to Time T18, the current amount $I_{ref0}$ flows as the reference data from the circuit XCS to the wiring XCL[i+1]. Specifically, as in the period from Time T13 to Time T14, when the wiring XCL illustrated in FIG. 2C is the wiring XCL[i+1], a high-level potential is input to the wiring DX[1], a low-level potential is input to the wiring DX[2] to the wiring DX[K], and the current $I_{ref0}=I_{Xut}$ flows from the circuit XCS to the wiring XCL[i+1].

Between Time T17 and Time T18, since a conduction state is made between the first terminal of the transistor F1m included in the cell IMref[i+1] and the wiring XCL[i+1], the current amount $I_{ref0}$ flows from the wiring XCL[i+1] to the cell IMref[i+1].

As in the cell IM[i+1,j], when the transistor F1m included in the cell IMref[i+1] is turned on, the transistor F2m included in the cell IMref[i+1] has a diode-connected structure. Therefore, when a current flows from the wiring XCL[i+1] to the cell IMref[i+1], the potentials of the gate of the transistor F2m and the second terminal of the transistor F2m are substantially equal to each other. The potential is determined by the amount of current flowing from the wiring XCL[i+1] to the cell IMref[i+1], the potential of the first terminal of the transistor F2m (here, GND), and the like. In this operation example, the current amount $I_{ref0}$ flows from the wiring XCL[i+1] to the cell IMref[i+1], whereby the potential of the gate of the transistor F2 (the node NNref[i+1]) becomes $V_{gm}[i+1]$, and the potential of the wiring XCL[i+1] is also $V_{gm}[i+1]$. That is, the voltage between the gate and the source of the transistor F2$m$ is $V_{gm}[i+1]$–GND, and the current amount $I_{ref0}$ as a current flowing between the first terminal and the second terminal of the transistor F2$m$ is set.

Here, the amount of current $I_{ref0}$ in the case where the threshold voltage of the transistor F2$m$ is $V_{thm}[i+1,j]$ and the transistor F2$m$ operates in a subthreshold region can be expressed with the following formula. Note that the coefficient of correction J is the same as that of the transistor F2 included in the cell IM[i+1,j].

[Formula 6]

$$I_{ref0} = I_a \exp\{J(V_{gm}[i+1] - V_{thm}[i+1])\} \quad (1.6)$$

Here, a coefficient of weight w[i+1,j] that is the first data is defined as follows.

[Formula 7]

$$w[i+1,j] = \exp\{J(V_g[i+1,j] - V_{th}[i+1,j] - V_{gm}[i+1] \pm V_{thm}[i+1])\} \quad (1.7)$$

Therefore, Formula (1.5) can be rewritten into the following formula.

[Formula 8]

$$I_0[i+1,] = w[i+1,j]I_{ref0} \leftrightarrow \alpha[i+1,j]I_{Wut} = w[i+1,j]I_{Xut} \quad (1.8)$$

When the current $I_{Wut}$ output from the current source CS of the circuit WCS in FIG. 2A and the current $I_{Xut}$ output from the current source CS of the circuit XCS in FIG. 2C are equal, w[i+1,j] is equal to $\alpha$[i+1,j]. That is, when $I_{Wut}$ and $I_{Xut}$ are equal, $\alpha$[i+1,j] corresponds to the value of the first data; accordingly, $I_{Wut}$ and $I_{Xut}$ are preferably equal.

<<From Time T18 to Time T19>>

In the period from Time T18 to Time T19, a low-level potential is applied to the wiring WSL[i+1]. Accordingly, in the i+1-th row of the cell array CA, a low-level potential is applied to each of the gates of the transistors F1 included in the cell IM[i+1,1] to the cell IM[i+1,n] and the gate of the transistor F1$m$ included in the cell IMref[i+1], and the transistors F1 and the transistor F1$m$ are turned off.

When the transistor F1 included in the cell IM[i+1,j] is turned off, $V_g[i+1,j] - V_{gm}[i+1]$, which is a difference between the potential of the gate of the transistor F2 (the node NN[i+1,j]) and the potential of the wiring XCL[i+1], is stored in the capacitor C5. Moreover, when the transistor F1 included in the cell IMref[i+1] is turned off, 0, which is a difference between the potential of the gate of the transistor F2$m$ (the node NNref[i+1]) and the potential of the wiring XCL[i+1], is stored in the capacitor C5$m$. In the operation from Time T18 to Time T19, the voltage stored in the capacitor C5$m$ might be a voltage that is not 0 (e.g., Vas) depending on transistor characteristics of the transistor F1$m$ and the transistor F2$m$ and the like. In this case, the potential of the node NNref[i+1] is the potential obtained by adding Vas to the potential of the wiring XCL[i+1].

<<From Time T19 to Time 20>>

In the period from Time T19 to Time T20, the ground potential GND is applied to the wiring XCL[i+1]. Specifically, for example, when the wiring XCL in FIG. 2C is the wiring XCL[i+1], the potential of the wiring XCL[i+1] can be set to the ground potential GND by setting the initialization potential of the wiring VINIL2 to the ground potential GND and turning on the switch SWX.

Thus, the potentials of the node NN[i,1] to the node NN[i+1,n] change because of capacitive coupling of the capacitors C5 included in the cell IM[i+1,1] to the cell IM[i+1,n] in the i+1-th row, and the potential of the node NNref[i+1] changes because of capacitive coupling of the capacitor C5$m$ included in the cell IMref[i+1].

The amount of change in the potentials of the node NN[i+1,1] to the node NN[i+1,n] equals to a potential obtained by multiplying the amount of change in the potential of the wiring XCL[i+1] by a capacitive coupling coefficient determined by the structures of the cell IM[i+1,1] to the cell IM[i+1,n] included in the cell array CA. The capacitive coupling coefficient is calculated using the capacitance of the capacitor C5, the gate capacitance of the transistor F2, the parasitic capacitance, and the like. In the case where the capacitive coupling coefficient due to the capacitor C5 in each of the cell IM[i+1,1] to the cell IM[i+1,n] is p, which is the same as the capacitive coupling coefficient due to the capacitor C5 in each of the cell IM[i,1] to the cell IM[i,n], the potential of the node NN[i+1,j] of the cell IM[i+1,j] decreases from the potential in the period from Time T18 to Time T19 by p($V_{gm}[i+1]$–GND).

Similarly, when the potential of the wiring XCL[i+1] changes, the potential of the node NNref[i+1] also changes because of capacitive coupling of the capacitor C5$m$ included in the cell IMref[i+1]. The potential of the node NNref[i+1] of the cell IMref[i+1] in the case where the capacitive coupling coefficient due to the capacitor C5$m$ is p like that due to the capacitor C5 decreases from the potential in the period from Time T18 to Time T19 by p($V_{gm}[i+1]$–GND). In the timing chart in FIG. 6, p is 1 as an example. Accordingly, the potential of the node NNref [i+1] is GND between Time T20 and Time T21.

Accordingly, the potential of the node NN[i+1,j] of the cell IM[i+1,j] decreases, so that the transistor F2 is turned off; similarly, the potential of the node NNref[i+1] of the cell IMref[i+1] decreases, so that the transistor F2$m$ is also turned off. Therefore, $I_{F2}[i+1,j]$ and $I_{F2m}[i+1]$ are each 0 in the period from Time T19 to Time T20.

<<From Time T20 to Time T21>>

In the period from Time T20 to Time T21, a low-level potential is applied to the wiring SWL1. Accordingly, a low-level potential is applied to each of the gates of the transistor F3[1] to the transistor F3[$n$], whereby the transistor F3[1] to the transistor F3[$n$] are brought into an off state.

<<From Time T21 to Time T22>>

In the period from Time T21 to Time T22, a high-level potential is applied to the wiring SWL2. Accordingly, a high-level potential is applied to each of the gates of the transistor F4[1] to the transistor F4[$n$], whereby the transistor F4[1] to the transistor F4[$n$] are brought into an on state.

<<From Time T22 to Time T23>>

In the period from Time T22 to Time T23, a current x[i]$I_{ref0}$, which is x[i] times as large as the amount of current $I_{ref0}$, flows from the circuit XCS to the wiring XCL[i] as the second data. Specifically, for example, when the wiring XCL in FIG. 2C is the wiring XCL[i], a high-level potential or a low-level potential is input to the wiring DX[1] to the wiring DX[K] in accordance with the value of x[i], and the current amount x[i]$I_{ref0}$=x[i]$I_{Xut}$ flows from the circuit XCS to the wiring XCL[i]. In this operation example, x[i] corresponds to the value of the second data. At this time, the potential of the wiring XCL[i] changes from 0 to $V_{gm}[i]+\Delta V[i]$.

When the potential of the wiring XCL[i] changes, the potentials of the node NN[i,1] to the node NN[i,n] also change because of the capacitive coupling of the capacitors C5 included in the cell IM[i,1] to the cell IM[i,n] in the i-th row of the cell array CA. Thus, the potential of the node NN[i,j] of the cell IM[i,j] becomes $V_g[i,j]+p\Delta V[i]$.

Similarly, when the potential of the wiring XCL[i] changes, the potential of the node NNref[i] also changes because of capacitive coupling of the capacitor C5m included in the cell IMref[i]. Thus, the potential of the node NNref[i] of the cell IMref[i] becomes $V_{gm}[i]+p\Delta V[i]$.

Accordingly, a current amount $I_1[i,j]$ of a current flowing between the first terminal and the second terminal of the transistor F2 and a current amount $I_{ref1}[i,j]$ of a current flowing between the first terminal and the second terminal of the transistor F2m in the period from Time T22 to Time T23 can be described as follows.

[Formula 9]

$$I_1[i, j] = I_a \exp\{J(V_g[i, j] + p\Delta V[i] - V_{th}[i, j])\} \qquad (1.9)$$
$$= J_0[i, j]\exp(Jp\Delta V[i])$$

[Formula 10]

$$I_{ref1}[i] = I_a \exp\{J(V_{gm}[i] + p\Delta V[i] - V_{thm}[i])\} \qquad (1.10)$$
$$= x[i]I_{ref0}$$

According to Formula (1.9) and Formula (1.10), x[i] can be expressed with the following formula.

[Formula 11]

$$x[i]=\exp(Jp\times V[i]) \qquad (1.11)$$

Therefore, Formula (1.9) can be rewritten into the following formula.

[Formula 12]

$$I_1[i,j]=x[i]W[i,j]I_{ref0} \qquad (1.12)$$

That is, the amount of current flowing between the first terminal and the second terminal of the transistor F2 included in the cell IM[i,j] is proportional to the product of the first data w[i,j] and the second data x[i].

In the period from Time T22 to Time T23, a current $x[i+1]I_{ref0}$, which is x[i+1] times as large as the amount of current $I_{ref0}$, flows from the circuit XCS to the wiring XCL[i+1] as the second data. Specifically, for example, when the wiring XCL illustrated in FIG. 2C is the wiring XCL[i+1], a high-level potential or a low-level potential is input to the wiring DX[1] to the wiring DX[K] in accordance with the value of x[i+1], and the current amount $x[i+1]I_{ref0}=x[i+1]I_{Xut}$ flows from the circuit XCS to the wiring XCL[i+1]. In this operation example, x[i+1] corresponds to the value of the second data. At this time, the potential of the wiring XCL[i+1] changes from 0 to $V_{gm}[i+1]+\Delta V[i+1]$.

When the potential of the wiring XCL[i+1] changes, the potentials of the node NN[i+1,1] to the node NN[i+1,n] also change because of the capacitive coupling of the capacitors C5 included in the cell IM[i+1,1] to the cell IM[i+1,n] in the i+1-th row of the cell array CA. Thus, the potential of the node NN[i+1,j] of the cell IM[i+1,j] becomes $V_g[i+1,j]+p\Delta V[i+1]$.

Similarly, when the potential of the wiring XCL[i+1] changes, the potential of the node NNref[i+1] also changes because of capacitive coupling of the capacitor C5m included in the cell IMref[i+1]. Thus, the potential of the node NNref[i+1] of the cell IMref[i+1] becomes $V_{gm}[i+1]+p\Delta V[i+1]$.

Accordingly, a current amount $I_1[i+1,j]$ of a current flowing between the first terminal and the second terminal of the transistor F2 and a current amount $I_{ref1}[i+1,j]$ of a current flowing between the first terminal and the second terminal of the transistor F2m in the period from Time T22 to Time T23 can be described as follows.

[Formula 13]

$$J_1[i+1, j] = I_a \exp\{J(V_g[i+1, j] + p\Delta V[i+1] - V_{th}[i+1, j])\} = \qquad (1.13)$$
$$I_0[i+1, j]\exp(Jp\Delta V[i+1])$$

[Formula 14]

$$I_{ref1}[i+1] = \qquad (1.14)$$
$$I_a\exp\{J(V_{gm}[i+1] + p\Delta V[i+1] - V_{thm}[i+1])\} = x[i+1]I_{ref0}$$

According to Formula (1.13) and Formula (1.14), x[i+1] can be expressed with the following formula.

[Formula 15]

$$x[i+1]=\exp(Jp\Delta V[i+1]) \qquad (1.15)$$

Therefore, Formula (1.13) can be rewritten into the following formula.

[Formula 16]

$$I_1[i+1,j]=x[i+1]w[i+1,j]I_{ref0} \qquad (1.16)$$

That is, the amount of current flowing between the first terminal and the second terminal of the transistor F2 included in the cell IM[i+1,j] is proportional to the product of the first data w[i+1,j] and the second data x[i+1].

Here, the sum of the current amounts of currents flowing from the converter circuit ITRZ[j] to the cell IM[i,j] and the cell IM[i+1,j] through the transistor F4[j] and the wiring WCL[j] is considered. According to Formula (1.12) and Formula (1.16), when the sum of the current amounts is $I_S[j]$, $I_S[j]$ can be expressed with the following formula.

[Formula 17]

$$I_S[j] = I_1[i, j] + I_1[i+1, j] \qquad (1.17)$$
$$= I_{ref0}(x[i]w[i, j] + x[i+1]w[i+1, j])$$

Thus, the amount of current output from the converter circuit ITRZ[j] is a current proportional to the sum of products of the coefficient of weights w[i,j] and w[i+1,j] that are the first data and the values x[i] and x[i+1] of the signals of the neurons that are the second data.

Although in the above-described operation example, the sum of the current amounts of currents flowing to the cell IM[i,j] and the cell IM[i+1,j] is described, the sum of the current amounts of currents flowing to a plurality of cells, i.e., the cell IM[1,j] to the cell IM[m,j] may be described. In this case, Formula (1.17) can be rewritten into the following formula.

[Formula 18]

$$I_S[i] = I_{ref0}\sum_{i=1}^{m} x[i]w[i, j] \qquad (1.18)$$

Thus, even in the case of the arithmetic circuit MAC1 including the cell array CA including three or more rows and two or more columns, a product-sum operation can be performed in the above-described manner. In the arithmetic circuit MAC1 of such a case, memory cells in one of the plurality of columns are used for retaining $I_{ref0}$ and $xI_{ref0}$ as the amount of current, whereby product-sum operations, the number of which corresponds to the number of rest of the columns among the plurality of columns, can be executed concurrently. That is, when the number of columns in a memory cell array is increased, a semiconductor apparatus that achieves high-speed product-sum operation can be provided.

The above operation example of the arithmetic circuit MAC1 is preferable when a product-sum operation of the positive first data and the positive second data is performed. Embodiment 2 will describe an operation example in which a product-sum operation of the positive or negative first data and the positive second data is performed and an operation example in which a product-sum operation of the positive or negative first data and the positive or negative second data is performed.

Although this embodiment describes the case where the transistors included in the arithmetic circuit MAC1 are OS transistors or Si transistors, one embodiment of the present invention is not limited thereto. The transistor included in the arithmetic circuit MAC1 can be, for example, a transistor including Ge and the like in a channel formation region, a transistor including a compound semiconductor such as ZnSe, CdS, GaAs, InP, GaN, or SiGe in a channel formation region, a transistor including a carbon nanotube in a channel formation region, a transistor including an organic semiconductor in a channel formation region, in addition to the Si transistor.

Note that this embodiment can be combined with any of the other embodiments in this specification as appropriate.

Embodiment 2

In Embodiment 1, the arithmetic circuit which performs the product-sum operation of the first data being positive or "0" and the second data being positive or "0" and its operation example are described; in this embodiment, an arithmetic circuit which can perform a product-sum operation of the first data being positive, negative, or "0" and the second data being positive or "0", and a product-sum operation of the first data being positive, negative, or "0" and the second data being positive, negative, or "0" is described.

<Configuration Example 1 of Arithmetic Circuit>

Figure 7:
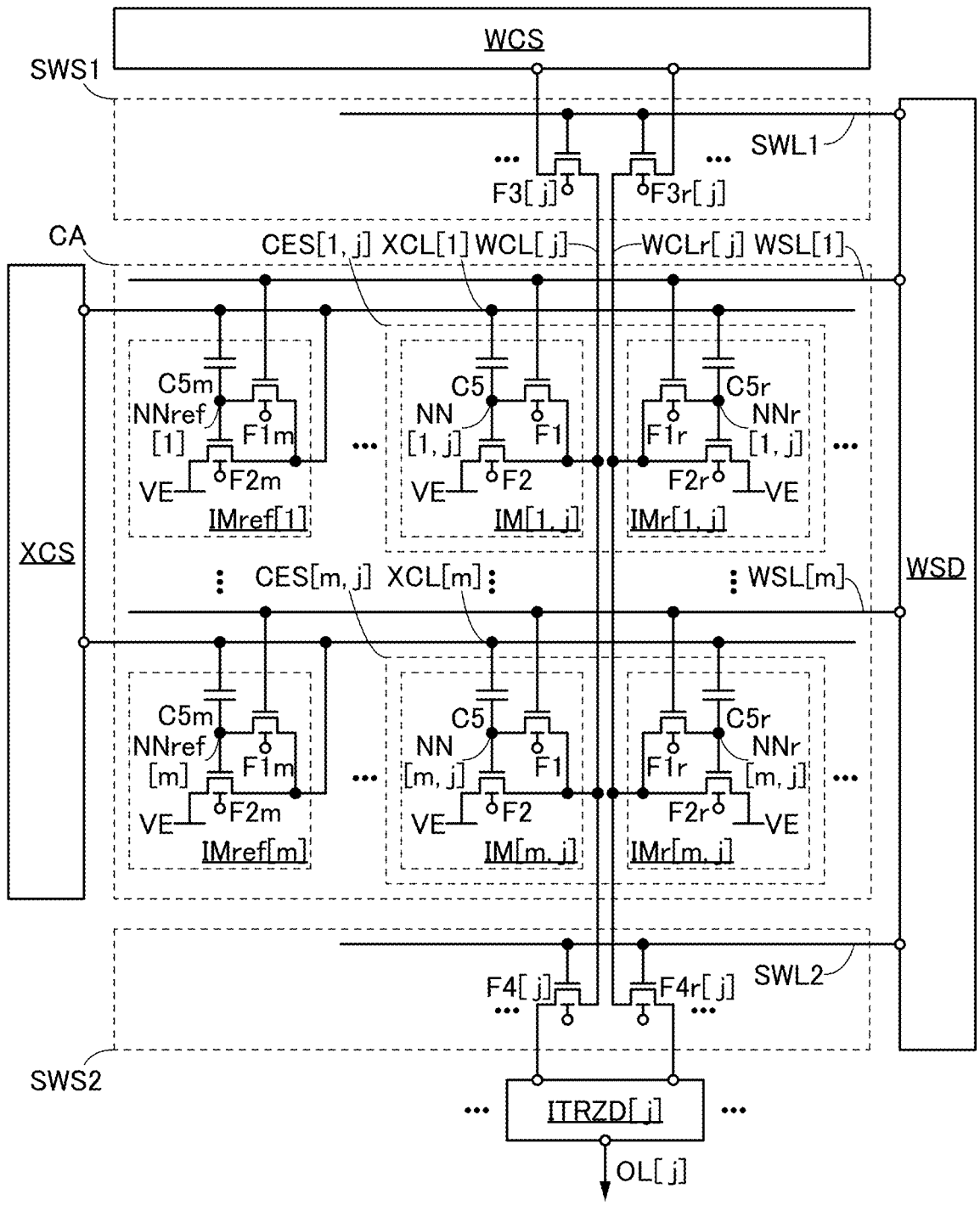
FIG. 7 is a block diagram showing a configuration example of a semiconductor device.

FIG. 7 illustrates a configuration example of an arithmetic circuit which performs a product-sum operation of the positive, negative, or "0" first data and the positive or "0" second data. An arithmetic circuit MAC2 in FIG. 7 has a configuration in which the arithmetic circuit MAC1 in FIG. 1 is changed. Thus, the portions in the arithmetic circuit MAC2 that are the same as in the arithmetic circuit MAC1 are not described.

The cell array CA illustrated in FIG. 7 includes a circuit CES[1,j] to a circuit CES[m,j], the circuit CES[1,j] includes a cell IM[1,j] and a cell IMr[1,j], and the circuit CES[m,j] includes a cell IM[m,j] and a cell IMr[m,j]. FIG. 7 selectively illustrates the circuit CES[1,j] and the circuit CES[m, j]. In this specification and the like, when the circuit CES [1,j] to the circuit CES[m,j], the cell IM[1,j], the cell IMr[1,j], the cell IM[m,j], the cell IMr[m,j] and the like are described, [m,n] and the like that are added to reference letters may be omitted.

The cell IM can have a configuration similar to that of the cell IM[1,1] to the cell IM[m,n] included in the cell array CA in the arithmetic circuit MAC1 in FIG. 1.

The cell IMr can have a configuration similar to that of the cell IM. FIG. 7 shows the cell IMr having a similar configuration to that of the cell IM, for example. To distinguish the transistors, the capacitors, and the like included in the cell IM and the cell IMr, "r" is added to the reference numerals representing the transistors and the capacitor included in the cell IMr.

Specifically, the cell IMr includes a transistor F1r, a transistor F2r, and a capacitor C5r. The transistor F1r corresponds to the transistor F1 in the cell IM, the transistor F2r corresponds to the transistor F2 in the cell IM, and the capacitor C5r corresponds to the capacitor C5 in the cell IM. Thus, for the electrical connection configuration between the transistor F1r, the transistor F2r, and the capacitor C5r, the descriptions on IM[1,1] to the cell IM[m,n] in Embodiment 1 are referred to.

In the cell IMr, a connection portion of the first terminal of the transistor F1r, the gate of the transistor F2r, and the first terminal of the capacitor C5r is a node NNr.

In the circuit CES[1,j], the second terminal of the capacitor C5 is electrically connected to the wiring XCL[1], the gate of the transistor F1 is electrically connected to the wiring WSL[1], and the second terminal of the transistor F1 and the second terminal of the transistor F2 are electrically connected to the wiring WCL[j]. A second terminal of the capacitor C5r is electrically connected to the wiring XCL [1], a gate of the transistor F1r is electrically connected to the wiring WSL[1], and a second terminal of the transistor F1r and a second terminal of the transistor F2r are electrically connected to a wiring WCLr[j].

Similarly, in the circuit CES[m,j], the second terminal of the capacitor C5 is electrically connected to the wiring XCL[m], the gate of the transistor F1 is electrically connected to the wiring WSL[m], and the second terminal of the transistor F1 and the second terminal of the transistor F2 are electrically connected to the wiring WCL[j]. The second terminal of the capacitor C5r is electrically connected to the wiring XCL[m], the gate of the transistor F1r is electrically connected to the wiring WSL[m], and the second terminal of the transistor F1r and the second terminal of the transistor F2r are electrically connected to the wiring WCLr[j].

The wiring WCL[j] and the wiring WCLr[j] function as, for example, wirings through which a current flows from the circuit WCS to the cell IM and the cell IMr included in the circuit CES like the wiring WCL[1] to the wiring WCL[n] described in Embodiment 1. As an example, the wiring WCL[j] and the wiring WCLr[j] function as wirings through which a current flows from a converter circuit ITRZD[j] to the cell IM and the cell IMr included in the circuit CES.

In the arithmetic circuit MAC2 in FIG. 7, the circuit SWS1 includes the transistor F3[j] and a transistor F3r[j]. A first terminal of the transistor F3[j] is electrically connected to the wiring WCL[j], the second terminal of the transistor F3[j] is electrically connected to the circuit WCS, and a gate of the transistor F3[j] is electrically connected to the wiring SWL1. A first terminal of the transistor F3r[j] is electrically connected to the wiring WCLr[j], a second terminal of the transistor F3r[j] is electrically connected to the circuit WCS, and a gate of the transistor F3r[j] is electrically connected to the wiring SWL1.

In the arithmetic circuit MAC2 in FIG. 7, the circuit SWS2 includes the transistor F4[j] and a transistor F4r[j]. A first terminal of the transistor F4[j] is electrically connected to the wiring WCL[j], a second terminal of the transistor F4[j] is electrically connected to the converter circuit ITRZD[j], and a gate of the transistor F4[j] is electrically connected to the wiring SWL2. A first terminal of the transistor F4r[j] is electrically connected to the wiring WCLr[j], a second terminal of the transistor F4r[j] is electrically connected to the converter circuit ITRZD[j], and a gate of the transistor F4r[j] is electrically connected to the wiring SWL2.

The converter circuit ITRZD[j] corresponds to the converter circuit ITRZ[1] to the converter circuit ITRZ[n] in the arithmetic circuit MAC1; for example, the converter circuit ITRZD[j] has a function of generating a voltage corresponding to the difference between the amount of current flowing from the converter circuit ITRZD[j] to the wiring WCL[j] and the amount of current flowing from the converter circuit ITRZD[j] to the wiring WCLr[j] and outputting the voltage to the wiring OL[j].

Figure 8A:
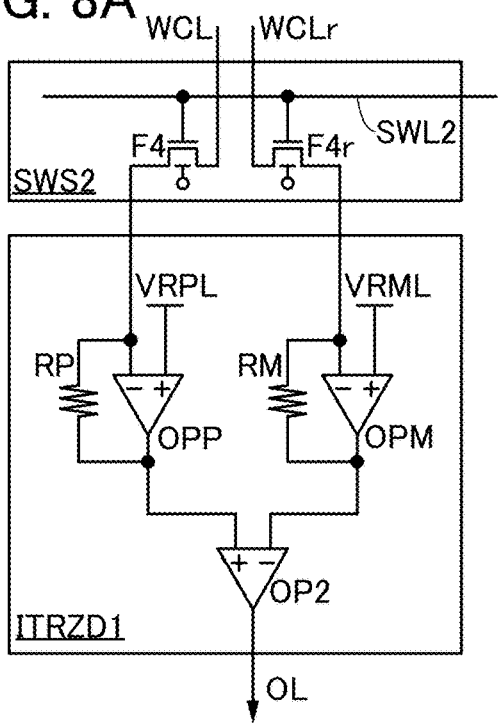
FIG. 8A to FIG. 8C are block diagrams each showing a configuration example of a circuit included in a semiconductor device.

FIG. 8A illustrates a specific configuration example of the converter circuit ITRZD[j]. A converter circuit ITRZD1 illustrated in FIG. 8A is an example of a circuit which can be used as the converter circuit ITRZD[j] in FIG. 7. FIG. 8A also illustrates the circuit SWS2, the wiring WCL, the wiring WCLr, the wiring SWL2, the transistor F4, and the transistor F4r to show the electrical connections between the converter circuit ITRZD1 and its nearby circuits. The wiring WCL[j] and the wiring WCLr[j] included in the arithmetic circuit MAC2 in FIG. 7 can be respectively used as the wiring WCL and the wiring WCLr, for example, and the transistor F4[j] and the transistor F4r[j] included in the arithmetic circuit MAC2 in FIG. 7 can be respectively used as the transistor F4 and the transistor F4r, for example.

The converter circuit ITRZD1 in FIG. 8A is electrically connected to the wiring WCL through the transistor F4. The converter circuit ITRZD1 is electrically connected to the wiring WCLr through the transistor F4r. The converter circuit ITRZD1 is electrically connected to the wiring OL. The converter circuit ITRZD1 has a function of converting the amount of current flowing from the converter circuit ITRZD1 to the wiring WCL or the amount of current flowing from the wiring WCL to the converter circuit ITRZD1 into a first voltage, a function of converting the amount of current flowing from the converter circuit ITRZD1 to the wiring WCLr or the amount of current flowing from the wiring WCLr to the converter circuit ITRZD1 into a second voltage, and a function of outputting to the wiring OL an analog voltage corresponding to the difference between the first voltage and the second voltage.

The converter circuit ITRZD1 in FIG. 8A includes a resistor RP, a resistor RM, an operational amplifier OPP, an operational amplifier OPM, and an operational amplifier OP2, for example.

An inverting input terminal of the operational amplifier OPP is electrically connected to a first terminal of the resistor RP and the second terminal of the transistor F4. A non-inverting input terminal of the operational amplifier OPP is electrically connected to a wiring VRPL. An output terminal of the operational amplifier OPP is electrically connected to a second terminal of the resistor RP and a non-inverting input terminal of the operational amplifier OP2. An inverting input terminal of the operational amplifier OPM is electrically connected to a first terminal of the resistor RM and a second terminal of the transistor F4r. A non-inverting input terminal of the operational amplifier OPM is electrically connected to a wiring VRML. An output terminal of the operational amplifier OPM is electrically connected to a second terminal of the resistor RM and an inverting input terminal of the operational amplifier OP2. An output terminal of the operational amplifier OP2 is electrically connected to the wiring OL.

The wiring VRPL functions as a wiring for supplying a constant voltage. The constant voltage can be a ground potential (GND), a low-level potential, or a high-level potential, for example. The wiring VRML functions as a wiring for supplying a constant voltage. The constant voltage can be a ground potential (GND), a low-level potential, or a high-level potential, for example. The constant voltages provided by the wiring VRPL and the wiring VRML may be equal or different. In particular, by setting the constant voltages supplied by the wiring VRPL and the wiring VRML to ground potentials (GND), the inverting input terminal of the operational amplifier OPP and the inverting input terminal of the operational amplifier OPM are virtually grounded.

The converter circuit ITRZD1 with the configuration in FIG. 8A can convert the amount of current flowing from the wiring WCL to the converter circuit ITRZD1 through the transistor F4 or the amount of current flowing from the converter circuit ITRZD1 to the wiring WCL through the transistor F4 into the first voltage. The converter circuit ITRZD1 can convert the amount of current flowing from the wiring WCLr to the converter circuit ITRZD1 through the transistor F4r or the amount of current flowing from the converter circuit ITRZD1 to the wiring WCLr through the transistor F4r into the second voltage. Then, the converter circuit ITRZD1 can output to the wiring OL an analog voltage corresponding to the difference between the first voltage and the second voltage.

Figure 8B:
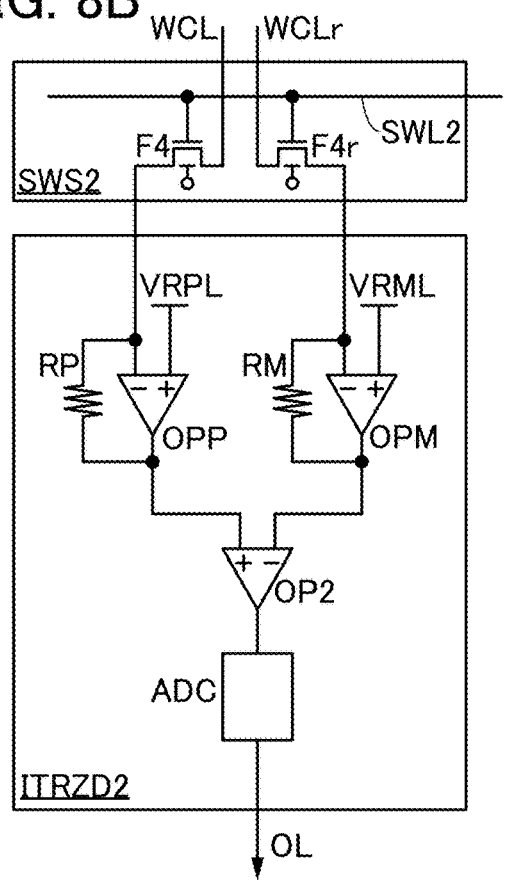

The converter circuit ITRZD1 in FIG. 8A outputs an analog voltage; however, the circuit configuration which can be used for the converter circuit ITRZD[j] in FIG. 7 is not limited thereto. For example, the converter circuit ITRZD1 may include, as in FIG. 4B, the analog-digital converter circuit ADC as illustrated in FIG. 8B. Specifically, in a converter circuit ITRZD2 in FIG. 8B, the input terminal of the analog-digital converter circuit ADC is electrically connected to the output terminal of the operational amplifier OP2 and the output terminal of the analog-digital converter circuit ADC is electrically connected to the wiring OL. With such a configuration, the converter circuit ITRZD2 in FIG. 8B can output a digital signal to the wiring OL.

Figure 8C:
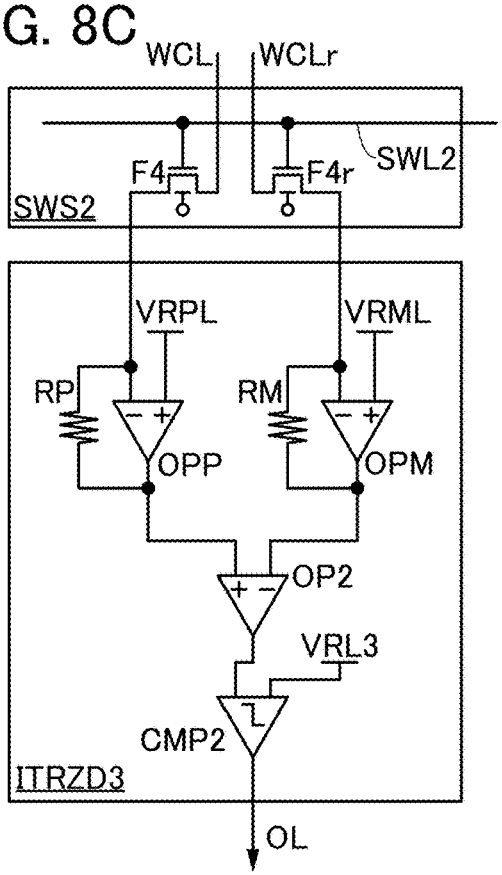

When the digital signal output to the wiring OL is 1 bit (binary) in the converter circuit ITRZD2, the converter circuit ITRZ2 may be replaced with a converter circuit ITRZD3 in FIG. 8C. The converter circuit ITRZ3 in FIG. 8C has a configuration in which the converter circuit ITRZD1 in FIG. 8A further includes a comparator CMP2, as in FIG. 4C. Specifically, the converter circuit ITRZD3 has a configuration in which a first input terminal of the comparator CMP2 is electrically connected to the output terminal of the operational amplifier OP2, and a second input terminal of the comparator CMP2 is electrically connected to a wiring VRL3, and an output terminal of the comparator CMP2 is electrically connected to the wiring OL. The wiring VRL3 functions as a wiring for supplying a potential to be compared to the potential of the first terminal of the comparator CMP2. With such a structure, the converter circuit ITRZD3 in FIG. 8C can output to the wiring OL a low-level potential or a high-level potential (a binary digital signal) in accordance with the large-small relation between the voltage supplied by the wiring VRL3 and the difference of the first voltage converted from the amount of current flowing between the source and the drain of the transistor F4 and the second voltage converted from the amount of current flowing between the source and the drain of the transistor F4r.

<<Example of Storing First Data>>

Next, In the arithmetic circuit MAC2 in FIG. 7, an example of the circuit CES storing the first data to perform a product-sum operation of the positive, negative, or "0" first data and the positive or "0" second data is described.

Since the circuit CES includes the cell IM and the cell IMr, the circuit CES can use the two circuits, i.e., the cell IM and the cell IMr to store the first data. Two current amounts are set for the circuit CES and potentials corresponding to the current amounts can be stored in the cell IM and the cell IMr. The first data can be represented with the current amount set in the cell IM and the current amount set in the cell IMr. The positive first data, the negative first data, or the "0" first data to be stored in the circuit CES is defined as follows.

To store the positive first data in the circuit CES[1,j], the cell IM[1,j] is set such that the current amount corresponding to the absolute value of the positive first data flows between the first terminal and the second terminal of the transistor F2 in the cell IM[1,j], for example. Specifically, the potential corresponding to the current amount is stored in the gate of the transistor F2 (the node NN[1,j]). In contrast, the cell IMr[1,j] is set such that a current does not flow between the first terminal and the second terminal of the transistor F2r in the cell IMr[1,j]. Specifically, the gate of the transistor F2r (node NNr[1,j]) stores the potential supplied by the wiring VE or the initialization potential supplied by the wiring VINIL1 of the circuit WCS in FIG. 2A, for example.

To store the negative first data in the circuit CES[1,j], the cell IMr[1,j] is set such that the current amount corresponding to the absolute value of the negative first data flows through the transistor F2r in the cell IMr[1,j], for example. Specifically, a potential corresponding to the current amount is retained in the gate of the transistor F2r (node NNr[1,j]). In contrast, the cell IM[1,j] is set such that a current does not flow through the transistor F2 in the cell IM[1,j]. Specifically, the gate of the transistor F2 (node NN[1,j]) stores the potential supplied by the wiring VE or the initialization potential supplied by the wiring VINIL1 of the circuit WCS in FIG. 2A, for example.

To store the "0" first data in the circuit CES[1,j], the transistor F2 of the cell IM[1,j] and the transistor F2r of the cell IMr[1,j] are set such that currents do not flow through these transistors, for example. Specifically, the gate of the transistor F2 (node NN[1,j]) and the gate of the transistor F2r (node NNr[1,j]) stores the potential supplied by the wiring VE or the initialization potential supplied by the wiring VINIL1 of the circuit WCS in FIG. 2A, for example.

To store the positive first data or the negative first data in another circuit CES, it is set that a current with the current amount corresponding to the first data flows through one of the path between the cell IM and the wiring WCL and the path between the cell IMr and the wiring WCLr while a current does not flow through the other of the path between the cell IM and the wiring WCL and the path between the cell IMr and the wiring WCLr, as in the circuit CES[1,j]. To store the "0" first data in another circuit CES, it is set that a current does not flow between the cell IM and the wiring WCL and between the cell IMr and the wiring WCLr as in the circuit CES[1,j].

For example, to store each case of "+3", "+2", "+1", "0", "−1", "−2", and "−3" in the circuit CES as the first data, the amount of current flowing from the wiring WCL to the cell IM and the amount of current flowing from the wiring WCLr to the cell IMr are set as described above, whereby each of "+3", "+2", "+1", "0", "−1", "−2", and "−3" as the first data can be defined as illustrated in the following table.

TABLE 1

| First data | Current flowing from the wiring WCL to the cell IM | Current flowing from the wiring WCLr to the cell IMr |
| --- | --- | --- |
| +3 | $3I_{W_{ut}}$ | 0 |
| +2 | $2I_{W_{ut}}$ | 0 |
| +1 | $I_{W_{ut}}$ | 0 |
| 0 | 0 | 0 |
| −1 | 0 | $I_{W_{ut}}$ |
| −2 | 0 | $2I_{W_{ut}}$ |
| −3 | 0 | $3I_{W_{ut}}$ |

Here, the case is examined in which each of the circuit CES[1,j] to the circuit CES[m,j] retains the first data and the second data is input to each of the wiring XCL[1] to the wiring XCL[m] in the arithmetic circuit MAC2 in FIG. 7. A low-level potential is supplied to the wiring SWL1 to turn off the transistor F3[j] and the transistor F3r[j], and a high level potential is supplied to the wiring SWL2 to turn on the transistor F4[j] and the transistor F4r[j]. The converter circuit ITRZD[j] thus becomes electrically continuous with the wiring WCL[j], and a current may flow from the converter circuit ITRZD[j] to the wiring WCL[j]. The converter circuit ITRZD[j] becomes electrically continuous also with the wiring WCLr[j], and a current may flow from the converter circuit ITRZD[j] to the wiring WCLr[j]. When the sum of the amount of current flowing from the converter circuit ITRZD[j] to the wiring WCL[j] is $I_S[j]$ and the sum of the amount of current flowing from the converter circuit ITRZD[j] to the wiring WCLr[j] is $I_{Sr}[j]$, $I_S[j]$ and $I_{Sr}[j]$ can be represented by the following formulae, considering the operation example of the arithmetic circuit MAC1 described in Embodiment 1.

[Formula 19]

$$I_S[j] = I_{ref0} \sum_{i=1}^{m} x[i]w[i, j] \quad (2.1)$$

$$I_{Sr}[j] = I_{ref0} \sum_{i=1}^{m} x[i]w_r[i, j] \quad (2.2)$$

Note that w[i,j] shown in Formula (2.1) is the value of the first data written to the cell IM[i,j], and $w_r[i,j]$ shown in Formula (2.2) is the value of the first data written to the cell IMr[i,j]. When the value of one of w[i,j] and $w_r[i,j]$ is not "0", the other of w[i,j] and $w_r[i,j]$ is set to the value "0", whereby the first data retained in the circuit CES[i,j] can follow the definition shown in Table 1, for example.

The converter circuit ITRZD[j] convert the sum $I_S[j]$ of the amount of current flowing in the wiring WCL into the first voltage, and the sum $I_{Sr}[j]$ of the amount of current flowing in the wiring WCLr into the second voltage, for example. Then, the converter circuit ITRZD[j] can output a voltage corresponding to the difference between the first voltage and the second voltage to the wiring OL.

The converter circuit ITRZD1 to the converter circuit ITRZD3 illustrated in FIG. 8A to FIG. 8C each have a circuit configuration which outputs a voltage to the wiring OL; however, one embodiment of the present invention is not limited thereto. For example, the converter circuit ITRZD[j] included in the arithmetic circuit MAC2 in FIG. 7 may have a circuit configuration outputting a current.

Figure 9:
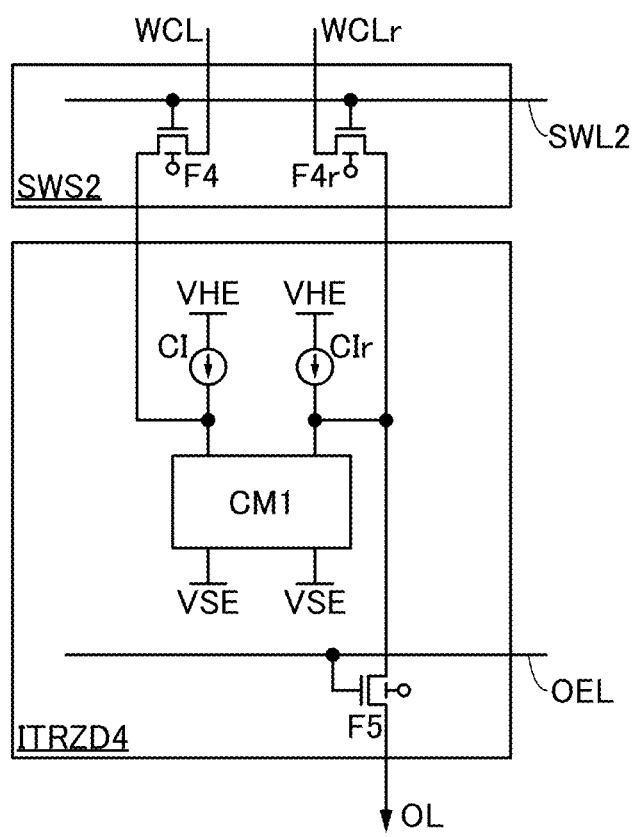
FIG. 9 is a block diagram showing a configuration example of a circuit included in a semiconductor device.

A converter circuit ITRZD4 illustrated in FIG. 9 can be used for the converter circuit ITRZD[j] included in the arithmetic circuit MAC2 in FIG. 7, and has a circuit configuration of outputting the results of a product-sum operation and an activation function operation in the form of a current amount.

FIG. 9 illustrates the circuit SWS2, the wiring WCL, the wiring WCLr, the wiring OL, the transistor F4, and the transistor F4r to show the electrical connections between the converter circuit ITRZD4 and its nearby circuits. The wiring WCL[j] and the wiring WCLr[j] included in the arithmetic circuit MAC2 in FIG. 7 can be respectively used as the wiring WCL and the wiring WCLr, for example, and the transistor F4[j] and the transistor F4r[j] included in the arithmetic circuit MAC2 in FIG. 7 can be respectively used as the transistor F4 and the transistor F4r, for example The converter circuit ITRZD4 in FIG. 9 is electrically connected to the wiring WCL through the transistor F4. The converter circuit ITRZD4 is electrically connected to the wiring WCLr through the transistor F4r. The converter circuit ITRZD4 is electrically connected to the wiring OL. The converter circuit ITRZD4 has a function of obtaining the difference current of one of the amount of current flowing from the converter circuit ITRZD4 to the wiring WCL and the amount of current flowing from the wiring WCL to the converter circuit ITRZD4, and one of the amount of current flowing from the converter circuit ITRZD4 to the wiring WCLr and the amount of current flowing from the wiring WCLr to the converter circuit ITRZD4. The converter circuit ITRZD4 has a function of making the difference current flow between the converter circuit ITRZD4 and the wiring OL.

The converter circuit ITRZD4 in FIG. 9 includes, for example, a transistor F5, a current source CI, a current source CIr, and a current mirror circuit CM1.

The second terminal of the transistor F4 is electrically connected to a first terminal of the current mirror circuit CM1 and an output terminal of the current source CI, and the second terminal of the transistor F4r is electrically connected to a second terminal of the current mirror circuit CM1, an output terminal of the current source CIr, and a first terminal of the transistor F5. An input terminal of the current source CI is electrically connected to a wiring VHE, and an input terminal of the current source CIr is electrically connected to the wiring VHE. A third terminal of the current mirror circuit CM1 is electrically connected to a wiring VSE, and a fourth terminal of the current mirror circuit CM1 is electrically connected to the wiring VSE.

The second terminal of the transistor F5 is electrically connected to the wiring OL and the gate of the transistor F5 is electrically connected to the wiring OEL.

The current mirror circuit CM1 has, for example, a function of making the current amount corresponding to the potential of the first terminal of the current mirror circuit CM1 flow between the first terminal and the third terminal of the current mirror circuit CM1 and between the second terminal and the fourth terminal of the current mirror circuit CM1.

The wiring VHE functions as a wiring for supplying a constant voltage, for example. Specifically, the constant voltage can be a high-level potential or the like, for example.

The wiring VSE functions as a wiring for supplying a constant voltage, for example. Specifically, the constant voltage can be, for example, a low-level potential, a ground potential, or the like.

The wiring OEL functions, for example, as a wiring for sending a signal to switch the on state and the off state of the transistor F5. Specifically, for example, a high-level potential or a low-level potential may be input to the wiring OEL.

The current source CI has a function of making a constant current flow between the input terminal and the output terminal of the current source CI. The current source CIr has a function of making a constant current flow between the input terminal and the output terminal of the current source CIr. The magnitude of the current flowing from the current source CI and the magnitude of the current flowing from the current source CIr are preferably equal in the converter circuit ITRZD4 in FIG. 9.

An operation example of the converter circuit ITRZD4 in FIG. 9 is described.

First, the amount of current flowing from the converter circuit ITRZD4 to the wiring WCL through the transistor F4 is $I_S$, and the amount of current flowing from the converter circuit ITRZD4 to the wiring WCLr through the transistor F4r is $I_{Sr}$. The current amount flowing from each of the current source CI and the current source CIr is $I_0$.

$I_S$ is the sum of the amount of current flowing through the cell IM[1,j] to the cell IM[m,j] positioned in the j-th row in the arithmetic circuit MAC2 in FIG. 7, for example. $I_{Sr}$ is the sum of the amount of current flowing through the cell IMr[1,j] to the cell IMr[m,j] positioned in the j-th row in the arithmetic circuit MAC2 in FIG. 7, for example.

When a high-level potential is input to the wiring SWL2, the transistor F4 and the transistor F4r are turned on. Accordingly, the amount of current flowing from the first terminal to the third terminal of the current mirror circuit CM1 is $I_0-I_S$. Due to the current mirror circuit CM1, the current amount $I_0-I_S$ flows from the second terminal to the second terminal of the current mirror circuit CM1.

Next, a high-level potential is input to the wiring OEL to turn on the transistor F5. When the amount of current flowing through the wiring OL is $I_{out}$, Iout is $I_0-(I_0-I_S)-I_{Sr}=I_S-I_{Sr}$.

In the arithmetic circuit MAC2 in FIG. 7, for storing the first data in the circuit CES to perform a product-sum operation of the positive, negative, or "0" first data and the positive or "0" second data, the above example of storing the first data is referred to.

That is, to store the positive first data in the circuit CES[i,j], the cell IM[i,j] is set such that the current amount corresponding to the absolute value of the positive first data flows between the first terminal and the second terminal of the transistor F2 of the cell IM[i,j], and the cell IMr[i,j] is set such that a current does not flow between the first terminal and the second terminal of the transistor F2r of the cell IMr[i,j]. To store the negative first data in the circuit CES[i,j], the cell IM[i,j] is set such that a current does not flow between the first terminal and the second terminal of the transistor F2 of the cell IM[i,j], and the cell IMr[i,j] is set such that the current amount corresponding to the absolute value of the negative first data flows between the first terminal and the second terminal of the transistor F2r of the cell IMr[i,j]. To store "0" first data in the circuit CES[i,j], the cell IM[i,j] is set such that a current does not flow between the first terminal and the second terminal of the transistor F2 of the cell IM[i,j], and the cell IMr[i,j] is set such that a current does not flow between the first terminal and the second terminal of the transistor F2r of the cell IMr[i,j]

When the second data is input to each of the wiring XCL[1] to the wiring XCL[m] of the arithmetic circuit MAC2 in FIG. 7, the current amount flowing between the first terminal and the second terminal of the transistor F2 of the cell IM[i,j] and the current amount flowing between the first terminal and the second terminal of the transistor F2 of the cell IMr[i,j] are each proportional to the second data.

$I_S$ is the sum of the amount of current flowing through the cell IM[1,j] to the cell IM[m,j] positioned in the j-th row. Thus, $I_S$ is the sum of the amount of current flowing in the cells IM included in the circuits CES in which the positive first data is stored out of the circuit CES[1,j] to the circuit CES[m,j]; Is can be represented in a manner similar to Formula (2.1), for example. That is, Is corresponds to the result of product-sum operation of the absolute value of the positive first data and the second data. $I_{Sr}$ is the sum of the amount of current flowing through the cell IMr[1,j] to the cell IMr[m,j] positioned in the j-th row. Thus, $Is_r$ is the sum of the amount of current flowing in the cells IMr included in the circuits CES in which the negative first data is stored out of the circuit CES[1,j] to the circuit CES[m,j]; $I_{Sr}$ can be represented in a manner similar to Formula (2.2), for example. That is, $I_{Sr}$ corresponds to the result of a product-sum operation of the absolute value of the negative first data and the second data.

Thus, the current amount $I_{out}=I_S-I_{Sr}$ flowing to the wiring OL corresponds to the difference between the result of the product-sum operation of the absolute value of the positive first data and the second data and the result of the product-sum operation of the absolute value of the negative first data and the second data. That is, $I_{out}=I_S-I_{Sr}$ corresponds to the result of the product-sum operation of the negative, "0", or positive first data stored in the circuit CES[1,j] to the circuit CES[m,j] and the second data input to each of the wiring XCL[1] to the wiring XCL[m].

When the sum of the amount of current flowing in the cell IM[1,j] to the cell IM[m,j] is larger than the sum of the amount of current flowing in the cell IMr[1,j] to the cell IMr[m,j], or Is is larger than $I_{Sr}$, $I_{out}$ is the current amount larger than 0 and flows from the converter circuit ITRZD4 to the wiring OL. In contrast, when the sum of the amount of current flowing in the cell IM[1,j] to the cell IM[m,j] is smaller than the sum of the amount of current flowing in the cell IMr[1,j] to the cell IMr[m,j], or $I_S$ is smaller than $I_{Sr}$, a current does not flow from the converter circuit ITRZD4 to the wiring OL in some cases. That is, when $I_S$ is smaller than $I_{Sr}$, $I_{out}$ can be approximately 0. Therefore, the converter circuit ITRZD4 can be regarded as a ReLU function, for example.

A ReLU function can be used as an activation function of a neural network, for example. In the arithmetic operation of the neural network, a product sum of the signal values (e.g., second data) from the neurons in the previous layer and the corresponding coefficient of weight (e.g., first data) is required to be calculated. In response to the result of the product sum, the value of an activation function is required to be calculated. Thus, when the activation function of the neural network is the ReLU function, the arithmetic operation of the neural network can be performed with the arithmetic circuit MAC2 including the converter circuit ITRZD4.

The hierarchical neural network will be described in Embodiment 5.

Next, a specific circuit configuration example of the converter circuit ITRZD4 in FIG. 9 is described.

Figure 10A:
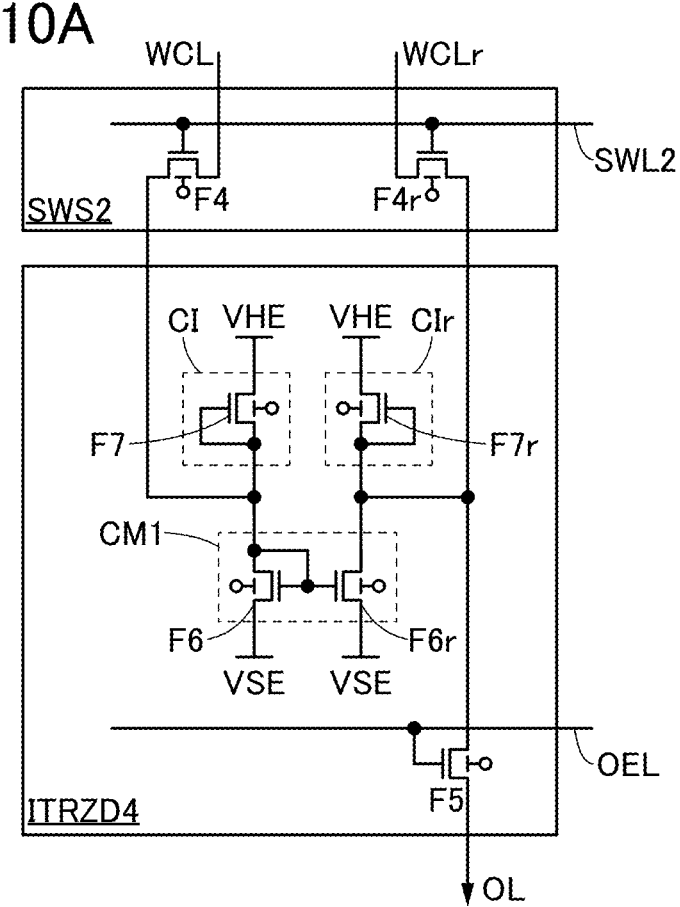
FIG. 10A is a circuit diagram showing a configuration example of a circuit included in a semiconductor device.

The converter circuit ITRZD4 illustrated in FIG. 10A is an example of the converter circuit ITRZD4 in FIG. 9. Specifically, FIG. 10A shows configuration examples of the current mirror circuit CM1, the current source CI, and the current source CIr.

In the converter circuit ITRZD4 in FIG. 10A, the current mirror circuit CM1 includes a transistor F6 and a transistor F6r, the current source CI includes a transistor F7, and the current source CIr includes a transistor F7r, for example. The transistor F6, the transistor F6r, the transistor F7, and the transistor F7r are n-channel transistors.

For example, the first terminal of the current mirror circuit CM1 is electrically connected to a first terminal of the transistor F6, a gate of the transistor F6, and a gate of the transistor F6r, and the third terminal of the current mirror circuit CM1 is electrically connected to a second terminal of the transistor F6. The second terminal of the current mirror circuit CM1 is electrically connected to a first terminal of the transistor F6r, and a fourth terminal of the current mirror circuit CM1 is electrically connected to a second terminal of the transistor F6r.

The output terminal of the current source CI is electrically connected to a first terminal of the transistor F7 and a gate of the transistor F7, and the input terminal of the current source CI is electrically connected to a second terminal of the transistor F7, for example.

The output terminal of the current source CIr is electrically connected to a first terminal of the transistor F7r and a gate of the transistor F7r, and the input terminal of the current source CIr is electrically connected to a second terminal of the transistor F7r.

The gate and the first terminal of each of the transistor F7 and the transistor F7r are electrically connected, and the second terminal thereof and the wiring VHE are electrically connected. Thus, the voltage between the gate and the source of each of the transistor F7 and the transistor F7r is 0 V, and when the threshold voltages of the transistor F7 and the transistor F7r are within an appropriate range, a constant current flows between the first terminal and the second terminal of each of the transistor F7 and the transistor F7r. In other words, the transistor F7 and the transistor F7r function as current sources.

The configurations of the current source CI and the current source CIr included in the converter circuit ITRZD4 in FIG. 9 are not limited to the current source CI and the current source CIr in FIG. 10A. The configurations of the current source CI and the current source CIr included in the converter circuit ITRZD4 can be changed depending on circumstances.

Figure 10B:
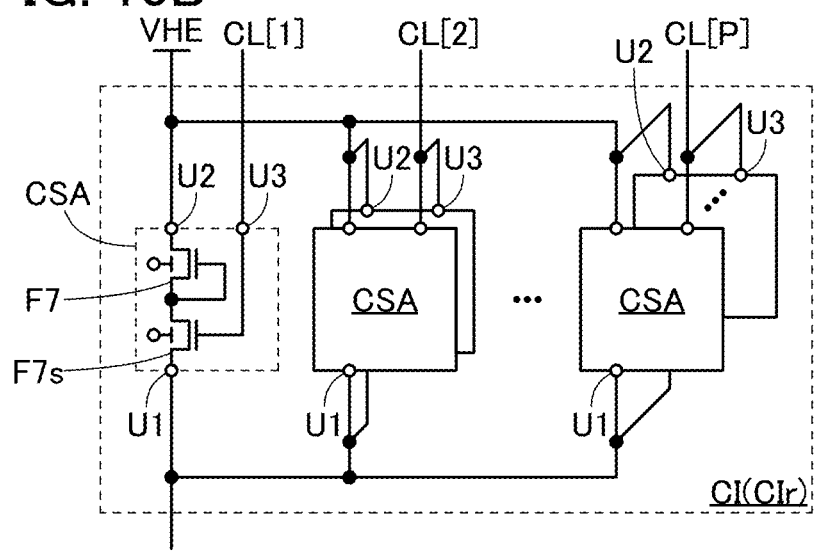
FIG. 10B is a block diagram showing a configuration example of a circuit included in a semiconductor device.

For example, the current source CI (current source CIr) in FIG. 10B can be used as the current source CI and the current source CIr included in the converter circuit ITRZD4 in FIG. 9.

The current source CI (current source CIr) in FIG. 10B has a plurality of current sources CSA, for example. Each of the plurality of current sources CSA includes the transistor F7, a transistor F7s, a terminal U1, a terminal U2, and a terminal U3.

For example, the current source CSA has a function of making the current amount $I_{CSA}$ flow between the terminal U2 and the terminal U1. When the current source CI (current source CIr) includes $2^P-1$ current source(s) CSA (P is an integer greater than or equal to 1), the current source CI (current source CIr) can make the current amount $s \times I_{CSA}$ (s is an integer more than or equal to 0 and less than or equal to $2^P-1$) flow to the output terminal.

When the current source CI (current source CIr) is manufactured, the transistors in each current sources CSA may have different electrical characteristics, resulting in errors in some cases. The errors of the constant currents $I_{CSA}$ output from the terminals U1 of the plurality of current sources CSA are preferably within 10%, more preferably within 5%, and further preferably within 1%. In this embodiment, the description is made based on the assumption that there is no error in the constant currents $I_{CSA}$ output from the terminals U1 of the plurality of current sources CSA included in the current source CI (current source CIr).

One of the plurality of current sources CSA, a first terminal of the transistor F7s is electrically connected to the terminal U1, and a gate of the transistor F7s is electrically connected to the terminal U3. A first terminal of the transistor F7 is electrically connected to a gate of the transistor F7 and a second terminal of the transistor F7s. A second terminal of the transistor F7 is electrically connected to the terminal U2.

Each terminal U1 of the plurality of current sources CSA is electrically connected to the output terminal of the current source CI (current source CIr). Each terminal U2 of the plurality of current sources CSA is electrically connected to the input terminal of the current source CI (current source CIr). That is, each terminal U2 of the plurality of current sources CSA is electrically continuous with the wiring VHE.

The terminal U3 of one current source CL[1] is electrically connected to the wiring CL[1], the terminals U3 of two current sources CS are electrically connected to the wiring CL[2], and the terminals U3 of $2^P-1$ current sources CS are electrically connected to the wiring CL[P].

The wiring CL[1] to the wiring CL[P] each function as a wiring for sending a control signal to make the current source(s) CSA, to which the wiring is connected, output the constant current $I_{CSA}$. Specifically, for example, when a high-level potential is supplied to the wiring CL[1], the current source CSA electrically connected to the wiring CL[1] supplies $I_{CSA}$ as a constant current to the terminal U1, and when a low-level potential is supplied to the wiring CL[1], the current source CSA electrically connected to the wiring CL[1] does not output $I_{CSA}$. When a high-level potential is supplied to the wiring CL[2], two current sources CSA electrically connected to the wiring CL[2] supply $2I_{CSA}$ in total as a constant current to the terminal U1, and when a low-level potential is supplied to the wiring CL[2], the current source CSA electrically connected to the wiring CL[2] does not output $2I_{CSA}$ in total, for example. When a high-level potential is supplied to the wiring CL[P], $2^{P-1}$ current sources CSA electrically connected to the wiring CL[P] supply $2^{P-1}I_{CSA}$ in total as a constant current to the terminal U1, and when a low-level potential is supplied to the wiring CL[P], the current source CSA electrically connected to the wiring CL[P] does not output $2^{P-1}I_{CSA}$ in total, for example.

Accordingly, when one or more wirings selected from the wiring CL[1] to the wiring CL[P] is/are supplied with high potentials, a current flows to the output terminal of the current source CI (current source CIr). The current amount can be determined through the combination of one or more wirings to which a high-level potential is supplied that are selected from the wiring CL[1] to the wiring CL[P]. For example, when a high-level potential is supplied to the wiring CL[1] and the wiring CL[2] and a low-level potential is supplied to the wiring CL[3] to the wiring CL[P], the current with $3I_{CSA}$ in total flows to the output terminal of the current source CI (current source CIr).

As described above, with the use of the current source CI (current source CIr) in FIG. 10B, the current amount flowing by the current source CI (current source CIr) to its output terminal can be changed depending on circumstances.

When the converter circuit ITRZD4 in FIG. 10A is used as the converter circuit ITRZD4 in FIG. 9, all the transistors included in the converter circuit ITRZD4 can be OS transistors. The cell array CA, the circuit WCS, the circuit XCS, and the like in the arithmetic circuit MAC2 can be formed using only OS transistors; the converter circuit ITRZD4 can be formed at the same time as the cell array CA, the circuit WCS, the circuit XCS, and the like. Thus, the manufacturing process of the arithmetic circuit MAC2 can be shortened in some cases. The same applies to the case where the current source CI (current source CIr) in FIG. 10B is used as the current source CI and the current source CIr of the converter circuit ITRZD4 in FIG. 10A.

For example, since the current source CI and the current source CIr included in the converter circuit ITRZD4 in FIG. 9 need to make the same current flow, the current source CI and the current source CIr can be replaced with a current mirror circuit.

Figure 11A:
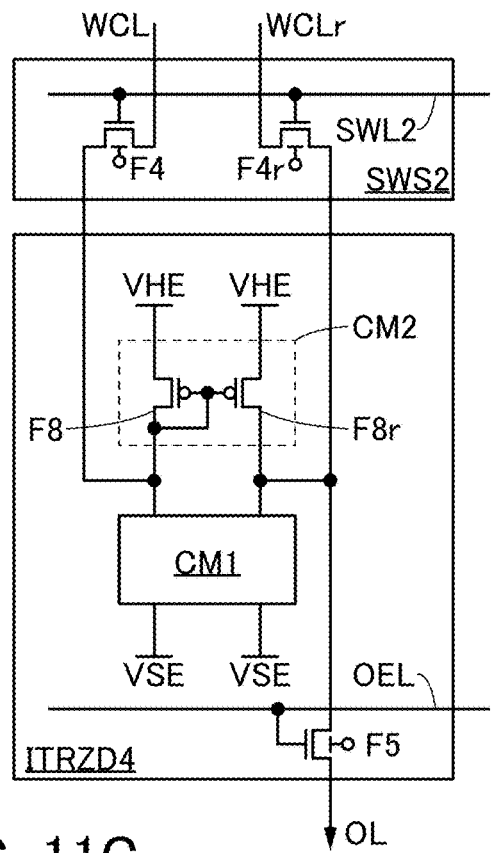
FIG. 11A and FIG. 11B are block diagrams each showing a configuration example of a circuit included in a semiconductor device.

The converter circuit ITRZD4 in FIG. 11A has a configuration in which the current source CI and the current source CIr included in the converter circuit ITRZD4 in FIG. 9 are replaced with a current mirror circuit CM2. The current mirror circuit CM2 includes a transistor F8 and a transistor F8r, for example. Note that the transistor F8 and the transistor F8r are p-channel transistors.

A first terminal of the transistor F8 is electrically connected to a gate of the transistor F8, a gate of the transistor F8r, the second terminal of the transistor F4, and the first terminal of the current mirror circuit CM1. A second terminal of the transistor F8 is electrically connected to the wiring VHE. A first terminal of the transistor F8r is electrically connected to the second terminal of the transistor F4r and the second terminal of the current mirror circuit CM1. A second terminal of the transistor F8r is electrically connected to the wiring VHE.

As shown in the converter circuit ITRZD4 in FIG. 11A, the current source CI and the current source CIr included in the converter circuit ITRZD4 in FIG. 9 are replaced with the current mirror circuit CM2, whereby currents with substantially the same current amount can flow through the connection point of the second terminal of the transistor F4 and the first terminal of the current mirror circuit CM1 and the connection point of the second terminal of the transistor F4r, the second terminal of the current mirror circuit CM1, and the first terminal of the transistor F5.

The current mirror circuit CM2 includes the transistor F8 and the transistor F8r in FIG. 11A; however, the circuit configuration of the current mirror circuit CM2 is not limited thereto. For example, as in FIG. 1C described later, the current mirror circuit CM2 may have a configuration in which the transistors included in the current mirror circuit CM2 have a cascode connection. As described above, the circuit configuration of the current mirror circuit CM2 in FIG. 11A may be changed depending on circumstances.

Figure 11B:
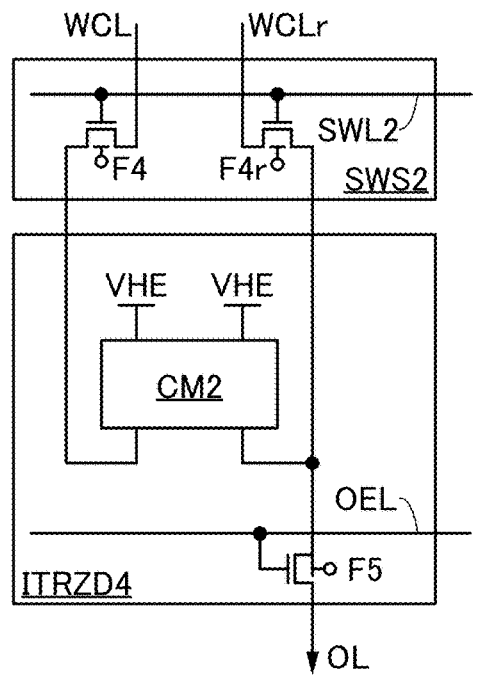

As in the configuration of the converter circuit ITRZD4 in FIG. 11B, the converter circuit ITRZD4 in FIG. 11A does not necessarily include the current mirror circuit CM1. In the converter circuit ITRZD4 in FIG. 11B, the amount of current flowing from the first terminal of the current mirror circuit CM2 to the second terminal of the transistor F4 can be substantially equal to the amount of current flowing from the second terminal of the current mirror circuit CM2 to the connection point of the second terminal of the transistor F4r, the wiring VSE, and the first terminal of the transistor F5. Therefore, in the case where $I_S$ is larger than the $I_{Sr}$, the amount of current $I_{out}$ flowing through the wiring OL in FIG. 11B can be $I_S-I_{Sr}$ as in the converter circuit ITRZD4 in FIG. 9.

The converter circuit ITRZD4 in FIG. 11B does not include the current mirror circuit CM1, and thus can have a circuit area smaller than that of the converter circuit ITRZD4 in FIG. 11A. Since no constant current flows from the current mirror circuit CM2 to the current mirror circuit CM1, the converter circuit ITRZD4 in FIG. 11B can have lower power consumption than the converter circuit ITRZD4 in FIG. 11A.

In FIG. 11B, the transistor F8 and the transistor F8r are not illustrated, and the current mirror circuit CM2 is illustrated as a block diagram. Thus, the configuration of the current mirror circuit CM2 in FIG. 11B can be determined depending on circumstances, as is the case with the current mirror circuit CM2 in FIG. 11A.

The current mirror circuit CM1 included in the converter circuit ITRZD4 in FIG. 9 is not limited to the current mirror circuit CM1 in FIG. 10A. The configuration of the current mirror circuit CM1 included in the converter circuit ITRZD4 in FIG. 10A can be changed depending on circumstances.

Figure 11C:
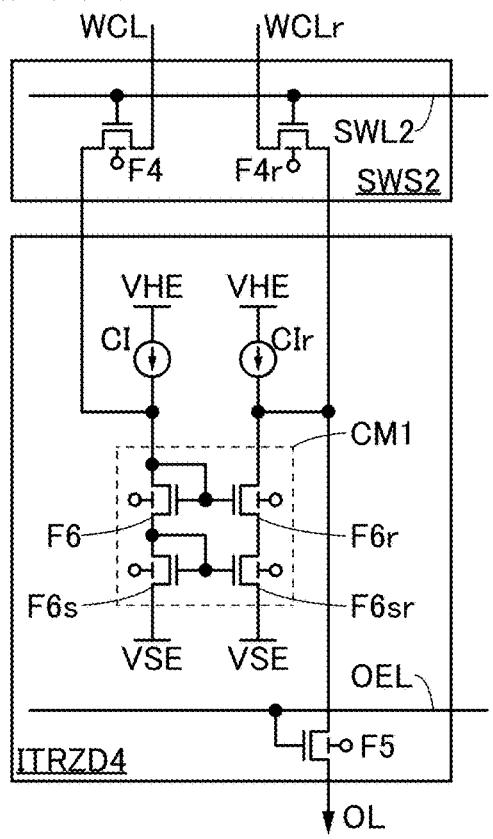
FIG. 11C is a circuit diagram showing a configuration example of a circuit included in a semiconductor device.

For example, the current mirror circuit CM1 illustrated in FIG. 11C can be used as the current mirror circuit CM1 included in the converter circuit ITRZD4 in FIG. 9. In the current mirror circuit CM1 illustrated in FIG. 11C, an n-channel transistor F6s and an n-channel transistor F6sr are further provided in the current mirror circuit CM1 in FIG. 10A; the transistor F6 and the transistor F6s are cascode-connected, and the transistor F6r and the transistor F6sr are cascode-connected. As shown in FIG. 11C, the transistors included in the current mirror circuit are cascode-connected, whereby the stability of the operation of the current mirror circuit can be improved.

<Configuration Example 2 of Arithmetic Circuit>

Figure 12:
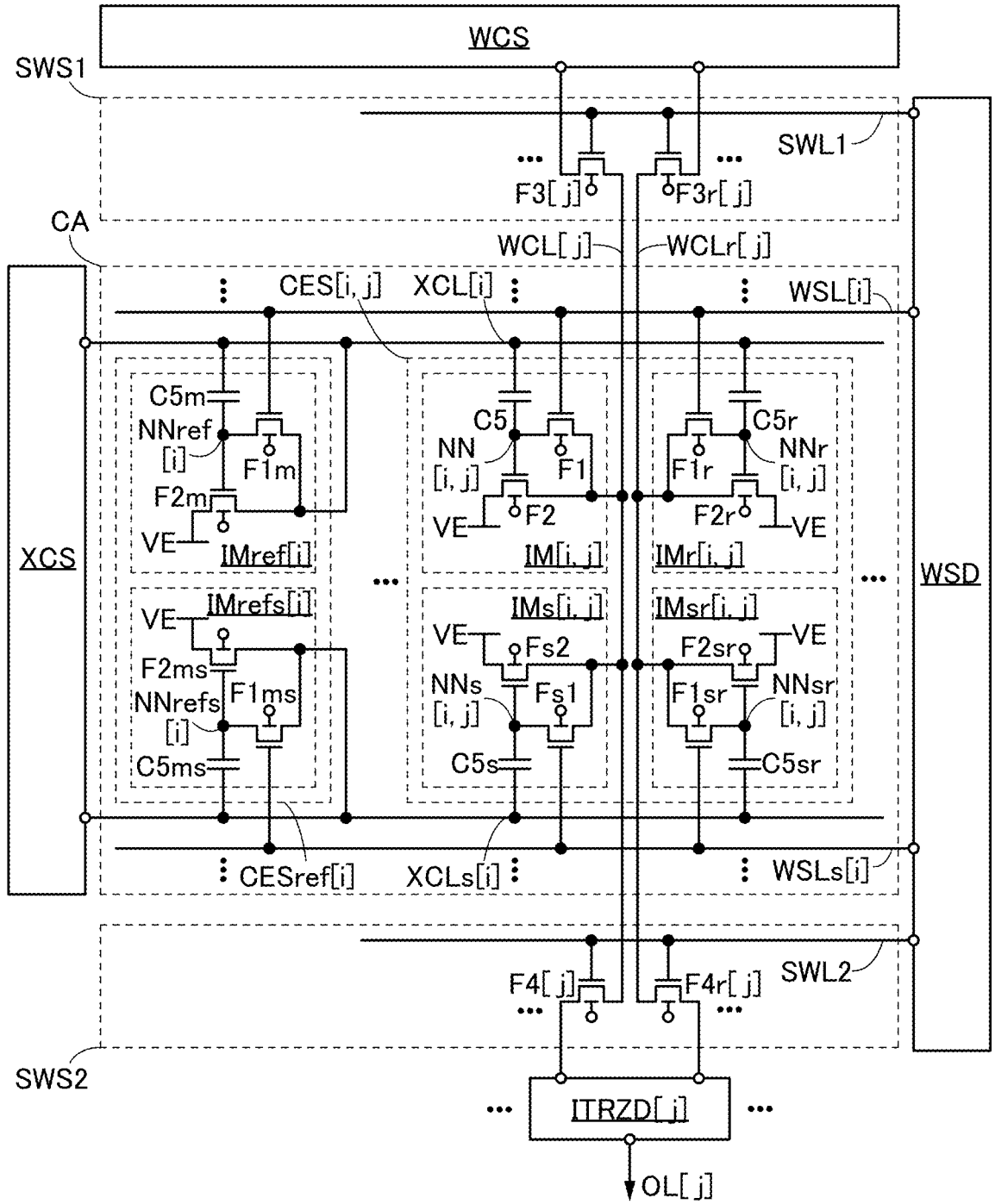
FIG. 12 is a block diagram showing a configuration example of a semiconductor device.

FIG. 12 shows a configuration example of an arithmetic circuit which performs a product-sum operation of the positive, negative, or "0" first data and the positive, negative, or "0" second data. An arithmetic circuit MAC3 illustrated in FIG. 12 has a structure in which the arithmetic circuit MAC2 in FIG. 7 is changed. Thus, the portions in the arithmetic circuit MAC3 that are the same as in the arithmetic circuit MAC1 and the arithmetic circuit MAC2 are not described.

The circuit CES[i,j] illustrated in FIG. 12 includes a cell IMs[i,j] and a cell IMsr[i,j] in addition to the cell IM[i,j] and the cell IMr[i,j]. In FIG. 12, the circuit CES[i,j] is illustrated, and the other circuit CES are omitted. In this specification and the like, when the circuit CES[i,j], the cell IM[i,j], the cell IMr[i,j], the cell IMs[i,j], the cell IMsr[i,j] and the like are described, [i,j] and the like that are added to the reference letters may be omitted.

The cell IMs and the cell IMsr can have configurations similar to that of the cell IM. FIG. 12 illustrates the cell IMs and the cell IMsr having configurations similar to that of the cell IM, for example. To distinguish the transistors, the capacitors, and the like included in the cell IM, the cell IMs, and the cell IMsr, "s" is added to the reference numerals representing the transistors and the capacitor included in the cell IMs and "sr" is added to the reference numerals representing the transistors and the capacitor included in the cell IMsr.

Specifically, the cell IMs includes a transistor F1s, a transistor F2s, and a capacitor C5s. The transistor F1s corresponds to the transistor F1 in the cell IM, the transistor F2s corresponds to the transistor F2 in the cell IM, and the capacitor C5s corresponds to the capacitor C5 in the cell IM. Thus, for the electrical connection configuration between the transistor F1s, the transistor F2s, and the capacitor C5s, the descriptions on IM[1,1] to the cell IM[m,n] in Embodiment 1 are referred to.

Furthermore, the cell IMsr includes a transistor F1sr, a transistor F2sr, and a capacitor C5sr. The transistor F1sr corresponds to the transistor F1 in the cell IM, the transistor F2sr corresponds to the transistor F2 in the cell IM, and the capacitor C5sr corresponds to the capacitor C5 in the cell IM. Thus, for the electrical connection configuration between the transistor F1sr, the transistor F2sr, and the capacitor C5sr, the descriptions on IM[1,1] to the cell IM[m,n] in Embodiment 1 are referred to, as in the case with the cell IMs.

In the cell IMs, a connection portion of the first terminal of the transistor F1s, a gate of the transistor F2s, and a first terminal of the capacitor C5s is a node NNs, and in the cell IMs, the connection portion of a first terminal of the transistor F1sr, a gate of the transistor F2sr, and a first terminal of the capacitor C5sr is a node NNsr.

In the circuit CES[i,j], the second terminal of the capacitor C5 is electrically connected to the wiring XCL[i], the gate of the transistor F1 is electrically connected to the wiring WSL[i], and the second terminal of the transistor F1 and the second terminal of the transistor F2 are electrically connected to the wiring WCL[j]. The second terminal of the capacitor C5r is electrically connected to the wiring XCL[i], the gate of the transistor F1r is electrically connected to the wiring WSL[i], and the second terminal of the transistor Fir and the second terminal of the transistor F2r are electrically connected to the wiring WCLr[j].

A second terminal of the capacitor C5s is electrically connected to a wiring XCLs[i], a gate of the transistor F1s is electrically connected to a wiring WSLs[i], and a second terminal of the transistor F1s and a second terminal of the transistor F2s are electrically connected to the wiring WCL[j]. A second terminal of the capacitor C5sr is electrically connected to the wiring XCLs[m], agate of the transistor F1sr is electrically connected to the wiring WSLs[m], and a second terminal of the transistor F1sr and a second terminal of the transistor F2sr are electrically connected to the wiring WCLr[j].

The circuit CESref[i] illustrated in FIG. 12 includes a cell IMrefs[i] in addition to the cell IMref[i]. In FIG. 12, the circuit CESref[i] is illustrated, and the other circuits CESref are omitted. In this specification and the like, when the circuit CESref[i], the cell IMref[i], the cell IMrefs[i] and the like are described, [i] and the like that are added to the reference letters may be omitted.

The cell IMrefs can have a configuration similar to that of the cell IMref. FIG. 12 illustrates the cell IMrefs having a similar configuration to that of the cell IMref, for example. To distinguish the transistors, the capacitors, and the like included in the cell IMref and the cell IMrefs, "s" is added to the reference letters representing the transistors and the capacitor included in the cell IMrefs.

Specifically, the cell IMrefs includes a transistor F1ms, a transistor F2ms, and a capacitor C5ms. The transistor F1ms corresponds to the transistor F1m in the cell IMref, the transistor F2ms corresponds to the transistor F2m in the cell IMref, and the capacitor C5ms corresponds to the capacitor C5m in the cell IMref. Thus, for the electrical connection configuration between the transistor Fims, the transistor F2ms, and the capacitor C5ms, the descriptions on IMref[1] to the cell IMref[m] in Embodiment 1 are referred to.

In the cell IMrefs, a connection portion of a first terminal of the transistor F1ms, a gate of the transistor F2ms, and the first terminal of the capacitor C5ms is a node NNrefs.

In the circuit CESref[i], a second terminal of the capacitor C5m is electrically connected to the wiring XCL[i], the gate of the transistor F1m is electrically connected to the wiring WSL[i], and the second terminal of the transistor F1m and the second terminal of the transistor F2m are electrically connected to the wiring XCL[i]. A second terminal of the capacitor C5ms is electrically connected to the wiring XCLs[i], a gate of the transistor F1ms is electrically connected to the wiring WSLs[i], and a second terminal of the transistor F1ms and a second terminal of the transistor F2ms are electrically connected to the wiring XCLs[i].

Like the wiring XCL[1] to the wiring XCL[n] described in Embodiment 1, the wiring XCL[i] and the wiring XCLs[i] function as wirings which supply currents from the circuit XCS to the cell IM, the cell IMr, the cell IMs, and the cell IMsr included in the circuit CES, and as wirings which supply currents from the circuit XCS to the cell IMref[i] and the cell IMrefs[i] included in the circuit CESref, for example.

Like the wiring WSL[1] to the wiring WSL[m] described in Embodiment 1, the wiring WSL[j] and the wiring WSLs[j] function as wirings to send a selection signal for writing the first data from the circuit WSD to the cell IM and the cell IMr included in the circuit CES, and wirings to send a selection signal for writing reference data from the circuit WSD to the cell IMref and the cell IMrefs included in the circuit CESref, for example.

As the converter circuit ITRZD[j] included in the arithmetic circuit MAC3 in FIG. 12, a circuit that can be used for the converter circuit ITRZD[j] included in the arithmetic circuit MAC2 in FIG. 7 can be used. In other words, as the converter circuit ITRZD[j] included in the arithmetic circuit MAC3, the converter circuit ITRZD1 to the converter circuit ITRZD3 illustrated in FIG. 8A to FIG. 8C can be used.

Next, an example in which the first data is stored in the circuit CES and an example in which the second data is input to the circuit CES, which are for performing a product-sum operation of the positive, negative, or "0" first data and the positive, negative, or "0" second data in the arithmetic circuit MAC3 in FIG. 12, are described.

Since the circuit CES includes the cell IM, the cell IMr, the cell IMs, and the cell IMsr, the circuit CES can use the four circuits, i.e., the cell IM, the cell IMr, the cell IMs, and the cell IMsr, to store the first data. In other words, four current amounts are set for the circuit CES and potentials corresponding to the current amounts can be stored in the cell IM, the cell IMr, the cell IMs, and the cell IMsr. Thus, the first data can be represented with the current amount set in the cell IM, the current amount set in the cell IMr, the current amount set in the cell IMs, and the current amount set in the cell IMsr. The positive first data, the negative first data, or the "0" first data to be stored in the circuit CES is defined as follows.

To store the positive first data in the circuit CES[i,j], the cell IM[i,j] is set such that the current amount corresponding to the absolute value of the positive first data flows through the transistor F2 in the cell IM[i,j] and the current amount corresponding to the absolute value of the positive first data flows through the transistor F2sr in the cell IMsr[i,j] for example. Specifically, the potential corresponding to the current amount is retained in the gate of the transistor F2 (node NN[i,j]) and the gate of the transistor F2sr (node NNsr[i,j]). The cell IMr[i,j] is set such that a current does not flow through the transistor F2r in the cell IMr[i,j] and a current does not flow through the transistor F2s in the cell IMs[i,j]. Specifically, the gate of the transistor F2r (node NNr[i,j]) and the gate of the transistor F2s (node NNs[i,j]) store the potential supplied by the wiring VE or the initialization potential supplied by the wiring VINIL1 of the circuit WCS in FIG. 2, for example.

To store the negative first data in the circuit CES[i,j], the cell IMr[i,j] is set such that the current amount corresponding to the absolute value of the negative first data flows through the transistor F2r in the cell IMr[i,j], and the current amount corresponding to the absolute value of the negative first data flows through the transistor F2s in the cell IMs[i,j] for example. Specifically, the potential corresponding to the current amount is stored in the gate of the transistor F2r (node NNr[i,j]) and the gate of the transistor F2s (node NNs[i,j]). The cell IM[i,j] is set such that a current does not flow through the transistor F2 in the cell IM[i,j] and a current does not flow through the transistor F2sr in the cell IMsr[i,j]. Specifically, the gate of the transistor F2 (node NN[i,j]) and the gate of the transistor F2sr (node NNsr[i,j]) stores the potential supplied by the wiring VE or the initialization potential supplied by the wiring VINIL1 of the circuit WCS in FIG. 2, for example.

To store the "0" first data in the circuit CES[i,j], the transistor F2 of the cell IM[i,j], the transistor F2r of the cell IMr[i,j], the transistor F2s of the cell IMs[i,j], and the transistor F2sr of the cell IMsr[i,j] are set such that currents do not flow through these transistors, for example. Specifically, the gate of the transistor F2 (node NN[i,j]), the gate of the transistor F2r (node NNr[i,j]), the gate of the transistor F2s (node NNs[i,j]), and the gate of the transistor F2sr (node NNsr[i,j]) store the potential supplied by the wiring VE or the initialization potential supplied by the wiring VINIL1 of the circuit WCS in FIG. 2, for example.

To store the positive first data or the negative first data in another circuit CES, it is set that currents with the current amount corresponding to the first data flow through one of the following pairs of the paths: a pair of the paths between the cell IM and the wiring WCL and between the cell IMsr and the wiring WCLr and a pair of the paths between the cell IMr and the wiring WCLr and between the cell IMs and the wiring WCL while currents do not flow between the other pair of the paths, as in the circuit CES[i,j] described above. To store the "0" first data in another circuit CES, it is set that currents do not flow between the cell IM and the wiring WCL, between the cell IMr and the wiring WCLr, between the cell IMs and the wiring WCL, and between the cell IMsr and the wiring WCLsr, as in the circuit CES[i,j] described above.

To store each of "+3", "+2", +1 "0", "−1", "−2", and "−3" in the circuit CES as the first data, for example, the amount of current flowing from the wiring WCL to the cell IM, the amount of current flowing from the wiring WCLr to the cell IMr, the amount of current flowing from the wiring WCL to the cell IMs, and the amount of current flowing from the wiring WCLsr to the cell IMsr are set as described above, whereby each "+3", "+2", "+1", "0", "−1", "−2", and "−3" as the first data can be defined as illustrated in the following table.

TABLE 2

| First data | Current flowing from the wiring WCL to the cell IM | Current flowing from the wiring WCLr to the cell IMr | Current flowing from the wiring WCL to the cell IMs | Current flowing from the wiring WCLr to the cell IMsr |
|---|---|---|---|---|
| +3 | $3I_{Wut}$ | 0 | 0 | $3I_{Wut}$ |
| +2 | $2I_{Wut}$ | 0 | 0 | $2I_{Wut}$ |
| +1 | $I_{Wut}$ | 0 | 0 | $I_{Wut}$ |
| 0 | 0 | 0 | 0 | 0 |
| −1 | 0 | $I_{Wut}$ | $I_{Wut}$ | 0 |
| −2 | 0 | $2I_{Wut}$ | $2I_{Wut}$ | 0 |
| −3 | 0 | $3I_{Wut}$ | $3I_{Wut}$ | 0 |

On the other hand, as a wiring for inputting the second data, the wiring XCL and the wiring XCLs are electrically connected to the circuit CES. Thus, two signals can be input as the second data to the circuit CES. In other words, the second data can be represented by the signal input to the wiring XCL and the signal input to the wiring XCLs and input to the circuit CES. The positive second data, the negative second data, or the "0" second data to be input to the circuit CES is defined as follows.

To input the positive second data in the circuit CES[i,j], the cell IMref[i] is set such that the current amount corresponding to the absolute value of the positive second data flows through the transistor F2m in the cell IMref[i], for example. Specifically, the potential corresponding to the current amount is stored in the gate of the transistor F2m (node NNref[i]). In contrast, the cell IMrefs[i] is set such that a current does not flow through the transistor F2ms in the cell IMrefs[i]. Specifically, the gate of the transistor F2ms (node NNrefs[i]) stores the potential supplied by the wiring VE or the initialization potential supplied by the wiring VINIL2 of the circuit XCS in FIG. 2C, for example.

To input the negative second data in the circuit CES[i,j], the cell IMrefs[i] is set such that the current amount corresponding to the absolute value of the negative second data flows through the transistor F2ms in the cell IMrefs[i], for example. Specifically, the potential corresponding to the current amount is stored in the gate of the transistor F2ms (node NNrefs[i]). In contrast, the cell IMref[i] is set such that a current does not flow through the transistor F2m in the cell IMref[i]. Specifically, the gate of the transistor F2m (node NNref[i]) stores the potential supplied by the wiring VE or the initialization potential supplied by the wiring VINIL2 of the circuit XCS in FIG. 2C, for example.

To input the "0" second data in the circuit CES[i,j], the transistor F2m of the cell IMref[i] and the transistor F2ms of the cell IMrefs[1] are set such that currents do not flow through these transistors, for example. Specifically, the gate of the transistor F2m (node NNref[i]) and the gate of the transistor F2ms (node NNrefs[i]) stores the potential supplied by the wiring VE or the initialization potential supplied by the wiring VINIL2 of the circuit XCS in FIG. 2C, for example.

To input the positive second data or the negative second data in another circuit CES, it is set that a current with the current amount corresponding to the second data flows through one of the path between the cell IMref and the wiring XCL and the path between the cell IMrefs and the wiring XCLs while a current does not flow through the other of the path between the cell IMref and the wiring XCL and the path between the cell IMrefs and the wiring XCLs, as in the circuit CESref[i]. To input the "0" second data in another circuit CES, it is set that a current does not flow between the cell IMref and the wiring XCL and between the cell IMrefs and the wiring XCLs, as in the circuit CESref[i].

For example, to store each case of "+3", "+2", "+1", "0", "−1", "−2", and "−3" in the circuit CES as the second data, the amount of current flowing from the wiring XCL to the cell IMref and the amount of current flowing from the wiring XCLs to the cell IMrefs are set as described above, whereby each of "+3", "+2", "+1", "0", "−1", "−2", and "−3" as the second data can be defined as illustrated in the following table.

TABLE 3

| Second data | Current flowing from the wiring XCL to the cell IMref | Current flowing from the wiring XCLs to the cell IMrefs |
|---|---|---|
| +3 | $3I_{Xut}$ | 0 |
| +2 | $2I_{Xut}$ | 0 |
| +1 | $I_{Xut}$ | 0 |

TABLE 3-continued

| Second data | Current flowing from the wiring XCL to the cell IMref | Current flowing from the wiring XCLs to the cell IMrefs |
|---|---|---|
| 0 | 0 | 0 |
| −1 | 0 | $I_{Xut}$ |
| −2 | 0 | $2I_{Xut}$ |
| −3 | 0 | $3I_{Xut}$ |

When one of "+3", "+2", "+1", "0", "−1", "−2", and "−3" is stored in the circuit CES as the first data and one of "+1", "0", and "−1" is input to the circuit CES as the second data, the amount of current flowing from the wiring WCL to the cell IM and the cell IMs in the circuit CES, and the amount of current flowing from the wiring WCLr to the cell IMr and the cell IMsr in the circuit CES are considered.

For example, when the second data input to the circuit CES is "+1", the potential corresponding to the absolute value of the "+1" second data is input to each of the second terminals of the capacitor C5 and the capacitor C5r from the wiring XCL, and the potential corresponding to the ground potential (GND) is input to each of the second terminals of the capacitor C5s and the capacitor C5sr of the circuit CES from the wiring XCLs. When the first data stored in the circuit CES is "+3", the potential corresponding to the absolute value of the "+3" first data is stored in each of the node NN and the node NNsr, and the ground potential (GND) is stored in each of the node NNr and the node NNs. Between the first terminal and the second terminal of the transistor F2 in the circuit CES, the current amount $3I_{ref0}$ flows according to Formula (1.12) or Formula (1.16). Between the first terminals and the second terminals of the transistor F2r, the transistor F2s, and the transistor F2sr, currents do not flow. In other words, a current with the current amount $3I_{ref0}$ flows from the wiring WCL to the cell IM, and currents do not flow from the wiring WCL to the cell IMs, from the wiring WCLr to the cell IMr, and does from the wiring WCLr to the cell IMsr.

For example, the second data input to the circuit CES is "+1" and the first data retained in the circuit CES is "−3". Thus, the potential corresponding to the absolute value of the "−3" first data is stored in each of the node NNr and the node NNs, and the ground potential (GND) is stored in each of the node NN and the node NNsr. Between the first terminals and the second terminals of the transistor F2r in the circuit CES, the current amount $3I_{ref0}$ flows according to Formula (1.12) or Formula (1.16). Between the first terminals and the second terminals of the transistor F2, the transistor F2s, and the transistor F2sr, currents do not flow. In other words, the current amount $3I_{ref0}$ flows from the wiring WCLr to the cell IMr, and currents do not flow from the wiring WCL to the cell IM, from the wiring WCL to the cell IMs, and from the wiring WCLr to the cell IMsr.

For example, when the second data input to the circuit CES is "−1", the potential corresponding to the absolute value of the "−1" second data is input to each of the second terminals of the capacitor C5s and the capacitor C5sr from the wiring XCLs, and the potential corresponding to the ground potential (GND) is input to each of the second terminals of the capacitor C5 and the capacitor C5r of the circuit CES from the wiring XCL. When the first data stored in the circuit CES is "+3", the potential corresponding to the absolute value of the "+3" first data is stored in each of the node NN and the node NNsr, and each of the node NNr and the node NNs stores a ground potential (GND). Between the first terminal and the second terminal of the transistor F2sr in the circuit CES, the current amount $3I_{ref0}$ flows according to Formula (1.12) or Formula (1.16). Between the first terminals and the second terminals of the transistor F2, the transistor F2r, and the transistor F2s, currents do not flow. In other words, the current amount $3I_{ref0}$ flows from the wiring WCLr to the cell IMsr, and currents do not flow from the wiring WCL to the cell IM, from the wiring WCLr to the cell IMr, and from the wiring WCL to the cell IMs.

For example, the second data input to the circuit CES is "−1" and the first data stored in the circuit CES is "−3". The potential corresponding to the absolute value of the "−3" first data is stored in each of the node NNr and the node NNs, and the ground potential (GND) is stored in each of the node NN and the node NNsr. Between the first terminal and the second terminal of the transistor F2s in the circuit CES, the current amount $3I_{ref0}$ flows according to Formula (1.12) or Formula (1.16). Between the first terminals and the second terminals of the transistor F2, the transistor F2r, and the transistor F2sr, currents do not flow. In other words, the current amount $3I_{ref0}$ flows from the wiring WCL to the cell IMs, and currents do not flow from the wiring WCL to the cell IM, from the wiring WCLr to the cell IMr, and from the wiring WCLr to the cell IMsr.

For example, when the second data input to the circuit CES is "0", a ground potential (GND) is input to each of the second terminal of the capacitor C5 and the capacitor C5r of the circuit CES from the wiring XCL, and a ground potential (GND) is input to each of the second terminals of the capacitor C5s and the capacitor C5sr of the circuit CES from the wiring XCLs. At this time, even the first data retained in the circuit CES has some value, currents do not flow between the first terminal and the second terminals of the transistor F2, the transistor F2r, the transistor F2s, and the transistor F2sr.

For example, when the first data stored in the circuit CES is "0", each of the node NN, the node NNr, the node NNs, and the node NNsr stores a ground potential (GND). At this time, even the second data input to the circuit CES has some value, currents do not flow between the first terminals and the second terminals of the transistor F2, the transistor F2r, the transistor F2s, and the transistor F2sr.

The cases where the first data is "+3", "−3", and "0" and the second data is "+1", "−1", and "0" have been described; when the same applies to the other cases, the amounts of current flowing in the wiring WCL and the wiring WCLr can be represented as the following table.

As described above, a product-sum operation of the positive, negative, or "0" first data and the positive, negative, or "0" second data can be performed by using the arithmetic circuit MAC2. A product-sum operation of the positive, negative, or "0" first data and the positive, negative, or "0" second data can be performed by using the arithmetic circuit MAC3.

One embodiment of the present invention is not limited to the circuit configurations of the arithmetic circuit MAC2 and the arithmetic circuit MAC3 described in this embodiment. The circuit configurations of the arithmetic circuit MAC2 and the arithmetic circuit MAC3 can be changed depending on circumstances. For example, gate capacitances of transistors can be used as the capacitor C5, the capacitor C5r, the capacitor C5s, the capacitor C5sr, the capacitor C5m, and the capacitor C5ms included in the arithmetic circuit MAC3 (not illustrated). In the arithmetic circuit MAC3, the capacitor C5, the capacitor C5r, the capacitor C5s, the capacitor C5sr, the capacitor C5m, and the capacitor C5ms are not necessarily provided when parasitic capacitances between the node NN, the node NNr, the node NNs, the node NNsr, the node NNref, and the node NNrefs and their nearby wirings are large.

Note that this embodiment can be combined with any of the other embodiments in this specification as appropriate.

Embodiment 3

In this embodiment, a configuration in which one of the arithmetic circuit MAC1, the arithmetic circuit MAC1A, the arithmetic circuit MAC2, and the arithmetic circuit MAC3 described in the above embodiment is combined with a sensor is described.

Figure 13A:
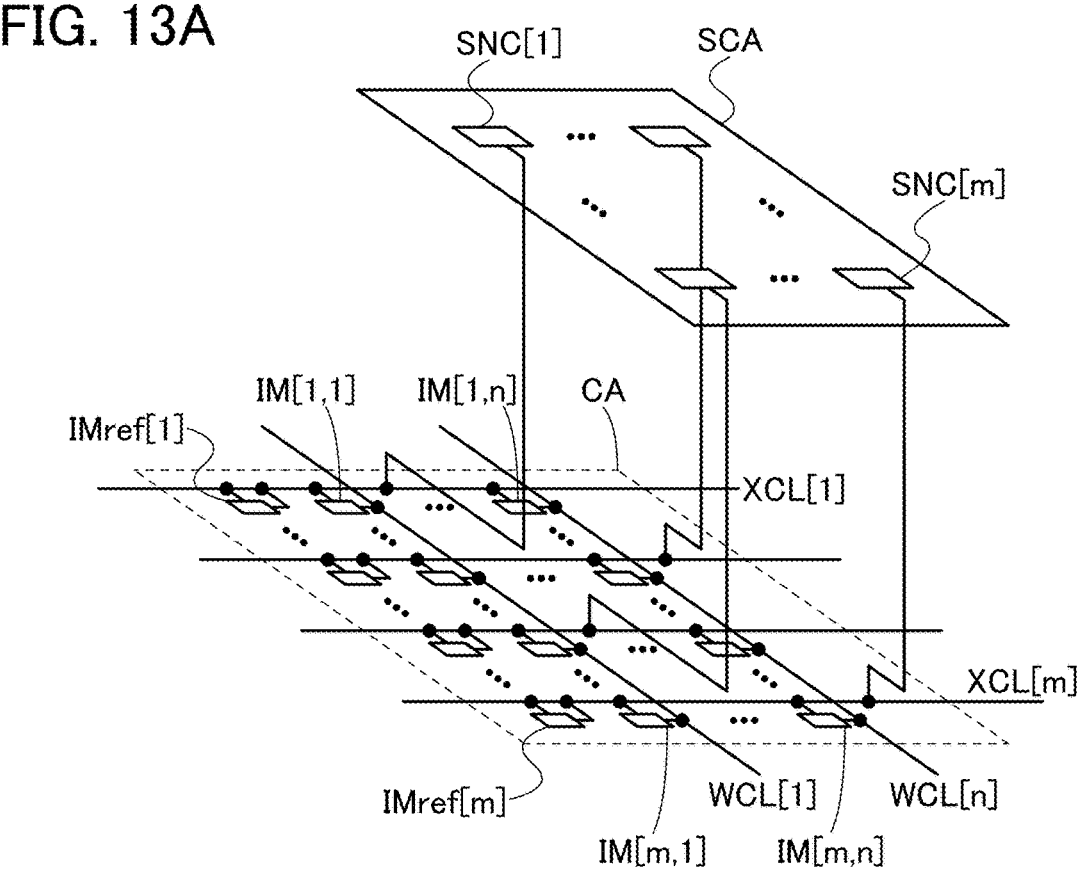
FIG. 13A and FIG. 13B are block diagrams each showing a configuration example of a circuit included in a semiconductor device.

FIG. 13A shows a configuration example in which the arithmetic circuit MAC1 and a circuit SCA including a sensor are combined. In FIG. 13A, the cell array CA of the arithmetic circuit MAC1 is selected and illustrated.

The circuit SCA includes a sensor SNC[1] to a sensor SNC[m], for example. In FIG. 13A, the sensor SNC[1] to the sensor SNC[m] are arranged in a matrix, for example.

TABLE 4

| First data | Second data | First data × Second data | Current flowing from wiring WCL to cell IM | Current flowing from wiring WCLr to cell IMr | Current flowing from wiring WCL to cell IMs | Current flowing from wiring WCLr to cell IMsr |
|---|---|---|---|---|---|---|
| +3 | +1 | +3 | $3I_{ref0}$ | 0 | 0 | 0 |
| +2 | +1 | +2 | $2I_{ref0}$ | 0 | 0 | 0 |
| +1 | +1 | +1 | $1I_{ref0}$ | 0 | 0 | 0 |
| 0 | +1 | 0 | 0 | 0 | 0 | 0 |
| −1 | +1 | −1 | 0 | $1I_{ref0}$ | 0 | 0 |
| −2 | +1 | −2 | 0 | $2I_{ref0}$ | 0 | 0 |
| −3 | +1 | −3 | 0 | $3I_{ref0}$ | 0 | 0 |
| +3 | 0 | 0 | 0 | 0 | 0 | 0 |
| +2 | 0 | 0 | 0 | 0 | 0 | 0 |
| +1 | 0 | 0 | 0 | 0 | 0 | 0 |
| 0 | 0 | 0 | 0 | 0 | 0 | 0 |
| −1 | 0 | 0 | 0 | 0 | 0 | 0 |
| −2 | 0 | 0 | 0 | 0 | 0 | 0 |
| −3 | 0 | 0 | 0 | 0 | 0 | 0 |
| +3 | −1 | −3 | 0 | 0 | 0 | $3I_{ref0}$ |
| +2 | −1 | −2 | 0 | 0 | 0 | $2I_{ref0}$ |
| +1 | −1 | −1 | 0 | 0 | 0 | $1I_{ref0}$ |
| 0 | −1 | 0 | 0 | 0 | 0 | 0 |
| −1 | −1 | +1 | 0 | 0 | $1I_{ref0}$ | 0 |
| −2 | −1 | +2 | 0 | 0 | $2I_{ref0}$ | 0 |
| −3 | −1 | +3 | 0 | 0 | $3I_{ref0}$ | 0 |

The sensor SNC[1] to the sensor SNC[m] have functions of converting sensed data to a current amount and outputting the current amount. As the sensor SNC[1] to the sensor SNC[m], an optical sensor including a photodiode, a pressure sensor, a gyroscope sensor, an acceleration sensor, a sound sensor, a temperature sensor, a humidity sensor, or the like can be used. In particular, when optical sensors are used as the sensor SNC[1] to the sensor SNC[m], the circuit SCA can be part of an image sensor.

The sensor SNC[1] to the sensor SNC[m] are preferably provided in a region close to the external area because these sense external data. For this reason, the circuit SCA is preferably provided over the arithmetic circuit MAC1 as illustrated in FIG. 13A; more specifically, the circuit SCA is preferably provided over the cell array CA.

The sensor SNC[1] to the sensor SNC[m] are electrically connected to the wiring XCL[1] to the wiring XCL[m], respectively.

Thus, when data is sensed in each of the sensor SNC[1] to the sensor SNC[m], the current amount in accordance with the data flows from each of the sensor SNC[1] to the sensor SNC[m] to the wiring XCL[1] to the corresponding wiring XCL[m].

The circuit SCA preferably has a configuration in which the sensor SNC[1] to the sensor SNC[m] consecutively perform sensing, and consecutively make currents flow to the wiring XCL[1] to the wiring XCL[m]. In this case, for example, signal lines for selecting the sensor SNC[1] to the sensor SNC[m] are provided in the circuit SCA so that signals or the like are consecutively sent to the signal line and the sensor SNC[1] to the sensor SNC[m] consecutively operate.

Figure 13B:
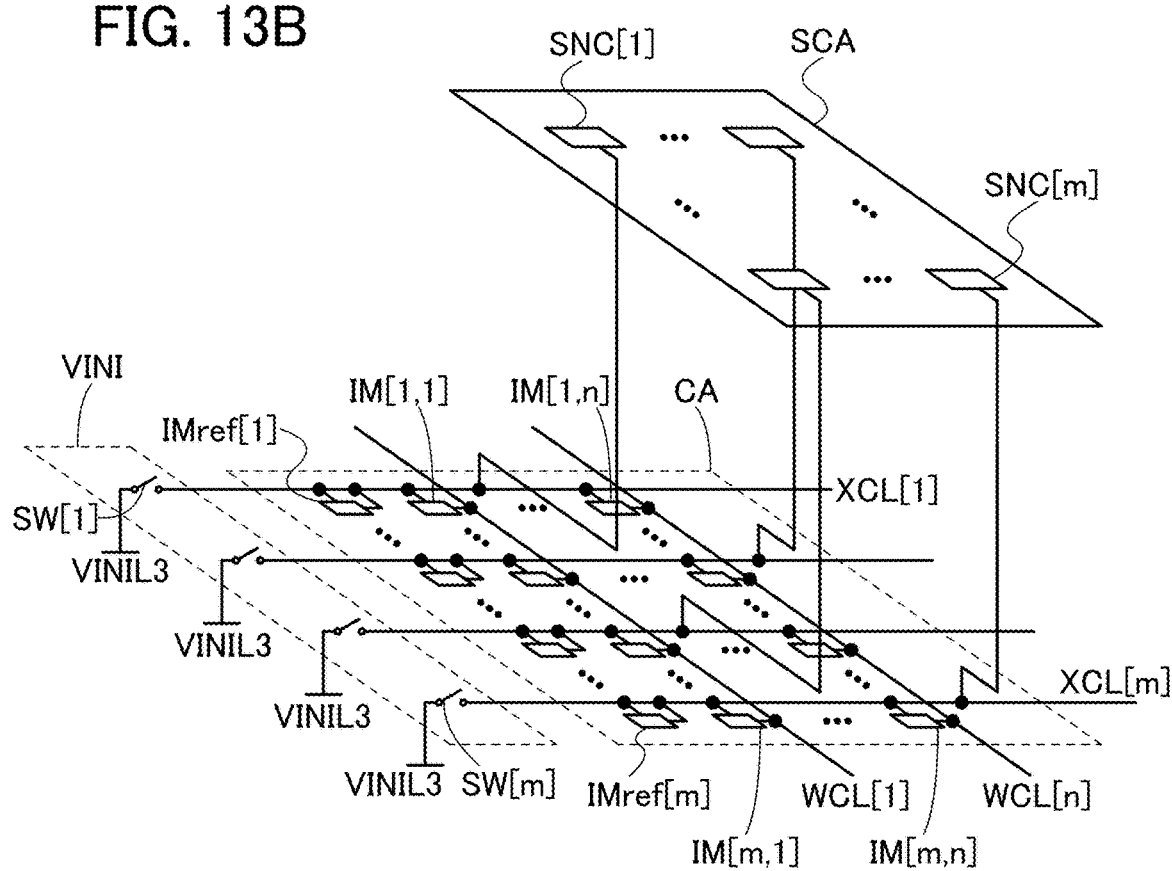

Specifically, for example, as illustrated in FIG. 13B, a circuit VINI may be provided to the wiring XCL[1] to the wiring XCL[m] in the circuit configuration of FIG. 13A. The circuit VINI includes a switch SW[1] to a switch SW[m]. First terminals of the switch SW[1] to the switch SW[m] are electrically connected to the wiring XCL[1] to the wiring XCL[m], and second terminals of the switch SW[1] to the switch SW[m] are electrically connected to a wiring VINIL3. The wiring VINIL3 functions as a wiring that supplies, for example, a constant potential such as a low-level potential, a ground potential, or the like. In particular, the constant potential is preferably lower than the potential supplied by the wiring VE. Here, the case is considered in which the switch SW[1] to the switch SW[m] are consecutively turned off so that one of the switch SW[1] to the switch SW[m] is in the off state and the other switches SW are in the on state. When the sensor SNC[1] to the sensor SNC[m] perform sensing at the same time, the sensor SNC[1] to the sensor SNC[m] make currents flow to the wiring XCL[1] to the wiring XCL[m]. In that case, the wiring XCL electrically connected to the switch SW in the on state out of the switch SW[1] to the switch SW[m] and the wiring VINIL3 are in the conduction state; the current flows to the wiring VINIL3. Thus, the potential of the wiring XCL electrically connected to the switch SW in the on state becomes substantially equal to the constant potential supplied by the wiring VINIL3. In contrast, the potentials of the wirings XCL electrically connected to the switches SW in the off state out of the switch SW[1] to the switch SW[m] are determined in accordance with the current amount of the current.

For example, in the case where the sensor SNC[1] to the sensor SNC[m] are optical sensors including photodiodes or the like, a filter is prepared so that only one of the sensor SNC[1] to the sensor SNC[m] is irradiated with light. Since the number of sensors SNC is m, the number of kinds of filters is also m. In addition, in the case where a filter that does not allow light to enter any of the sensor SNC[1] to the sensor SNC[m] is prepared, the number of kinds of filters is m+1. When the circuit SCA is irradiated with light, the filters are consecutively changed, whereby the sensor SNC[1] to the sensor SNC[m] can consecutively perform sensing.

For example, in the case where the sensor SNC[1] to the sensor SNC[m] are optical sensors including photodiodes or the like, each of the arithmetic circuit MAC1, the arithmetic circuit MAC1A, the arithmetic circuit MAC2, and the arithmetic circuit MAC3 may have a configuration in which the sensor SNC[1] to the sensor SNC[m] are independently irradiated with light. With a configuration that the sensor SNC[1] to the sensor SNC[m] are irradiated with light independently of each other, the sensor SNC[1] to the sensor SNC[m] can be consecutively irradiated with light to perform consecutive sensing.

Here, an operation example of the arithmetic circuit MAC1 to which the circuit SCA and the circuit VINI in FIG. 13B are provided is described.

The timing chart in FIG. 6 is referred to for the operation example. Thus, in the descriptions of the operation example of the arithmetic circuit MAC1 to which the circuit SCA in FIG. 13B and the circuit VINI are provided, the same descriptions with <Operation example 1 of arithmetic circuit> in Embodiment 1 are omitted.

The constant potential supplied by the wiring VINIL3 is a ground potential.

From Time T13 to Time T15 in the timing chart in FIG. 6, the current amount $I_{ref0}$ flows from the sensor SNC[i] of the circuit SCA to the wiring XCL[i]. For example, $I_{ref}i$ is the amount of reference current output by the sensor SNC[i] in FIG. 13B which performs sensing. In the circuit VINI, when the switch SW[i] is turned off, the potential of the wiring XCL[i] is, for example, $V_{gm}[i]$.

From Time T13 to Time T15 in the timing chart in FIG. 6, the sensor SNC[1] to the sensor SNC[m] other than the sensor SNC[i] may or may not perform sensing. At this time, the switch SW[1] to the switch SW[m] other than the switch SW[i] are turned on, whereby the potentials of the wiring XCL[1] to the wiring XCL[m] other than the wiring XCL[i] become ground potentials, for example.

From Time T17 to Time T19 in the timing chart in FIG. 6, the current amount $I_{ref0}$ flows from the sensor SNC[i+1] of the circuit SCA to the wiring XCL[i+1]. For example, $I_{ref0}$ is the amount of current output by the sensor SNC[i+1] in FIG. 13B which performs sensing. In the circuit VINI, the switch SW[i+1] is turned off, whereby the potential of the wiring XCL[i+1] is, for example, $V_{gm}[i+1]$.

From Time T17 to Time T19 in the timing chart in FIG. 6, the sensor SNC[1] to the sensor SNC[m] other than the sensor SNC[i+1] may or may not perform sensing. At this time, the switch SW[1] to the switch SW[m] other than the switch SW[i+1] are turned on, whereby the potentials of the wiring XCL[1] to the wiring XCL[m] other than the wiring XCL[i+1] become ground potentials, for example.

From Time T22 to Time T23 in the timing chart in FIG. 6, the current amount $x[i]I_{ref0}$ which is $x[i]$ times larger than $I_{ref0}$ flows from the sensor SNC[i] of the circuit SCA to the wiring XCL[i]. For example, $x[i]I_{ref0}$ is a current output by the sensor SNC[i] in FIG. 13B which performs sensing. In the circuit VINI, when the switch SW[i] is turned off, the potential of the wiring XCL[i] changes to, for example, $V_{gm}[i]+\Delta V[i]$.

From Time T22 to Time T23 in the timing chart in FIG. 6, the current amount $x[i+1]I_{ref0}$ which is $x[i+1]$ times larger than $I_{ref0}$ flows from the sensor SNC[i+1] of the circuit SCA to the wiring XCL[i+1]. For example, x[i+1]$I_{ref0}$ is a current output by the sensor SNC[i+1] in FIG. 13B which performs sensing. In the circuit VINI, the switch SW[i+1] is turned off, whereby the potential of the wiring XCL[i+1] changes to, for example, $V_{gm}$[i+1]+ΔV[i+1].

Then, as in the timing chart in FIG. 6, the amount of current flowing between the converter circuit ITRZ[j] and the wiring WCL[j] is the sum of the amount of current $I_1$[i,j] flowing between the first terminal and the second terminal of the transistor F2 included in the cell IM[i,j] and the amount of current $I_1$[i+1,j] flowing between the first terminal and the second terminal of the transistor F2 included in the cell IM[i+1,j] (corresponding to Formula (1.17)). Thus, the amount of current output from the converter circuit ITRZ[j] to the wiring WCL[j] is the amount of current proportional to the sum of products of the coefficients of weight w[i,j] and w[i+1,j] that are the first data and the values x[i] and x[i+1] of the signals of the neurons that are the second data, i.e., x[i]w[i,j]+x[i+1]w[i+1,j].

The arithmetic circuit MAC1 including the circuit SCA can perform an arithmetic operation of a hierarchical neural network from its first layer (input layer) to its second layer (middle layer), for example. That is, the data (value) obtained by sensing of the sensor SNC[1] to the sensor SNC[m] corresponds to the signal sent from the first-layer neuron to the second-layer neuron. When the coefficient of weight between the first layer neuron and the second layer neuron is stored in the cell IM[1,j] to the cell IM[m,j], the arithmetic circuit MAC1 can perform a product-sum operation of the data (value) and the coefficient of weight.

The hierarchical neural network will be described in Embodiment 5.

Figure 14:
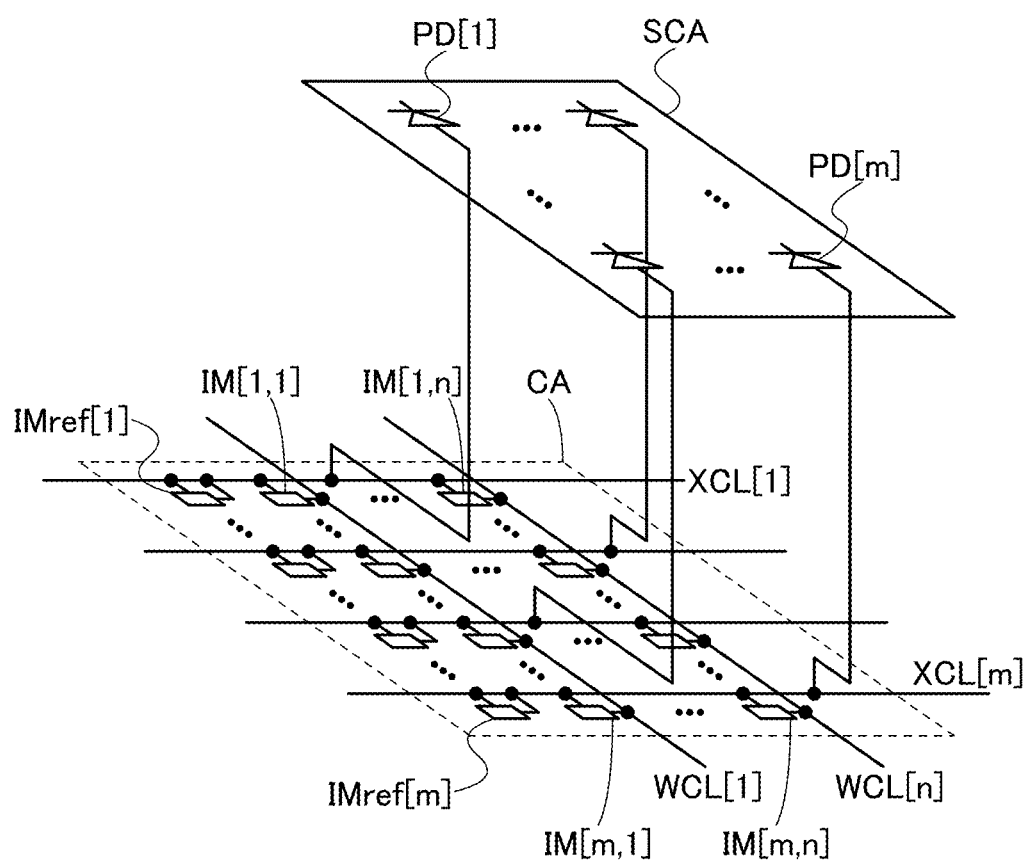
FIG. 14 is a block diagram showing a configuration example of a circuit included in a semiconductor device.

In FIG. 14, the circuit SCA including a photodiode PD[1] to a photodiode PD[m] as the sensor SNC[1] to the sensor SNC[m] in FIG. 13A is illustrated, for example. That is, the circuit SCA in FIG. 14 is assumed to be an optical sensor.

When an optical sensor is used in this way, the intensity of light delivered to the optical sensor is preferably within the range of the light delivered to the optical sensor in its usage condition.

Note that this embodiment can be combined with any of the other embodiments in this specification as appropriate.

Embodiment 4

In this embodiment, an odor sensor which is a configuration example described in Embodiment 3 in which one of the arithmetic circuit MAC1, the arithmetic circuit MAC1A, the arithmetic circuit MAC2, and the arithmetic circuit MAC3 is combined with a sensor is described. An example of an electronic device in which one of the arithmetic circuit MAC1, the arithmetic circuit MAC1A, the arithmetic circuit MAC2, and the arithmetic circuit MAC3 is combined with a tactile sensor is described. An example of an electronic device in which one of the arithmetic circuit MAC1, the arithmetic circuit MAC1A, the arithmetic circuit MAC2, and the arithmetic circuit MAC3 is combined with a taste sensor is described.

<Odor Sensor>

Figure 15:
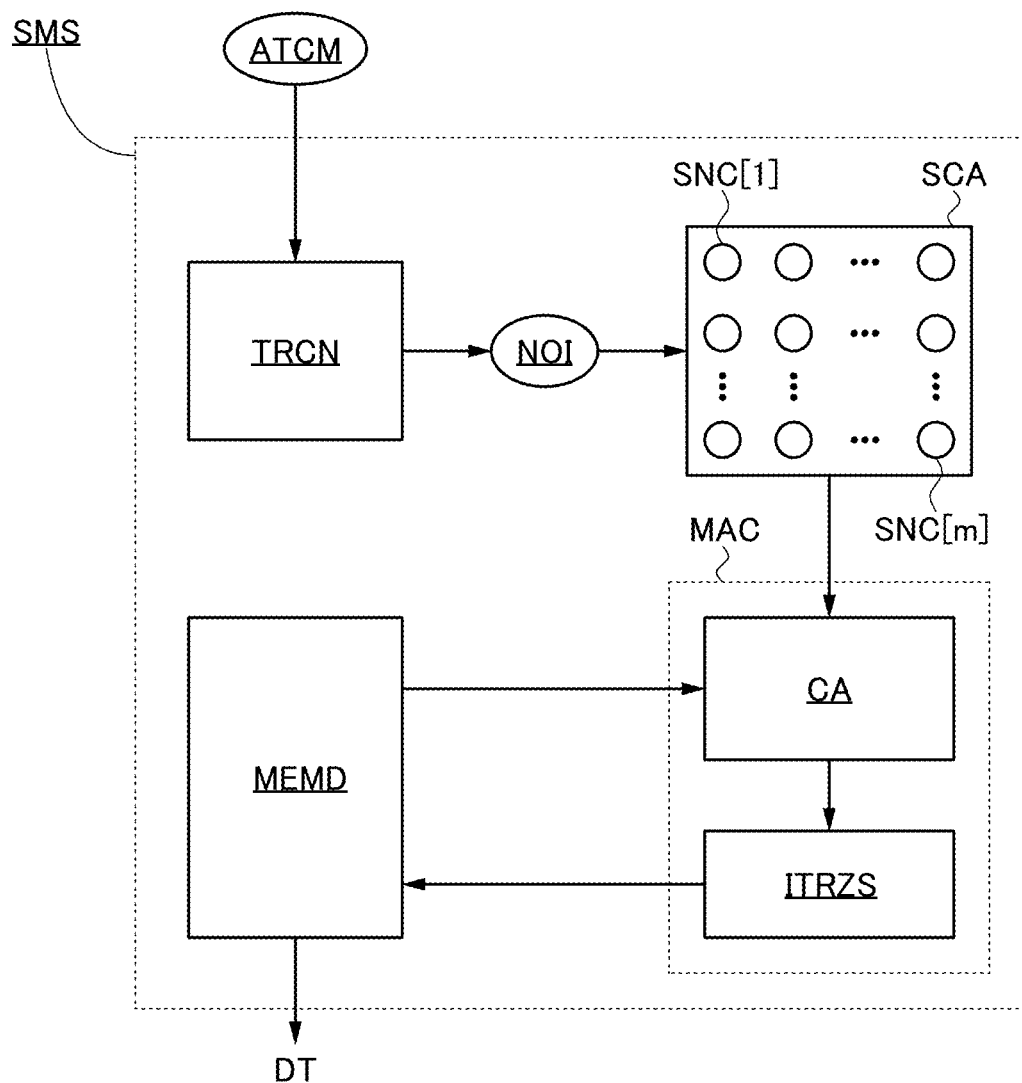
FIG. 15 is a block diagram showing a configuration example of an odor sensor.

FIG. 15 is a block diagram of a configuration example of an odor sensor. An odor sensor SMS includes a path TRCN, the circuit SCA including a sensor, the arithmetic circuit MAC, and a memory portion MEMD.

The path TRCN is a path to send an atmospheric component ATCM to the circuit SCA. The path TRCN may have a function of selectively capturing only a targeted odor molecule and condensing it.

In the case where the path TRCN has the function, the path TRCN preferably includes a nano-level path, a nanopiller, a nanowire, or the like. When the path TRCN includes a nano-level path, a nanopiller, a nanowire, or the like, odor molecules unnecessary to be detected by the odor sensor SMS included in the atmospheric component ATCM can be removed. Thus, through the path TRCN, an odor component NOI which is a rest of the atmospheric component ATCM from which unnecessary odor molecules are removed can be sent to the circuit SCA.

Like the circuit SCA described in Embodiment 3, the circuit SCA includes the sensor SNC[1] to the sensor SNC[m], for example. The sensor SNC[1] to the sensor SNC[m] are arranged in a matrix in FIG. 15, for example. The sensor SNC[1] to the sensor SNC[m] are arranged in a matrix in FIG. 15 as an example; however, the sensor SNC[1] to the sensor SNC[m] are not necessarily arranged in a matrix. The sensor SNC[1] to the sensor SNC[m] can be arranged depending on circumstances.

In this embodiment, the sensor SNC[1] to the sensor SNC[m] illustrated in FIG. 15 are detector elements for detecting odor molecules. The sensor SNC[1] to the sensor SNC[m] can be sensors detecting the same odor components or sensors detecting different odor components. A plurality of sensors may sense the same odor components. An example of the sensor SNC[1] to the sensor SNC[m] is described later.

The arithmetic circuit MAC is a circuit as which one of the arithmetic circuit MAC1 and the arithmetic circuit MAC1A described in Embodiment 1 and the arithmetic circuit MAC2 and the arithmetic circuit MAC3 described in Embodiment 2 can be used.

As illustrated in FIG. 15, the arithmetic circuit MAC includes the cell array CA and a converter circuit ITRZS, for example. The cell array CA illustrated in FIG. 1, FIG. 5, FIG. 7, or FIG. 12 can be used as the cell array CA. In the case where the cell array CA illustrated in FIG. 1 is used as the cell array CA in FIG. 15, the configurations illustrated in FIG. 13A and FIG. 13B are referred to for the relation of the circuit SCA and the cell array CA. The converter circuit ITRZS in FIG. 15 collectively shows the converter circuit ITRZ[1] to the converter circuit ITRZ[n] in FIG. 1, the converter circuit ITRZ[1] to the converter circuit ITRZ[n] in FIG. 5, the converter circuit ITRZD[j] in FIG. 7, or the converter circuit ITRZD[j] in FIG. 12. In FIG. 15, the circuit WCS, the circuit WSD, the circuit SWS1, the circuit SWS2, and the like are omitted.

The memory portion MEMD has a function of storing the result of the calculation in the arithmetic circuit MAC, for example. The memory portion MEMD has a function of outputting the result as data DT to the outside of the odor sensor SMS. When the arithmetic circuit MAC performs operations repeatedly, the memory portion MEMD may have a function of temporarily storing data in the middle of the arithmetic operation.

Figure 16A:
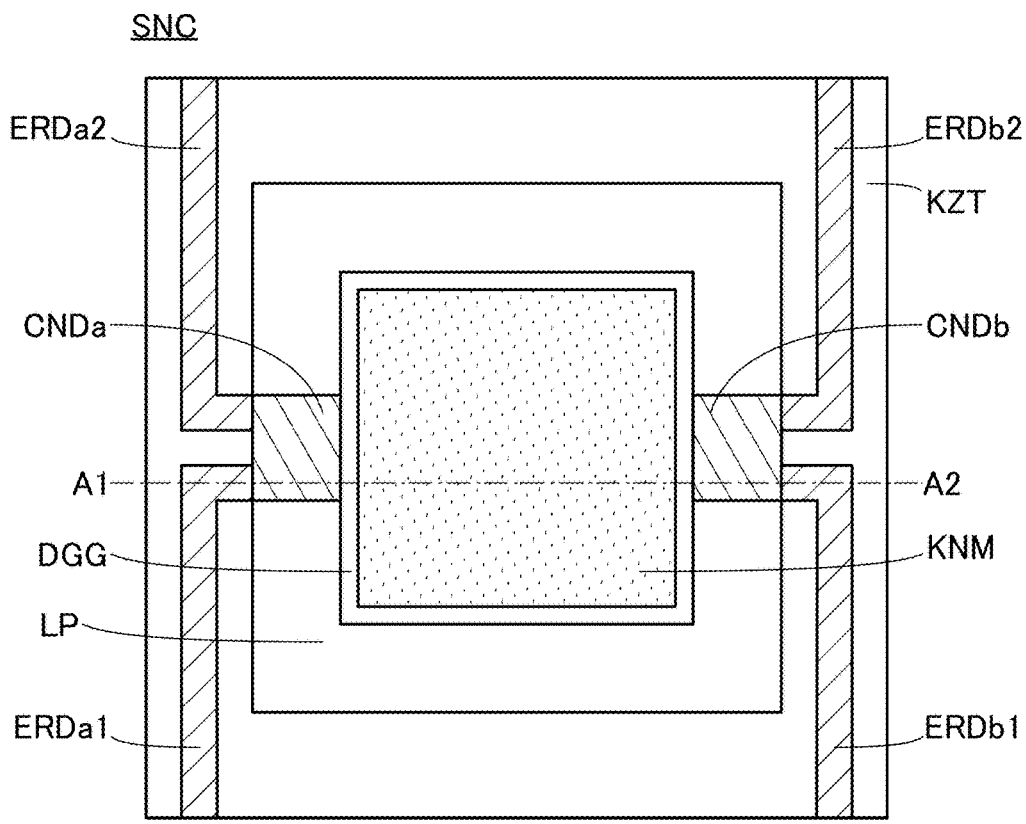
FIG. 16A is a top view showing an example of a detector element included in an odor sensor.
Figure 16B:
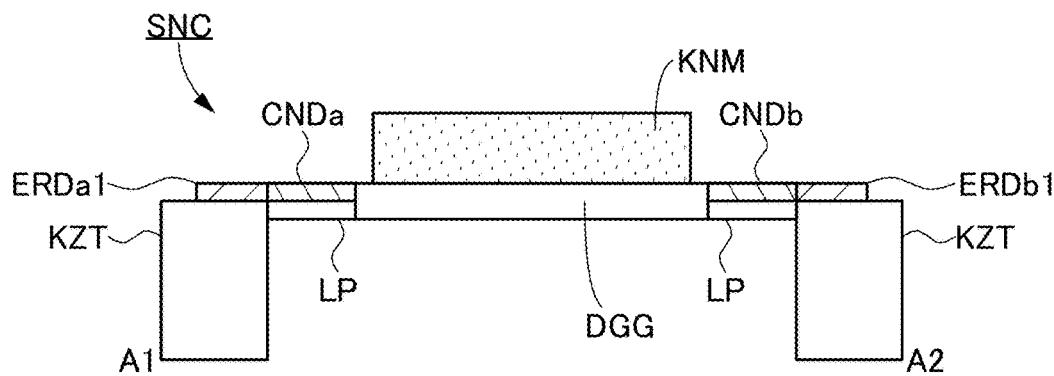
FIG. 16B and FIG. 16C are cross-sectional views showing an example of a detector element included in an odor sensor.

The sensor SNC[1] to the sensor SNC[m] for detecting odor molecules can be, for example, the sensor SNC illustrated in FIG. 16A and FIG. 16B. FIG. 16A shows a top view of the sensor SNC, and FIG. 16B shows a cross-sectional view taken along the dashed-dotted line A1-A2 in FIG. 16A.

For example, the sensor SNC includes a structure body KZT, a wiring ERDa1, a wiring ERDa2, a wiring ERDb1, a wiring ERDb2, a strain gauge DGG, a connection portion LP, a conductor CNDa, a conductor CNDb, and a sensing film KNM.

The strain gauge DGG is connected to the structure body KZT through the connection portion LP. The sensing film KNM is provided on the strain gauge DGG.

The strain gauge DGG and the connection portion LP are preferably flexible insulators. As the structure body KZT, an insulator highly resistant to strain is preferable.

The sensing film KNM has a property of expanding and contracting when a specific odor molecule is attached.

The wiring ERDa1 and the wiring ERDa2 are positioned over the structure body KZT. The wiring ERDb1 and the wiring ERDb2 are also positioned over the structure body KZT.

The conductor CNDa and the conductor CNDb are positioned over the connection portion LP. The conductor CNDa is provided such that the wiring ERDa1 and the wiring ERDa2 are in the conduction state. Similarly, the conductor CNDb is provided such that the wiring ERDb1 and the wiring ERDb2 are in the electrical conduction state.

A constant voltage is input between the wiring ERDa1 and the wiring ERDa2, for example. A current flows in the wiring ERDa1 and the wiring ERDa2 through the conductor CNDa, and the amount of the current is $I_a$. A constant voltage is also input between the wiring ERDb1 and the wiring ERDb2, for example. A current flows in the wiring ERDb1 and the wiring ERDb2 through the conductor CNDb, and the amount of the current is Ib.

Figure 16C:
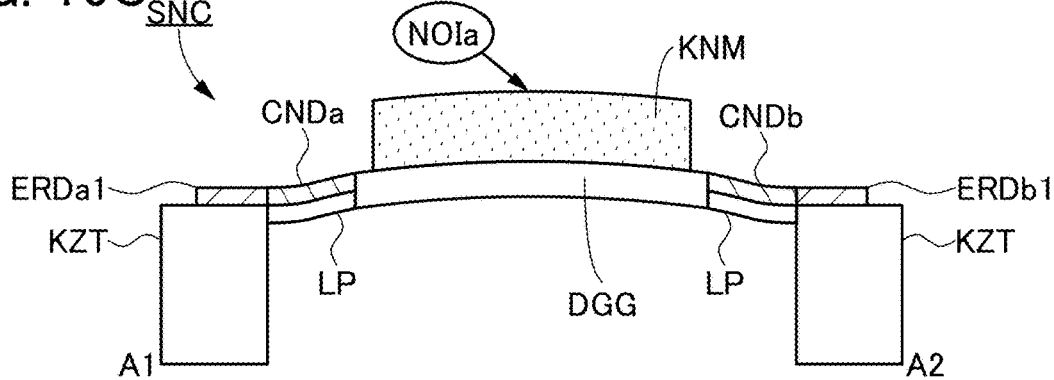

Here, a case where an odor molecule NOIa included in the odor component NOI sent from the path TRCN is attached to the sensing film KNM is considered. For example, when the odor molecule NOIa is attached to the sensing film KNM, the surface of the sensing film KNM which is not in contact with the strain gauge expands. Thus, as illustrated in FIG. 16C, strain is generated in the sensing film KNM and the strain gauge DGG, force is applied to the connection portion LP, the conductor CNDa, and the conductor CNDb, and the shapes of the connection portion LP, the conductor CNDa, and the conductor CNDb also change.

The shapes of the conductor CNDa and the conductor CNDb change, whereby the resistance values of the conductor CNDa and the conductor CNDb changes. When the amount of change in the current flowing through the conductor CNDa is $\Delta I_a$ due to the change, the amount of current flowing through the wiring ERDa1 and the wiring ERDa2 is represented as $I_a + \Delta I_a$. Similarly, when the amount of change in the current flowing through the conductor CNDb is $\Delta I_b$ due to the change, the amount of current flowing through the wiring ERDb1 and the wiring ERDb2 is represented as $I_b + \Delta I_b$.

A current flowing from the sensor SNC may be one of the current flowing through the wiring ERDa1 and the wiring ERDa2 and the current flowing through the wiring ERDa1 and the wiring ERDa2. A current flowing from the sensor SNC may be the sum of the current flowing through the wiring ERDa1 and the wiring ERDa2 and the current flowing through the wiring ERDa1 and the wiring ERDa2. A current flowing from the sensor SNC may be the average of the current flowing through the wiring ERDa1 and the wiring ERDa2 and the current flowing through the wiring ERDa1 and the wiring ERDa2.

In FIG. 15, the current flowing from the sensor SNC flows into the cell array CA of the arithmetic circuit MAC. Specifically, as illustrated in FIG. 13A and FIG. 13B, currents from the sensor SNC[1] to the sensor SNC[m] flow to the wiring XCL[1] to the wiring XCL[m].

For example, the amount of current flowing from the sensor SNC[i] is $I_a[i]$ before the odor component NOI is attached to the sensing film KNM of the sensor SNC[i] (i is an integer more than or equal to 1 and less than or equal to m). Further, the current flows through the wiring XCL[i] between Time T13 and Time T14 in the timing chart in FIG. 6.

For example, the amount of current flowing from the sensor SNC[i] is $x[i]I_a[i] = I_a[i] + \Delta I_a[i]$ after the odor component NOI is attached to the sensing film KNM of the sensor SNC[i]. The current flows through the wiring XCL[i] between Time T22 and Time T23 in the timing chart in FIG. 6.

As described above, a current from the sensor SNC[1] to the sensor SNC[m] flows from the circuit SCA to the cell array CA in the arithmetic circuit MAC, a second data x[1] to x[m] corresponding to the odor component NOI can be input to the arithmetic circuit MAC. Thus, the product-sum operation of the first data stored in the cell IM in the cell array CA and the second data can be performed. In other words, the neural network arithmetic operation can be performed using the odor component NOI as an input data.

The arithmetic operation of the neural network is a pattern recognition algorithm to the odor component NOI. The first data (coefficient of weight) used in the neural network is stored in the node NM in the cell IM through the machine learning or the like. Thus, from the pattern of a current flowing from the circuit SCA to the cell array CA corresponding to the odor component NOI, the odor, the molecular size, the shape, and the like of the odor component NOI can be recognized and the result can be output as the data DT from the odor sensor SMS.

<Tactile Sensor>

Figure 17:
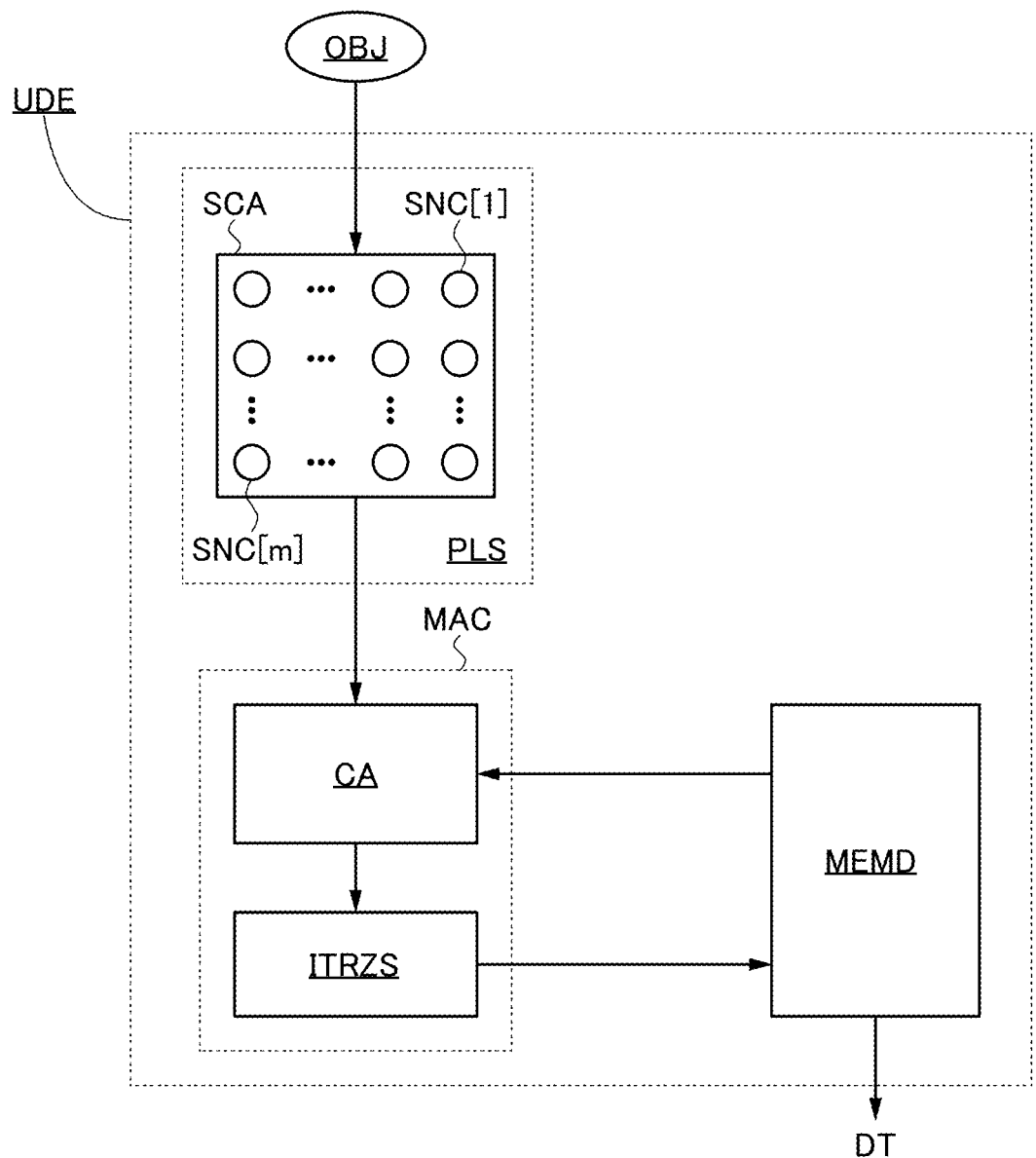
FIG. 17 is a block diagram showing a configuration example of an electronic device including a pressure sensor or a tactile sensor.

FIG. 17 is a block diagram illustrating a configuration example of an electronic device including a tactile sensor. An electronic device UDE includes, for example, a sensor portion PLS functioning as a tactile sensor, the arithmetic circuit MAC, and the memory portion MEMD. The sensor portion PLS includes the circuit SCA, and as the circuit SCA, the circuit SCA described in Embodiment 3 can be used, for example.

As an example of the circuit SCA in FIG. 17, the sensor SNC[1] to the sensor SNC[m] are included in the circuit SCA as in the circuit SCA described in Embodiment 3. In FIG. 17, the sensor SNC[1] to the sensor SNC[m] are arranged in a matrix as an example; however, these are not necessarily arranged in a matrix. The sensor SNC[1] to the sensor SNC[m] can be arranged depending on circumstances.

The sensor SNC[1] to the sensor SNC[m] in FIG. 17 are pressure sensors, and detector elements detecting pressure from the outside. An object OBJ is illustrated in FIG. 17; the sensor SNC[1] to the sensor SNC[m] are in contact with the object OBJ, and a detection signal is sent to the arithmetic circuit MAC. The signal can be, for example, a voltage, a current, or a change thereof.

Any one of the arithmetic circuit MAC1 and the arithmetic circuit MAC1A described in Embodiment 1 and the arithmetic circuit MAC2 and the arithmetic circuit MAC3 described in Embodiment 2 can be used as the arithmetic circuit MAC.

As illustrated in FIG. 17, the arithmetic circuit MAC includes the cell array CA and the converter circuit ITRZS, for example. As the cell array CA and the converter circuit ITRZS in FIG. 17, the descriptions of the arithmetic circuit MAC in FIG. 15 are referred to.

The memory portion MEMD has a function of storing the result of a calculation in the arithmetic circuit MAC, for example. The memory portion MEMD has a function of outputting the result as the data DT to the outside of the electronic device UDE. When the arithmetic circuit MAC performs operations repeatedly, the memory portion MEMD may have a function of temporarily storing data in the middle of the arithmetic operation.

Figure 18A:
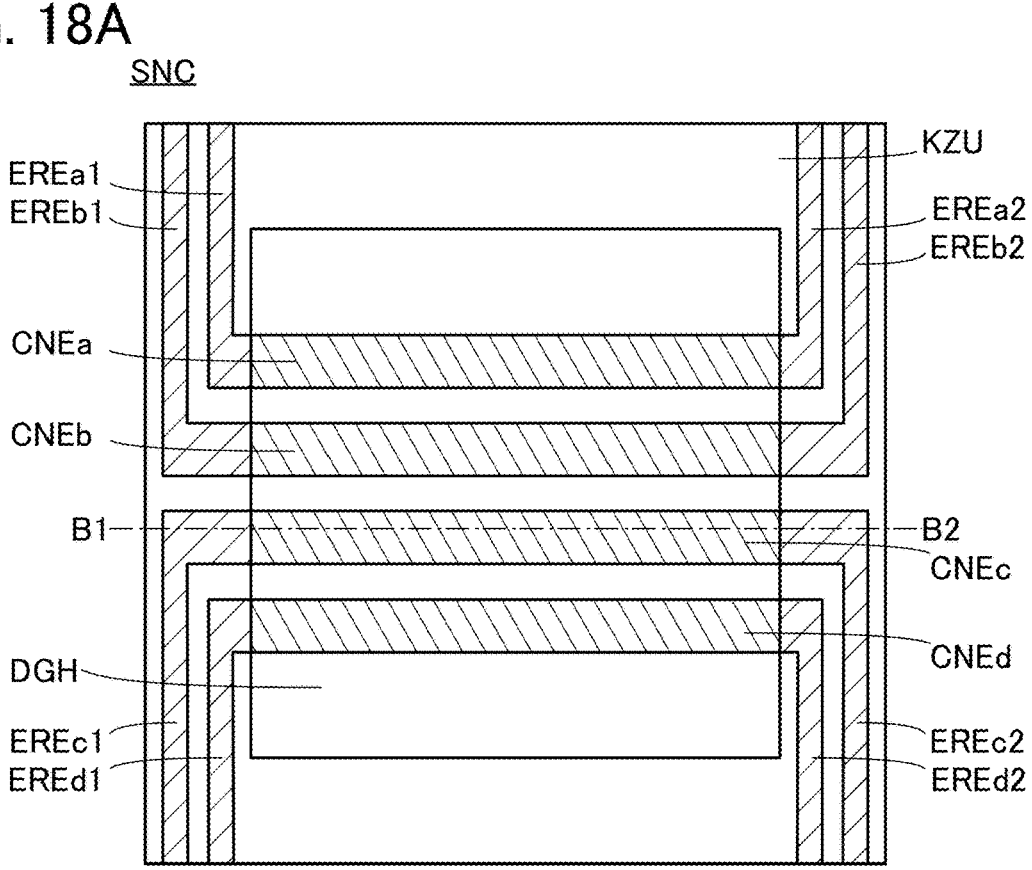
FIG. 18A is a top view showing an example of a detector element included in a pressure sensor.
Figure 18B:
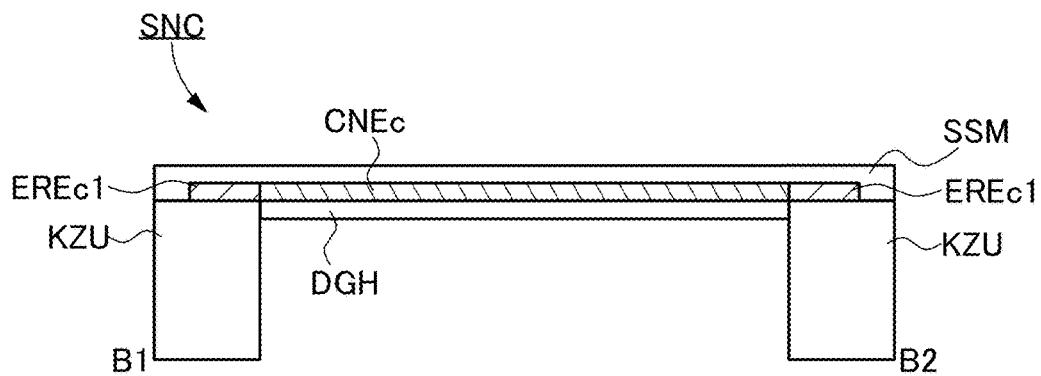
FIG. 18B and FIG. 18C are cross-sectional views showing an example of a detector element included in a pressure sensor.

For example, the sensor SNC illustrated in FIG. 18A and FIG. 18B can be used as the sensor SNC[1] to the sensor SNC[m] included in the sensor portion PLS. FIG. 18A shows a top view of the sensor SNC, and FIG. 18B is a cross-sectional view taken along the dashed-dotted line B1-B2 in FIG. 18A.

As an example, the sensor SNC includes a structure KZU, a wiring EREa1, a wiring EREa2, a wiring EREb1, a wiring EREb2, a wiring EREc1, a wiring EREc2, a wiring EREd1, a wiring EREd2, a conductor CNEa, a conductor CNEb, a conductor CNEc, a conductor CNEd, an insulator SSM, and a strain gauge DGH.

The strain gauge DGH is connected to the structure body KZU. The conductor CNEa, the conductor CNEb, the conductor CNEc, and the conductor CNEd are provided over the strain gauge DGH.

The wiring EREa1 and the wiring EREa2 are provided over the structure body KZU and in the conduction state with the conductor CNEa therebetween. The wiring EREb1 and the wiring EREb2 are provided over the structure body KZU to be in the conduction state with the conductor CNEb therebetween. The wiring EREc1 and the wiring EREc2 are provided over the structure body KZU to be in the conduction state with the conductor CNEc therebetween. The wiring EREd1 and the wiring EREd2 are provided over the structure body KZU to be in the conduction state with the conductor CNEd therebetween.

The insulator SSM is provided over the structure body KZU and the strain gauge DGH to cover the wiring EREa1, the wiring EREa2, the wiring EREb1, the wiring EREb2, the wiring EREc1, the wiring EREc2, the wiring EREd1, the wiring EREd2, the conductor CNEa, the conductor CNEb, the conductor CNEc, and the conductor CNEd. The insulator SSM is not illustrated in FIG. 18A.

The strain gauge DGH and the insulator SSM are preferably flexible insulators. As the structure body KZU, an insulator highly resistant to strain is preferable.

Figure 18C:
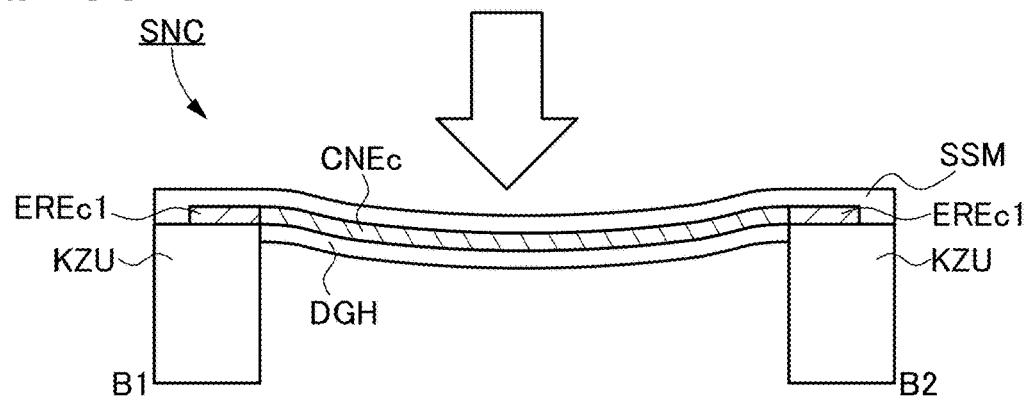

When force is applied from the outside in the sensor SNC illustrated in FIG. 18A and FIG. 18B, the sensor SNC distorts by applying force to the strain gauge DGH as illustrated in FIG. 18C. Thus, the conductor CNEa, the conductor CNEb, the conductor CNEc, the conductor CNEd, and the insulator SSM distorts with the strain gauge DGH, and the shapes of the conductor CNEa, the conductor CNEb, the conductor CNEc, the conductor CNEd, and the insulator SSM also change.

The shapes of the conductor CNEa, the conductor CNEb, the conductor CNEc, and the conductor CNEd, change, and the resistance values of the conductor CNEa, the conductor CNEb, the conductor CNEc, and the conductor CNEd change. The resistance values of the conductor CNEa, the conductor CNEb, the conductor CNEc, and the conductor CNEd change after a pressure detection; the sensor SNC makes constant currents flow through the wiring EREa1, the wiring EREa2, the wiring EREb1, the wiring EREb2, the wiring EREc1, the wiring EREc2, the wiring EREd1, and the wiring EREd2 to the conductor CNEa, the conductor CNEb, the conductor CNEc, and the conductor CNEd, whereby the pressure can be detected by the changes of the voltages of the conductor CNEa, the conductor CNEb, the conductor CNEc, and the conductor CNEd.

Figure 19A:
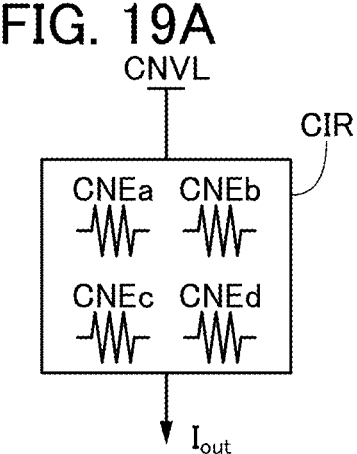
FIG. 19A to FIG. 19C are circuit diagrams showing an example of a circuit configuration included in a pressure sensor.

In the case where the sensor SNC is a tactile sensor, for example, the circuit illustrated in FIG. 19A can be used as the circuit including the conductor CNEa, the conductor CNEb, the conductor CNEc, and the conductor CNEd. A circuit CIR includes at least one of the conductor CNEa, the conductor CNEb, the conductor CNEc, and the conductor CNEd. A wiring CNVL functions as a wiring which supplies a constant voltage.

FIG. 19A shows a circuit configuration in which, when a constant voltage is supplied from the wiring CNVL to the circuit CIR, the output current $I_{out}$ can be obtained. When pressure is detected with the sensor SNC, the resistances of the conductor CNEa, the conductor CNEb, the conductor CNEc, and the conductor CNEd change, and thus the current $I_{out}$ changes before/after the detection of the pressure.

Figure 19B:
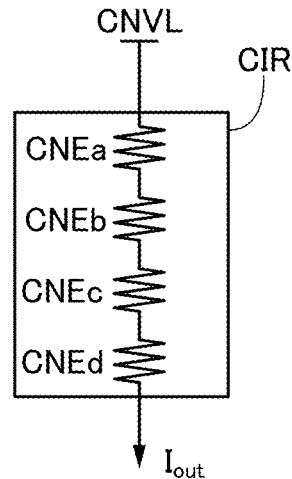
Figure 19C:
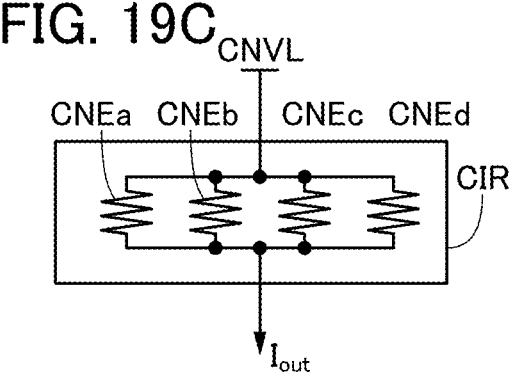

As a configuration example of the circuit CIR illustrated in FIG. 19A, the conductor CNEa, the conductor CNEb, the conductor CNEc, and the conductor CNEd may be electrically connected in series as illustrated in FIG. 19B. The conductor CNEa, the conductor CNEb, the conductor CNEc, and the conductor CNEd may be electrically connected in parallel as illustrated in FIG. 19C.

The current $I_{out}$ output from the circuit CIR in FIG. 19A is input to the arithmetic circuit MAC in FIG. 17. Specifically, for example, the amount of current flowing from the sensor SNC[i] is $I_{out}[i]$ before pressure is detected by the sensor SNC[i] (i is an integer more than or equal to 1 and less than or equal to m). Further, the current flows through the wiring XCL[i] between Time T13 and Time T14 in the timing chart in FIG. 6.

For example, the amount of current flowing from the sensor SNC[i] is $x[i]I_{out}[i]=I_{out}[i]+\Delta I_{out}[i]$ after pressure is detected by the sensor SNC[i]. The current flows through the wiring XCL[i] between Time T22 and Time T23 in the timing chart in FIG. 6.

As described above, a current from the sensor SNC[1] to the sensor SNC[m] flows from the circuit SCA to the cell array CA in the arithmetic circuit MAC, whereby the second data x[1] to x[m] corresponding to the pressure detected with the sensor SNC[1] to the sensor SNC[m] can be input to the arithmetic circuit MAC. Thus, the product-sum operation of the first data stored in the cell IM in the cell array CA and the second data can be performed. In other words, the neural network arithmetic operation can be performed using a pressure as an input data.

The structure of the electronic device of one embodiment of the present invention is not limited to the structure of the electronic device UDE in FIG. 17, which includes the sensor SNC illustrated in FIG. 18A and FIG. 18B as the sensor SNC provided to the sensor portion PLS. For example, a circuit that can be used in the sensor portion PLS of the electronic device UDE in FIG. 17 may have a configuration of a sensor portion PLSA illustrated in FIG. 20A.

Figure 20A:
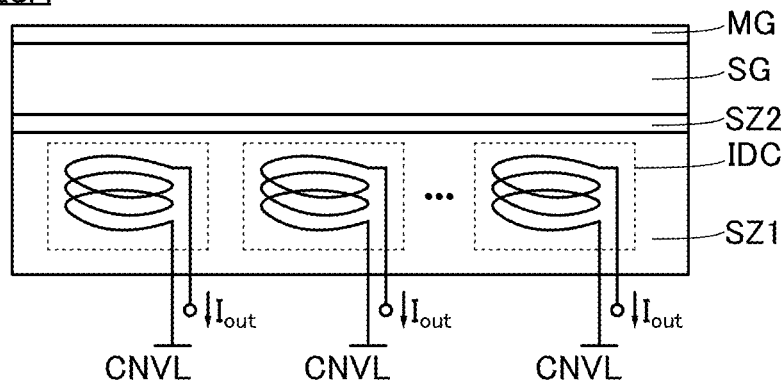
FIG. 20A and FIG. 20B are schematic cross-sectional views showing a structure example of a tactile sensor.

The sensor portion PLSA illustrated in FIG. 20A includes an insulator SZ1, a coil IDC, an insulator SZ2, a material SG, and a material MG.

The coil IDC functioning as the sensor SNC is embedded in the insulator SZ1. The insulator SZ2 is provided over the insulator SZ1, the material SG is provided over the insulator SZ2, and the material MG is provided over the material SG.

One terminal of the coil IDC is, for example, electrically connected to the wiring CNVL. The wiring CNVL functions as a wiring for supplying a constant voltage, like the wiring CNVL in FIG. 19A to FIG. 19C. Thus, when the wiring CNVL supplies a constant voltage and a voltage is generated between one terminal and the other terminal of the coil IDC, a steady current $I_{out}$ is generated between one terminal and the other terminal of the coil IDC after a sufficient period.

The material SG is preferably an elastic material, specifically, elastomer. Specifically, for example, a synthetic resin such as silicone rubber can be used as the material SG.

As a material for the material MG, for example, elastomer including a metal material emitting magnetism is preferably used. Specifically, thermosetting elastomer including a metal material emitting a magnetic field (e.g., metal powder) can be used as the material MG.

As the insulator SZ2, an insulator that does not block the magnetic field generated by the metal material included in the material MG is preferably used, for example.

In the sensor portion PLSA illustrated in FIG. 20A, when the shape of the material MG is changed by pushing or the like, the position of the metal material included in the material MG changes. The position of the metal material changes, whereby the magnetic field generated by the metal material changes; thus, in the coil IDC near the metal material whose position changes, electromotive force through electromagnetic induction is generated.

Figure 20B:
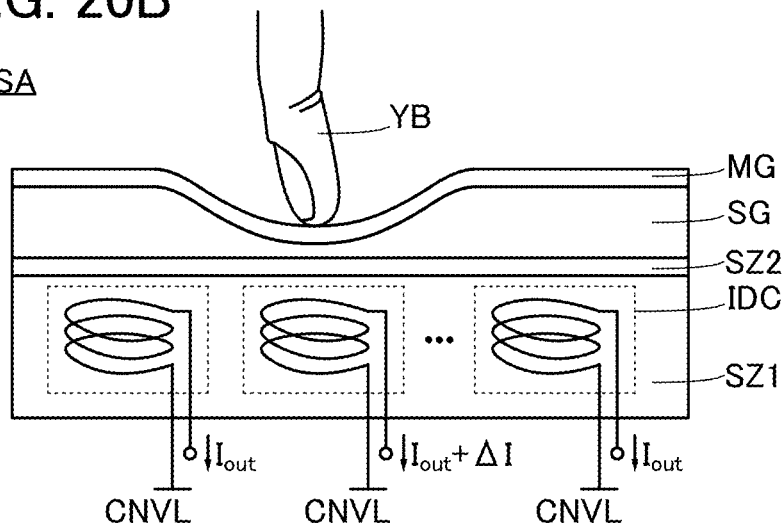

For example, when the material MG is dented by pushing of a finger YB, the position of the metal material included in the material MG changes and the magnetic field generated by the metal material changes; thus, in the coil IDC near the finger YB, electromotive induction occurs, as illustrated in FIG. 20B. Accordingly, electromotive force is generated in the coil IDC near the finger YB.

At this time, the amount of steady current flowing in the coil IDC temporarily changes. For example, when the amount of change in a current flowing through the coil IDC near the finger YB is $\Delta I$, the amount of current flowing between one terminal and the other terminal of the coil IDC is $I_{out}+\Delta I$. At this time, x satisfying $xI_{out}=I_{out}+\Delta I$ is defined.

The currents $I_{out}$ and $I_{out}+\Delta I$ output from the tactile sensor illustrated in FIG. 20A and FIG. 20B are input to the arithmetic circuit MAC in FIG. 17. Specifically, before an object touches the tactile sensor, the current amount $I_{out}$ flows from the tactile sensor to the wiring XCL. The current flows through the wiring XCL between Time T13 and Time T14 in the timing chart in FIG. 6.

When an object touches the tactile sensor, for example, the current amount $I_{out}+\Delta I$ flows from the tactile sensor to the wiring XCL. The current flows through the wiring XCL[i] between Time T22 and Time T23 in the timing chart in FIG. 6.

As described above, a current from the tactile sensor in FIG. 20A as the sensor SNC[1] to the sensor SNC[m] flows from the circuit SCA to the cell array CA in the arithmetic circuit MAC, whereby the second data x[1] to x[m] corresponding to the shape of the object touching the sensor SNC[1] to the sensor SNC[m] can be input to the arithmetic circuit MAC. Thus, the product-sum operation of the first data stored in the cell IM in the cell array CA and the second data can be performed. In other words, the neural network arithmetic operation can be performed using the shape of an object as an input data.

<<Application Example of Tactile Sensor>>

Next, an application example of the electronic device UDE in FIG. 17 for which a tactile sensor is used as the sensor portion PLS is described.

Figure 21A:
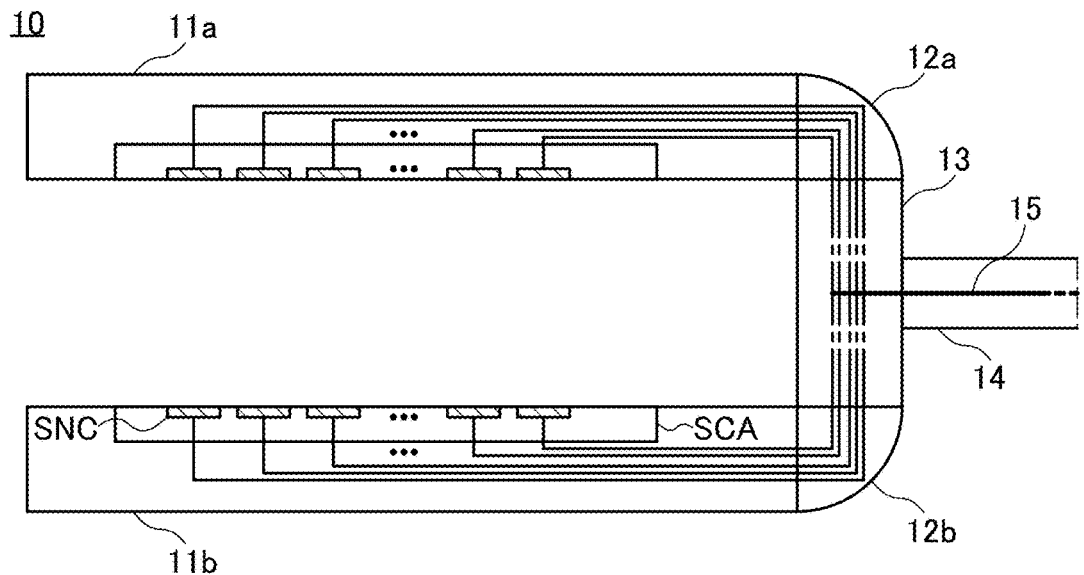

FIG. 21A shows a configuration example where the electronic device UDE is used in a hand portion of an industrial manipulator. Specifically, the circuit SCA included in the electronic device UDE in FIG. 17 is embedded in a finger portion 11a and a finger portion 11b of the hand portion 10 in FIG. 21A to expose the sensors SNC to the outside.

The hand portion 10 includes the finger portion 11a, the finger portion 11b, a joint portion 12a, a joint portion 12b, an extending portion 13, a support portion 14, and a bus wiring 15, for example.

For example, the finger portion 11a and the finger portion 11b function as part to hold an object. The hand portion 10 is configured to have a structure for holding an object in FIG. 21A; however, one embodiment of the present invention is not limited to the structure of the hand portion 10. For example, the hand portion 10 may be configured to push an object in one direction with the finger portion 11a or the finger portion 11b (not illustrated).

The joint portion 12a has a function of changing an angle formed between the finger portion 11a and the extending portion 13, for example. Similarly, the joint portion 12b has a function of changing an angle formed between the finger portion 11b and the extending portion 13, for example. The joint portion 12a and the joint portion 12b change the angles formed between the finger portion 11a and the finger portion 11b and the extending portion 13, whereby an object can be held with the finger portion 11a and the finger portion 11b.

The extending portion 13 has a function of adjusting the length between the joint portion 12a and the joint portion 12b, for example. The length of the extending portion 13 can be adjusted to the size of an object held with the hand portion 10.

The support portion 14 has a function of supporting the entire hand portion 10, for example. The support portion 14 can include, for example, a mechanism to make the hand portion 10 closer to an object, a driving shaft to direct the hand portion 10 to an object, and the like, which are not illustrated in FIG. 21.

A plurality of sensors SNC of the circuit SCA provided in the finger portion 11a and the finger portion 11b is electrically connected to the bus wiring 15 for supplying a current and/or a voltage. The wiring is provided inside the finger portion 11a, the finger portion 11b, the joint portion 12a, the joint portion 12b, the extending portion 13, and the support portion 14 as an example. It is particularly preferable that a current flowing at the time when the sensors SNC detect a change in pressure or a touch of an object is input to the main device of the hand portion 10 (not illustrated) or the wiring XCL[1] to the wiring XCL[m] (see FIG. 13A and FIG. 13B) of the arithmetic circuit MAC included in the main device through the bus wiring 15. Thus, the bus wiring 15 is preferably electrically connected to the wiring XCL[1] to the wiring XCL[m] of the arithmetic circuit MAC.

An operation example of the hand portion 10 holding an object is described.

Figure 21B:
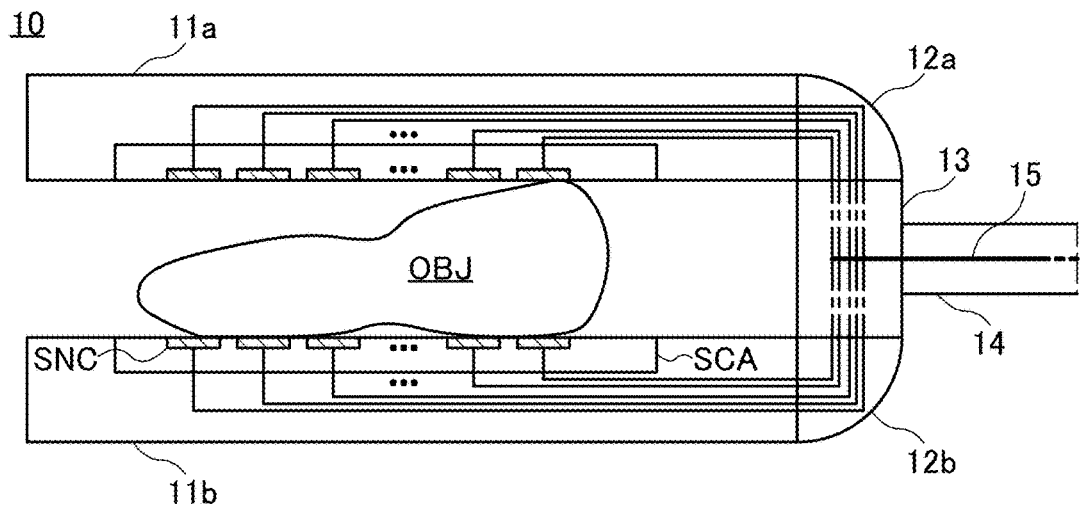

FIG. 21B shows the hand portion 10 holding the object OBJ. At this time, a detectable region of the sensor SNC of the circuit SCA provided to the finger portion 11a and the finger portion 11b touches the object OBJ, whereby the amount of current flowing from the sensor SNC touching the object OBJ to the main device through the bus wiring 15 changes. Through the change of the current amount, the main device can recognize that the object OBJ touches the finger portion 11a and/or the finger portion 11b of the hand portion 10.

Not to drop the object OBJ held with the finger portion 11a and the finger portion 11b, it is necessary that the shape of the object OBJ is recognized with the main device and the joint portion 12a, the joint portion 12b, the joint portion 13, and the like are adjusted in accordance with the shape of the object OBJ. For example, as illustrated in FIG. 21B, the hand portion 10 holds the object OBJ with the finger portion 11a and the finger portion 11b parallel to each other; depending on the shape of the object OBJ, the circuit SCA includes the sensor SNC not touching the object OBJ. The amount of current flowing from the sensor SNC not touching the object OBJ to the main device through the bus wiring 15 does not change; thus, the main device can recognize that the finger portion 11a and/or the finger portion 11b of the hand portion 10 does not touch the object OBJ.

Thus, with the amount of change in a current flowing from each of the plurality of sensors SNC of the circuit SCA included in the finger portion 11a and the finger portion 11b to the bus wiring 15, the region where the object OBJ touches the circuit SCA of the finger portion 11a and the finger portion 11b can be represented. Thus, a current flows from the plurality of sensors SNC through the bus wiring 15 to the arithmetic circuit MAC, whereby the region can be regarded as an input data to the arithmetic circuit MAC.

The sensors SNC included in the circuit SCA of the finger portion 11a and the finger portion 11b are the sensor SNC[1] to the sensor SNC[m] (m is an integer more than or equal to 1). In FIG. 21A, a current output from the sensor SNC[i] (i is an integer more than or equal to 1 and less than or equal to m) is $I_{out}[i]$ and in FIG. 21B, a current output from the sensor SNC[i] is $x[i]I_{out}[i]$. At this time, the region of the circuit SCA of the finger portion 11a and the finger portion 11b touching the object OBJ can be represented with x[1] to x[m]. By inputting x[1] to x[m] to the arithmetic circuit MAC as the second data, a product-sum operation of the first data stored in the cell IM in the cell array CA and the second data can be performed. That is, an arithmetic operation of the neural network can be performed using the input data of the region where the circuit SCA of the finger portion 11a and the finger portion 11 touches the object OBJ and where the circuit SCA does not touch the object OBJ.

The arithmetic operation of the neural network is a pattern recognition algorithm to the region where the circuit SCA of the finger portion 11a and the finger portion 11b touches the object held by the hand portion 10 and where the circuit SCA does not touch the object held by the hand portion 10. The first data (coefficient of weight) used in the neural network is stored in the node NM in the cell IM through the machine learning or the like. Thus, from the patterns of currents flowing from the circuit SCA to the cell array CA corresponding to the region where the circuit SCA of the finger portion 11a and the finger portion 11 touches the object held by the hand portion 10 and where the circuit SCA does not touch the object held by the hand portion 10, the shape, size, and the like of the object OBJ can be recognized.

Data of the object OBJ recognized with a pattern recognition may be fed back, and the hand portion 10 can change the way of holding the object OBJ. Specifically, from the recognized object OBJ data, the joint portion 12a, the joint portion 12b, the extending portion 13, and the like can be adjusted in accordance with the shape of the object OBJ. Thus, as illustrated in FIG. 21C, the hand portion 10 can more stably hold the object OBJ than that in FIG. 21B.

Figure 21C:
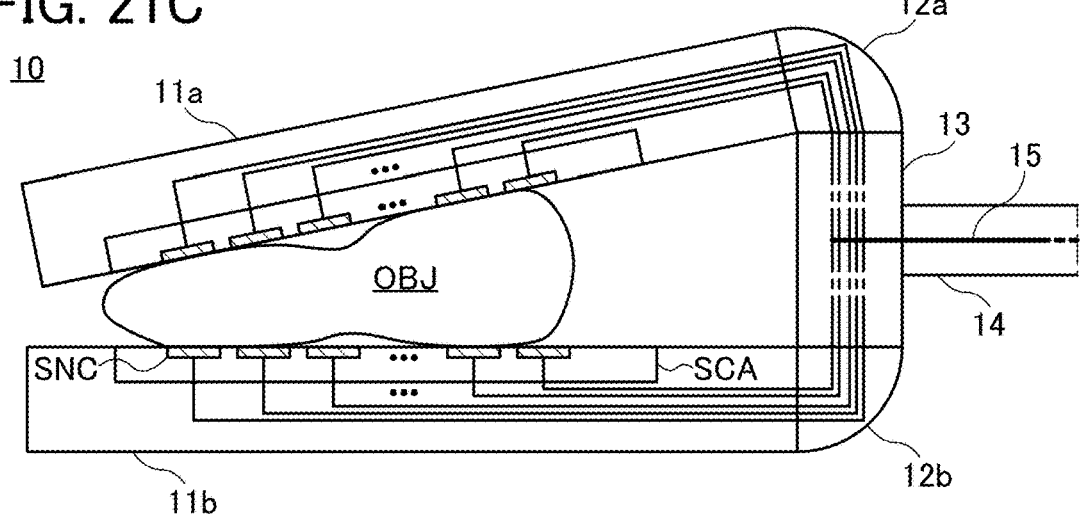

A hand portion of an industrial manipulator is not limited to the hand portion 10 in FIG. 21A to FIG. 21C. For example, the hand portion of an industrial manipulator may have a structure illustrated in FIG. 22A.

Figure 22A:
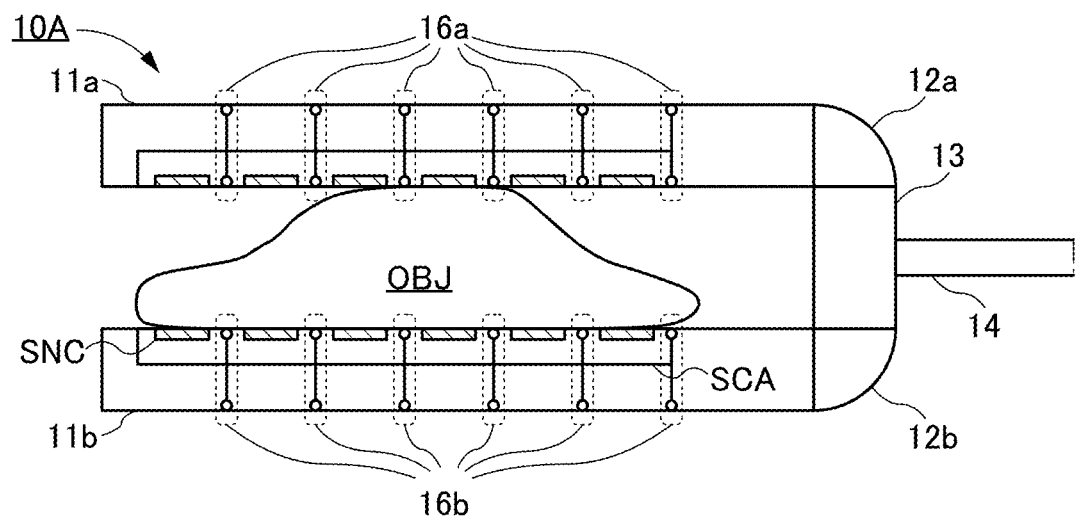

A hand portion 10A illustrated in FIG. 22A differs from the hand portion 10 in FIG. 21A in that a plurality of joint portions 16a is included in the finger portion 11a and a plurality of joint portions 16b is included in the finger portion 11b. FIG. 22A illustrates that the object OBJ is held with the finger portion 11a and the finger portion 11b.

The joint portion 16a and the joint portion 16b included in the finger portion 11a and the finger portion 11b may be one, not plural. In FIG. 22A, the joint portion 16a or the joint portion 16b is provided between different sensors SNC; the position of the joint portion 16a or the joint portion 16b can be decided freely in accordance with an object held with the hand portion 10A.

In FIG. 22A, the bus wiring 15 electrically connected to the plurality of sensors SNC is omitted.

The joint portion 16a and the joint portion 16b in FIG. 22 have mechanisms to bend the finger portion 11a and the finger portion 11b to the inside or the outside. Thus, the hand portion 10A can change the shapes of the finger portion 11a and the finger portion 11b depending on the shape of the object held.

Figure 22B:
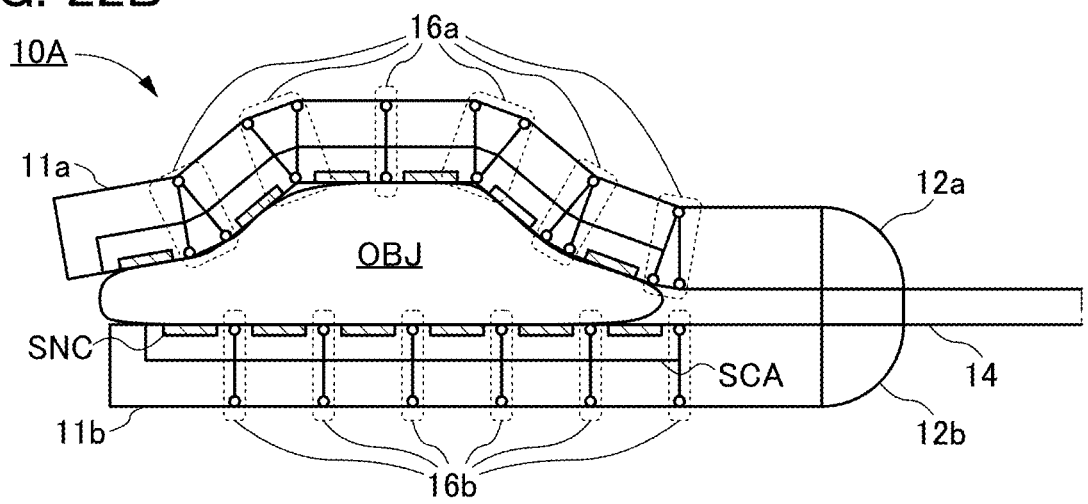

For example, as in the case of FIG. 21B and FIG. 21C described above, the shape of the object OBJ is calculated with the plurality of sensors SNC included in the circuit SCA and the arithmetic circuit MAC, and the joint portion 16a of the finger portion 11a and the joint portion 16b of the finger portion 11b can be adjusted to the calculated data at the step of FIG. 22A. Thus, as illustrated in FIG. 22B, the hand portion 10A can more stably hold the object OBJ than that in FIG. 22A.

The electronic device of one embodiment of the present invention can be used for a device or the like in addition to the above-described manipulator. For example, the electronic device of one embodiment of the present invention can be used for a medical device for a palpation or the like.

<Taste Sensor>

Figure 23:
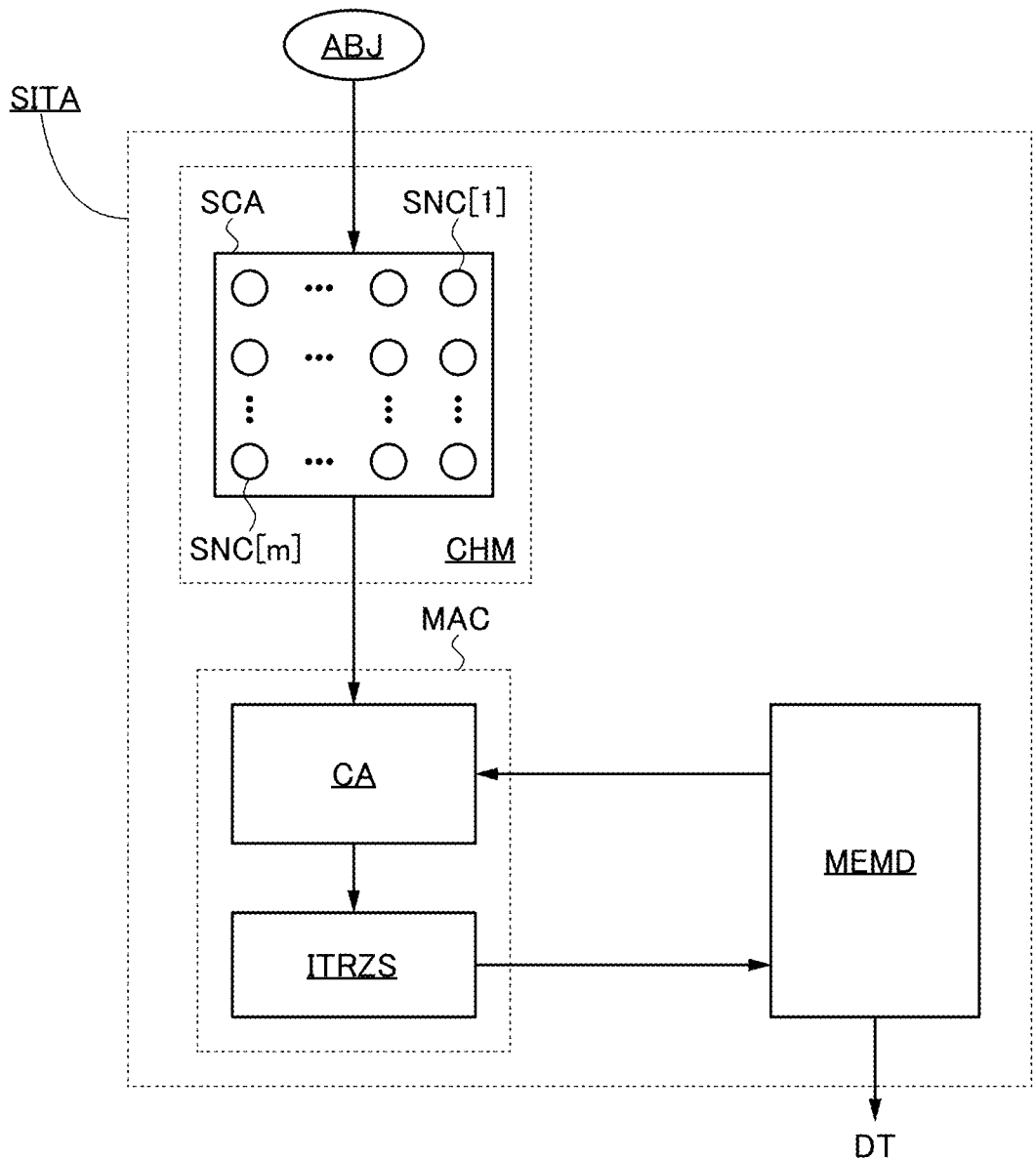
FIG. 23 is a block diagram showing a configuration example of an electronic device including a taste sensor.

FIG. 23 is a block diagram illustrating a structure example of an electronic device including a taste sensor. As an example, an electronic device SITA includes a sensor portion CHM functioning as a taste sensor, the arithmetic circuit MAC, and the memory portion MEMD. The sensor portion CHM includes the circuit SCA, and the circuit SCA in Embodiment 3 can be used as the circuit SCA, for example.

As an example of the circuit SCA in FIG. 23, the sensor SNC[1] to the sensor SNC[m] are included in the circuit SCA as in the circuit SCA described in Embodiment 3. The sensor SNC[1] to the sensor SNC[m] are arranged in a matrix as in FIG. 23 as an example; however, the sensor SNC[1] to the sensor SNC[m] are not necessarily arranged in a matrix. The sensor SNC[1] to the sensor SNC[m] can be arranged depending on circumstances.

The sensor SNC[1] to the sensor SNC[m] in FIG. 23 are taste sensors and detection elements detecting a specific taste component included in an evaluated material. A specific taste component is a material giving a human tongue a reaction of five basic tastes, spiciness, astringency, and the like. An evaluated object ABJ is illustrated in FIG. 23; the sensor SNC[1] to the sensor SNC[m] touch the evaluated object ABJ, and a detection signal is sent to the arithmetic circuit MAC. The signal can be, for example, a voltage, a current, or a change thereof.

The arithmetic circuit MAC can have a configuration similar to that of the arithmetic circuit MAC described in the odor sensor or the tactile sensor. For the arithmetic circuit MAC in FIG. 23, the arithmetic circuit MAC described in the odor sensor or the tactile sensor is referred to.

The memory portion MEMD can have a configuration similar to that of the memory portion MEMD described in the odor sensor or the tactile sensor. For the memory portion MEMD in FIG. 23, the memory portion MEMD described in the odor sensor or the tactile sensor is referred to.

Figure 24A:
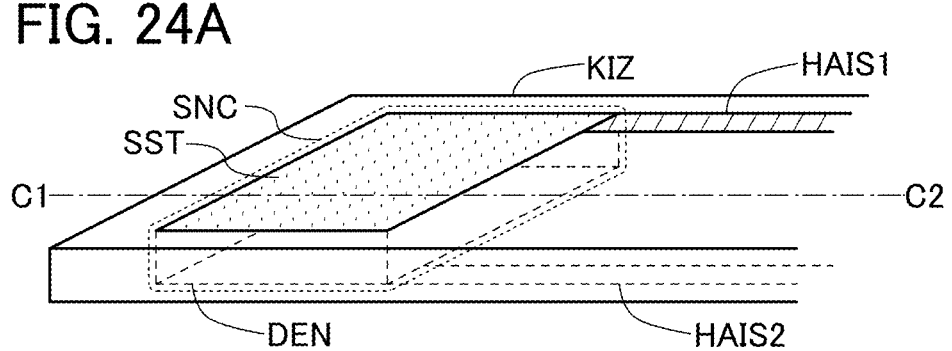
FIG. 24A is a perspective view showing a structure example of a taste sensor.
Figure 24B:
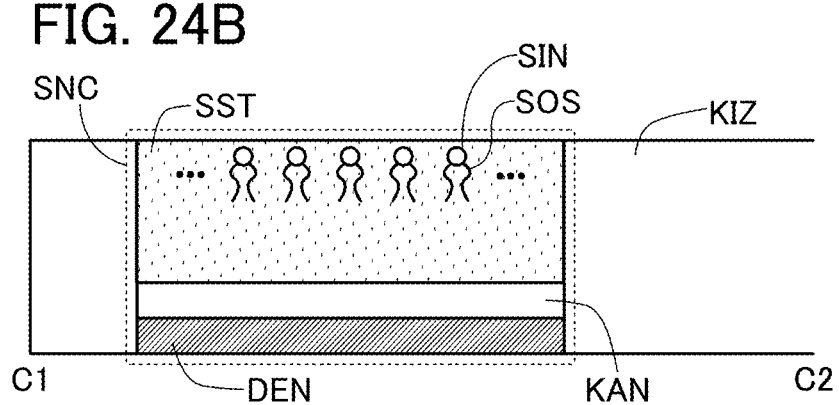
FIG. 24B is a cross-sectional view showing a structure example of a taste sensor.

Next, the sensor SNC[1] to the sensor SNC[m] included in the sensor portion CHM are described. The sensor SNC illustrated in FIG. 24A and FIG. 24B can be used as the sensor SNC[1] to the sensor SNC[m], for example. FIG. 24A is a perspective view of a structure example of a sensing element including the sensor SNC. FIG. 24B is a cross-sectional view taken along the dashed-dotted line C1-C2 in FIG. 24A.

The sensor SNC in FIG. 24A is, for example, mounted on a base material KIZ. The sensor SNC is electrically connected to a wiring HAIS1 and a wiring HAIS2.

As an example, the sensor SNC includes a lipid film SST, a buffer film KAN, and a reference electrode DEN as illustrated in FIG. 24B. The reference electrode DEN is provided to overlap with the lipid film SST with the buffer film KAN therebetween in FIG. 24B; the reference electrode DEN and the lipid film SST do not necessarily overlap.

When the lipid film SST touches a taste component, the lipid film SST functions as a sensor electrode to obtain a potential corresponding to the taste component; the lipid film SST includes lipid, plastisizer, polyvinyl chloride, and the like. The lipid includes a lipid molecule including a hydrophilic portion SIN and a hydrophobic portion SOS as an example. As illustrated in FIG. 24B, water or reference solution soaks the lipid film SST and lipid molecules are automatically aligned such that the hydrophilic portion SIN points to the outside of the film and the hydrophobic portion SOS points to the inside of the film in the vicinity of the surface of the lipid film SST. As the reaction of the lipid film SST to an umami material, a surface charge density, a surface potential, a connection proportion of hydrogen ions, and the like change and thus the potential of the lipid film SST changes.

In the lipid film SST, kinds of lipid and a plastisizer are changed or a ratio of lipid and a plastisizer is adjusted depending on taste components, e.g., sweetness, bitterness, sourness, savoriness, saltiness, spiciness, and, astringency, that are sensed. For example, in the case of a sensor sensing a taste component giving a human tongue astringency, the hydrophobic property of the lipid film SST is improved by decreasing the amount of lipid including charges. For example, in the case of a sensor sensing a taste component giving a human tongue saltiness, the hydrophilic property of the lipid film SST is improved by increasing the amount of lipid including charges to easily cause electrostatic reaction with ions.

The buffer film KAN has a function of preventing a transfer of charges between the lipid film SST and the reference electrode DEN. Thus, the buffer film KAN is preferably an insulator.

The reference electrode DEN functions as an electrode to obtain a reference potential of a corresponding taste component.

The lipid film SST is electrically connected to the wiring HAIS1, for example. The reference electrode DEN is electrically connected to the wiring HAIS2, for example.

The sensor SNC in FIG. 24A and FIG. 24B are soaked with a solution and the like including the evaluated material ABJ, whereby a potential difference is caused between the lipid film SST and the reference electrode DEN. The potential difference is determined with the evaluated material ABJ and the concentration of the solution; thus, the potential difference may be analyzed when the taste of the evaluated material ABJ is determined.

Figure 24C:
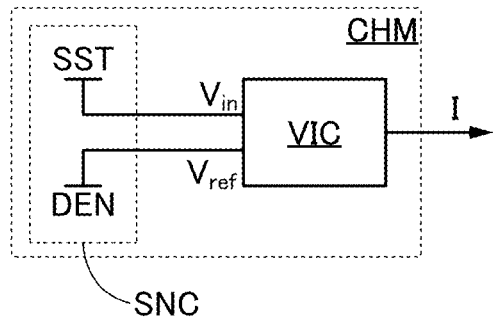
FIG. 24C is a block diagram showing a configuration example of a circuit included in an electronic device.

In particular, when the difference between the potentials obtained with the electronic device SITA in FIG. 23 is analyzed, it is preferable that the potential difference be converted into a current value to be input to the arithmetic circuit MAC. For example, the sensor portion CHM preferably has a structure illustrated in a block diagram illustrated in FIG. 24C, in which a potential $V_{in}$ obtained with the lipid film SST and a potential $V_{ref}$ obtained with the reference electrode DEN are input to a voltage-current converter circuit VIC, and the voltage-current converter circuit VIC outputs a current I in accordance with the potential difference between $V_{in}$ and $V_{ref}$. The current I is input to the arithmetic circuit MAC from the sensor portion CHM in the electronic device SITA in FIG. 23.

The voltage-current converter circuit VIC includes two input terminals and one output terminal, and has a function of converting the potential difference between the potentials input to the two input terminals into a current and outputting the current to the output terminal.

For example, a current output from the output terminal of the voltage-current converter circuit VIC is $I_{out}[i]$ before a solution and the like including the evaluated material ABJ soaks the sensor SNC[i] in FIG. 23. The current $I_{out}[i]$ flows through the wiring XCL[i] between Time T13 and Time T14 in the timing chart in FIG. 6. "Before a solution and the like including the evaluated material ABJ soaks the sensor SNC[i]" includes the case where the sensor SNC[i] is in contact with the outside air, the case where the sensor SNC[i] is in contact with a reference liquid (e.g., a solution not including the evaluated material ABJ, e.g., pure water), and the like.

For example, a current output from the output terminal of the voltage-current converter circuit VIC is $x[i]I_{out}[i]=I_{out}[i]+\Delta I_{out}[i]$ before the sensor SNC[i] in FIG. 23 is soaked with a solution including the evaluated material ABJ. The current flows through the wiring XCL[i] between Time T22 and Time T23 in the timing chart in FIG. 6.

As described above, a current from the sensor SNC[1] to the sensor SNC[m] flows from the circuit SCA to the cell array CA in the arithmetic circuit MAC, whereby the second data x[1] to x[m] corresponding to a plurality of taste data detected by the sensor SNC[1] to the sensor SNC[m] can be input to the arithmetic circuit MAC. Thus, a product-sum operation of the first data stored in the cell IM in the cell array CA and the second data can be performed. In other words, the neural network arithmetic operation can be performed using a plurality of taste data as input data.

The arithmetic operation of the neural network is a pattern recognition algorithm to a plurality of taste data detected with the sensor SNC[1] to the sensor SNC[m]. The first data (coefficient of weight) used in the neural network is stored in the node NM in the cell IM through the machine learning or the like. Thus, from the pattern of a current flowing from the circuit SCA to the cell array CA corresponding to the evaluated material ABJ, what type of taste is given to a human tongue by the evaluated material ABJ can be recognized and the result can be output from the electronic device SITA as the data DT.

Figure 25A:
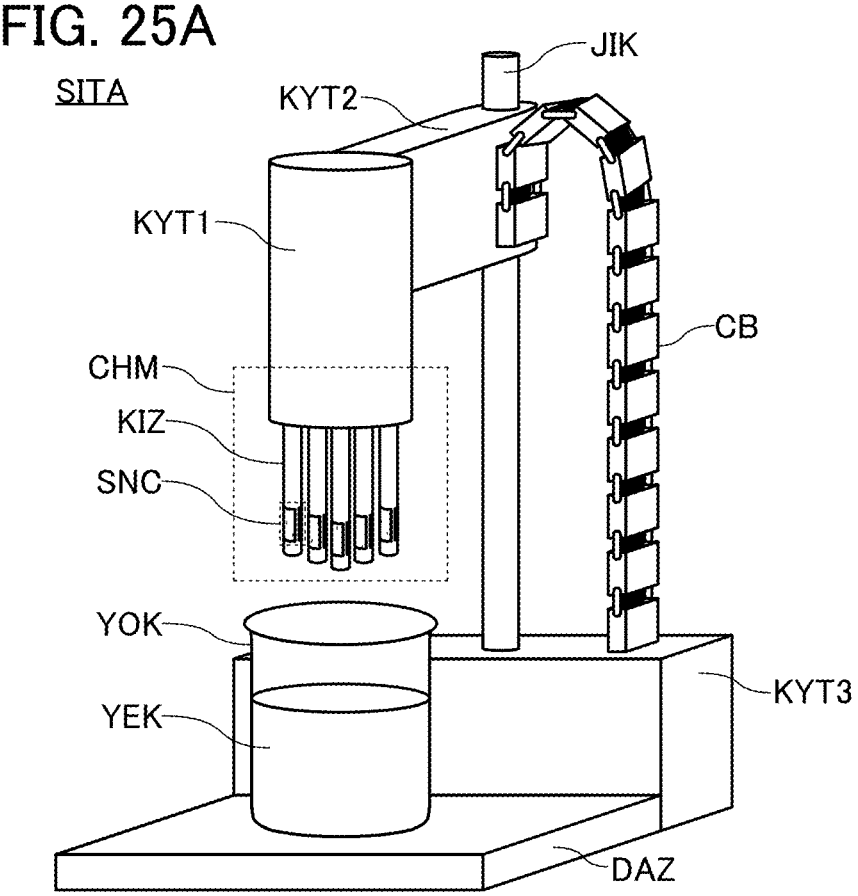
FIG. 25A is a perspective view showing a structure example of an electronic device including a taste sensor.

FIG. 25A shows a perspective view of an example of the electronic device SITA in FIG. 23. In the electronic device SITA in FIG. 25A, a plurality of sensors SNC and a plurality of base materials KIZ in FIG. 24A and FIG. 24B are provided as the sensor portion CHM; when the electronic device SITA operates, the plurality of sensors SNC are soaked with a solution YEK including the evaluated material ABJ. The electronic device SITA has a function of sensing plural kinds of taste components included in the evaluated material with the plurality of sensors SNC with a single driving.

The electronic device SITA in FIG. 25A includes a first housing KYT1, a second housing KYT2, a third housing KYT3, an axis JIK, a base DAZ, and a cable bare (registered trademark) CB in addition to the sensor SNC and the base material KIZ. FIG. 25A also illustrates a container YOK and the solution YEK including the evaluated material ABJ.

Figure 25B:
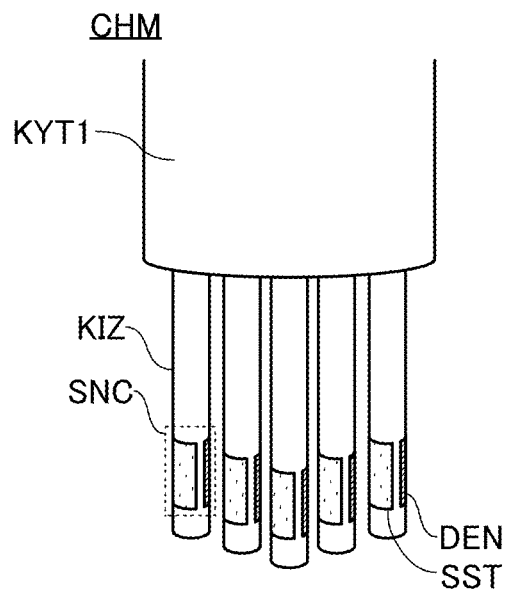
FIG. 25B and FIG. 25C are perspective views each showing a structure example of a plurality of taste sensors included in an electronic device.

FIG. 25B is an enlarged view of the sensor portion CHM of the electronic device SITA in FIG. 25A. The first housing KYT1 is a structure body to which a plurality of base materials KIZ with the sensor SNC can be attached as illustrated in FIG. 25B. One of the plurality of sensors SNC can be a sensor that detects a taste selected from one of the five basic tastes, spiciness, astringency, and the like. For example, sweetness and the like includes a plurality of taste components such as sucrose, xylitol, synthetic sweetener; the base material KIZ with the sensor SNC for each taste component to be detected is prepared. In this manner, each of a plurality of sensors SNC is a taste sensor detecting a different taste, whereby the plurality of sensors SNC can detect the taste components included in the evaluated material ABJ with a single operation of the electronic device SITA.

The first housing KYT1 can have a structure in which the wiring HAIS1 and the wiring HAIS2 illustrated in FIG. 24A are electrically connected to the internal circuit of the first housing KYT1. The first housing KYT1 and the wiring HAIS2 are not illustrated in FIG. 25B. The first housing KYT1 is structurally connected to the second housing KYT2. The electronic device SITA illustrated in FIG. 25A may have a structure in which the first housing KYT1 and the second housing KYT2 are collectively provided. The wiring HAIS1 and the wiring HAIS2 provided in the base material KIZ are electrically connected to the second housing KYT2 through the first housing KYT1.

The second housing KYT2 is a structure body which can perform an elevation and a descent along the axis JIK. For example, the second housing KYT2 includes a component for operation such as a motor, and with the component, the second housing KYT2 itself can be elevated or descended. The second housing KYT2 is elevated or descended along the axis JIK, whereby the first housing KYT1 can be elevated or descended at the same time. Thus, the sensors SNC attached to the plurality of base materials KIZ can be moved up and down.

The base DAZ and the axis JIK are structurally connected to the third housing KYT3. The third housing KYT3 may have a function of controlling the elevation and descent of the second housing KYT2. In this case, a wiring electrically connecting the third housing KYT3 and the second housing KYT2 is preferably provided.

The third housing KYT3 includes the arithmetic circuit MAC and the memory portion MEMD illustrated in FIG. 23. In this case, a wiring electrically connecting the third housing KYT3 and the sensor SNC is preferably provided. That is, the electronic device SITA may be configured to send data about an taste component included in the evaluated material detected with the sensor SNC to the third housing KYT3 and analyze the data with the arithmetic circuit MAC included in third housing KYT3.

In the case where electrical signals are transmitted through a plurality of wirings between the third housing KYT3 and the first housing KYT1 and/or the second housing KYT2, as illustrated in FIG. 25A, the electronic device SITA preferably includes a cable bare CB. The cable bare CB includes a plurality of wirings, and the plurality of wirings electrically connects the third housing KYT3 and the second housing KYT2. The plurality of wirings are bundled with the cable bare CB, so that the plurality of wirings can be prevented from coming apart even when the first housing KYT1 and the second housing KYT2 elevate and descend. In the electronic device SITA, the cable bare CB is not necessarily used. Without the cable bare CB, an FPC (Flexible Printed Circuit) can be used instead of the plurality of wirings.

In the above descriptions, the third housing KYT3 includes the arithmetic circuit MAC and the memory portion MEMD in FIG. 23; however, the structure of the electronic device including the semiconductor device of one embodiment of the present invention is not limited thereto. For example, the arithmetic circuit MAC and the memory unit MEMD in FIG. 23 may be included in the first housing KYT1 or the second housing KYT2, or the arithmetic circuit MAC and the memory portion MEMD may be included in different housings.

The base DAZ functions as a space to which the container YOK is provided. The base DAZ may function as a support to make the electronic device SITA stand alone. In the case where the second housing KYT2 does not have a function of elevating and descending along the axis JIK, the base DAZ may have a function of elevating and descending. Thus, the electronic device SITA can soak the sensor SNC with the solution YEK with the base DAZ elevating.

The structure of the electronic device including the semiconductor device of one embodiment of the present invention is not limited to FIG. 25A and FIG. 25B. The electronic device including the semiconductor device of one embodiment of the present invention may have a structure in which the structures illustrated in FIG. 25A and FIG. 25B are changed.

Figure 25C:
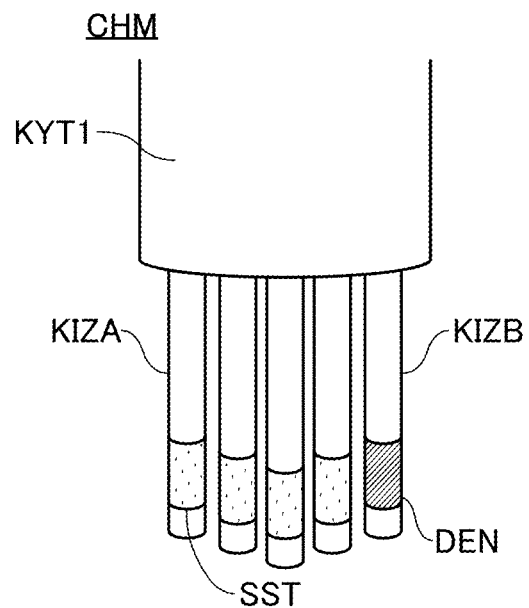

For example, the structure of the base KIZ attached to the first housing KYT1 in FIG. 25B may be changed as illustrated in FIG. 25C. FIG. 25C shows a plurality of base materials KIZA with the lipid films SST and one base material KIZB with the reference electrode DEN are attached to the first housing KYT1, for example. In other words, in the structure in FIG. 25C, reference electrodes DEN to obtain a reference potential are combined to one. Thus, the reference potential can be obtained with one reference electrode DEN (base material KIZB), whereby the number of wirings can be less than that in FIG. 25B. When the structure in FIG. 25C is used for the electronic device SITA, as for the electronic device SITA having the structure in FIG. 25B, the potential differences between the reference potential and a plurality of potentials corresponding to the evaluated material ABJ included in the solution YEK obtained with lipid films SST attached to the plurality of base materials KIZA can be obtained.

As described in this embodiment, by combining the arithmetic circuit MAC described in the above embodiment and the sensor, an electronic device including an odor sensor or a tactile sensor, or an electronic device including a taste sensor can be manufactured.

Note that this embodiment can be combined with any of the other embodiments in this specification as appropriate.

Embodiment 5

A hierarchical neural network is described in this embodiment. An arithmetic operation of a hierarchical neural network can be performed by using the semiconductor device described in the above embodiments.

<Hierarchical Neural Network>

Figure 26A:
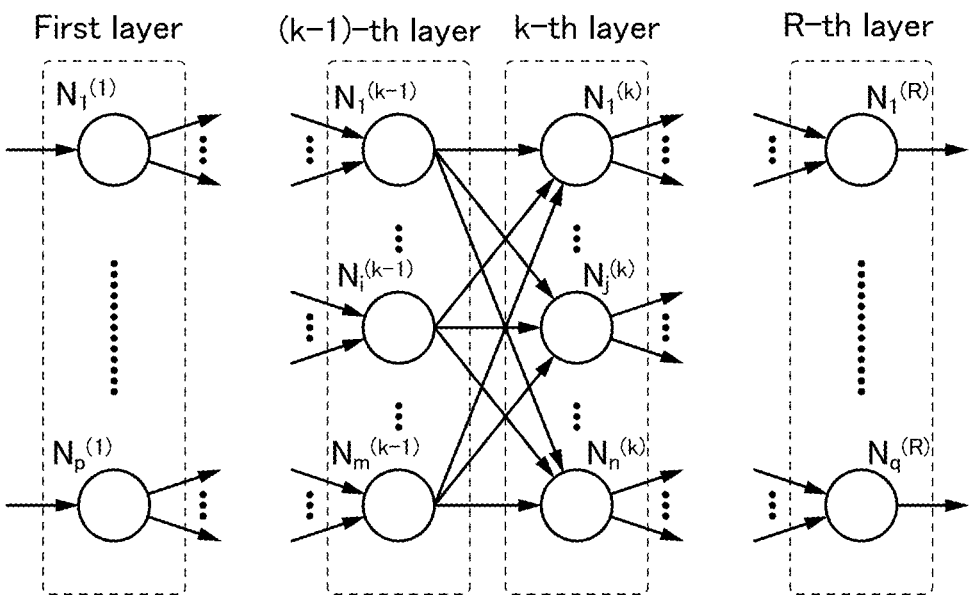
FIG. 26A and FIG. 26B are diagrams showing hierarchical neural networks.

A hierarchical neural network includes one input layer, one or a plurality of intermediate layers (hidden layers), and one output layer, for example, and is configured with a total of at least three layers. A hierarchical neural network 100 illustrated in FIG. 26A is one example, and the neural network 100 includes a first layer to an R-th layer (here, R can be an integer greater than or equal to 4). Specifically, the first layer corresponds to the input layer, the R-th layer corresponds to the output layer, and the other layers correspond to the intermediate layers. Note that FIG. 26A illustrates the (k−1)-th layer and the k-th layer (here, k is an integer greater than or equal to 3 and less than or equal to R−1) as the intermediate layers, and does not show the other intermediate layers.

Each of the layers of the neural network 100 includes one or a plurality of neurons. In FIG. 26A, the first layer includes a neuron $N_1^{(1)}$ to a neuron $N_p^{(1)}$ (here, p is an integer greater than or equal to 1); the (k−1)-th layer includes a neuron $N_1^{(k-1)}$ to a neuron $N_m^{(k-1)}$ (here, m is an integer greater than or equal to 1); the k-th layer includes a neuron $N_1^{(k)}$ to a neuron $N_n^{(k)}$ (here, n is an integer greater than or equal to 1); and the R-th layer includes a neuron $N_1^{(R)}$ to a neuron $N_q^{(R)}$ (here, q is an integer greater than or equal to 1).

FIG. 26A illustrates a neuron $N_i^{(k-1)}$ (here, i is an integer greater than or equal to 1 and less than or equal to m) in the (k−1)-th layer and a neuron $N_j^{(k)}$ (here, j is an integer greater than or equal to 1 and less than or equal to n) in the k-th layer, in addition to the neuron $N_1^{(1)}$, the neuron $N_p^{(1)}$, the neuron $N_1^{(k-1)}$, the neuron $N_m^{(k-1)}$, the neuron $N_1^{(k)}$, the neuron $N_n^{(k)}$, the neuron $N_1^{(R)}$, and the neuron $N_q^{(R)}$; the other neurons are not illustrated.

Next, signal transmission from a neuron in one layer to a neuron in the subsequent layer and signals input to and output from the neurons are described. Note that description here is made focusing on the neuron $N_j^{(k)}$ in the k-th layer.

Figure 26B:
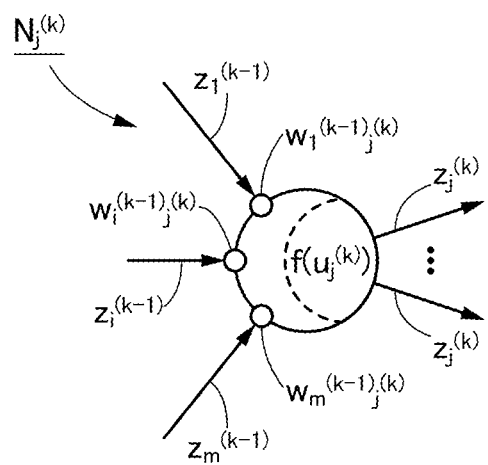

FIG. 26B illustrates the neuron $N_j^{(k)}$ in the k-th layer, signals input to the neuron $N_j^{(k)}$, and a signal output from the neuron $N_j^{(k)}$.

Specifically, $z_1^{(k-1)}$ to $z_m^{(k-1)}$ that are output signals from the neuron $N_1^{(k-1)}$ to the neuron $N_m^{(k-1)}$ in the (k−1)-th layer are output to the neuron $N_j^{(k)}$. Then, the neuron $N_j^{(k)}$ generates $z_j^{(k)}$ in accordance with $z_1^{(k-1)}$ to $z_m^{(k-1)}$, and outputs $z_j^{(k)}$ as the output signal to the neurons in the (k+1)-th layer (not illustrated).

The efficiency of transmitting a signal input from a neuron in one layer to a neuron in the subsequent layer depends on the connection strength (hereinafter, referred to as coefficient of weight) of the synapse that connects the neurons to each other. In the neural network 100, a signal output from a neuron in one layer is multiplied by the corresponding coefficient of weight and then is input to a neuron in the subsequent layer. When i is an integer greater than or equal to 1 and less than or equal to m and the coefficient of weight of the synapse between the neuron $N_i^{(k-1)}$ in the (k−1)-th layer and the neuron $N_j^{(k)}$ in the k-th layer is $w_i^{(k-1)}{}_j^{(k)}$, a signal input to the neuron $N_j^{(k)}$ in the k-th layer can be expressed with Formula (5.1).

[Formula 20]

$$w_i^{(k-1)}{}_j^{(k)} \cdot z_i^{(k-1)} \qquad (5.1)$$

That is, when the signals are transmitted from the neuron $N_1^{(k-1)}$ to the neuron $N_m^{(k-1)}$ in the (k−1)-th layer to the neuron $N_j^{(k)}$ in the k-th layer, the signals $z_1^{(k-1)}$ to $z_m^{(k-1)}$ are multiplied by respective coefficient of weights ($w_1^{(k-1)}{}_j^{(k)}$ to $w_m^{(k-1)}{}_j^{(k)}$). Then, $w_1^{(k-1)}{}_j^{(k)} \cdot z_1^{(k-1)}$ to $w_m^{(k-1)}{}_j^{(k)} \cdot z_m^{(k-1)}$ are input to the neuron $N_j^{(k)}$ in the k-th layer. At this time, the total sum $u_j^{(k)}$ of the signals input to the neuron $N_j^{(k)}$ in the k-th layer is expressed by Formula (5.2).

[Formula 21]

$$u_j^{(k)} = \sum_{i=1}^{m} w_i^{(k-1)}{}_j^{(k)} \cdot z_i^{(k-1)} \qquad (5.2)$$

In addition, a bias may be added to the product-sum result of the coefficient of weights $w_1^{((k-1)}{}_j^{(k)})$ to $w_m^{(k-1)}{}_j^{(k)}$ and the signals $z_1^{(k-1)}$ to $z_m^{(k-1)}$ of the neurons. When the bias is denoted by b, Formula (5.2) can be rewritten as the following formula.

[Formula 22]

$$u_j^{(k)} = \sum_{i=1}^{m} w_i^{(k-1)}{}_j^{(k)} \cdot z_i^{(k-1)} + b \qquad (5.3)$$

The neuron $N_j^{(k)}$ generates the output signal $z_j^{(k)}$ in accordance with $u_j^{(k)}$. Here, the output signal $z_j^{(k)}$ from the neuron $N_j^{(k)}$ is defined with the following formula.

[Formula 23]

$$z_j^{(k)} = f(u_j^{(k)}) \qquad (5.4)$$

A function $f(u_j^{(k)})$ is an activation function in a hierarchical neural network, and a step function, a linear ramp function, a sigmoid function, or the like can be used. Note that the activation function may be the same or different among all neurons. In addition, the neuron activation function may be the same or different between the layers.

Signals output from the neurons in the layers, coefficient of weights w, or bias b may be an analog value or a digital value. For example, a binary or ternary digital value may be used. A value having a larger number of bits may be used. In the case of an analog value, for example, a linear ramp function or a sigmoid function is used as the activation function. In the case of a binary digital value, a step function with an output of −1 or 1 or an output of 0 or 1 is used. Alternatively, the neurons in the layers may each output a ternary or higher-level signal; in this case, a step function with an output of −1, 0, or 1 or a step function with an output of 0, 1, or 2 is used as a ternary activation function. Furthermore, as an activation function for outputting five values, a step function with an output of −2, −1, 0, 1, or 2 may be used, for example. Using a digital value as at least one of the signals output from the neurons in the layers, the coefficient of weights w, and the bias b enables a reduction of the circuit scale, a reduction of power consumption, or an increase of operation speed, for example. Furthermore, the use of an analog value as at least one of the signal output from each neuron in the layers, the coefficient of weight w, and the bias b can improve the arithmetic operation accuracy.

The neural network 100 performs operation in which by input of an input signal to the first layer (the input layer), output signals are sequentially generated in the layers from the first layer (the input layer) to the last layer (the output layer) according to Formula (5.1), Formula (5.2) (or Formula (5.3)), and Formula (5.4) on the basis of the signals input from the previous layers, and the output signals are output to the subsequent layers. The signal output from the last layer (the output layer) corresponds to the calculation results of the neural network 100.

In the case where the arithmetic circuit MAC1 described in Embodiment 1 is used as the above-described hidden layer, the coefficient of weight $w_{s[k-1]}{}^{(k-1)}{}_{s[k]}{}^{(k)}$ (s[k-1] is an integer more than or equal to 1 and less than or equal to m, and s[k] is an integer more than or equal to n) is used as the first data, the current amount corresponding to the first data is stored in each of the cells IM in the same column sequentially, the output signal $z_{s[k-1]}{}^{(k-1)}$ from the neuron $Ns_{[k-1]}{}^{(k-1)}$ in the (k-1)-th layer is used as the second data, and the current amount corresponding to the second data is made to flow from the circuit XCS to the wiring XCL in each row, so that the product-sum of the first data and the second data can be obtained from the current amount Is input to the converter circuit ITRZ. In addition, the value of the activation function is obtained using the value of the sum of products, so that the value of the activation function can be, as a signal, the output signal $z_{s[k]}{}^{(k)}$ of the neuron $Ns_{[k]}{}^{(k)}$ in the k-th layer.

In the case where the arithmetic circuit MAC1 described in Embodiment 1 is used as the above-described output layer, the coefficient of weight $w_{s[R-1]}{}^{(R-1)}{}_{s[R]}{}^{(R)}$ (s[R-1] is an integer more than or equal to 1 and s[R] is an integer more than or equal to 1 and less than or equal to q) is used as the first data, the current amount corresponding to the first data is stored in each of the cells IM in the same column sequentially, the output signal $z_{s[R-1]}{}^{(L-1)}$ from the neuron $N_{s[R-1]}{}^{(R-1)}$ in the (R-1)-th layer is used as the second data, and the current amount corresponding to the second data is made to flow from the circuit XCS to the wiring XCL in each row, so that the sum of products of the first data and the second data can be obtained from the current amount Is input to the converter circuit ITRZ. In addition, the value of the activation function is obtained using the value of the sum of products, so that the value of the activation function can be, as a signal, the output signal $z_{s[R]}{}^{(R)}$ of the neuron $N_{s[R]}{}^{(R)}$ in the R-th layer.

Note that the input layer described in this embodiment may function as a buffer circuit that outputs an input signal to the second layer.

When the arithmetic circuit MAC2 described in Embodiment 2 in which the converter circuit ITRZD4 in FIG. 9 is used as the converter circuit ITRZD[j] is used as the hidden layer, the coefficient of weight $w_{s[k-1]}{}^{(k-1)}{}_{s[k]}{}^{(k)}$ is the first data, the amount of current corresponding to the first data is stored consecutively in the cells IM and the cells IMr of the circuit CES in the same row, an output signal $z_{s[k-1]}{}^{(k-1)}$ from the neuron $N_{s[k-1]}{}^{(k-1)}$ in the (k-1)-th layer is the second data, and the current amount corresponding to the second data flows from the circuit XCS to the wiring XCL in each row, whereby the value of the activation function corresponding to the product-sum operation of the first data and the second data from the current amounts IS and ISr input to the converter circuit ITRZD4. That is, the value can be an output signal $z_{s[k]}{}^{(k)}$ from a neuron $N_{s[k]}{}^{(k)}$ in the k-th layer as a signal. Since the converter circuit ITRZD4 outputs the current amount corresponding to the value, the output signal $z_{s[k]}{}^{(k)}$ from the neuron $N_{s[k]}{}^{(k)}$ in the k-th layer input to the (k+1)-th layer can be a current, for example. That is, in the case where the arithmetic circuit MAC2 is used as the hidden layer of the (k+1)-th layer, the output signal $z_s[k]$ (from the neuron $N_{s[k]}{}^{(k)}$ in the k-th layer input to the wiring XCL of the arithmetic circuit MAC2 is not generated in the circuit XCS but can be a current output from the converter circuit ITRZD4 of the arithmetic circuit MAC2 of the hidden layer in the k-th layer.

Figure 27:
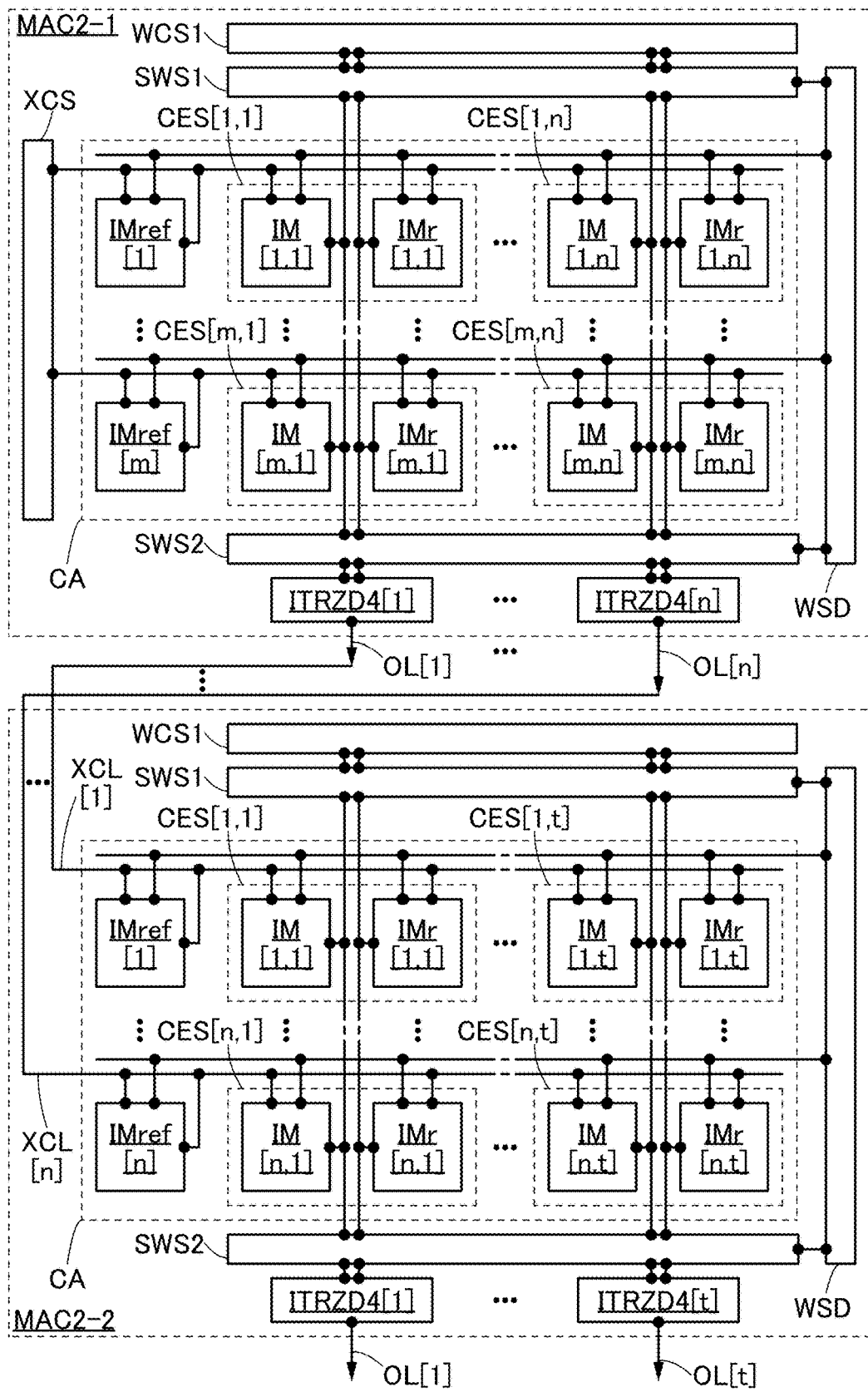
FIG. 27 is a block diagram showing a configuration example of a semiconductor device.

Specifically, by using the arithmetic circuit in FIG. 27, the arithmetic operation of the hierarchical neural network can be performed. The arithmetic circuit in FIG. 27 includes, as an example, an arithmetic circuit MAC2-1 having a configuration similar to that of the arithmetic circuit MAC2 in FIG. 7 and an arithmetic circuit MAC2-2 having a configuration where the circuit XCS is not provided in the arithmetic circuit MAC2 in FIG. 7. In the cell array CA of the arithmetic circuit MAC2-1, m×n circuits are arranged in a matrix, and in the cell array CA of the arithmetic circuit MAC2-2, n×t circuits CES (t is an integer more than or equal to 1) are arranged in a matrix. A wiring OL[1] to a wiring OL[n] of the arithmetic circuit MAC2-1 are electrically connected to a wiring XCL[1] to a wiring XCL[n] of the arithmetic circuit MAC2-2, respectively.

For example, in the arithmetic circuit MAC2-1 in FIG. 27, the coefficient of weight between the neurons in the (k-1)-th layer and the neurons in the k-th layer is the first data and stored in the circuit CES[1,1] to the circuit CES[m,n] of the cell array CA, and the output signal $z_{s[k-1]}{}^{(k-1)}$ from a neuron $N_{s[k-1]}{}^{(k-1)}$ in the (k-1)-th layer is the second data and a current amount corresponding to the second data flows from the circuit XCS to the wiring XCL in each row, whereby output signals $z_1{}^{(k)}$ to $z_n{}^{(k)}$ of a neuron $N_1{}^{(k)}$ to a neuron $N_n{}^{(k)}$ in the k-th layer can be output from the wiring OL[1] to the wiring OL[n]. The values of the output signals $z_1{}^{(k)}$ to $z_a{}^{(k)}$ can be represented as the amounts of current output from the converter circuit ITRZD4[1] to the converter circuit ITRZD4[n].

In the arithmetic circuit MAC2-2 in FIG. 27, the coefficient of weight between the neurons in the k-th layer and the neurons in the (k+1)-th layer is the first data and stored in the circuit CES[1,1] to the circuit CES[n,t] of the cell array CA; the amount of current flowing in the wiring XCL in each row, i.e., output signals $z_1{}^{(k)}$ to $z_n{}^{(k)}$ from the neuron $N_1{}^{(k)}$ to the neuron $N_n{}^{(k)}$ in the k-th layer is the second data; thus, a wiring OL[s[k+1]] (s[k+1] is an integer more than or equal to 1 and less than or equal to t) can output an output signal $z_{s[k+1]}{}^{(k+1)}$ of the neuron $N_{s[k+1]}{}^{(k+1)}$ in the (k+1)-th layer.

As described in Embodiment 2, one of the converter circuits ITRZD4 in FIG. 9, FIG. 10A, and FIG. 11A to FIG. 1C is used as the converter circuit ITRZD4[1] to the converter circuit ITRZD4[n] of the arithmetic circuit MAC2-1 in FIG. 27, whereby the converter circuit ITRZD4[1] to the converter circuit ITRZD4[n] function as ReLU functions. When the result of the product-sum operation in the circuit CES[1,j] to the circuit CES[m,j] is "negative", the amount of current flowing from the converter circuit ITRZD4 to the wiring OL[j] is preferably ideally 0. However, in some cases, a minute amount of current flows from the converter circuit ITRZD4 to the wiring OL[j], or a minute amount of current flows from the wiring OL[j] to the converter circuit ITRZD4.

Figure 28:
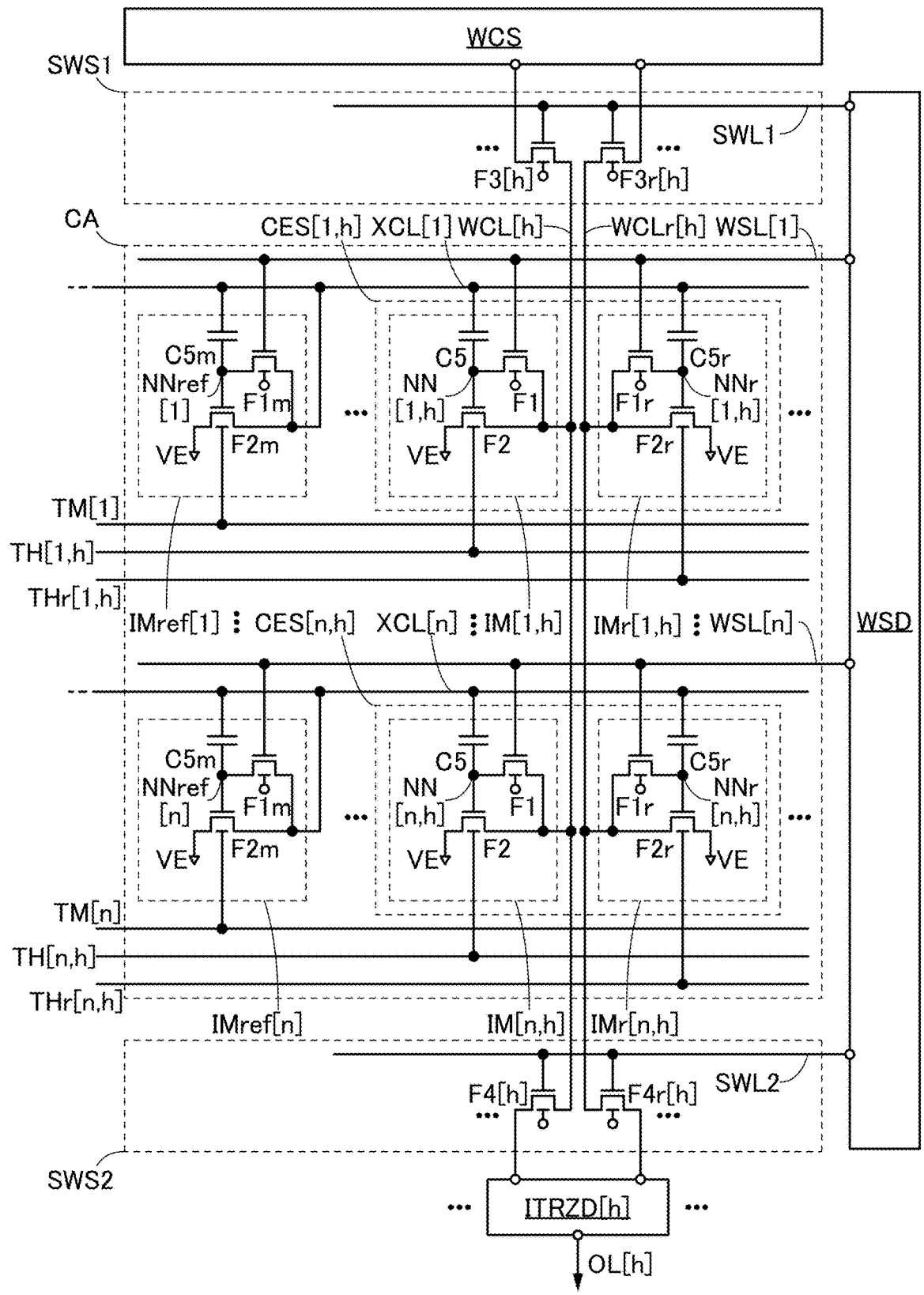
FIG. 28 is a block diagram showing a configuration example of a semiconductor device.

FIG. 28 shows a configuration example of the arithmetic circuit MAC2-2 to perform arithmetic operations in the following layers of the hierarchical neural network properly. The arithmetic circuit MAC2-2 illustrated in FIG. 28 has a configuration in which the circuit CES arranged in the cell array CA in the arithmetic circuit MAC2 in FIG. 7 is changed from an m×n matrix to an n×t matrix and the circuit XCS is not provided. The circuits CES of the cell array CA of the arithmetic circuit MAC2-2 are arranged in an n×t matrix, and thus the values in the parenthesis such as [ ] with the reference numerals of the wiring, the circuit, and the like in FIG. 28 are changed.

The arithmetic circuit MAC2-2 in FIG. 28 illustrates an example of a circuit configuration in which a wiring TM[1], a wiring TM[n], a wiring TH[1,$h$] (h is an integer more than or equal to 1 and less than or equal to t), a wiring TH[n,h], a wiring THr[1,$h$], and a wiring THr[n,h] are provided in the arithmetic circuit MAC2-2. In the arithmetic circuit MAC2-2 in FIG. 28, the wiring TM[1] is electrically connected to the back gate of the transistor F2$m$ in the cell IMref[1], the wiring TM[n] is electrically connected to the back gate of the transistor F2$m$ in the cell IMref[n], the wiring TH[1,$h$] is electrically connected to the back gate of the transistor F2 in the cell IM[1,$h$], the wiring THr[1,$h$] is electrically connected to the back gate of the transistor F2$r$ in the cell IMr[1,$h$], the wiring TH[n,h] is electrically connected to the back gate of the transistor F2 in the cell IM[n,h], and the wiring THr[n,h] is electrically connected to the back gate of the transistor F2$r$ in the cell IMr[n,h].

A low-level potential is supplied to the wiring TM[1], the wiring TM[n], the wiring TH[1,$h$], the wiring TH[n,h], the wiring THr[1,$h$], and the wiring THr[n,h], whereby the threshold voltages of the transistors whose back gates are electrically connected to these wirings can be high. This can prevent a minute current amount flowing through the wiring OL of the arithmetic circuit MAC2-1 from flowing to the wiring VE through the cell IMref of the arithmetic circuit MAC2-2. That is, the output characteristics of the converter circuit ITRZD4[1] to the converter circuit ITRZD4[$n$] can be close to ReLU functions. Thus, arithmetic operations in the following layer of the hierarchical neural network can be performed properly.

For example, the configuration of the arithmetic circuit MAC2-2 in FIG. 28 can be used for the arithmetic circuit MAC2-1 in FIG. 27. With such a configuration, the threshold voltages of the transistor F2, the transistor F2$r$, and the transistor F2$m$ which are included in the arithmetic circuit MAC2-1 can be changed as in the arithmetic circuit MAC2-2.

The wiring TM[1], the wiring TM[n], the wiring TH[1,$h$], the wiring TH[n,h], the wiring THr[1,$h$], and the wiring THr[n,h] are illustrated in FIG. 28; however, the arithmetic circuit MAC2-2 in FIG. 28 can have a configuration in which the wiring TM[1], the wiring TH[1,$h$], and the wiring THr[1,$h$] are combined to one, and the wiring TM[n], the wiring TH[n,h], and the wiring THr[n,h] are combined to one.

With the arithmetic circuit in FIG. 27, as described above, the value of the output signal of the neuron (current amount) output from the arithmetic circuit MAC2-1 can be directly input to the arithmetic circuit MAC2-2, whereby arithmetic operations of a hierarchical neural network can be performed from, for example, the first layer consecutively. The output signals from the wiring OL[1] to the wiring OL[n] of the arithmetic circuit MAC2-1 need not be temporarily stored with an external circuit or the like; thus, a memory device to temporarily store the signal need not be provided. With the arithmetic circuit in FIG. 27, the circuit area can be reduced and power necessary for transmitting data to be temporarily stored can be reduced.

Note that this embodiment can be combined with any of the other embodiments in this specification as appropriate.

Embodiment 6

This embodiment describes structure examples of the semiconductor device described in the above embodiment and structure examples of a transistor that can be applied to the semiconductor device.

<Structure Example of Semiconductor Device>

Figure 29:
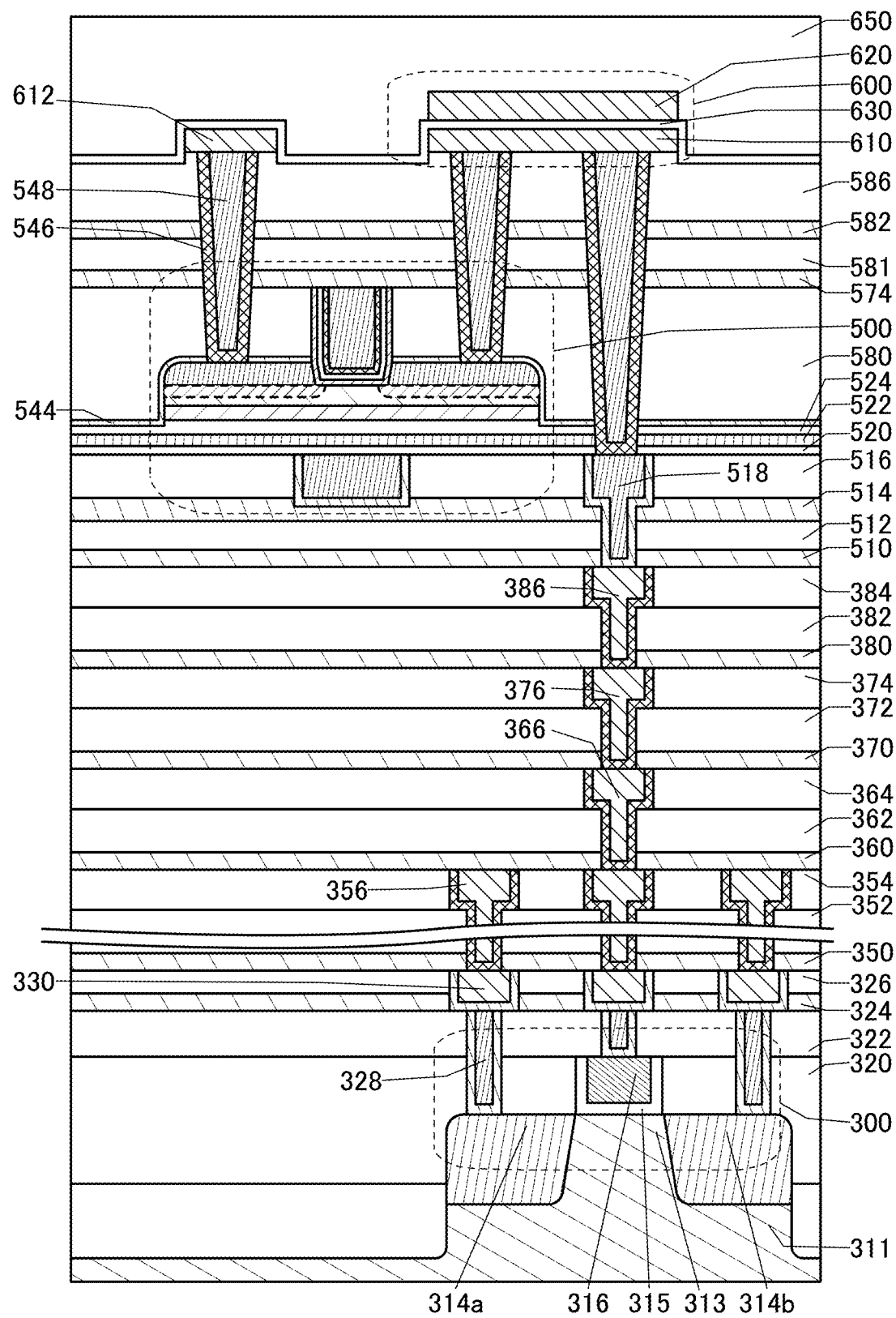
FIG. 29 is a schematic cross-sectional view showing a structure example of a semiconductor device.
Figure 31A:
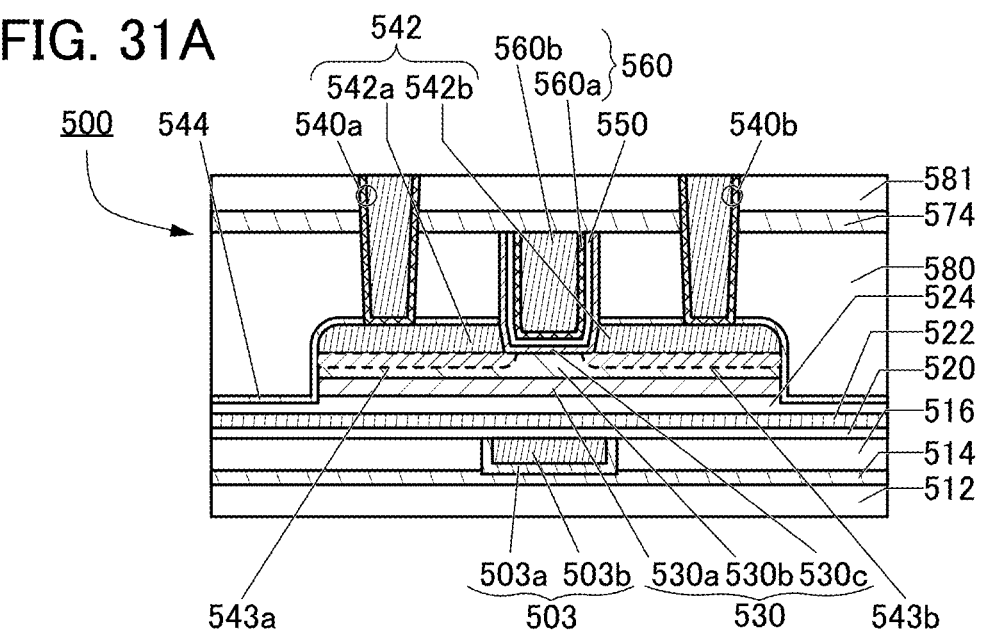
FIG. 31A to FIG. 31C are schematic cross-sectional views each showing a transistor structure example.
Figure 31B:
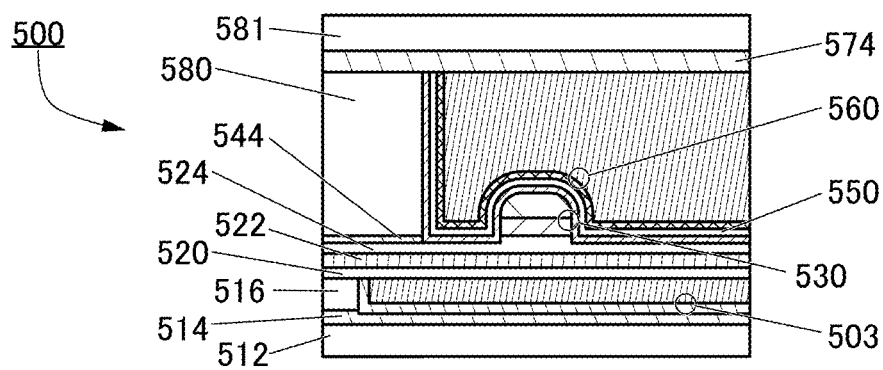
Figure 31C:
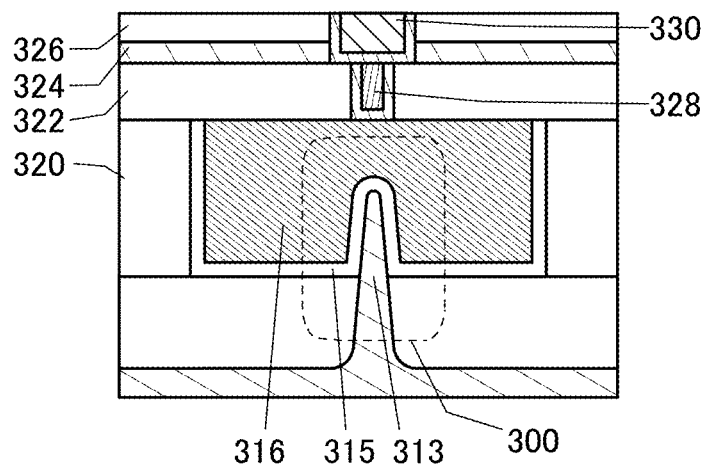

A semiconductor device illustrated in FIG. 29 includes a transistor 300, a transistor 500, and a capacitor 600. FIG. 31A is a cross-sectional view of the transistor 500 in the channel length direction, FIG. 31B is a cross-sectional view of the transistor 500 in the channel width direction, and FIG. 31C is a cross-sectional view of the transistor 300 in the channel width direction.

The transistor 500 is a transistor including a metal oxide in a channel formation region (an OS transistor). The transistor 500 has features that the off-state current is small and that the field-effect mobility does not change even at high temperatures. The transistor 500 is used as a transistor included in a semiconductor device, for example, the arithmetic circuit MAC1, the arithmetic circuit MAC1A, the arithmetic circuit MAC2, the arithmetic circuit MAC3, or the like described in the above embodiment, whereby a semiconductor device whose operating capability does not deteriorate even at a high temperature can be obtained. In particular, by utilizing the feature of a small off-state current, the transistor 500 can be used as the transistor F1 and the transistor F1$m$, and a potential written in the cell IM, the cell IMref, and the like can be stored for a long time.

The semiconductor device described in this embodiment includes the transistor 300, the transistor 500, and the capacitor 600 as illustrated in FIG. 29, for example. The transistor 500 is provided above the transistor 300, and the capacitor 600 is provided above the transistor 300 and the transistor 500, for example. The capacitor 600 can be used as the capacitor or the like included in the arithmetic circuit MAC1, the arithmetic circuit MAC1A, the arithmetic circuit circuits MAC2, the arithmetic circuit MAC3, or the like described in the above embodiment. Note that depending on a circuit configuration, the capacitor 600 illustrated in FIG. 29 is not necessarily provided.

The transistor 300 is provided over a substrate 311 and includes a conductor 316, an insulator 315, a semiconductor region 313 that is part of the substrate 311, and a low-resistance region 314$a$ and a low-resistance region 314$b$ each functioning as a source region or a drain region. Note that the transistor 300 can be used as, for example, the transistors in the arithmetic circuit MAC1, the arithmetic circuit MAC1A, the arithmetic circuit MAC2, the arithmetic circuit MAC3, or the like described in the above embodiment. Specifically, the transistor 300 can be used as a transistor included in the operational amplifier OP1 or the like included in the converter circuit ITRZ1 to the converter circuit ITRZ3 in FIG. 4A to FIG. 4C, for example. Note that FIG. 29 illustrates a structure in which a gate of the transistor 300 is electrically connected to one of a source and a drain of the transistor 500 through a pair of electrodes of the capacitor 600; however, depending on the configurations of the arithmetic circuit MAC1, the arithmetic circuit MAC1A, the arithmetic circuit MAC2, and the arithmetic circuit MAC3, and the like, a structure in which one of a source and a drain of the transistor 300 is electrically connected to one of the source and the drain of the transistor 500 through the pair of electrodes of the capacitor 600 may be employed, a structure in which one of the source and the drain of the transistor 300 is electrically connected to a gate of the transistor 500 through the pair of electrodes of the capacitor 600 may be employed, or a structure in which each terminal of the transistor 300 is not electrically connected to each terminal of the transistor 500 and each terminal of the capacitor 600 may be employed.

A semiconductor substrate (e.g., a single crystal substrate or a silicon substrate) is preferably used as the substrate 311.

In the transistor 300, the top surface and the side surface in the channel width direction of the semiconductor region 313 are covered with the conductor 316 with the insulator 315 therebetween, as illustrated in FIG. 31C. Such a Fin-type transistor 300 can have an increased effective channel width, and thus the transistor 300 can have improved on-state characteristics. In addition, contribution of an electric field of a gate electrode can be increased, so that the off-state characteristics of the transistor 300 can be improved.

Note that the transistor 300 can be either a p-channel transistor or an n-channel transistor.

A region of the semiconductor region 313 where a channel is formed, a region in the vicinity thereof, the low-resistance region 314a and the low-resistance region 314b each functioning as the source region or the drain region, or the like preferably contain a semiconductor such as a silicon-based semiconductor, further preferably contain single crystal silicon. Alternatively, the regions may be formed using a material containing Ge (germanium), SiGe (silicon germanium), GaAs (gallium arsenide), GaAlAs (gallium aluminum arsenide), GaN (gallium nitride) or the like. A structure may be employed in which silicon whose effective mass is controlled by applying stress to the crystal lattice and changing the lattice spacing is used. Alternatively, the transistor 300 may be an HEMT (High Electron Mobility Transistor) with the use of GaAs and GaAlAs, or the like.

The low-resistance region 314a and the low-resistance region 314b contain an element that imparts n-type conductivity, such as arsenic or phosphorus, or an element that imparts p-type conductivity, such as boron, in addition to a semiconductor material used for the semiconductor region 313.

For the conductor 316 functioning as a gate electrode, a semiconductor material such as silicon containing an element that imparts n-type conductivity, such as arsenic or phosphorus, or an element that imparts p-type conductivity, such as boron, or a conductive material such as a metal material, an alloy material, or a metal oxide material can be used.

Note that since the work function of a conductor depends on the material of the conductor, the threshold voltage of the transistor can be adjusted by selecting the material of the conductor. Specifically, it is preferable to use a material such as titanium nitride or tantalum nitride for the conductor. Moreover, in order to ensure both conductivity and embeddability, it is preferable to use stacked layers of metal materials such as tungsten and aluminum for the conductor, and it is particularly preferable to use tungsten in terms of heat resistance.

Figure 30:
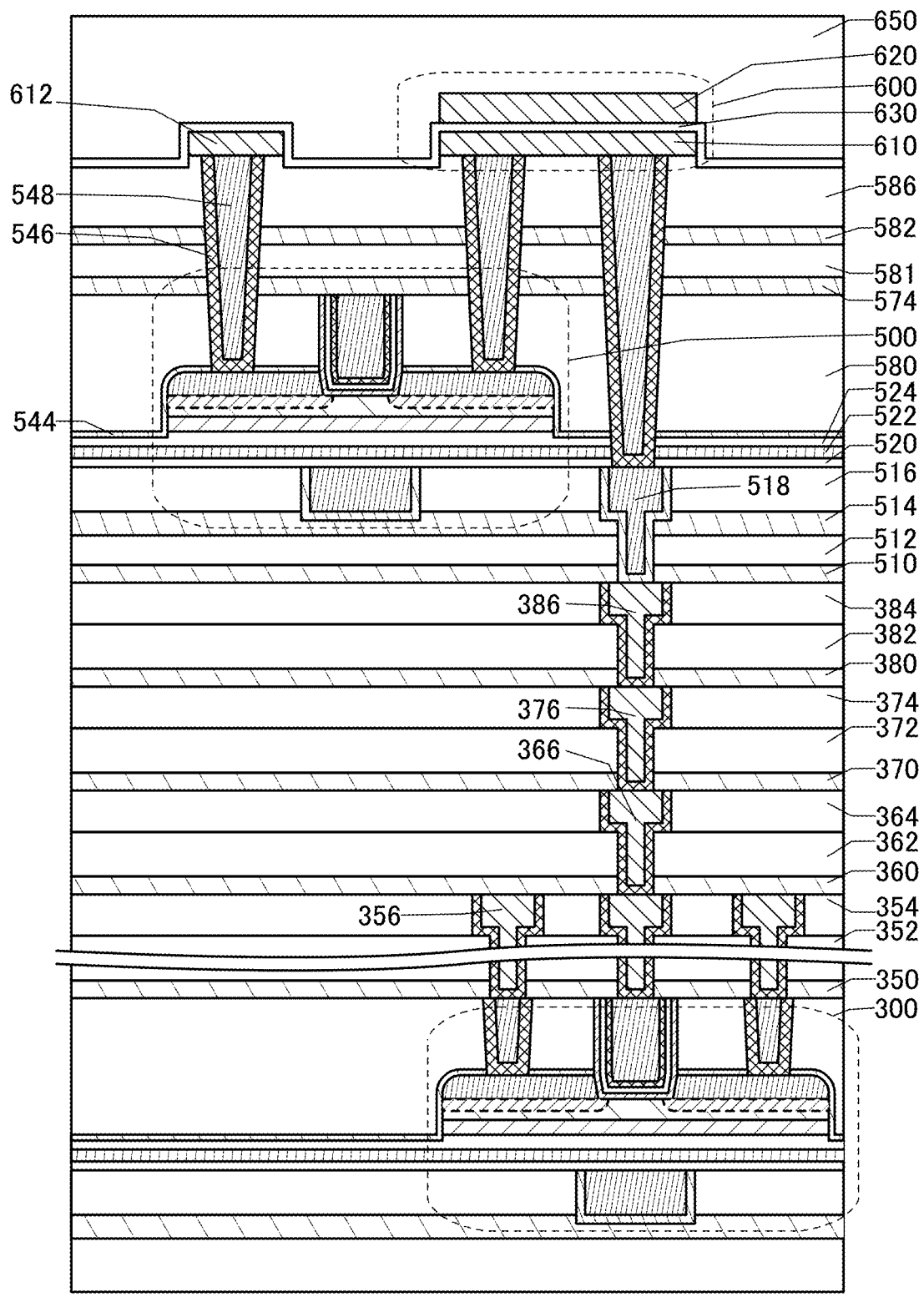
FIG. 30 is a schematic cross-sectional view showing a structure example of a semiconductor device.

Note that the transistor 300 illustrated in FIG. 29 is just an example and the structure is not limited thereto; an appropriate transistor can be used in accordance with a circuit structure or a driving method. For example, when a semiconductor apparatus is a single-polarity circuit using only OS transistors, the transistor 300 has a structure similar to the structure of the transistor 500 using an oxide semiconductor, as illustrated in FIG. 30. Note that the details of the transistor 500 are described later.

An insulator 320, an insulator 322, an insulator 324, and an insulator 326 are stacked in this order to cover the transistor 300.

For the insulator 320, the insulator 322, the insulator 324, and the insulator 326, silicon oxide, silicon oxynitride, silicon nitride oxide, silicon nitride, aluminum oxide, aluminum oxynitride, aluminum nitride oxide, or aluminum nitride can be used, for example.

Note that in this specification, silicon oxynitride refers to a material that contains oxygen at a higher proportion than nitrogen, and silicon nitride oxide refers to a material that contains nitrogen at a higher proportion than oxygen. Furthermore, in this specification, aluminum oxynitride refers to a material that contains oxygen at a higher proportion than nitrogen, and aluminum nitride oxide refers to a material that contains nitrogen at a higher proportion than oxygen.

The insulator 322 may have a function of a planarization film for planarizing a level difference caused by the transistor 300 or the like provided below the insulator 322. For example, a top surface of the insulator 322 may be planarized through planarization treatment using a chemical mechanical polishing (CMP) method or the like to increase planarity.

As the insulator 324, it is preferable to use a film having a barrier property that prevents diffusion of hydrogen or impurities from the substrate 311, the transistor 300, or the like into a region where the transistor 500 is provided.

For the film having a barrier property against hydrogen, silicon nitride formed using a CVD method can be used, for example. Here, diffusion of hydrogen to a semiconductor element including an oxide semiconductor, such as the transistor 500, degrades the characteristics of the semiconductor element in some cases. Therefore, a film that inhibits hydrogen diffusion is preferably used between the transistor 500 and the transistor 300. The film that inhibits hydrogen diffusion is specifically a film from which a small amount of hydrogen is released.

The amount of released hydrogen can be analyzed using thermal desorption spectroscopy (TDS) or the like, for example. The amount of hydrogen released from the insulator 324 that is converted into hydrogen atoms per area of the insulator 324 is less than or equal to $10 \times 10^{15}$ atoms/cm$^2$, preferably less than or equal to $5 \times 10^{15}$ atoms/cm$^2$, in the TDS analysis in a film-surface temperature range of 50° C. to 500° C., for example.

Note that the permittivity of the insulator 326 is preferably lower than that of the insulator 324. For example, the relative permittivity of the insulator 326 is preferably lower than 4, further preferably lower than 3. The relative permittivity of the insulator 326 is, for example, preferably 0.7 times or less, further preferably 0.6 times or less the relative permittivity of the insulator 324. When a material with a low permittivity is used for an interlayer film, parasitic capacitance generated between wirings can be reduced.

In addition, a conductor 328, a conductor 330, and the like that are connected to the capacitor 600 or the transistor 500 are embedded in the insulator 320, the insulator 322, the insulator 324, and the insulator 326. Note that the conductor 328 and the conductor 330 each have a function of a plug or a wiring. Furthermore, a plurality of conductors functioning as plugs or wirings is collectively denoted with the same reference numeral in some cases. Moreover, in this specification and the like, a wiring and a plug connected to the wiring may be a single component. That is, there are cases where part of a conductor functions as a wiring and part of a conductor functions as a plug.

As a material of each of plugs and wirings (e.g., the conductor 328 and the conductor 330), a single layer or a stacked layer of a conductive material such as a metal material, an alloy material, a metal nitride material, or a metal oxide material can be used. It is preferable to use a high-melting-point material that has both heat resistance and conductivity, such as tungsten or molybdenum, and it is preferable to use tungsten. Alternatively, a low-resistance conductive material such as aluminum or copper is preferably used. The use of a low-resistance conductive material can reduce wiring resistance.

A wiring layer may be provided over the insulator 326 and the conductor 330. For example, in FIG. 29, an insulator 350, an insulator 352, and an insulator 354 are stacked in this order. Furthermore, a conductor 356 is formed in the insulator 350, the insulator 352, and the insulator 354. The conductor 356 has a function of a plug or a wiring that is connected to the transistor 300. Note that the conductor 356 can be provided using a material similar to those for the conductor 328 and the conductor 330.

Note that for example, as the insulator 350, like the insulator 324, an insulator having a barrier property against hydrogen is preferably used. Furthermore, the conductor 356 preferably contains a conductor having a barrier property against hydrogen. In particular, the conductor having a barrier property against hydrogen is formed in an opening of the insulator 350 having a barrier property against hydrogen. With this structure, the transistor 300 and the transistor 500 can be separated by the barrier layer, so that diffusion of hydrogen from the transistor 300 into the transistor 500 can be inhibited.

Note that for the conductor having a barrier property against hydrogen, tantalum nitride is preferably used, for example. In addition, the use of a stack including tantalum nitride and tungsten, which has high conductivity, can inhibit diffusion of hydrogen from the transistor 300 while the conductivity of the wiring is maintained. In that case, a structure is preferable in which a tantalum nitride layer having a barrier property against hydrogen is in contact with the insulator 350 having a barrier property against hydrogen.

A wiring layer may be provided over the insulator 354 and the conductor 356. For example, in FIG. 29, an insulator 360, an insulator 362, and an insulator 364 are stacked in this order. Furthermore, a conductor 366 is formed in the insulator 360, the insulator 362, and the insulator 364. The conductor 366 has a function of a plug or a wiring. Note that the conductor 366 can be provided using a material similar to those for the conductor 328 and the conductor 330.

Note that for example, as the insulator 360, like the insulator 324, an insulator having a barrier property against hydrogen is preferably used. Furthermore, the conductor 366 preferably contains a conductor having a barrier property against hydrogen. In particular, the conductor having a barrier property against hydrogen is formed in an opening of the insulator 360 having a barrier property against hydrogen. With this structure, the transistor 300 and the transistor 500 can be separated by the barrier layer, so that diffusion of hydrogen from the transistor 300 into the transistor 500 can be inhibited.

A wiring layer may be provided over the insulator 364 and the conductor 366. For example, in FIG. 29, an insulator 370, an insulator 372, and an insulator 374 are stacked in this order. Furthermore, a conductor 376 is formed in the insulator 370, the insulator 372, and the insulator 374. The conductor 376 has a function of a plug or a wiring. Note that the conductor 376 can be provided using a material similar to those for the conductor 328 and the conductor 330.

Note that for example, as the insulator 370, like the insulator 324, an insulator having a barrier property against hydrogen is preferably used. Furthermore, the conductor 376 preferably contains a conductor having a barrier property against hydrogen. In particular, the conductor having a barrier property against hydrogen is formed in an opening of the insulator 370 having a barrier property against hydrogen. With this structure, the transistor 300 and the transistor 500 can be separated by the barrier layer, so that diffusion of hydrogen from the transistor 300 into the transistor 500 can be inhibited.

A wiring layer may be provided over the insulator 374 and the conductor 376. For example, in FIG. 29, an insulator 380, an insulator 382, and an insulator 384 are stacked in this order. Furthermore, a conductor 386 is formed in the insulator 380, the insulator 382, and the insulator 384. The conductor 386 has a function of a plug or a wiring. Note that the conductor 386 can be provided using a material similar to those for the conductor 328 and the conductor 330.

Note that for example, as the insulator 380, like the insulator 324, an insulator having a barrier property against hydrogen is preferably used. Furthermore, the conductor 386 preferably contains a conductor having a barrier property against hydrogen. In particular, the conductor having a barrier property against hydrogen is formed in an opening of the insulator 380 having a barrier property against hydrogen. With this structure, the transistor 300 and the transistor 500 can be separated by the barrier layer, so that diffusion of hydrogen from the transistor 300 into the transistor 500 can be inhibited.

Although the wiring layer including the conductor 356, the wiring layer including the conductor 366, the wiring layer including the conductor 376, and the wiring layer including the conductor 386 are described above, the semiconductor device of this embodiment is not limited thereto. Three or less wiring layers that are similar to the wiring layer including the conductor 356 may be provided, or five or more wiring layers that are similar to the wiring layer including the conductor 356 may be provided.

An insulator 510, an insulator 512, an insulator 514, and an insulator 516 are stacked sequentially and provided over the insulator 384. A substance having a barrier property against oxygen or hydrogen is preferably used for any of the insulator 510, the insulator 512, the insulator 514, and the insulator 516.

For example, as the insulator 510 and the insulator 514, it is preferable to use a film having a barrier property that prevents diffusion of hydrogen or impurities from the substrate 311, a region where the transistor 300 is provided, or the like into the region where the transistor 500 is provided. Therefore, a material similar to that for the insulator 324 can be used.

For the film having a barrier property against hydrogen, silicon nitride formed using a CVD method can be used, for example. Here, diffusion of hydrogen to a semiconductor element including an oxide semiconductor, such as the transistor 500, degrades the characteristics of the semiconductor element in some cases. Therefore, a film that inhibits hydrogen diffusion is preferably used between the transistor 500 and the transistor 300. The film that inhibits hydrogen diffusion is specifically a film from which a small amount of hydrogen is released.

As the film having a barrier property against hydrogen, a metal oxide such as aluminum oxide, hafnium oxide, or tantalum oxide is preferably used for the insulator 510 and the insulator 514, for example.

In particular, aluminum oxide has an excellent blocking effect that prevents transmission of oxygen and impurities such as hydrogen and moisture which would cause a change in the electrical characteristics of the transistor. Accordingly, aluminum oxide can prevent entry of impurities such as hydrogen and moisture into the transistor 500 in and after the manufacturing process of the transistor. In addition, release of oxygen from the oxide included in the transistor 500 can be inhibited. Therefore, aluminum oxide is suitably used for the protective film of the transistor 500.

In addition, for the insulator 512 and the insulator 516, a material similar to that for the insulator 320 can be used, for example. Furthermore, when a material with a comparatively low permittivity is used for these insulators, parasitic capacitance generated between wirings can be reduced. A silicon oxide film or a silicon oxynitride film can be used for the insulator 512 and the insulator 516, for example.

Furthermore, a conductor 518, a conductor included in the transistor 500 (a conductor 503 for example), and the like are embedded in the insulator 510, the insulator 512, the insulator 514, and the insulator 516. Note that the conductor 518 has a function of a plug or a wiring that is connected to the capacitor 600 or the transistor 300. The conductor 518 can be provided using a material similar to those for the conductor 328 and the conductor 330.

In particular, the conductor 518 in a region in contact with the insulator 510 and the insulator 514 is preferably a conductor having a barrier property against oxygen, hydrogen, and water. With this structure, the transistor 300 and the transistor 500 can be separated by the layer having a barrier property against oxygen, hydrogen, and water; hence, the diffusion of hydrogen from the transistor 300 into the transistor 500 can be inhibited.

The transistor 500 is provided above the insulator 516.

As illustrated in FIG. 31A and FIG. 31B, the transistor 500 includes the conductor 503 positioned to be embedded in the insulator 514 and the insulator 516, an insulator 520 positioned over the insulator 516 and the conductor 503, an insulator 522 positioned over the insulator 520, an insulator 524 positioned over the insulator 522, an oxide 530a positioned over the insulator 524, an oxide 530b positioned over the oxide 530a, a conductor 542a and a conductor 542b positioned apart from each other over the oxide 530b, an insulator 580 that is positioned over the conductor 542a and the conductor 542b and is provided with an opening formed to overlap with a region between the conductor 542a and the conductor 542b, an oxide 530c positioned on a bottom and a side surface of the opening, an insulator 550 positioned on a formation surface of the oxide 530c, and a conductor 560 positioned on a formation surface of the insulator 550. Note that the conductor 542a and the conductor 542b are collectively referred to as a conductor 542 in this specification and the like.

As illustrated in FIG. 31A and FIG. 31B, an insulator 544 is preferably provided between the insulator 580 and the oxide 530a, the oxide 530b, the conductor 542a, and the conductor 542b. In addition, as illustrated in FIG. 31A and FIG. 31B, the conductor 560 preferably includes a conductor 560a provided inside the insulator 550 and a conductor 560b provided to be embedded inside the conductor 560a. As illustrated in FIG. 31A and FIG. 31B, the insulator 574 is preferably positioned over the insulator 580, the conductor 560, and the insulator 550.

Note that in the following description, the oxide 530a, the oxide 530b, and the oxide 530c are sometimes collectively referred to as an oxide 530.

The structure of the transistor 500 is shown, in which the three layers of the oxide 530a, the oxide 530b, and the oxide 530c are stacked in the region where the channel is formed and in its vicinity thereof; however, one embodiment of the present invention is not limited to the structure. For example, a single layer of the oxide 530b, a two-layer structure of the oxide 530b and the oxide 530a, a two-layer structure of the oxide 530b and the oxide 530c, or a stacked-layer structure of four or more layers may be employed. Furthermore, although the conductor 560 is shown to have a stacked-layer structure of two layers in the transistor 500, one embodiment of the present invention is not limited thereto. For example, the conductor 560 may have a single-layer structure or a stacked-layer structure of three or more layers. Moreover, the transistor 500 illustrated in FIG. 29, FIG. 31A, and FIG. 31B is an example and the structure is not limited thereto; an appropriate transistor is used in accordance with a circuit configuration or a driving method.

Here, the conductor 560 functions as a gate electrode of the transistor, and each of the conductor 542a and the conductor 542b function as a source electrode or a drain electrode. As described above, the conductor 560 is formed to be embedded in the opening of the insulator 580 and the region interposed between the conductor 542a and the conductor 542b. The positions of the conductor 560, the conductor 542a, and the conductor 542b are selected in a self-aligned manner with respect to the opening in the insulator 580. That is, in the transistor 500, the gate electrode can be positioned between the source electrode and the drain electrode in a self-aligned manner. Therefore, the conductor 560 can be formed without an alignment margin, resulting in a reduction in the area occupied by the transistor 500. Accordingly, miniaturization and high integration of the semiconductor device can be achieved.

In addition, since the conductor 560 is formed in the region between the conductor 542a and the conductor 542b in a self-aligned manner, the conductor 560 does not have a region overlapping with the conductor 542a or the conductor 542b. Thus, parasitic capacitance formed between the conductor 560 and the conductor 542a and the conductor 542b can be reduced. As a result, the switching speed of the transistor 500 can be improved, and the transistor 500 can have high frequency characteristics.

The conductor 560 sometimes functions as a first gate (also referred to as top gate) electrode. In addition, the conductor 503 sometimes functions as a second gate (also referred to as bottom gate) electrode. In that case, the threshold voltage of the transistor 500 can be controlled by changing a potential applied to the conductor 503 independently of a potential applied to the conductor 560. In particular, the threshold voltage of the transistor 500 can be higher than 0 V and the off-state current can be reduced by applying a negative potential to the conductor 503. Thus, a drain current at the time when a potential applied to the conductor 560 is 0 V can be lower in the case where a negative potential is applied to the conductor 503 than in the case where a negative potential is not applied to the conductor 503.

The conductor 503 is positioned to overlap with the oxide 530 and the conductor 560. Thus, in the case where potentials are applied to the conductor 560 and the conductor 503, an electric field generated from the conductor 560 and an electric field generated from the conductor 503 are connected, so that a channel formation region formed in the oxide 530 can be covered. In this specification and the like, a transistor structure in which a channel formation region is electrically surrounded with electric fields of a first gate electrode and a second gate electrode is referred to as a surrounded channel (S-channel) structure.

In addition, the conductor 503 has a structure similar to that of the conductor 518; a conductor 503a is formed in contact with an inner wall of an opening in the insulator 514 and the insulator 516, and a conductor 503b is formed on the inner side. Although the transistor 500 having a structure in which the conductor 503a and the conductor 503b are stacked is illustrated, one embodiment of the present invention is not limited thereto. For example, the conductor 503 may be provided as a single layer or to have a stacked-layer structure of three or more layers.

Here, for the conductor 503a, a conductive material that has a function of inhibiting diffusion of impurities such as a hydrogen atom, a hydrogen molecule, a water molecule, and a copper atom (through which the impurities are unlikely to pass) is preferably used. Alternatively, it is preferable to use a conductive material that has a function of inhibiting diffusion of oxygen (e.g., at least one of an oxygen atom, an oxygen molecule, and the like) (through which the above oxygen is unlikely to pass). Note that in this specification, a function of inhibiting diffusion of impurities or oxygen means a function of inhibiting diffusion of any one or all of the above impurities and the above oxygen.

For example, when the conductor 503a has a function of inhibiting diffusion of oxygen, a reduction in conductivity of the conductor 503b due to oxidation can be inhibited.

In addition, in the case where the conductor 503 also functions as a wiring, a conductive material with high conductivity that contains tungsten, copper, or aluminum as its main component is preferably used for the conductor 503b. In addition, in the case where the conductivity of the wiring can be kept high, the conductor 503a is not necessarily provided. Note that the conductor 503b is illustrated as a single layer but may have a stacked-layer structure, for example, a stack of any of the above conductive materials and titanium or titanium nitride.

The insulator 520, the insulator 522, and the insulator 524 have a function of a second gate insulating film.

Here, as the insulator 524 that is in contact with the oxide 530, an insulator that contains oxygen more than oxygen in the stoichiometric composition is preferably used. That is, an excess-oxygen region is preferably formed in the insulator 524. When such an insulator containing excess oxygen is provided in contact with the oxide 530, oxygen vacancies in the oxide 530 can be reduced and the reliability of the transistor 500 can be improved. Note that in this specification and the like, an oxygen vacancy in the metal oxide is referred to as $V_O$ in some cases.

When impurities or oxygen vacancies (Vo) are in a channel formation region of the metal oxide included in a transistor, electrical characteristics of the transistor may vary and the reliability thereof may worsen. In some cases, hydrogen in the vicinity of an oxygen vacancy (Vo) forms a defect in which hydrogen enters an oxygen vacancy (Vo) (hereinafter sometimes referred to as VoH), which generates an electron serving as a carrier. Therefore, when the channel formation region in the oxide semiconductor includes oxygen vacancies, the transistor tends to have normally-on characteristics (a channel is generated even when no voltage is applied to the gate electrode and a current flows through the transistor). Therefore, the impurities, oxygen vacancies, and VoH are preferably reduced as much as possible in the channel formation region of the oxide semiconductor. In other words, the oxide semiconductor preferably includes an i-type (intrinsic) or substantially i-type channel formation region with a low carrier concentration.

As the insulator including an excess-oxygen region, specifically, an oxide material that releases part of oxygen by heating is preferably used. An oxide that releases oxygen by heating is an oxide film in which the amount of released oxygen converted into oxygen atoms is greater than or equal to $1.0 \times 10^{18}$ atoms/cm$^3$, preferably greater than or equal to $1.0 \times 10^{19}$ atoms/cm$^3$, further preferably greater than or equal to $2.0 \times 10^{19}$ atoms/cm$^3$ or greater than or equal to $3.0 \times 10^{20}$ atoms/cm$^3$ in TDS (Thermal Desorption Spectroscopy) analysis. Note that the temperature of the film surface in the TDS analysis is preferably in a range of higher than or equal to 100° C. and lower than or equal to 700° C., or higher than or equal to 100° C. and lower than or equal to 400° C.

One or more of heat treatment, microwave treatment, and RF treatment may be performed in a state in which the insulator including the excess-oxygen region and the oxide 530 are in contact with each other. By the treatment, water or hydrogen in the oxide 530 can be removed. For example, in the oxide 530, dehydrogenation can be performed when a reaction in which a bond of VoH is cut occurs, i.e., a reaction of "$V_OH \rightarrow V_O+H$" occurs. Part of hydrogen generated at this time is bonded to oxygen to be H$_2$O, and removed from the oxide 530 or an insulator near the oxide 530 in some cases. Part of hydrogen is diffused into or gettered (also referred to as gettering) by the conductor 542a and the conductor 542b in some cases.

For the microwave treatment, for example, an apparatus including a power supply that generates high-density plasma or an apparatus including a power supply that applies RF to the substrate side is suitably used. For example, the use of an oxygen-containing gas and high-density plasma enables high-density oxygen radicals to be generated, and application of the RF to the substrate side allows the oxygen radicals generated by the high-density plasma to be efficiently introduced into the oxide 530 or an insulator in the vicinity of the oxide 530. The pressure in the microwave treatment is higher than or equal to 133 Pa, preferably higher than or equal to 200 Pa, further preferably higher than or equal to 400 Pa. As a gas introduced into an apparatus for performing the microwave treatment, for example, oxygen and argon are used and the oxygen flow rate ($O_2/(O_2+Ar)$) is lower than or equal to 50%, preferably higher than or equal to 10% and lower than or equal to 30%.

In a manufacturing process of the transistor 500, heat treatment is preferably performed with the surface of the oxide 530 exposed. The heat treatment is performed at higher than or equal to 100° C. and lower than or equal to 450° C., preferably higher than or equal to 350° C. and lower than or equal to 400° C., for example. Note that the heat treatment is performed in a nitrogen gas or inert gas atmosphere, or an atmosphere containing an oxidizing gas at 10 ppm or more, 1% or more, or 10% or more. For example, the heat treatment is preferably performed in an oxygen atmosphere. Accordingly, oxygen can be supplied to the oxide 530 to reduce oxygen vacancies (Vo). The heat treatment may be performed under reduced pressure. Alternatively, the heat treatment may be performed in such a manner that heat treatment is performed in a nitrogen gas or inert gas atmosphere, and then another heat treatment is performed in an atmosphere containing an oxidizing gas at 10 ppm or more, 1% or more, or 10% or more in order to compensate for released oxygen. Alternatively, the heat treatment may be performed in such a manner that heat treatment is performed in an atmosphere containing an oxidizing gas at 10 ppm or more, 1% or more, or 10% or more, and then another heat treatment is successively performed in a nitrogen gas or inert gas atmosphere.

Note that the oxygen adding treatment performed on the oxide 530 can promote a reaction in which oxygen vacancies in the oxide 530 are filled with supplied oxygen, in other words, a reaction of "$V_O+O \rightarrow null$" is promoted. Furthermore, hydrogen remaining in the oxide 530 reacts with supplied oxygen, so that the hydrogen can be removed as H₂O (dehydration). This can inhibit recombination of hydrogen remaining in the oxide 530 with oxygen vacancies and formation of VoH.

In addition, in the case where the insulator 524 includes an excess-oxygen region, it is preferable that the insulator 522 have a function of inhibiting diffusion of oxygen (e.g., an oxygen atom, an oxygen molecule, or the like) (through which oxygen is unlikely to pass).

When the insulator 522 has a function of inhibiting diffusion of oxygen or impurities, oxygen contained in the oxide 530 is not diffused into the insulator 520 side, which is preferable. Furthermore, the conductor 503 can be inhibited from reacting with oxygen contained in the insulator 524 or the oxide 530.

The insulator 522 is preferably a single layer or stacked layers using an insulator containing a high-k material such as aluminum oxide, hafnium oxide, an oxide containing aluminum and hafnium (hafnium aluminate), tantalum oxide, zirconium oxide, lead zirconate titanate (PZT), strontium titanate (SrTiO₃), or (Ba,Sr)TiO₃ (BST). As miniaturization and high integration of transistors progress, a problem such as leakage current may arise because of a thinner gate insulating film. When a high-k material is used for an insulator functioning as the gate insulating film, a gate potential during transistor operation can be reduced while the physical thickness is maintained.

It is particularly preferable to use an insulator containing an oxide of one or both of aluminum and hafnium, which is an insulating material having a function of inhibiting diffusion of impurities, oxygen, and the like (through which the above oxygen is less likely to pass). As the insulator containing an oxide of one or both of aluminum and hafnium, aluminum oxide, hafnium oxide, an oxide containing aluminum and hafnium (hafnium aluminate), or the like is preferably used. In the case where the insulator 522 is formed using such a material, the insulator 522 functions as a layer that inhibits release of oxygen from the oxide 530 and mixing of impurities such as hydrogen from the periphery of the transistor 500 into the oxide 530.

Alternatively, aluminum oxide, bismuth oxide, germanium oxide, niobium oxide, silicon oxide, titanium oxide, tungsten oxide, yttrium oxide, or zirconium oxide may be added to these insulators, for example. Alternatively, these insulators may be subjected to nitriding treatment. Silicon oxide, silicon oxynitride, or silicon nitride may be stacked over the above insulator.

In addition, it is preferable that the insulator 520 be thermally stable. For example, silicon oxide and silicon oxynitride, which have thermal stability, are suitable. Furthermore, when an insulator that is a high-k material is combined with silicon oxide or silicon oxynitride, the insulator 520 having a stacked-layer structure that has thermal stability and a high relative permittivity can be obtained.

Note that in the transistor 500 in FIG. 31A and FIG. 31B, the insulator 520, the insulator 522, and the insulator 524 are shown as the second gate insulating film having a stacked-layer structure of three layers; however, the second gate insulating film may be a single layer or may have a stacked-layer structure of two layers or four or more layers. In such cases, without limitation to a stacked-layer structure formed of the same material, a stacked-layer structure formed of different materials may be employed.

In the transistor 500, a metal oxide functioning as an oxide semiconductor is preferably used as the oxide 530 including the channel formation region. For example, as the oxide 530, a metal oxide such as an In-M-Zn oxide (the element M is one or more selected from aluminum, gallium, yttrium, copper, vanadium, beryllium, boron, titanium, iron, nickel, germanium, zirconium, molybdenum, lanthanum, cerium, neodymium, hafnium, tantalum, tungsten, magnesium, and the like) is preferably used. In particular, the In-M-Zn oxide which can be used for the oxide 530 is preferably a CAAC-OS (C-Axis Aligned Crystalline Oxide Semiconductor) or a CAC-OS (Cloud-Aligned Composite Oxide Semiconductor). Furthermore, an In—Ga oxide, an In—Zn oxide, an In oxide, or the like may be used as the oxide 530.

Furthermore, a metal oxide with a low carrier concentration is preferably used in the transistor 500. In order to reduce the carrier concentration of the metal oxide, the concentration of impurities in the metal oxide is reduced so that the density of defect states can be reduced. In this specification and the like, a state with a low impurity concentration and a low density of defect states is referred to as a highly purified intrinsic or substantially highly purified intrinsic state. Examples of impurities in a metal oxide include hydrogen, nitrogen, alkali metal, alkaline earth metal, iron, nickel, and silicon.

In particular, hydrogen contained in a metal oxide reacts with oxygen bonded to a metal atom to become water, and thus forms oxygen vacancies in the metal oxide in some cases. In the case where hydrogen enters an oxygen vacancy in the oxide 530, the oxygen vacancy and the hydrogen are bonded to each other to form VoH in some cases. The VoH serves as a donor and an electron that is a carrier is generated in some cases. In other cases, bonding of part of hydrogen to oxygen bonded to a metal atom generates electrons serving as carriers. Thus, a transistor using a metal oxide containing a large amount of hydrogen is likely to have normally-on characteristics. Moreover, hydrogen in a metal oxide easily moves by stress such as heat and an electric field; thus, the reliability of a transistor may be low when the metal oxide contains a plenty of hydrogen. In one embodiment of the present invention, VoH in the oxide 530 is preferably reduced as much as possible so that the oxide 530 becomes a highly purified intrinsic or substantially highly purified intrinsic oxide. It is important to remove impurities such as moisture and hydrogen in a metal oxide (sometimes described as dehydration or dehydrogenation treatment) and to compensate for oxygen vacancies by supplying oxygen to the metal oxide (sometimes described as oxygen supplying treatment) to obtain a metal oxide whose VoH is sufficiently reduced. When a metal oxide in which impurities such as VoH are sufficiently reduced is used for a channel formation region of a transistor, stable electrical characteristics can be given.

A defect in which hydrogen has entered an oxygen vacancy can function as a donor of a metal oxide. However, it is difficult to evaluate the defects quantitatively. Thus, the metal oxide is sometimes evaluated on the basis of not its donor concentration but its carrier concentration. Therefore, in this specification and the like, the carrier concentration assuming the state where an electric field is not applied is sometimes used, instead of the donor concentration, as the parameter of the metal oxide. That is, "carrier concentration" in this specification and the like can be replaced with "donor concentration" in some cases.

Consequently, when a metal oxide is used for the oxide 530, hydrogen in the metal oxide is preferably reduced as much as possible. Specifically, the hydrogen concentration of the metal oxide obtained using secondary ion mass spectrometry (SIMS) is set lower than $1\times10^{20}$ atoms/cm³, preferably lower than $1\times10^{19}$ atoms/cm³, further preferably lower than $5\times10^{18}$ atoms/cm³, still further preferably lower than $1\times10^{18}$ atoms/cm$^3$. When a metal oxide with a sufficiently low concentration of impurities such as hydrogen is used for a channel formation region of a transistor, the transistor can have stable electrical characteristics.

In the case where a metal oxide is used as the oxide 530, the metal oxide is an intrinsic (also referred to as i-type) or substantially intrinsic semiconductor that has a large band gap, and the carrier concentration of the metal oxide in the channel formation region is preferably lower than $1\times10^{18}$ cm$^{-3}$, further preferably lower than $1\times10^{17}$ cm$^{-3}$, still further preferably lower than $1\times10^{16}$ cm$^{-3}$, yet further preferably lower than $1\times10^{13}$ cm$^{-3}$, yet still further preferably lower than $1\times10^{12}$ cm$^{-3}$. Note that the lower limit of the carrier concentration of the metal oxide in the channel formation region is not particularly limited and can be, for example, $1\times10^{-9}$ cm$^{-3}$.

In the case where a metal oxide is used as the oxide 530, contact between the oxide 530 and each of the conductor 542a and the conductor 542b may diffuse oxygen in the oxide 530 into the conductor 542a and the conductor 542b, resulting in oxidation of the conductor 542a and the conductor 542b. It is highly possible that oxidation of the conductor 542a and the conductor 542b lowers the conductivity of the conductor 542a and the conductor 542b. Note that diffusion of oxygen from the oxide 530 into the conductor 542a and the conductor 542b can be rephrased as absorption of oxygen in the oxide 530 by the conductor 542a and the conductor 542b.

When oxygen in the oxide 530 is diffused into the conductor 542a and the conductor 542b, a different layer is sometimes formed between the conductor 542a and the oxide 530b and between the conductor 542b and the oxide 530b. The different layer contains a larger amount of oxygen than the conductor 542a and the conductor 542b and thus presumably has an insulating property. In this case, a three-layer structure of the conductor 542a or the conductor 542b, the different layer, and the oxide 530b can be regarded as a three-layer structure of a metal, an insulator, and a semiconductor and is sometimes referred to as a MIS (Metal-Insulator-Semiconductor) structure or referred to as a diode-connected structure mainly formed of the MIS structure.

The above different layer is not necessarily formed between the oxide 530b and the conductor 542a and the conductor 542b; for example, the different layer may be formed between the oxide 530c and the conductor 542a and the conductor 542b, or between the oxide 530b and the conductor 542a and the conductor 542b, and between the oxide 530c and the conductor 542a and the conductor 542b.

The metal oxide functioning as the channel formation region in the oxide 530 has a band gap of preferably 2 eV or higher, further preferably 2.5 eV or higher. With use of a metal oxide having such a wide band gap, the off-state current of the transistor can be reduced.

When the oxide 530 includes the oxide 530a under the oxide 530b, it is possible to inhibit diffusion of impurities into the oxide 530b from the components formed below the oxide 530a. Moreover, including the oxide 530c over the oxide 530b makes it possible to inhibit diffusion of impurities into the oxide 530b from the components formed above the oxide 530c.

Note that the oxide 530 preferably has a stacked-layer structure of a plurality of oxide layers that differ in the atomic ratio of metal atoms. Specifically, the atomic ratio of the element M to the constituent elements in the metal oxide used as the oxide 530a is preferably higher than the atomic ratio of the element M to the constituent elements in the metal oxide used as the oxide 530b. In addition, the atomic ratio of the element M to In in the metal oxide used as the oxide 530a is preferably higher than the atomic ratio of the element M to In in the metal oxide used as the oxide 530b. Furthermore, the atomic ratio of In to the element M in the metal oxide used as the oxide 530b is preferably higher than the atomic ratio of In to the element M in the metal oxide used as the oxide 530a. As the oxide 530c, it is possible to use a metal oxide that can be used as the oxide 530a or the oxide 530b.

Specifically, as the oxide 530a, a metal oxide in which an atomic ratio of In to Ga and Zn is In:Ga:Zn=1:3:4 or 1:1:0.5 is favorably used. In addition, as the oxide 530b, a metal oxide in which an atomic ratio of In to Ga and Zn is In:Ga:Zn=4:2:3 or 1:1:1 is favorably used. In addition, as the oxide 530c, a metal oxide in which an atomic ratio of In to Ga and Zn is In:Ga:Zn=1:3:4 or an atomic ratio of Ga to Zn is Ga:Zn=2:1 or Ga:Zn=2:5 is favorably used. Specific examples of the case where the oxide 530c has a stacked-layer structure include a stacked-layer structure of a layer in which an atomic ratio of In to Ga and Zn is In:Ga:Zn=4:2:3 and a layer with In:Ga:Zn=1:3:4; a stacked-layer structure of a layer in which an atomic ratio of Ga to Zn is Ga:Zn=2:1 and a layer in which an atomic ratio of In to Ga and Zn is In:Ga:Zn=4:2:3; a stacked-layer structure of a layer in which an atomic ratio of Ga to Zn is Ga:Zn=2:5 and a layer in which an atomic ratio of In to Ga and Zn is In:Ga:Zn=4:2:3; and a stacked-layer structure of gallium oxide and a layer in which an atomic ratio of In to Ga and Zn is In:Ga:Zn=4:2:3.

For example, in the case where the atomic ratio of In to the element M in the metal oxide used as the oxide 530a is lower than the atomic ratio of In to the element M in the metal oxide used as the oxide 530b, an In—Ga—Zn oxide having a composition with an atomic ratio of In:Ga:Zn=5:1:6 or a neighborhood thereof, In:Ga:Zn=5:1:3 or a neighborhood thereof, In:Ga:Zn=10:1:3 or a neighborhood thereof, or the like can be used as the oxide 530b.

As the oxide 530b, it is also possible to use a metal oxide having a composition of In:Zn=2:1, a composition of In:Zn=5:1, a composition of In:Zn=10:1, or a composition in the neighborhood of any one of these compositions, other than the above-described compositions.

These oxide 530a, the oxide 530b, and the oxide 530c are preferably combined to satisfy the above relation of the atomic ratios. For example, it is preferable that the oxide 530a and the oxide 530c each be a metal oxide having a composition of In:Ga:Zn=1:3:4 or a composition in the neighborhood thereof and the oxide 530b be a metal oxide having a composition of In:Ga:Zn=4:2:3 to 4:2:4.1 or a composition in the neighborhood thereof. Note that the above composition represents the atomic ratio of an oxide formed over a base or the atomic ratio of a sputtering target. Moreover, it is suitable that the proportion of In is increased in the composition of the oxide 530b because the transistor can have a higher on-state current, higher field-effect mobility, or the like.

In addition, the energy of the conduction band minimum of each of the oxide 530a and the oxide 530c is preferably higher than the energy of the conduction band minimum of the oxide 530b. In other words, the electron affinity of each of the oxide 530a and the oxide 530c is preferably smaller than the electron affinity of the oxide 530b.

Here, the energy level of the conduction band minimum gradually changes at junction portions of the oxide 530a, the oxide 530b, and the oxide 530c. In other words, the energy level of the conduction band minimum at the junction portions of the oxide 530a, the oxide 530b, and the oxide 530c continuously changes or is continuously connected. To change the energy level gradually, the densities of defect states in mixed layers formed at an interface between the oxide 530a and the oxide 530b and an interface between the oxide 530b and the oxide 530c are favorably made low.

Specifically, when the oxide 530a and the oxide 530b or the oxide 530b and the oxide 530c contain a common element (as a main component) in addition to oxygen, a mixed layer with a low density of defect states can be formed. For example, in the case where the oxide 530b is an In—Ga—Zn oxide, it is preferable to use an In—Ga—Zn oxide, a Ga—Zn oxide, gallium oxide, or the like as the oxide 530a and the oxide 530c.

At this time, the oxide 530b serves as a main carrier path. When the oxide 530a and the oxide 530c have the above structure, the density of defect states at the interface between the oxide 530a and the oxide 530b and the interface between the oxide 530b and the oxide 530c can be made low. Thus, the influence of interface scattering on carrier conduction is small, and the transistor 500 can have a high on-state current.

The conductor 542a and the conductor 542b functioning as the source electrode and the drain electrode are provided over the oxide 530b. For the conductor 542a and the conductor 542b, it is preferable to use a metal element selected from aluminum, chromium, copper, silver, gold, platinum, tantalum, nickel, titanium, molybdenum, tungsten, hafnium, vanadium, niobium, manganese, magnesium, zirconium, beryllium, indium, ruthenium, iridium, strontium, and lanthanum; an alloy containing the above metal element; an alloy containing a combination of the above metal elements; or the like. For example, it is preferable to use tantalum nitride, titanium nitride, tungsten, a nitride containing titanium and aluminum, a nitride containing tantalum and aluminum, ruthenium oxide, ruthenium nitride, an oxide containing strontium and ruthenium, an oxide containing lanthanum and nickel, or the like. Tantalum nitride, titanium nitride, a nitride containing titanium and aluminum, a nitride containing tantalum and aluminum, ruthenium oxide, ruthenium nitride, an oxide containing strontium and ruthenium, and an oxide containing lanthanum and nickel are preferable because they are oxidation-resistant conductive materials or materials that maintain their conductivity even after absorbing oxygen. Furthermore, a metal nitride film of tantalum nitride or the like is preferable because it has a barrier property against hydrogen or oxygen.

In addition, although the conductor 542a and the conductor 542b each having a single-layer structure are illustrated in FIG. 31A and FIG. 31B, a stacked-layer structure of two or more layers may be employed. For example, it is preferable to stack a tantalum nitride film and a tungsten film. Alternatively, a titanium film and an aluminum film may be stacked. Alternatively, a two-layer structure where an aluminum film is stacked over a tungsten film, a two-layer structure where a copper film is stacked over a copper-magnesium-aluminum alloy film, a two-layer structure where a copper film is stacked over a titanium film, or a two-layer structure where a copper film is stacked over a tungsten film may be employed.

Other examples include a three-layer structure where a titanium film or a titanium nitride film is formed, an aluminum film or a copper film is stacked over the titanium film or the titanium nitride film, and a titanium film or a titanium nitride film is formed over the aluminum film or the copper film; and a three-layer structure where a molybdenum film or a molybdenum nitride film is formed, an aluminum film or a copper film is stacked over the molybdenum film or the molybdenum nitride film, and a molybdenum film or a molybdenum nitride film is formed over the aluminum film or the copper film. Note that a transparent conductive material containing indium oxide, tin oxide, or zinc oxide may be used.

As illustrated in FIG. 31A, a region 543a and a region 543b are sometimes formed as low-resistance regions at an interface between the oxide 530 and the conductor 542a (the conductor 542b) and in the vicinity of the interface. In that case, the region 543a functions as one of a source region and a drain region, and the region 543b functions as the other of the source region and the drain region. Furthermore, the channel formation region is formed in a region between the region 543a and the region 543b.

When the conductor 542a (the conductor 542b) is provided to be in contact with the oxide 530, the oxygen concentration in the region 543a (the region 543b) sometimes decreases. In addition, a metal compound layer that contains the metal contained in the conductor 542a (the conductor 542b) and the component of the oxide 530 is sometimes formed in the region 543a (the region 543b). In such a case, the carrier concentration of the region 543a (the region 543b) increases, and the region 543a (the region 543b) becomes a low-resistance region.

The insulator 544 is provided to cover the conductor 542a and the conductor 542b and inhibits oxidation of the conductor 542a and the conductor 542b. At this time, the insulator 544 may be provided to cover a side surface of the oxide 530 and to be in contact with the insulator 524.

A metal oxide containing one or more selected from hafnium, aluminum, gallium, yttrium, zirconium, tungsten, titanium, tantalum, nickel, germanium, neodymium, lanthanum, magnesium, and the like can be used as the insulator 544. Moreover, silicon nitride oxide, silicon nitride, or the like can be used as the insulator 544.

It is particularly preferable to use an insulator containing an oxide of one or both of aluminum and hafnium, such as aluminum oxide, hafnium oxide, or an oxide containing aluminum and hafnium (hafnium aluminate), as the insulator 544. In particular, hafnium aluminate has higher heat resistance than a hafnium oxide film. Therefore, hafnium aluminate is preferable because it is unlikely to be crystallized by heat treatment in a later step. Note that the insulator 544 is not an essential component when the conductor 542a and the conductor 542b are oxidation-resistant materials or do not significantly lose the conductivity even after absorbing oxygen. Design is appropriately set in consideration of required transistor characteristics.

With the insulator 544, diffusion of impurities such as water and hydrogen contained in the insulator 580 into the oxide 530b through the oxide 530c and the insulator 550 can be inhibited. Furthermore, oxidation of the conductor 560 due to excess oxygen contained in the insulator 580 can be inhibited.

The insulator 550 functions as a first gate insulating film. The insulator 550 is preferably positioned in contact with the inner side (the top surface and the side surface) of the oxide 530c. Like the insulator 524 described above, the insulator 550 is preferably formed using an insulator that contains excess oxygen and releases oxygen by heating.

Specifically, it is possible to use any of silicon oxide, silicon oxynitride, silicon nitride oxide, silicon nitride, silicon oxide to which fluorine is added, silicon oxide to which carbon is added, silicon oxide to which carbon and nitrogen are added, and porous silicon oxide, each of which contains excess oxygen. In particular, silicon oxide and silicon oxynitride are preferable because they are thermally stable.

When an insulator from which oxygen is released by heating is provided as the insulator 550 in contact with the top surface of the oxide 530c, oxygen can be effectively supplied from the insulator 550 to the channel formation region of the oxide 530b through the oxide 530c. Furthermore, as in the insulator 524, the concentration of impurities such as water or hydrogen in the insulator 550 is preferably lowered. The thickness of the insulator 550 is preferably greater than or equal to 1 nm and less than or equal to 20 nm.

To efficiently supply excess oxygen contained in the insulator 550 to the oxide 530, a metal oxide may be provided between the insulator 550 and the conductor 560. The metal oxide preferably inhibits diffusion of oxygen from the insulator 550 to the conductor 560. Providing the metal oxide that inhibits diffusion of oxygen inhibits diffusion of excess oxygen from the insulator 550 to the conductor 560. That is, reduction in the amount of excess oxygen supplied to the oxide 530 can be inhibited. Moreover, oxidation of the conductor 560 due to excess oxygen can be inhibited. For the metal oxide, a material that can be used for the insulator 544 is used.

Note that the insulator 550 may have a stacked-layer structure like the second gate insulating film. As miniaturization and high integration of transistors progress, a problem such as leakage current may arise because of a thinner gate insulating film; for that reason, when the insulator functioning as a gate insulating film has a stacked-layer structure of a high-k material and a thermally stable material, a gate potential at the time when the transistor operates can be lowered while the physical thickness of the gate insulating film is maintained. Furthermore, the stacked-layer structure can be thermally stable and have a high relative permittivity.

Although the conductor 560 functioning as the first gate electrode has a two-layer structure in FIG. 31A and FIG. 31B, the conductor 560 may have a single-layer structure or a stacked-layer structure of three or more layers.

For the conductor 560a, it is preferable to use a conductive material having a function of inhibiting diffusion of impurities such as a hydrogen atom, a hydrogen molecule, a water molecule, a nitrogen atom, a nitrogen molecule, a nitrogen oxide molecule ($N_2O$, NO, $NO_2$, and the like), and a copper atom. Alternatively, it is preferable to use a conductive material having a function of inhibiting diffusion of oxygen (e.g., at least one of an oxygen atom, an oxygen molecule, and the like). When the conductor 560a has a function of inhibiting diffusion of oxygen, it is possible to inhibit a reduction in conductivity of the conductor 560b due to oxidation caused by oxygen contained in the insulator 550. As a conductive material having a function of inhibiting oxygen diffusion, tantalum, tantalum nitride, ruthenium, or ruthenium oxide is preferably used, for example. For the conductor 560a, the oxide semiconductor that can be used as the oxide 530 can be used. In that case, when the conductor 560b is deposited by a sputtering method, the conductor 560a can have a reduced electrical resistance value to be a conductor. Such a conductor can be referred to as an OC (Oxide Conductor) electrode.

In addition, a conductive material containing tungsten, copper, or aluminum as its main component is preferably used for the conductor 560b. Furthermore, the conductor 560b also functions as a wiring and thus a conductor having high conductivity is preferably used as the conductor 560b. For example, a conductive material containing tungsten, copper, or aluminum as its main component can be used. Moreover, the conductor 560b may have a stacked-layer structure, for example, a stacked-layer structure of the above conductive material and titanium or titanium nitride.

The insulator 580 is provided over the conductor 542a and the conductor 542b with the insulator 544 therebetween. The insulator 580 preferably includes an excess-oxygen region. For example, the insulator 580 preferably contains silicon oxide, silicon oxynitride, silicon nitride oxide, silicon nitride, silicon oxide to which fluorine is added, silicon oxide to which carbon is added, silicon oxide to which carbon and nitrogen are added, porous silicon oxide, a resin, or the like. In particular, silicon oxide and silicon oxynitride are preferable because they are thermally stable. In particular, silicon oxide and porous silicon oxide are preferable because an excess-oxygen region can be easily formed in a later step.

The insulator 580 preferably includes an excess-oxygen region. When the insulator 580 from which oxygen is released by heating is provided in contact with the oxide 530c, oxygen in the insulator 580 can be efficiently supplied to the oxide 530 through the oxide 530c. The concentration of impurities such as water or hydrogen in the insulator 580 is preferably lowered.

The opening of the insulator 580 is formed to overlap with the region between the conductor 542a and the conductor 542b. Accordingly, the conductor 560 is formed to be embedded in the opening in the insulator 580 and the region sandwiched between the conductor 542a and the conductor 542b.

The gate length needs to be short for miniaturization of the semiconductor device, but it is necessary to prevent a reduction in conductivity of the conductor 560. When the conductor 560 is made thick to achieve this, the conductor 560 might have a shape with a high aspect ratio. In this embodiment, the conductor 560 is provided to be embedded in the opening of the insulator 580; thus, even when the conductor 560 has a shape with a high aspect ratio, the conductor 560 can be formed without collapsing during the process.

The insulator 574 is preferably provided in contact with a top surface of the insulator 580, a top surface of the conductor 560, and a top surface of the insulator 550. When the insulator 574 is deposited using a sputtering method, excess-oxygen regions can be provided in the insulator 550 and the insulator 580. Accordingly, oxygen can be supplied from the excess-oxygen regions to the oxide 530.

For example, a metal oxide containing one or more selected from hafnium, aluminum, gallium, yttrium, zirconium, tungsten, titanium, tantalum, nickel, germanium, magnesium, and the like can be used as the insulator 574.

In particular, aluminum oxide has a high barrier property, and even a thin aluminum oxide film having a thickness of greater than or equal to 0.5 nm and less than or equal to 3.0 nm can inhibit diffusion of hydrogen and nitrogen. Accordingly, aluminum oxide deposited using a sputtering method serves as an oxygen supply source and can also have a function of a barrier film against impurities such as hydrogen.

In addition, an insulator 581 functioning as an interlayer film is preferably provided over the insulator 574. As in the insulator 524 and the like, the concentration of impurities such as water or hydrogen in the insulator 581 is preferably lowered.

Furthermore, a conductor 540a and a conductor 540b are positioned in openings formed in the insulator 581, the insulator 574, the insulator 580, and the insulator 544. The conductor 540a and the conductor 540b are provided to face each other with the conductor 560 therebetween. The structures of the conductor 540a and the conductor 540b are similar to structures of a conductor 546 and a conductor 548 that will be described later.

An insulator 582 is provided over the insulator 581. A substance having a barrier property against oxygen or hydrogen is preferably used for the insulator 582. Therefore, a material similar to that for the insulator 514 can be used for the insulator 582. For the insulator 582, a metal oxide such as aluminum oxide, hafnium oxide, or tantalum oxide is preferably used, for example.

In particular, aluminum oxide has an excellent blocking effect that prevents transmission of oxygen and impurities such as hydrogen and moisture which would cause a change in the electrical characteristics of the transistor. Accordingly, aluminum oxide can prevent entry of impurities such as hydrogen and moisture into the transistor 500 in and after the manufacturing process of the transistor. In addition, release of oxygen from the oxide included in the transistor 500 can be inhibited. Therefore, aluminum oxide is suitably used for the protective film of the transistor 500.

In addition, an insulator 586 is provided over the insulator 582. For the insulator 586, a material similar to that for the insulator 320 can be used. Furthermore, when a material with a comparatively low permittivity is used for these insulators, parasitic capacitance generated between wirings can be reduced. A silicon oxide film, a silicon oxynitride film, or the like can be used for the insulator 586, for example.

Furthermore, the conductor 546, the conductor 548, and the like are embedded in the insulator 520, the insulator 522, the insulator 524, the insulator 544, the insulator 580, the insulator 574, the insulator 581, the insulator 582, and the insulator 586.

The conductor 546 and the conductor 548 have functions of plugs or wirings that are connected to the capacitor 600, the transistor 500, or the transistor 300. The conductor 546 and the conductor 548 can be provided using a material similar to those for the conductor 328 and the conductor 330.

Note that after the transistor 500 is formed, an opening may be formed to surround the transistor 500 and an insulator having a high barrier property against hydrogen or water may be formed to cover the opening. Surrounding the transistor 500 with the insulator having a high barrier property can prevent entry of moisture and hydrogen from the outside. Alternatively, a plurality of transistors 500 may be collectively surrounded with the insulator having a high barrier property against hydrogen or water. In the case where an opening is formed to surround the transistor 500, for example, the formation of an opening reaching the insulator 514 or the insulator 522 and the formation of the insulator having a high barrier property in contact with the insulator 514 or the insulator 522 are suitable because these formation steps can also serve as some of the manufacturing steps of the transistor 500. For the insulator having a high barrier property against hydrogen or water, a material similar to that for the insulator 522 can be used, for example.

Next, the capacitor 600 is provided above the transistor 500. The capacitor 600 includes a conductor 610, a conductor 620, and an insulator 630.

In addition, a conductor 612 may be provided over the conductor 546 and the conductor 548. The conductor 612 has a function of a plug or a wiring that is connected to the transistor 500. The conductor 610 has a function of an electrode of the capacitor 600. Note that the conductor 612 and the conductor 610 can be formed at the same time.

For the conductor 612 and the conductor 610, a metal film containing an element selected from molybdenum, titanium, tantalum, tungsten, aluminum, copper, chromium, neodymium, and scandium; a metal nitride film containing the above element as its component (a tantalum nitride film, a titanium nitride film, a molybdenum nitride film, or a tungsten nitride film); or the like can be used. Alternatively, it is possible to use a conductive material such as indium tin oxide, indium oxide containing tungsten oxide, indium zinc oxide containing tungsten oxide, indium oxide containing titanium oxide, indium tin oxide containing titanium oxide, indium zinc oxide, or indium tin oxide to which silicon oxide is added.

The conductor 612 and the conductor 610 each have a single-layer structure in FIG. 29; however, the structure is not limited thereto, and a stacked-layer structure of two or more layers may be employed. For example, between a conductor having a barrier property and a conductor having high conductivity, a conductor that is highly adhesive to the conductor having a barrier property and the conductor having high conductivity may be formed.

The conductor 620 is provided to overlap with the conductor 610 with the insulator 630 therebetween. For the conductor 620, a conductive material such as a metal material, an alloy material, or a metal oxide material can be used. It is preferable to use a high-melting-point material that has both heat resistance and conductivity, such as tungsten or molybdenum, and it is particularly preferable to use tungsten. In the case where the conductor 620 is formed concurrently with another component such as a conductor, Cu (copper), Al (aluminum), or the like, which is a low-resistance metal material, can be used.

An insulator 650 is provided over the conductor 620 and the insulator 630. The insulator 650 can be provided using a material similar to that for the insulator 320. The insulator 650 may function as a planarization film that covers an uneven shape thereunder.

With the use of this structure, change in electrical characteristics can be inhibited and the reliability can be improved in a semiconductor device using a transistor including an oxide semiconductor. Alternatively, a semiconductor device using a transistor including an oxide semiconductor can be miniaturized or highly integrated.

Next, other structure examples of the OS transistors illustrated in FIG. 29 and FIG. 30 are described.

Figure 32A:
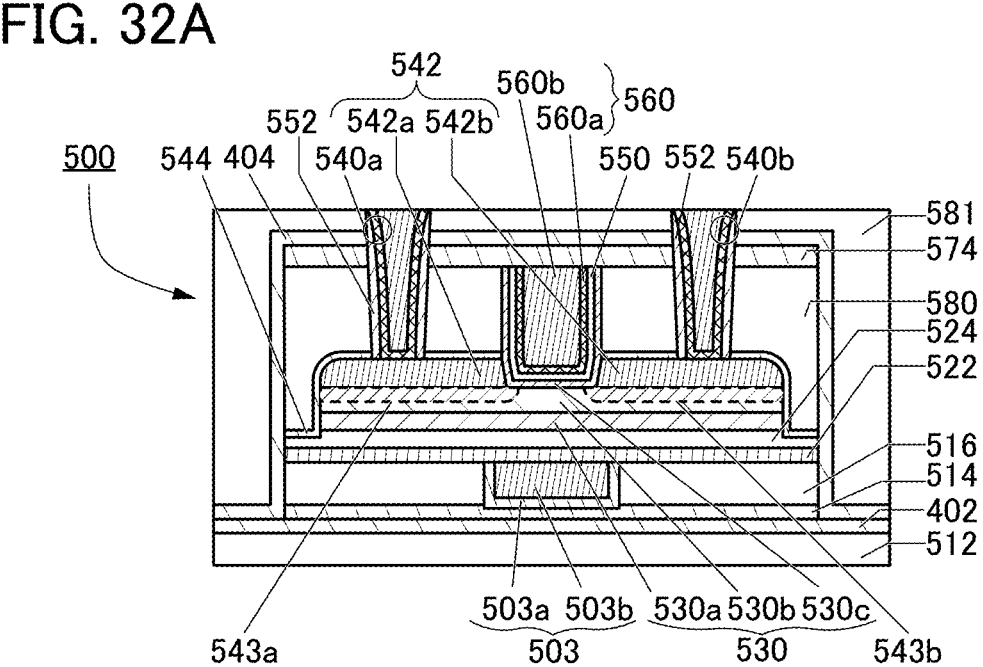
FIG. 32A and FIG. 32B are schematic cross-sectional views each showing a structure example of a transistor.
Figure 32B:
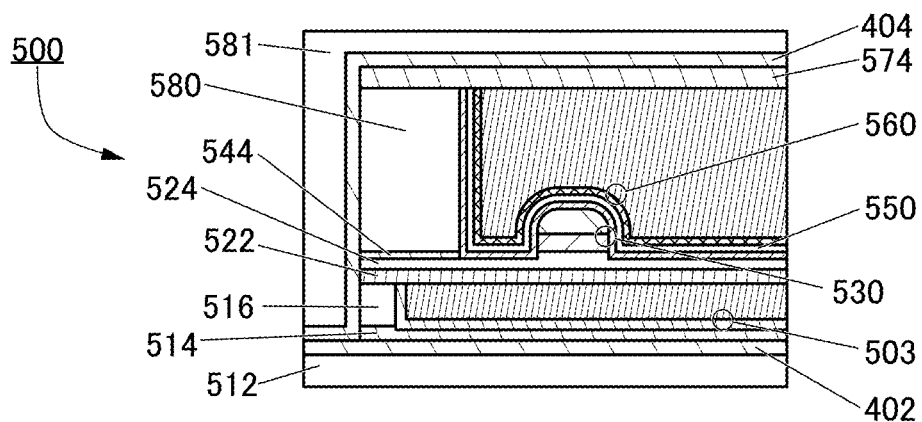

FIG. 32A and FIG. 32B illustrate a modification example of the transistor 500 illustrated in FIG. 31A and FIG. 31B. FIG. 32A is a cross-sectional diagram of the transistor 500 in the channel length direction and FIG. 32B is a cross-sectional diagram of the transistor 500 in the channel width direction. Note that the structure illustrated in FIG. 32A and FIG. 32B can be employed for other transistors, such as the transistor 300, included in the semiconductor device of one embodiment of the present invention.

The transistor 500 illustrated in FIG. 32A and FIG. 32B includes the insulator 402 and the insulator 404, which is different from the transistor 500 illustrated in FIG. 31A and FIG. 31B. Furthermore, the transistor 500 having the structure illustrated in FIG. 32A and FIG. 32B is different from the transistor 500 having the structure illustrated in FIG. 31A and FIG. 31B in that the insulator 552 is provided in contact with a side surface of the conductor 540a and a side surface of the conductor 540b. Moreover, the transistor 500 having the structure illustrated in FIG. 32A and FIG. 32B is different from the transistor 500 having the structure illustrated in FIG. 31A and FIG. 31B in that the insulator 520 is not included.

In the transistor 500 having the structure illustrated in FIG. 32A and FIG. 32B, the insulator 402 is provided over the insulator 512. In addition, the insulator 404 is provided over the insulator 574 and the insulator 402.

In the transistor 500 having the structure illustrated in FIG. 32A and FIG. 32B, the insulator 514, the insulator 516, the insulator 522, the insulator 524, the insulator 544, the insulator 580, and the insulator 574 are provided and covered with the insulator 404. That is, the insulator 404 is in contact with the top surface of the insulator 574, the side surface of the insulator 574, the side surface of the insulator 580, the side surface of the insulator 544, the side surface of the insulator 524, the side surface of the insulator 522, the side surface of the insulator 516, the side surface of the insulator 514, and the top surface of the insulator 402. Thus, the oxide 530 and the like are isolated from the outside with the insulator 404 and the insulator 402.

It is preferable that the insulator 402 and the insulator 404 have higher capability of inhibiting diffusion of hydrogen (e.g., at least one of a hydrogen atom, a hydrogen molecule, and the like) or a water molecule. For example, the insulator 402 and the insulator 404 are preferably formed using silicon nitride or silicon nitride oxide that is a material having a high hydrogen barrier property. This can inhibit the diffusion of hydrogen or the like into the oxide 530, whereby the deterioration of the characteristics of the transistor 500 can be inhibited. Consequently, the reliability of the semiconductor device of one embodiment of the present invention can be increased.

The insulator 552 is provided in contact with the insulator 581, the insulator 404, the insulator 574, the insulator 580, and the insulator 544. The insulator 552 preferably has a function of inhibiting diffusion of hydrogen or water molecules. For example, for the insulator 552, an insulator such as silicon nitride, aluminum oxide, or silicon nitride oxide that is a material having a high hydrogen barrier property is preferably used. In particular, it is preferable to use silicon nitride as the insulator 552 because of its high hydrogen barrier property. By using a material having a high hydrogen barrier property for the insulator 552, the diffusion of impurities such as water or hydrogen from the insulator 580 and the like into the oxide 530 through the conductor 540a and the conductor 540b can be inhibited. Furthermore, oxygen contained in the insulator 580 can be inhibited from being absorbed by the conductor 540a and the conductor 540b. As described above, the reliability of the semiconductor device of one embodiment of the present invention can be increased.

Figure 33:
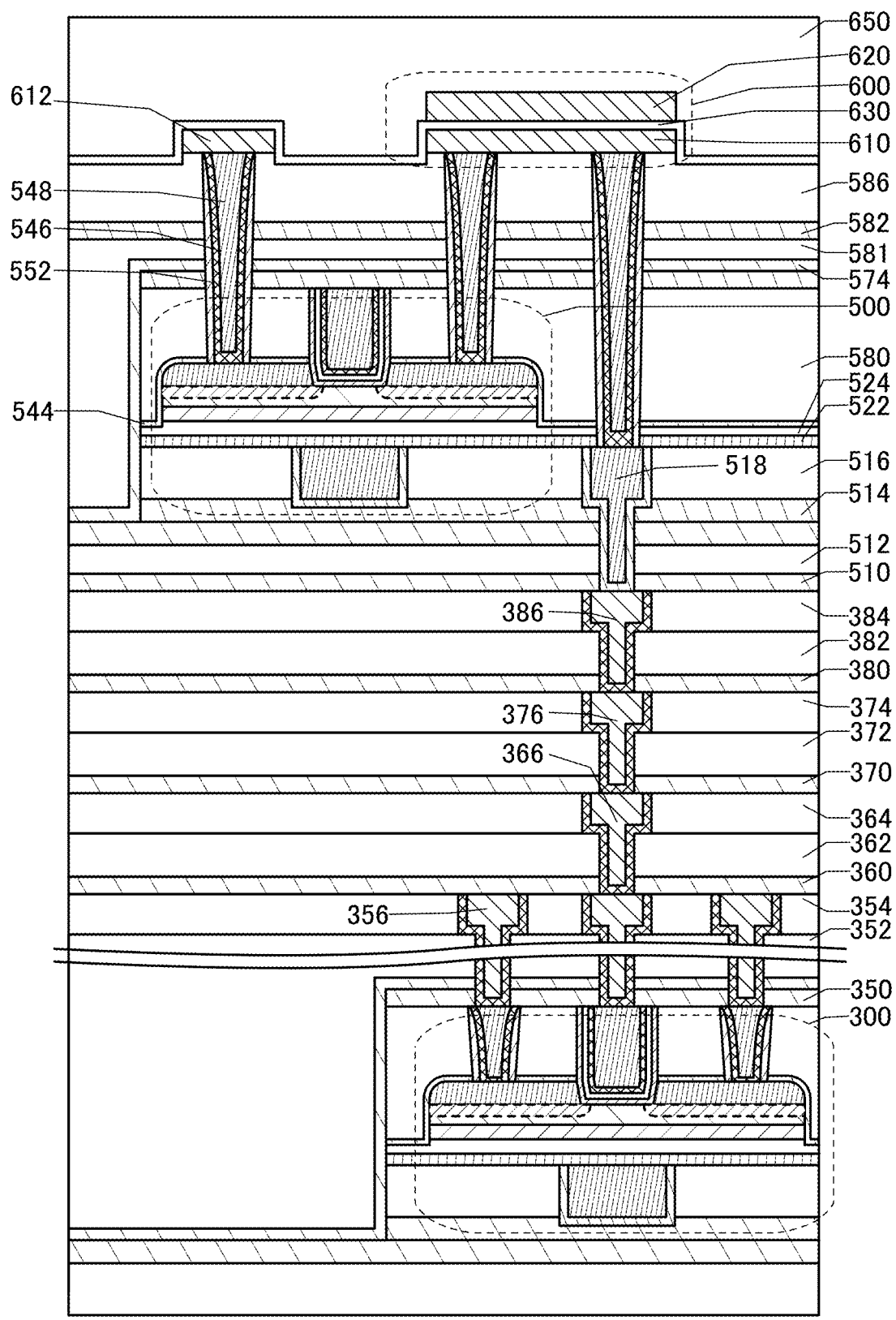
FIG. 33 is a schematic cross-sectional view showing a structure example of a semiconductor device.

FIG. 33 is a cross-sectional view showing a structure example of the semiconductor apparatus in the case where the transistor 500 and the transistor 300 have the structure illustrated in FIG. 32A and FIG. 32B. The insulator 552 is provided on the side surface of the conductor 546.

Figure 34A:
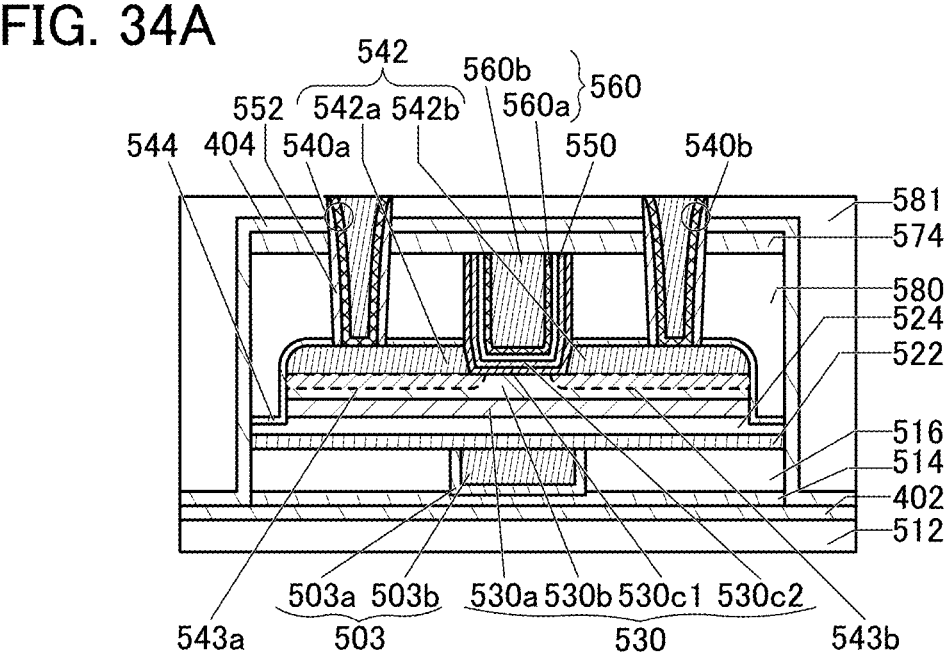
FIG. 34A and FIG. 34B are schematic cross-sectional views each showing a structure example of a transistor.
Figure 34B:
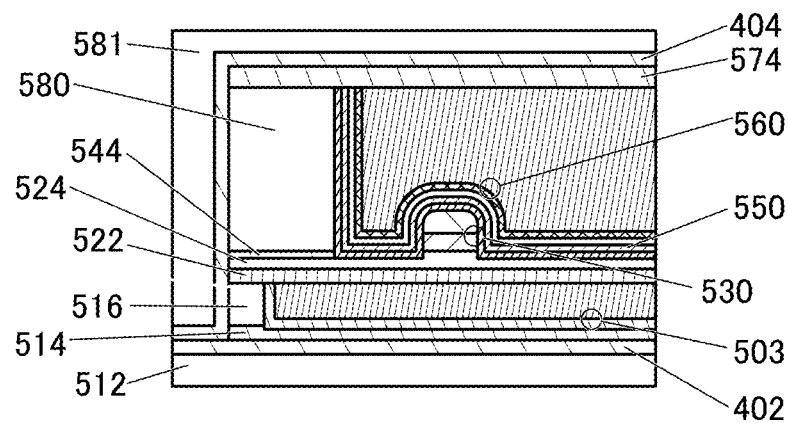

The transistor structure of the transistor 500 illustrated in FIG. 32A and FIG. 32B may be changed according to circumstances. As the modification example of the transistor 500 illustrated in FIG. 32A and FIG. 32B, a transistor illustrated in FIG. 34A and FIG. 34B can be employed, for example. FIG. 34A is a cross-sectional view of the transistor in the channel length direction, and FIG. 34B is a cross-sectional view of the transistor in the channel width direction. The transistor illustrated in FIG. 34A and FIG. 34B is different from the transistor illustrated in FIG. 32A and FIG. 32B in that the oxide 530c has a two-layer structure of an oxide 530c1 and an oxide 530c2.

The oxide 530c1 is in contact with the top surface of the insulator 524, the side surface of the oxide 530a, the top surface and the side surface of the oxide 530b, the side surfaces of the conductor 542a and the conductor 542b, the side surface of the insulator 544, and the side surface of the insulator 580. The oxide 530c2 is in contact with insulator 550.

An In—Zn oxide can be used as the oxide 530c1, for example. For the oxide 530c2, it is possible to use a material similar to a material used for the oxide 530c when the oxide 530c has a single-layer structure. For example, as the oxide 530c2, a metal oxide with In:Ga:Zn=1:3:4 [atomic ratio], Ga:Zn=2:1 [atomic ratio], or Ga:Zn=2:5 [atomic ratio] can be used.

When the oxide 530c has a two-layer structure of the oxide 530c1 and the oxide 530c2, the on-state current of the transistor can be increased as compared with the case where the oxide 530c has a single-layer structure. Thus, the transistor can be used as a power MOS transistor, for example. Note that the oxide 530c included in the transistor illustrated in FIG. 31A and FIG. 31B can also have a two-layer structure of the oxide 530c1 and the oxide 530c2.

The transistor having the structure illustrated in FIG. 34A and FIG. 34B can be used as the transistor 300 illustrated in FIG. 29 or FIG. 30, for example. In addition, for example, the transistor 300 can be used as a transistor or the like included in the semiconductor device described in the above embodiments, for example, the arithmetic circuit MAC1, the arithmetic circuit MAC1A, the arithmetic circuit MAC2, and the arithmetic circuit MAC3 described in the above embodiments, as described above. Note that the transistor illustrated in FIG. 34A and FIG. 34B can be used as a transistor included in the semiconductor device of one embodiment of the present invention, other than the transistors 300 and 500.

Figure 35:
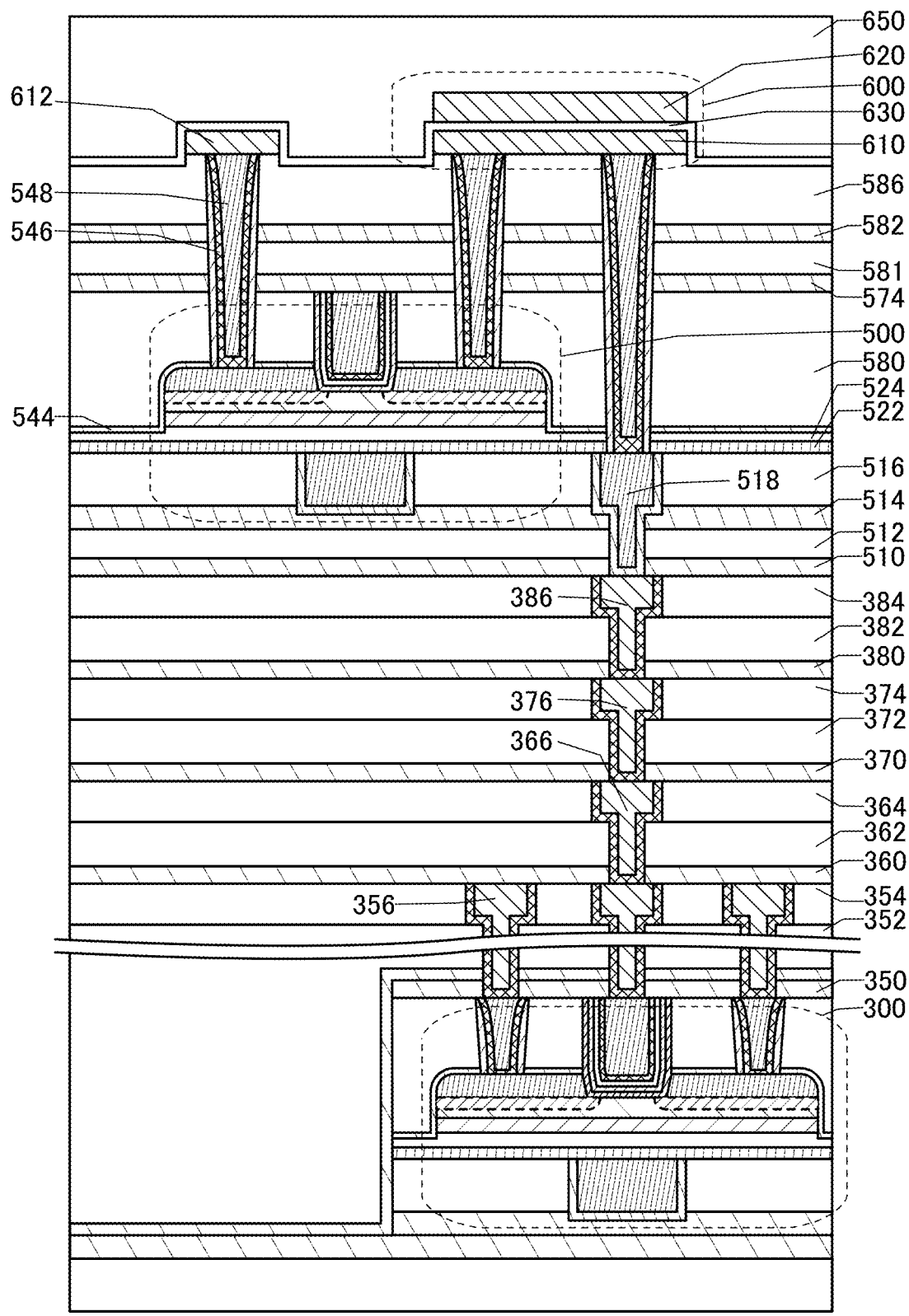
FIG. 35 is a schematic cross-sectional view showing a structure example of a semiconductor device.

FIG. 35 is a cross-sectional view showing a structure example of a semiconductor apparatus in which the transistor 500 has the structure of the transistor illustrated in FIG. 31A and the transistor 300 has the structure of the transistor illustrated in FIG. 34A. Note that as in FIG. 33, the insulator 552 is provided on the side surface of the conductor 546. As illustrated in FIG. 35, in the semiconductor apparatus of one embodiment of the present invention, the transistor 300 and the transistor 500 can have different structures while both the transistor 300 and the transistor 500 can be OS transistors.

Next, a capacitor that can be used in the semiconductor devices in FIG. 29, FIG. 30, FIG. 33, and FIG. 35 is described.

Figure 36A:
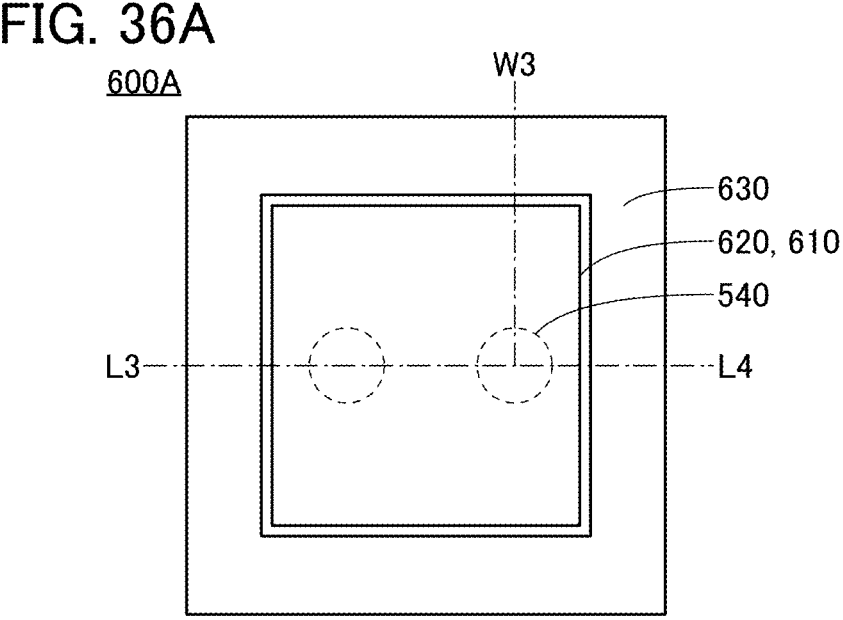
FIG. 36A is a top view showing a structure example of a capacitor.
Figure 36B:
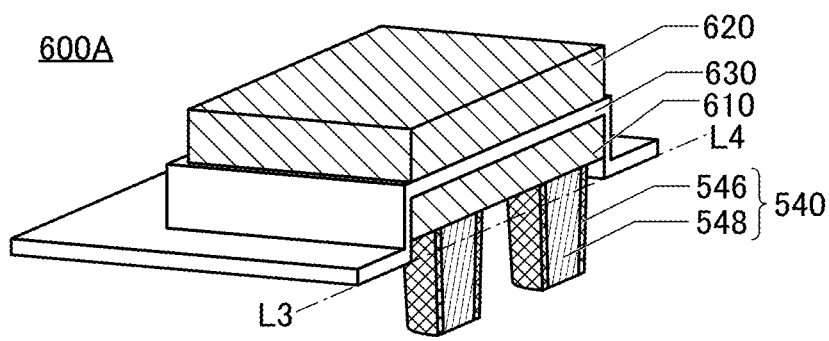
FIG. 36B and FIG. 36C are cross-sectional perspective views showing a structure example of a capacitor.
Figure 36C:
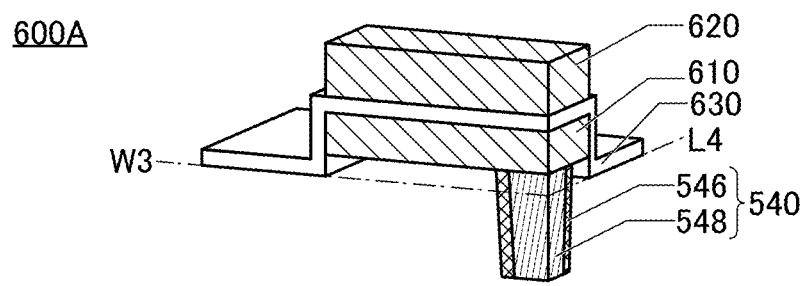

FIG. 36A to FIG. 36C illustrate a capacitor 600A as an example of the capacitor 600 that can be used in the semiconductor devices illustrated in FIG. 29, FIG. 30, FIG. 33, and FIG. 35. FIG. 36A is a top view of the capacitive element 600A, FIG. 36B is a perspective view illustrating a cross section of the capacitive element 600A along the dashed-dotted line L3-L4, and FIG. 36C is a perspective view illustrating a cross section of the capacitive element 600A along the dashed-dotted line W3-L4.

The conductor 610 functions as one of a pair of electrodes of the capacitor 600A, and the conductor 620 functions as the other of the pair of electrodes of the capacitor 600A. The insulator 630 functions as a dielectric between the pair of electrodes.

The insulator 630 can be provided to have a single-layer structure or a stacked-layer structure using, for example, silicon oxide, silicon oxynitride, silicon nitride oxide, silicon nitride, aluminum oxide, aluminum oxynitride, aluminum nitride oxide, aluminum nitride, hafnium oxide, hafnium oxynitride, hafnium nitride oxide, hafnium nitride, or zirconium oxide. Furthermore, in this specification, hafnium oxynitride refers to a material that contains oxygen at a higher proportion than nitrogen, and hafnium nitride oxide refers to a material that contains nitrogen at a higher proportion than oxygen.

Alternatively, for the insulator 630, a stacked-layer structure using a material with high dielectric strength such as silicon oxynitride and a high permittivity (high-k) material may be used, for example. In the capacitor 600A having such a structure, a sufficient capacitance can be ensured owing to the high permittivity (high-k) insulator, and the dielectric strength can be increased owing to the insulator with high dielectric strength, so that the electrostatic breakdown of the capacitor 600A can be inhibited.

As the insulator of a high permittivity (high-k) material (a material having a high relative permittivity), gallium oxide, hafnium oxide, zirconium oxide, an oxide containing aluminum and hafnium, an oxynitride containing aluminum and hafnium, an oxide containing silicon and hafnium, an oxynitride containing silicon and hafnium, a nitride containing silicon and hafnium, or the like can be given.

Alternatively, for example, a single layer or stacked layers of an insulator containing a high-k material, such as aluminum oxide, hafnium oxide, tantalum oxide, zirconium oxide, lead zirconate titanate (PZT), strontium titanate ($SrTiO_3$), or $(Ba,Sr)TiO_3$ (BST), may be used as the insulator 630. In the case where the insulator 630 has stacked layers, a three-layer structure in which zirconium oxide, aluminum oxide, and zirconium oxide are formed in this order, or a four-layer structure in which zirconium oxide, aluminum oxide, zirconium oxide, and aluminum oxide are formed in this order can be employed, for example. For the insulator 630, a compound containing hafnium and zirconium may be employed. When the semiconductor device is miniaturized and highly integrated, a dielectric used for a gate insulator and a capacitor becomes thin, which might cause a problem of leakage current of a transistor and a capacitor. When a high-k material is used as an insulator functioning as the dielectric used for the gate insulator and the capacitor, a gate potential during operation of the transistor can be lowered and the capacitance of the capacitor can be ensured while the physical thickness is kept.

A bottom portion of the conductor 610 in the capacitor 600 is electrically connected to the conductor 546 and the conductor 548. The conductor 546 and the conductor 548 function as plugs or wirings for connection to another circuit element. In FIG. 36A to FIG. 36C, the conductor 546 and the conductor 548 are collectively denoted as a conductor 540.

For clarification of the drawing, the insulator 586 in which the conductor 546 and the conductor 548 are embedded and the insulator 650 that covers the conductor 620 and the insulator 630 are omitted in FIG. 36A to FIG. 36C.

Although the capacitive element 600 illustrated in FIG. 29, FIG. 30, FIG. 33, FIG. 35, FIG. 36A, FIG. 36B, and FIG. 36C is a planar capacitive element, the shape of the capacitive element is not limited thereto. For example, the capacitive element 600 may be a cylindrical capacitive element 600B illustrated in FIG. 37A to FIG. 37C.

Figure 37A:
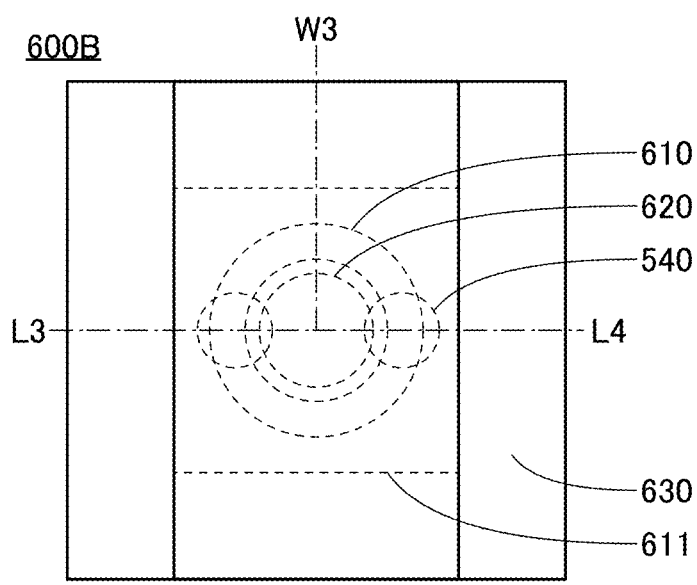
FIG. 37A is a top view showing a structure example of a capacitor.
Figure 37B:
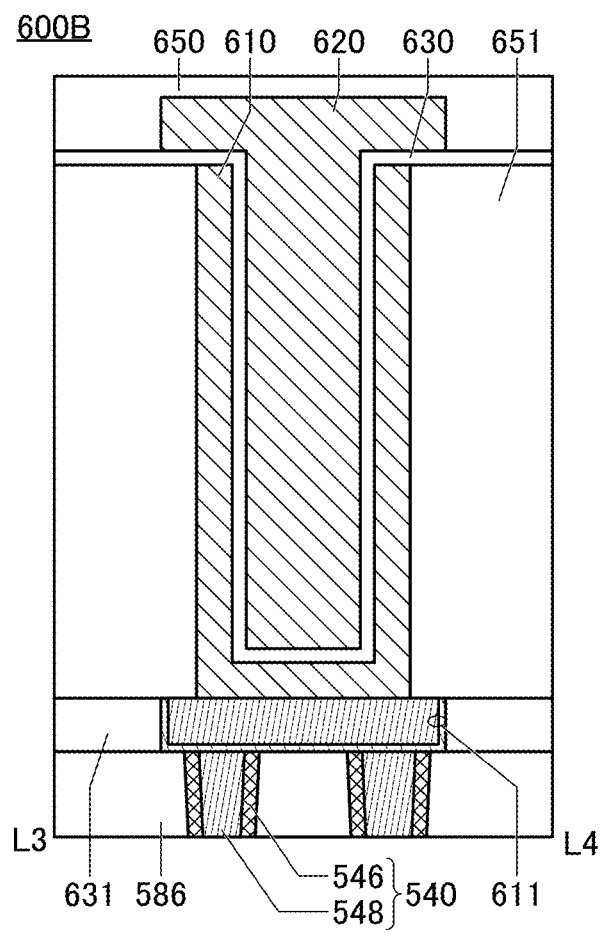
FIG. 37B is a cross-sectional perspective view showing a structure example of a capacitor.
Figure 37C:
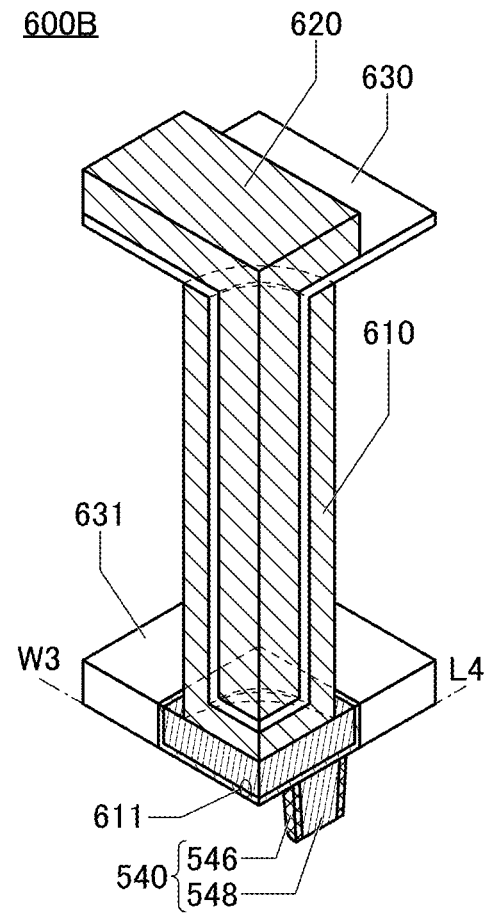
FIG. 37C is a cross-sectional perspective view showing a structure example of a capacitor.

FIG. 37A is a top view of the capacitive element 600B, FIG. 37B is a cross-sectional view of the capacitive element 600B along the dashed-dotted line L3-L4, and FIG. 37C is a perspective view illustrating a cross section of the capacitive element 600B along the dashed-dotted line W3-L4.

In FIG. 37B, the capacitor 600B includes an insulator 631 over the insulator 586 in which the conductor 540 is embedded, an insulator 651 having an opening, the conductor 610 functioning as one of a pair of electrodes, and the conductor 620 functioning as the other of the pair of electrodes.

For clarification of the drawing, the insulator 586, the insulator 650, and the insulator 651 are omitted in FIG. 37C.

For the insulator 631, a material similar to that for the insulator 586 can be used, for example.

A conductor 611 is embedded in the insulator 631 to be electrically connected to the conductor 540. For the conductor 611, a material similar to those for the conductor 330 and the conductor 518 can be used, for example.

For the insulator 651, a material similar to that for the insulator 586 can be used, for example.

The insulator 651 has an opening portion as described above, and the opening portion overlaps with the conductor 611.

The conductor 610 is formed on the bottom portion and the side surface of the opening portion. In other words, the conductor 610 overlaps with the conductor 611 and is electrically connected to the conductor 611.

The conductor 610 is formed in such a manner that an opening portion is formed in the insulator 651 using an etching method or the like, and then the conductor 610 is deposited using a sputtering method, an ALD method, or the like. After that, the conductor 610 deposited over the insulator 651 can be removed using a CMP (Chemical Mechanical Polishing) method or the like while the conductor 610 deposited in the opening portion is left.

The insulator 630 is positioned over the insulator 651 and over the formation surface of the conductor 610. Note that the insulator 630 functions as a dielectric between the pair of electrodes in the capacitor.

The conductor 620 is formed over the insulator 630 so as to fill the opening portion of the insulator 651.

The insulator 650 is formed to cover the insulator 630 and the conductor 620.

The capacitance value of the cylindrical capacitive element 600B illustrated in FIG. 37A to FIG. 37C can be higher than that of the planar capacitive element 600A.

Note that this embodiment can be combined with any of the other embodiments in this specification as appropriate.

Embodiment 7

Described in this embodiment is a metal oxide (hereinafter also referred to as an oxide semiconductor) that can be used in the OS transistor described in the above embodiment.

The metal oxide preferably contains at least indium or zinc. In particular, indium and zinc are preferably contained. In addition, aluminum, gallium, yttrium, tin, or the like is preferably contained. Furthermore, one or more kinds selected from boron, silicon, titanium, iron, nickel, germanium, zirconium, molybdenum, lanthanum, cerium, neodymium, hafnium, tantalum, tungsten, magnesium, cobalt, and the like may be contained.

<Classification of Crystal Structure>

First, the classifications of the crystal structures of oxide semiconductor are explained with FIG. 38A. FIG. 38A is a diagram showing the classifications of crystal structures of an oxide semiconductor, typically IGZO (a metal oxide containing In, Ga, and Zn).

As illustrated in FIG. 38A, an oxide semiconductor is roughly classified into "Amorphous", "Crystalline", and "Crystal". The term "Amorphous" includes completely amorphous. The term "Crystalline" includes CAAC (c-axis-aligned crystalline), nc (nanocrystalline), and CAC (Cloud-Aligned Composite) (excluding single crystal and poly crystal). Note that the term "Crystalline" excludes single crystal, poly crystal, and completely amorphous. The term "Crystal" includes single crystal and poly crystal.

Note that the structures in the thick frame in FIG. 38A are in an intermediate state between "Amorphous" and "Crystal", and belong to a new crystalline phase. That is, these structures are completely different from "Amorphous", which is energetically unstable, and "Crystal".

Note that a crystal structure of a film or a substrate can be evaluated with an X-ray diffraction (XRD) spectrum. FIG. 38B shows an XRD spectrum, which is obtained using GIXD (Grazing-Incidence XRD) measurement, of a CAAC-IGZO film classified into "Crystalline" (the vertical axis represents intensity in arbitrary unit (a. u.)). Note that a GIXD method is also referred to as a thin film method or a Seemann-Bohlin method. The XRD spectrum that is illustrated in FIG. 38B and obtained using GIXD measurement is hereinafter simply referred to as an XRD spectrum. The CAAC-IGZO film in FIG. 38B has a composition in the neighborhood of In:Ga:Zn=4:2:3 [atomic ratio]. The CAAC-IGZO film in FIG. 38B has a thickness of 500 nm.

As illustrated in FIG. 38B, a clear peak indicating crystallinity is detected in the XRD spectrum of the CAAC-IGZO film. Specifically, a peak indicating c-axis alignment is detected at 2θ of around 31° in the XRD spectrum of the CAAC-IGZO film. As illustrated in FIG. 38B, the peak at 2θ of around 310 is asymmetric with respect to the axis of the angle at which the peak intensity is detected.

A crystal structure of a film or a substrate can also be evaluated with a diffraction pattern obtained using a nanobeam electron diffraction (NBED) method (such a pattern is also referred to as a nanobeam electron diffraction pattern). FIG. 38C shows a diffraction pattern of the CAAC-IGZO film. FIG. 38C shows a diffraction pattern obtained with the NBED method in which an electron beam is incident in the direction parallel to the substrate. The composition of the CAAC-IGZO film in FIG. 38C is In:Ga:Zn=4:2:3 [atomic ratio] or the neighborhood thereof. In the nanobeam electron diffraction method, electron diffraction is performed with a probe diameter of 1 nm.

As illustrated in FIG. 38C, a plurality of spots indicating c-axis alignment is observed in the diffraction pattern of the CAAC-IGZO film.

<<Structure of Oxide Semiconductor>>

Oxide semiconductors might be classified in a manner different from one illustrated in FIG. 38A when classified in terms of the crystal structure. Oxide semiconductors are classified into a single crystal oxide semiconductor and a non-single-crystal oxide semiconductor, for example. Examples of the non-single-crystal oxide semiconductor include the above-described CAAC-OS and nc-OS. Other examples of the non-single-crystal oxide semiconductor include a polycrystalline oxide semiconductor, an amorphous-like oxide semiconductor (a-like OS), and an amorphous oxide semiconductor.

Here, the above-described CAAC-OS, nc-OS, and a-like OS are described in detail.

[CAAC-OS]

The CAAC-OS is an oxide semiconductor that has a plurality of crystal regions each of which has c-axis alignment in a particular direction. Note that the particular direction refers to the film thickness direction of a CAAC-OS film, the normal direction of the surface where the CAAC-OS film is formed, or the normal direction of the surface of the CAAC-OS film. The crystal region refers to a region having a periodic atomic arrangement. When an atomic arrangement is regarded as a lattice arrangement, the crystal region also refers to a region with a uniform lattice arrangement. The CAAC-OS has a region where a plurality of crystal regions is connected in the a-b plane direction, and the region has distortion in some cases. Note that distortion refers to a portion where the direction of a lattice arrangement changes between a region with a uniform lattice arrangement and another region with a uniform lattice arrangement in a region where a plurality of crystal regions is connected. That is, the CAAC-OS is an oxide semiconductor having c-axis alignment and having no clear alignment in the a-b plane direction.

Note that each of the plurality of crystal regions is formed of one or more fine crystals (crystals each of which has a maximum diameter of less than 10 nm). In the case where the crystal region is formed of one fine crystal, the maximum diameter of the crystal region is less than 10 nm. In the case where the crystal region is formed of a large number of fine crystals, the size of the crystal region may be approximately several tens of nanometers.

In the case of an In-M-Zn oxide (the element M is one or more kinds selected from aluminum, gallium, yttrium, tin, titanium, and the like), the CAAC-OS tends to have a layered crystal structure (also referred to as a stacked-layer structure) in which a layer containing indium (In) and oxygen (hereinafter, an In layer) and a layer containing the element M, zinc (Zn), and oxygen (hereinafter, an (M,Zn) layer) are stacked. Indium and the element M can be replaced with each other. Therefore, indium may be contained in the (M,Zn) layer. In addition, the element M may be contained in the In layer. Note that Zn may be contained in the In layer. Such a layered structure is observed as a lattice image in a high-resolution TEM image, for example.

When the CAAC-OS film is subjected to structural analysis by out-of-plane XRD measurement with an XRD apparatus using θ/2θ scanning, for example, a peak indicating c-axis alignment is detected at 2θ of 31° or around 31°. Note that the position of the peak indicating c-axis alignment (the value of 2θ) may change depending on the kind, composition, or the like of the metal element contained in the CAAC-OS.

For example, a plurality of bright spots is observed in the electron diffraction pattern of the CAAC-OS film. Note that one spot and another spot are observed point-symmetrically with a spot of the incident electron beam passing through a sample (also referred to as a direct spot) as the symmetric center.

When the crystal region is observed from the particular direction, a lattice arrangement in the crystal region is basically a hexagonal lattice arrangement; however, a unit lattice is not always a regular hexagon and is a non-regular hexagon in some cases. A pentagonal lattice arrangement, a heptagonal lattice arrangement, and the like are included in the distortion in some cases. Note that a clear grain boundary cannot be observed even in the vicinity of the distortion in the CAAC-OS. That is, formation of a crystal grain boundary is inhibited due to the distortion of lattice arrangement. This is probably because the CAAC-OS can tolerate distortion owing to a low density of arrangement of oxygen atoms in the a-b plane direction, an interatomic bond distance changed owing to substitution of a metal atom, and the like.

Note that a crystal structure in which a clear grain boundary is observed is what is called polycrystal. It is highly probable that the grain boundary becomes a recombination center and captures carriers and thus decreases the on-state current and field-effect mobility of a transistor, for example. Thus, the CAAC-OS in which no clear grain boundary is observed is one of crystalline oxides having a crystal structure suitable for a semiconductor layer of a transistor. Note that Zn is preferably contained to form the CAAC-OS. For example, an In—Zn oxide and an In—Ga—Zn oxide are suitable because they can inhibit generation of a grain boundary as compared with an In oxide.

The CAAC-OS is an oxide semiconductor with high crystallinity in which no clear grain boundary is observed. Thus, in the CAAC-OS, a reduction in electron mobility due to the grain boundary is unlikely to occur. Moreover, since the crystallinity of an oxide semiconductor might be decreased due to the entry of impurities, formation of defects, or the like, the CAAC-OS can be regarded as an oxide semiconductor that has small amounts of impurities and defects (e.g., oxygen vacancies). Thus, an oxide semiconductor including the CAAC-OS is physically stable. Therefore, the oxide semiconductor including the CAAC-OS is resistant to heat and has high reliability. In addition, the CAAC-OS is stable with respect to high temperature in the manufacturing process (what is called thermal budget). Accordingly, the use of the CAAC-OS for the OS transistor can extend the degree of freedom of the manufacturing process.

[nc-OS]

In the nc-OS, a microscopic region (e.g., a region with a size greater than or equal to 1 nm and less than or equal to 10 nm, in particular, a region with a size greater than or equal to 1 nm and less than or equal to 3 nm) has a periodic atomic arrangement. In other words, the nc-OS includes a fine crystal. Note that the size of the fine crystal is, for example, greater than or equal to 1 nm and less than or equal to 10 nm, particularly greater than or equal to 1 nm and less than or equal to 3 nm; thus, the fine crystal is also referred to as a nanocrystal. Furthermore, there is no regularity of crystal orientation between different nanocrystals in the nc-OS. Thus, the orientation in the whole film is not observed. Accordingly, the nc-OS cannot be distinguished from an a-like OS or an amorphous oxide semiconductor by some analysis methods. For example, when an nc-OS film is subjected to structural analysis by out-of-plane XRD measurement with an XRD apparatus using θ/2θ scanning, a peak indicating crystallinity is not detected. Furthermore, a diffraction pattern like a halo pattern is observed when the nc-OS film is subjected to electron diffraction (also referred to as selected-area electron diffraction) using an electron beam with a probe diameter larger than the diameter of a nanocrystal (e.g., larger than or equal to 50 nm). Meanwhile, in some cases, a plurality of spots in a ring-like region with a direct spot as the center are observed in the obtained electron diffraction pattern when the nc-OS film is subjected to electron diffraction (also referred to as nanobeam electron diffraction) using an electron beam with a probe diameter nearly equal to or smaller than the diameter of a nanocrystal (e.g., 1 nm or larger and 30 nm or smaller).

[a-Like OS]

The a-like OS is an oxide semiconductor having a structure between those of the nc-OS and the amorphous oxide semiconductor. The a-like OS includes a void or a low-density region. That is, the a-like OS has low crystallinity as compared with the nc-OS and the CAAC-OS. Moreover, the a-like OS has higher hydrogen concentration in the film than the nc-OS and the CAAC-OS.

<<Structure of Oxide Semiconductor>>

Next, the above-described CAC-OS is described in detail. Note that the CAC-OS relates to the material composition.

[CAC-OS]

The CAC-OS refers to one composition of a material in which elements constituting a metal oxide are unevenly distributed with a size greater than or equal to 0.5 nm and less than or equal to 10 nm, preferably greater than or equal to 1 nm and less than or equal to 3 nm, or a similar size, for example. Note that a state in which one or more metal elements are unevenly distributed and regions including the metal element(s) are mixed with a size greater than or equal to 0.5 nm and less than or equal to 10 nm, preferably greater than or equal to 1 nm and less than or equal to 3 nm, or a similar size in a metal oxide is hereinafter referred to as a mosaic pattern or a patch-like pattern.

In addition, the CAC-OS has a composition in which materials are separated into a first region and a second region to form a mosaic pattern, and the first regions are distributed in the film (this composition is hereinafter also referred to as a cloud-like composition). That is, the CAC-OS is a composite metal oxide having a composition in which the first regions and the second regions are mixed.

Note that the atomic ratios of In, Ga, and Zn to the metal elements contained in the CAC-OS in an In—Ga—Zn oxide are denoted with [In], [Ga], and [Zn], respectively. For example, the first region in the CAC-OS in the In—Ga—Zn oxide has [In] higher than that in the composition of the CAC-OS film. Moreover, the second region has [Ga] higher than that in the composition of the CAC-OS film. For example, the first region has higher [In] and lower [Ga] than the second region. Moreover, the second region has higher [Ga] and lower [In] than the first region.

Specifically, the first region includes indium oxide, indium zinc oxide, or the like as its main component. The second region includes gallium oxide, gallium zinc oxide, or the like as its main component. That is, the first region can be referred to as a region containing In as its main component. The second region can be referred to as a region containing Ga as its main component.

Note that a clear boundary between the first region and the second region cannot be observed in some cases.

For example, energy dispersive X-ray spectroscopy (EDX) is used to obtain EDX mapping, and according to the EDX mapping, the CAC-OS in the In—Ga—Zn oxide can be found to have a structure in which the region containing In as its main component (the first region) and the region containing Ga as its main component (the second region) are unevenly distributed and mixed.

In the case where the CAC-OS is used for a transistor, a switching function (on/off switching function) can be given to the CAC-OS owing to the complementary action of the conductivity derived from the first region and the insulating property derived from the second region. A CAC-OS has a conducting function in part of the material and has an insulating function in another part of the material; as a whole, the CAC-OS has a function of a semiconductor. Separation of the conducting function and the insulating function can maximize each function. Accordingly, when the CAC-OS is used for a transistor, high on-state current (Ion), high field-effect mobility (μ), and excellent switching operation can be achieved.

An oxide semiconductor has various structures with different properties. Two or more kinds among the amorphous oxide semiconductor, the polycrystalline oxide semiconductor, the a-like OS, the CAC-OS, the nc-OS, and the CAAC-OS may be included in an oxide semiconductor of one embodiment of the present invention.

<Transistor Including Oxide Semiconductor>

Next, the case where the above oxide semiconductor is used for a transistor is described.

When the above oxide semiconductor is used for a transistor, a transistor with high field-effect mobility can be achieved. In addition, a transistor having high reliability can be achieved.

An oxide semiconductor having a low carrier concentration is preferably used in a transistor. For example, the carrier concentration of an oxide semiconductor is lower than or equal to $1\times10^{17}$ cm$^{-3}$, preferably lower than or equal to $1\times10^{15}$ cm$^{-3}$, further preferably lower than or equal to $1\times10^{13}$ cm$^{-3}$, still further preferably lower than or equal to $1\times10^{11}$ cm$^{-3}$, yet further preferably lower than $1\times10^{10}$ cm$^{-3}$, and higher than or equal to $1\times10-9$ cm$^{-3}$. In order to reduce the carrier concentration of an oxide semiconductor film, the impurity concentration in the oxide semiconductor film is reduced so that the density of defect states can be reduced. In this specification and the like, a state with a low impurity concentration and a low density of defect states is referred to as a highly purified intrinsic or substantially highly purified intrinsic state. Note that an oxide semiconductor having a low carrier concentration may be referred to as a highly purified intrinsic or substantially highly purified intrinsic oxide semiconductor.

A highly purified intrinsic or substantially highly purified intrinsic oxide semiconductor film has a low density of defect states and thus has a low density of trap states in some cases.

Charge trapped by the trap states in the oxide semiconductor takes a long time to disappear and might behave like fixed charge. Thus, a transistor whose channel formation region is formed in an oxide semiconductor with a high density of trap states has unstable electrical characteristics in some cases.

Accordingly, in order to obtain stable electrical characteristics of a transistor, reducing the impurity concentration in an oxide semiconductor is effective. In order to reduce the impurity concentration in the oxide semiconductor, it is preferable that the impurity concentration in an adjacent film be also reduced. Examples of impurities include hydrogen, nitrogen, an alkali metal, an alkaline earth metal, iron, nickel, and silicon.

<Impurity>

Here, the influence of each impurity in the oxide semiconductor is described.

When silicon or carbon, which is one of Group 14 elements, is contained in the oxide semiconductor, defect states are formed in the oxide semiconductor. Thus, the concentration of silicon or carbon in the oxide semiconductor and the concentration of silicon or carbon in the vicinity of an interface with the oxide semiconductor (the concentration obtained by secondary ion mass spectrometry (SIMS)) are each set lower than or equal to $2\times10^{18}$ atoms/cm$^3$, preferably lower than or equal to $2\times10^{17}$ atoms/cm$^3$.

When the oxide semiconductor contains an alkali metal or an alkaline earth metal, defect states are formed and carriers are generated in some cases. Thus, a transistor using an oxide semiconductor that contains an alkali metal or an alkaline earth metal is likely to have normally-on characteristics. Thus, the concentration of an alkali metal or an alkaline earth metal in the oxide semiconductor, which is obtained using SIMS, is lower than or equal to $1\times10^{18}$ atoms/cm$^3$, preferably lower than or equal to $2\times10^{16}$ atoms/cm$^3$.

Furthermore, when the oxide semiconductor contains nitrogen, the oxide semiconductor easily becomes n-type by generation of electrons serving as carriers and an increase in carrier concentration. As a result, a transistor using an oxide semiconductor containing nitrogen as a semiconductor is likely to have normally-on characteristics. When nitrogen is contained in the oxide semiconductor, a trap state is sometimes formed. This might make the electrical characteristics of the transistor unstable. Therefore, the concentration of nitrogen in the oxide semiconductor, which is obtained by SIMS, is set lower than $5\times10^{19}$ atoms/cm$^3$, preferably lower than or equal to $5\times10^{18}$ atoms/cm$^3$, further preferably lower than or equal to $1\times10^{18}$ atoms/cm$^3$, still further preferably lower than or equal to $5\times10^{17}$ atoms/cm$^3$.

Hydrogen contained in the oxide semiconductor reacts with oxygen bonded to a metal atom to be water, and thus forms an oxygen vacancy in some cases. Entry of hydrogen into the oxygen vacancy generates an electron serving as a carrier in some cases. Furthermore, bonding of part of hydrogen to oxygen bonded to a metal atom causes generation of an electron serving as a carrier in some cases. Thus, a transistor using an oxide semiconductor containing hydrogen is likely to have normally-on characteristics. Accordingly, hydrogen in the oxide semiconductor is preferably reduced as much as possible. Specifically, the hydrogen concentration in the oxide semiconductor, which is obtained using SIMS, is set lower than $1\times10^{20}$ atoms/cm$^3$, preferably lower than $1\times10^{19}$ atoms/cm$^3$, further preferably lower than $5\times10^{18}$ atoms/cm$^3$, still further preferably lower than $1\times10^{18}$ atoms/cm$^3$.

When an oxide semiconductor with sufficiently reduced impurities is used for the channel formation region of the transistor, stable electrical characteristics can be given.

Note that this embodiment can be combined with any of the other embodiments in this specification as appropriate.

Embodiment 8

This embodiment will show examples of a semiconductor wafer where the semiconductor device or the like described in the above embodiment is formed and electronic components incorporating the semiconductor device.

<Semiconductor Wafer>

First, an example of a semiconductor wafer where a semiconductor device or the like is formed is described with reference to FIG. 39A.

Figure 39A:
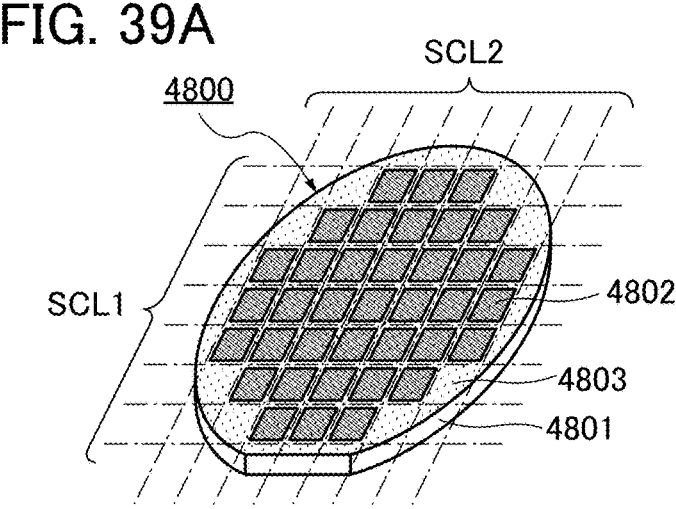
FIG. 39A is a perspective view showing an example of a semiconductor wafer.

A semiconductor wafer 4800 illustrated in FIG. 39A includes a wafer 4801 and a plurality of circuit portions 4802 provided on the top surface of the wafer 4801. A portion without the circuit portion 4802 on the top surface of the wafer 4801 is a spacing 4803 that is a region for dicing.

The semiconductor wafer 4800 can be fabricated by forming the plurality of circuit portions 4802 on the surface of the wafer 4801 by a pre-process. After that, a surface of the wafer 4801 opposite to the surface provided with the plurality of circuit portions 4802 may be ground to thin the wafer 4801. Through this step, warpage or the like of the wafer 4801 is reduced and the size of the component can be reduced.

A dicing step is performed as the next step. The dicing is performed along scribe lines SCL1 and scribe lines SCL2 (referred to as dicing lines or cutting lines in some cases) indicated with dashed-dotted lines. Note that to perform the dicing step easily, it is preferable that the spacing 4803 be provided so that the plurality of scribe lines SCL1 are parallel to each other, the plurality of scribe lines SCL2 are parallel to each other, and the scribe lines SCL1 are perpendicular to the scribe lines SCL2.

Figure 39B:
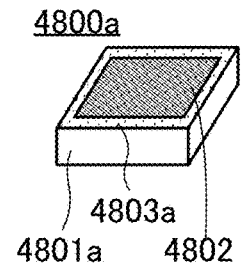
FIG. 39B is a perspective view showing an example of a chip.

With the dicing step, a chip 4800a as illustrated in FIG. 39B can be cut out from the semiconductor wafer 4800. The chip 4800a includes a wafer 4801a, the circuit portion 4802, and a spacing 4803a. Note that it is preferable to make the spacing 4803*a* as small as possible. In this case, the width of the spacing 4803 between adjacent circuit portions 4802 is substantially the same as a length of a cutting allowance of the scribe line SCL1 or a cutting allowance of the scribe line SCL2.

Note that the shape of the element substrate of one embodiment of the present invention is not limited to the shape of the semiconductor wafer 4800 illustrated in FIG. 39A. The element substrate may be a rectangular semiconductor wafer, for example. The shape of the element substrate can be changed as appropriate, depending on a manufacturing process of an element and an apparatus for manufacturing the element.

<Electronic Component>

Figure 39C:
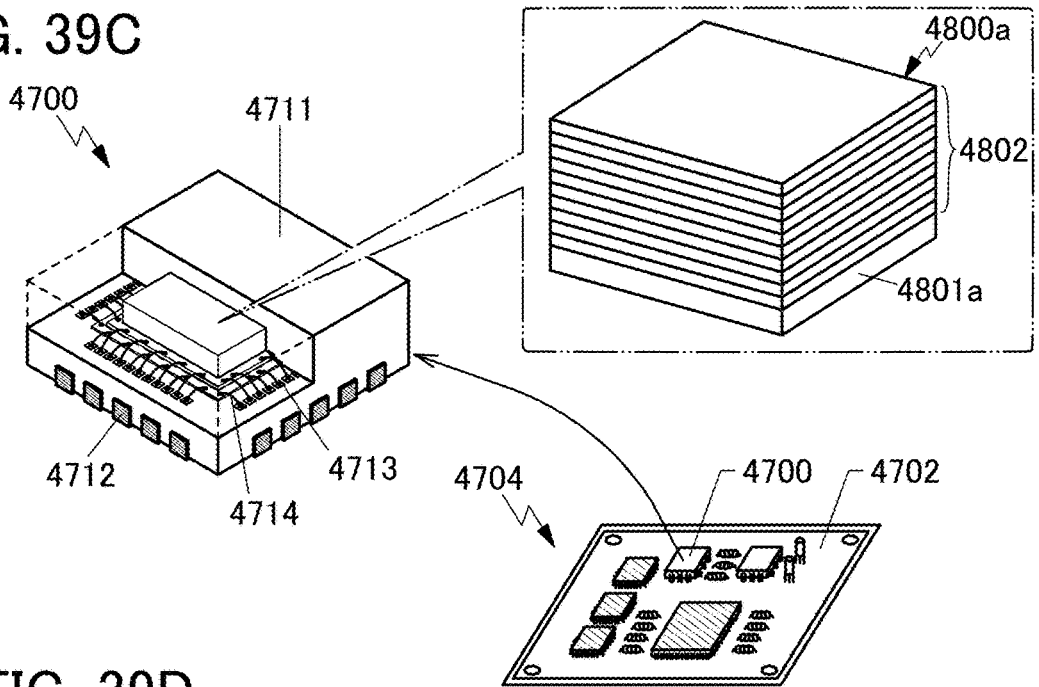
FIG. 39C and FIG. 39D are perspective views showing examples of electronic components.

FIG. 39C is a perspective view of an electronic component 4700 and a substrate (a mounting board 4704) on which the electronic component 4700 is mounted. The electronic component 4700 illustrated in FIG. 39C includes a chip 4800*a* in a mold 4711. Note that the chip 4800*a* illustrated in FIG. 39C may have a structure in which the circuit portions 4802 are stacked. To illustrate the inside of the electronic component 4700, some portions are omitted in FIG. 39C. The electronic component 4700 includes a land 4712 outside the mold 4711. The land 4712 is electrically connected to an electrode pad 4713, and the electrode pad 4713 is electrically connected to the chip 4800*a* through a wire 4714. The electronic component 4700 is mounted on a printed circuit board 4702, for example. A plurality of such electronic components is combined and electrically connected to each other on the printed circuit board 4702, whereby the mounting board 4704 is completed.

Figure 39D:
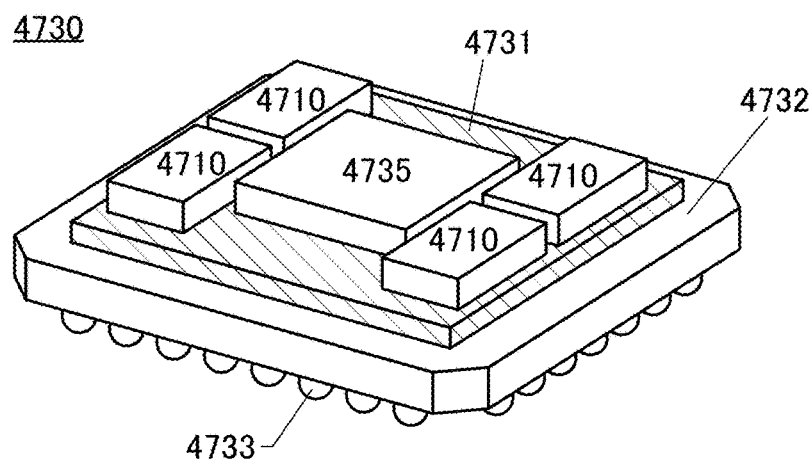

FIG. 39D is a perspective view of an electronic component 4730. The electronic component 4730 is an example of a SiP (System in package) or an MCM (Multi Chip Module).

In the electronic component 4730, an interposer 4731 is provided on a package substrate 4732 (printed circuit board), and a semiconductor device 4735 and a plurality of semiconductor devices 4710 are provided on the interposer 4731.

The electronic component 4730 includes the semiconductor devices 4710. Examples of the semiconductor devices 4710 include the semiconductor device described in the above embodiment and a high bandwidth memory (HBM). An integrated circuit (a semiconductor device) such as a CPU, a GPU, an FPGA, or a memory device can be used as the semiconductor device 4735.

As the package substrate 4732, a ceramic substrate, a plastic substrate, a glass epoxy substrate, or the like can be used. As the interposer 4731, a silicon interposer, a resin interposer, or the like can be used.

The interposer 4731 includes a plurality of wirings and has a function of electrically connecting a plurality of integrated circuits with different terminal pitches. The plurality of wirings have a single-layer structure or a layered structure. Moreover, the interposer 4731 has a function of electrically connecting an integrated circuit provided on the interposer 4731 to an electrode provided on the package substrate 4732. Accordingly, the interposer is sometimes referred to as a redistribution substrate or an intermediate substrate. A through electrode is provided in the interposer 4731 and the through electrode is used to electrically connect an integrated circuit and the package substrate 4732 in some cases. In the case of using a silicon interposer, a TSV (through-silicon via) can also be used as the through electrode.

A silicon interposer is preferably used as the interposer 4731. The silicon interposer can be manufactured at lower cost than an integrated circuit because the silicon interposer is not necessarily provided with an active element. Meanwhile, since wirings of the silicon interposer can be formed through a semiconductor process, the formation of minute wirings, which is difficult for a resin interposer, is easily achieved.

An HBM needs to be connected to many wirings to achieve a wide memory bandwidth. Therefore, an interposer on which an HBM is mounted requires minute and densely formed wirings. For this reason, a silicon interposer is preferably used as the interposer on which an HBM is mounted.

In an SiP, an MCM, or the like using a silicon interposer, a decrease in reliability due to a difference in the coefficient of expansion between an integrated circuit and the interposer is less likely to occur. Furthermore, a surface of a silicon interposer has high planarity, and a poor connection between the silicon interposer and an integrated circuit provided thereon less likely occurs. It is particularly preferable to use a silicon interposer for a 2.5D package (2.5D mounting) in which a plurality of integrated circuits is arranged side by side on the interposer.

A heat sink (a radiator plate) may be provided to overlap with the electronic component 4730. In the case of providing a heat sink, the heights of integrated circuits provided on the interposer 4731 are preferably equal to each other. For example, in the electronic component 4730 described in this embodiment, the heights of the semiconductor devices 4710 and the semiconductor device 4735 are preferably equal to each other.

To mount the electronic component 4730 on another substrate, an electrode 4733 may be provided on the bottom portion of the package substrate 4732. FIG. 39D illustrates an example in which the electrode 4733 is formed of a solder ball. Solder balls are provided in a matrix on the bottom portion of the package substrate 4732, whereby BGA (Ball Grid Array) mounting can be achieved. Alternatively, the electrode 4733 may be formed of a conductive pin. When conductive pins are provided in a matrix on the bottom portion of the package substrate 4732, PGA (Pin Grid Array) mounting can be achieved.

The electronic component 4730 can be mounted on another substrate by various mounting methods other than BGA and PGA. For example, a mounting method such as a staggered pin grid array (SPGA), a land grid array (LGA), a quad flat package (QFP), a quad flat J-leaded package (QFJ), or a quad flat non-leaded package (QFN) can be employed.

Note that this embodiment can be combined with any of the other embodiments in this specification as appropriate.

Embodiment 9

Figure 40:
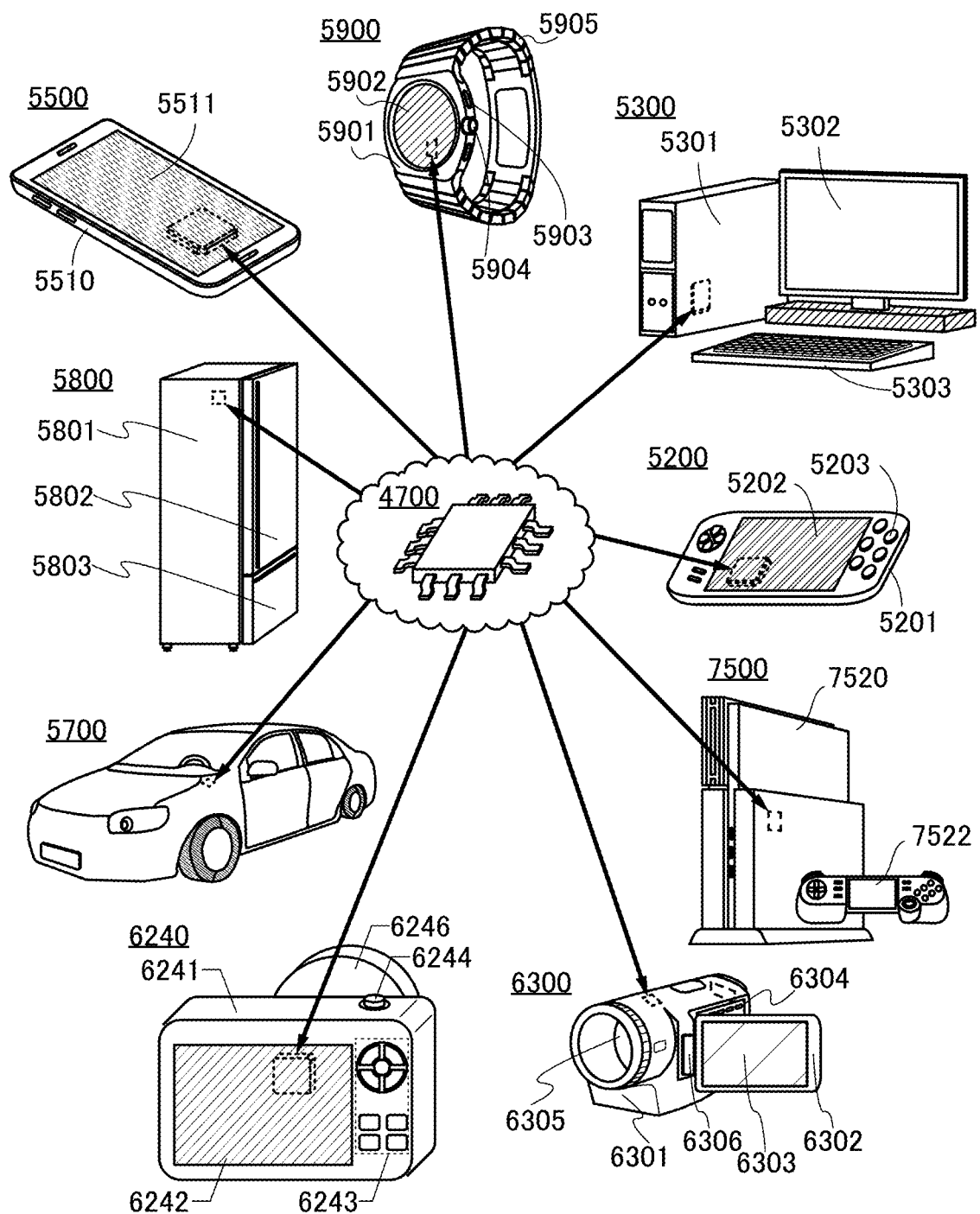
FIG. 40 is a perspective view showing examples of electronic devices.

This embodiment will show examples of electronic devices including the semiconductor device described in the above embodiment. FIG. 40 illustrates electronic devices each including the electronic component 4700 including the semiconductor device.

[Mobile Phone]

An information terminal 5500 illustrated in FIG. 40 is a mobile phone (smartphone), which is a type of information terminal. The information terminal 5500 includes a housing 5510 and a display portion 5511, and as input interfaces, a touch panel is provided in the display portion 5511 and a button is provided in the housing 5510.

The information terminal 5500 can execute an application utilizing artificial intelligence with the use of the semiconductor device described in the above embodiment. Examples of the application utilizing artificial intelligence include an application for interpreting a conversation and displaying its content on the display portion 5511; an application for recognizing letters, diagrams, and the like input to the touch panel of the display portion 5511 by a user and displaying them on the display portion 5511; and an application for biometric authentication using fingerprints, voice prints, or the like. The information terminal 5500 can execute the applications with the use of the semiconductor device described in the above embodiment with low power consumption.

[Wearable Terminal]

FIG. 40 illustrates an information terminal 5900 as an example of a watch-type wearable terminal. The information terminal 5900 includes a housing 5901, a display portion 5902, an operation button 5903, an operator 5904, a band 5905, and the like.

The wearable terminal can execute an application utilizing artificial intelligence with the use of the semiconductor device described in the above embodiment, like the information terminal 5500. Examples of the application utilizing artificial intelligence include an application for managing the health condition of the user of the wearable terminal and a navigation system that selects the optimal route and navigates the user on the basis of the input of the destination. The information terminal 5900 including the semiconductor device of the above described embodiments can execute the above described applications and systems with low power consumption.

[Information Terminal]

FIG. 40 illustrates a desktop information terminal 5300. The desktop information terminal 5300 includes a main body 5301 of the information terminal, a display 5302, and a keyboard 5303.

The desktop information terminal 5300 can execute an application utilizing artificial intelligence with the use of the semiconductor device described in the above embodiment, like the information terminal 5500 described above. Examples of the application utilizing artificial intelligence include design-support software, text correction software, and software for automatic menu generation. Furthermore, with the use of the desktop information terminal 5300, novel artificial intelligence can be developed.

Note that although FIG. 40 illustrates the smartphone, the desktop information terminal, and the wearable terminal as examples of the electronic device, one embodiment of the present invention can also be applied to information terminals other than smartphones, desktop information terminals, and wearable terminals. Examples of information terminals other than smartphones, desktop information terminals, and wearable terminals include a PDA (Personal Digital Assistant), a laptop information terminal, and a workstation.

[Household Appliance]

FIG. 40 illustrates an electric refrigerator-freezer 5800 as an example of a household appliance. The electric refrigerator-freezer 5800 includes a housing 5801, a refrigerator door 5802, a freezer door 5803, and the like.

When the semiconductor device described in the above embodiment is used for the electric refrigerator-freezer 5800, the electric refrigerator-freezer 5800 including artificial intelligence can be achieved. Utilizing the artificial intelligence enables the electric refrigerator-freezer 5800 to have a function of automatically making a menu based on foods stored in the electric refrigerator-freezer 5800, expiration dates of the foods, or the like, a function of automatically adjusting temperature to be appropriate for the foods stored in the electric refrigerator-freezer 5800, and the like.

Although the electric refrigerator-freezer is described as an electronic device in the example, other examples of the electronic device include a vacuum cleaner, a microwave oven, an electric oven, a rice cooker, a water heater, an IH (Induction Heating) cooker, a water server, a heating-cooling combination appliance such as an air conditioner, a washing machine, a drying machine, and an audio visual appliance.

[Game Machines]

FIG. 40 illustrates a portable game machine 5200 as an example of a game machine. The portable game machine 5200 includes a housing 5201, a display portion 5202, a button 5203, and the like.

FIG. 40 illustrates a stationary game machine 7500 as another example of a game machine. The stationary game machine 7500 includes a main body 7520 and a controller 7522. The controller 7522 can be connected to the main body 7520 with or without a wire. Although not illustrated in FIG. 40, the controller 7522 can include a display portion that displays a game image, and an input interface besides a button, such as a touch panel, a stick, a rotating knob, and a sliding knob, for example. The shape of the controller 7522 is not limited to that in FIG. 40, and the shape of the controller 7522 may be changed variously in accordance with the genres of games. For example, for a shooting game such as an FPS (First Person Shooter) game, a gun-shaped controller having a trigger button can be used. As another example, for a music game or the like, a controller having a shape of a musical instrument, audio equipment, or the like can be used. Furthermore, the stationary gaming machine may include a camera, a depth sensor, a microphone, and the like so that the game player can play a game using a gesture and/or a voice instead of a controller.

An image of the game machine can be output with a display device such as a television device, a personal computer display, a game display, or a head-mounted display.

When the semiconductor device described in the above embodiment is used in the portable game machine 5200, the portable game machine 5200 with low power consumption can be achieved. Furthermore, heat generation from a circuit can be reduced owing to low power consumption; thus, the influence of heat generation on the circuit itself, the peripheral circuit, and the module can be reduced.

Furthermore, when the semiconductor device described in the above embodiment is used for the portable game machine 5200, the portable game machine 5200 including artificial intelligence can be achieved.

In general, the progress of a game, the actions and words of game characters, and expressions of a phenomenon and the like in the game are programed in the game; however, the use of artificial intelligence in the portable game machine 5200 enables expressions not limited by the game program. For example, it becomes possible to change expressions such as questions posed by the player, the progress of the game, time, and actions and words of game characters.

When a game requiring a plurality of players is played on the portable game console 5200, the artificial intelligence can create a virtual game player; thus, the game can be played alone with the game player created by the artificial intelligence as an opponent.

Although FIG. 40 illustrates the portable game machine as an example of a game machine, the electronic device of one embodiment of the present invention is not limited thereto. Examples of the electronic device of one embodiment of the present invention include a home stationary game machine, an arcade game machine installed in entertainment facilities (e.g., a game center and an amusement park), and a throwing machine for batting practice installed in sports facilities.

[Moving Vehicle]

The semiconductor device described in the above embodiment can be used for an automobile, which is a moving vehicle, and around the driver's seat in an automobile.

FIG. 40 illustrates an automobile 5700 as an example of a moving vehicle.

An instrument panel that can display a speedometer, a tachometer, a mileage, a fuel meter, a gearshift state, air-conditioning setting, and the like is provided around the driver's seat in the automobile 5700. In addition, a display device showing the above information may be provided around the driver's seat.

In particular, the display device can compensate for the view obstructed by the pillar or the like, the blind areas for the driver's seat, and the like by displaying an image taken by an imaging device (not illustrated) provided for the automobile 5700, which improves safety. That is, display of an image taken by an imaging device provided on the outside of the automobile 5700 can fill in blind areas and improve safety.

Since the semiconductor device described in the above embodiment can be used as the components of artificial intelligence, the semiconductor device can be used for an automatic driving system of the automobile 5700, for example. The semiconductor device can also be used for a system for navigation, risk prediction, or the like. The display device may display navigation information, risk prediction information, or the like. Furthermore, with the use of the semiconductor device, the automated driving system with low power consumption can be achieved; therefore, for example, in the case where the system is mounted on an electric vehicle, the power consumption by the system is reduced, and as a result, a mileage of the vehicle can be increased.

Note that although an automobile is described above as an example of a moving vehicle, the moving vehicle is not limited to an automobile. Examples of moving objects include a train, a monorail train, a ship, and a flying object (a helicopter, an unmanned aircraft (a drone), an airplane, and a rocket), and these moving objects can include a system utilizing artificial intelligence when equipped with the semiconductor device of one embodiment of the present invention.

[Camera]

The semiconductor device described in the above embodiments can be used for a camera.

FIG. 40 illustrates a digital camera 6240 as an example of an imaging device. The digital camera 6240 includes a housing 6241, a display portion 6242, operation buttons 6243, a shutter button 6244, and the like, and an attachable lens 6246 is attached to the digital camera 6240. Although the lens 6246 of the digital camera 6240 is detachable from the housing 6241 for replacement here, the lens 6246 may be integrated with the housing 6241. A stroboscope, a viewfinder, or the like may be additionally attached to the digital camera 6240.

When the semiconductor device described in the above embodiment is used in the digital camera 6240, the digital camera 6240 with low power consumption can be achieved. Furthermore, heat generation from a circuit can be reduced owing to low power consumption; thus, the influence of heat generation on the circuit itself, the peripheral circuit, and the module can be reduced.

Furthermore, when the semiconductor device described in the above embodiment is used for the digital camera 6240, the digital camera 6240 including artificial intelligence can be achieved. Utilizing the artificial intelligence enables the digital camera 6240 to have a function of automatically recognizing a subject such as a face or an object, a function of adjusting a focus on the subject, a function of automatically using a flash in accordance with environments, a function of toning a taken image, and the like.

[Video Camera]

The semiconductor device described in the above embodiment can be used for a video camera.

FIG. 40 illustrates a video camera 6300 as an example of an imaging device. The video camera 6300 includes a first housing 6301, a second housing 6302, a display portion 6303, operation keys 6304, a lens 6305, a joint 6306, and the like. The operation keys 6304 and the lens 6305 are provided in the first housing 6301, and the display portion 6303 is provided in the second housing 6302. The first housing 6301 and the second housing 6302 are connected to each other with the joint 6306, and the angle between the first housing 6301 and the second housing 6302 can be changed with the joint 6306. Images displayed on the display portion 6303 may be changed in accordance with the angle at the joint 6306 between the first housing 6301 and the second housing 6302.

When images taken by the video camera 6300 are recorded, the images need to be encoded in accordance with a data recording format. With the use of artificial intelligence, the video camera 6300 can perform the pattern recognition by artificial intelligence in encoding of the images. The pattern recognition is used to calculate a difference in the human, the animal, the object, and the like between continuously taken image data, so that the data can be compressed. Furthermore, by applying the semiconductor device described in the above embodiment to the video camera 6300, power consumption needed for the above operation and the like of the video camera 6300 can be reduced.

[External Device for Personal Computer]

The semiconductor device described in the above embodiment can be used in a calculator such as a PC (Personal Computer) and an external device for an information terminal.

Figure 41A:
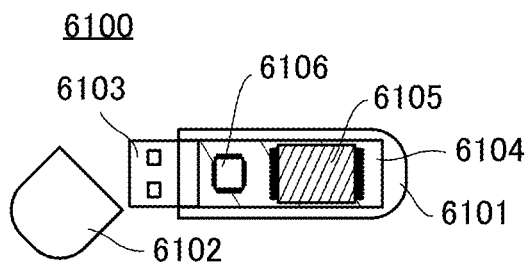
FIG. 41A to FIG. 41C are perspective views showing examples of electronic devices.

FIG. 41A illustrates, as an example of the external device, a portable external device 6100 that includes a chip capable of arithmetic processing and is externally attached to a PC. The external device 6100 can perform arithmetic processing using the chip when connected to a PC with a USB (Universal Serial Bus), for example. FIG. 41A shows the portable external device 6100; however, the external device of one embodiment of the present invention is not limited thereto and may be a relatively large external device including a cooling fan or the like, for example.

The external device 6100 includes a housing 6101, a cap 6102, a USB connector 6103, and a substrate 6104. The substrate 6104 is held in the housing 6101. The substrate 6104 is provided with a circuit for driving the semiconductor device or the like described in the above embodiment. For example, a chip 6105 (e.g., the semiconductor device described in the above embodiment, the electronic component 4700, or a memory chip) and a controller chip 6106 are attached to the substrate 6104. The USB connector 6103 functions as an interface for connection to an external device.

The use of the external device 6100 for the PC and the like can increase the arithmetic processing properties of the PC.

Thus, a PC with insufficient processing capability can perform arithmetic operation of artificial intelligence, moving image processing, and the like.

[Broadcasting System]

The semiconductor device described in the above embodiment can be used for a broadcasting system.

Figure 41B:
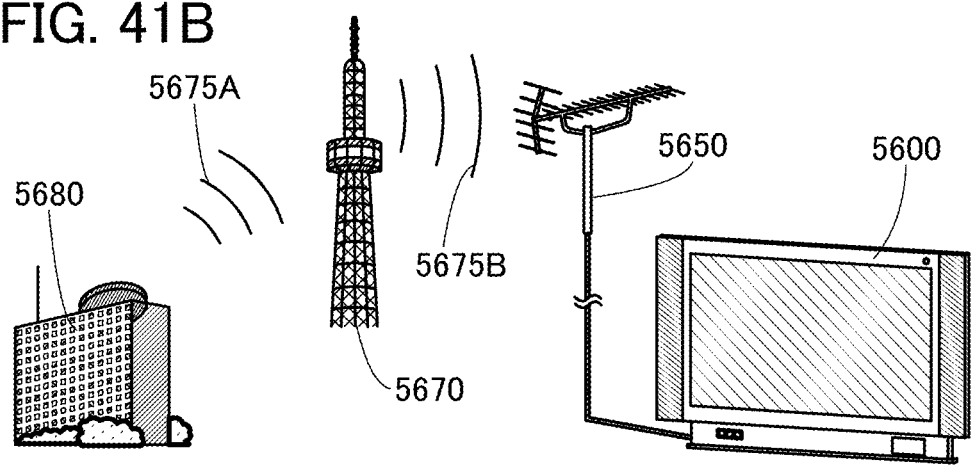

FIG. 41B schematically illustrates data transmission in a broadcasting system. Specifically, FIG. 41B illustrates a path in which a radio wave (a broadcasting signal) transmitted from a broadcast station 5680 reaches a television receiver (TV) 5600 of each household. The TV 5600 includes a receiving device (not illustrated), and the broadcast signal received by an antenna 5650 is transmitted to the TV 5600 through the receiving device.

Although a UHF (Ultra High Frequency) antenna is illustrated as the antenna 5650 in FIG. 41B, a BS/110° CS antenna, a CS antenna, or the like can also be used as the antenna 5650.

A radio wave 5675A and a radio wave 5675B are broadcast signals for terrestrial broadcasting; a radio wave tower 5670 amplifies the received radio wave 5675A and transmits the radio wave 5675B. Each household can view terrestrial TV broadcasting on the TV 5600 by receiving the radio wave 5675B with the antenna 5650. Note that the broadcasting system is not limited to the terrestrial broadcasting illustrated in FIG. 41B and may be satellite broadcasting using an artificial satellite, data broadcasting using an optical line, or the like.

The above-described broadcasting system may be a broadcasting system that utilizes artificial intelligence by including the semiconductor device described in the above embodiment. When the broadcast data is transmitted from the broadcast station 5680 to the TV 5600 of each household, the broadcast data is compressed with an encoder. When the antenna 5650 receives the compressed broadcast data, the compressed broadcast data is decompressed with a decoder of the receiving device in the TV 5600. Utilizing the artificial intelligence enables, for example, recognition of a display pattern included in a displayed image in motion compensation prediction, which is one of the compressing methods for the encoder. In-frame prediction utilizing artificial intelligence, for example, can also be performed. As another example, when the broadcast data with low resolution is received and the broadcast data is displayed on the TV 5600 with high resolution, image interpolation such as upconversion can be performed in the broadcast data decompression by the decoder.

The above-described broadcasting system utilizing artificial intelligence is suitable for ultra-high definition television (UHDTV: 4K and 8K) broadcasting, which needs a large amount of broadcast data.

As the application of artificial intelligence in the TV 5600, a recording device with artificial intelligence may be provided in the TV 5600, for example. With such a structure, the artificial intelligence can learn the user's preference, so that TV programs that suit the user's preference can be recorded automatically in the recording device.

[Authentication System]

The semiconductor device described in the above embodiment can be used for an authentication system.

Figure 41C:
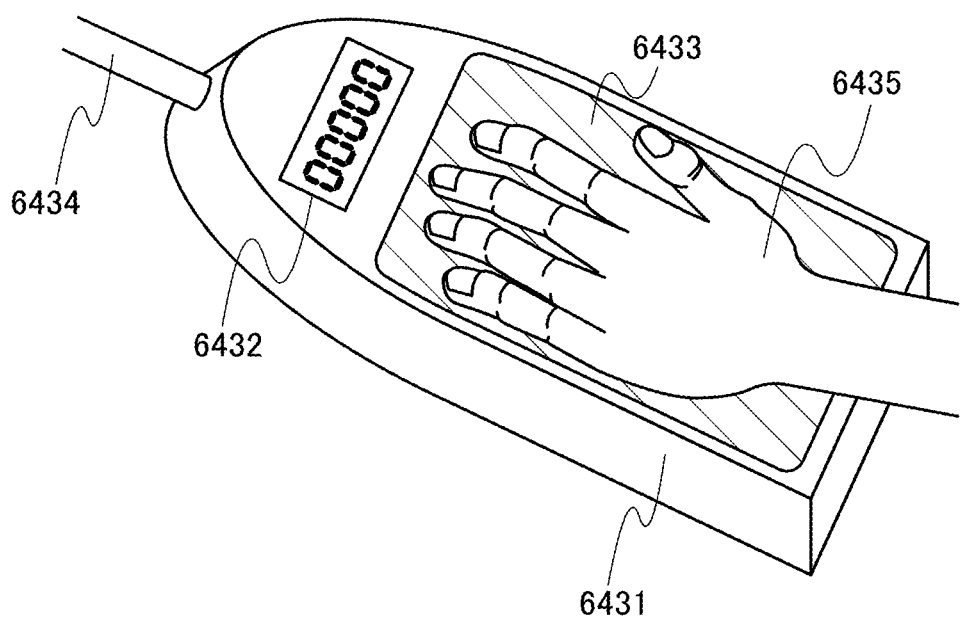

FIG. 41C illustrates a palm print authentication device including a housing 6431, a display portion 6432, a palm print reading portion 6433, and a wiring 6434.

In FIG. 41C, a palm print of a hand 6435 is obtained using the palm print authentication device. The obtained palm print is subjected to the pattern recognition utilizing artificial intelligence, so that personal authentication of the palm print can be performed. Thus, a system that performs highly secure authentication can be constructed. Without limitation to the palm print authentication device, the authentication system of one embodiment of the present invention may be a device that performs biometric authentication by obtaining biological information of fingerprints, veins, faces, iris, voice prints, genes, physiques, or the like.

[Alarm]

The semiconductor device described in the above embodiments can be used for an alarm.

Figure 42A:
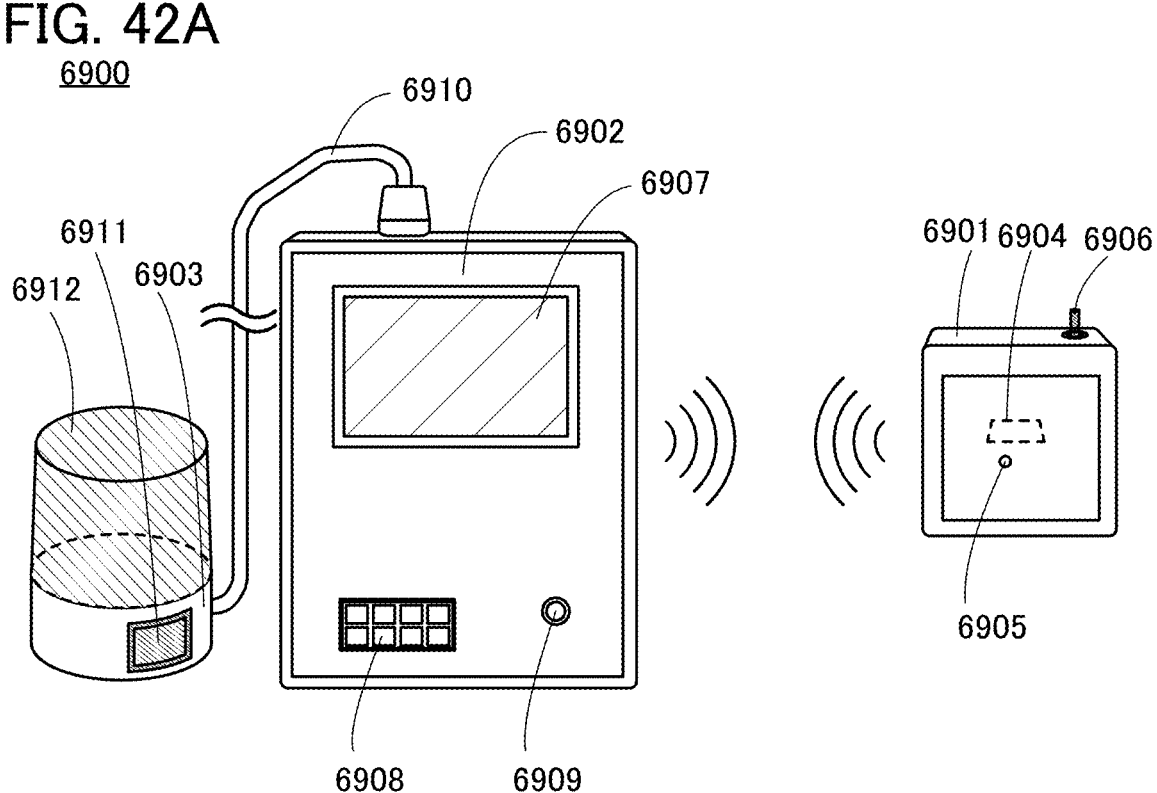
FIG. 42A to FIG. 42C are schematic diagrams each showing an example of an electronic device.

FIG. 42A illustrates an alarm 6900, which includes a sensor 6901, a receiver 6902, and a transmitter 6903.

The sensor 6901 includes a sensor circuit 6904, an air vent 6905, an operation key 6906, and the like. The detection object that passes through the air vent 6905 is sensed with the sensor circuit 6904. The sensor circuit 6904 can be, for example, a detector in which water leakage, electric leakage, gas leakage, fire, the water level of a river that may overflow, the seismic intensity of an earthquake, a radiation, or the like is the detection object. In particular, in the case where the detection object includes smoke in a fire, gas leakage, a radiation, or the like, the odor sensor SMS described in Embodiment 4 can be used.

For example, when the sensor circuit 6904 senses the detection object with a predetermined value or more, the sensor 6901 sends information thereof to the receiver 6902. The receiver 6902 includes a display unit 6907, operation keys 6908, an operation key 6909, a wiring 6910, and the like. The receiver 6902 controls the operation of the transmitter 6903 in accordance with the information from the sensor 6901. The transmitter 6903 includes a speaker 6911, a lighting device 6912, and the like. The transmitter 6903 has a function of giving an alarm in accordance with a command from the transmitter 6903. Although FIG. 42A illustrates an example in which the transmitter 6903 gives a sound alarm using the speaker 6911 and gives an optical alarm using the lighting device 6912 such as red light, the transmitter 6903 may give any one of the alarms or another alarm.

In the case where the sensor circuit functions as a fire alarm, the receiver 6902 may command fire preventive equipment such as a shutter to perform a predetermined operation when an alarm is given. Although FIG. 42A illustrates an example in which signals are wirelessly transmitted and received between the receiver 6902 and the sensor 6901, signals may be transmitted and received via a wiring or the like. In addition, although FIG. 42A illustrates an example in which a signal is transmitted from the receiver 6902 to the transmitter 6903 via the wiring 6910, a signal may be wirelessly transmitted. Furthermore, by using the odor sensor SMS described in Embodiment 4, what kind of burnable material is burning can be identified in some cases from the smoke generated by the fire. In particular, a method for extinguishing a fire is different depending on burnable materials; thus, to identify the burnable material causing a fire can lead to extinguishing the fire quickly.

[Robot]

The semiconductor device described in the above embodiments can be used for a robot.

Figure 42B:
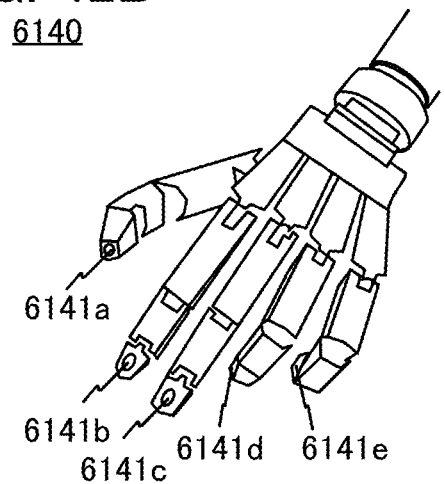

FIG. 42B illustrates an example of a robot. A robot 6140 includes a tactile sensor 6141a to a tactile sensor 6141e. The robot 6140 can grasp an object with the use of the tactile sensor 6141a to the tactile sensor 6141e. For example, the tactile sensor 6141a to the tactile sensor 6141e have a function such that a current flows through the object in accordance with a contact area at the time of touching the object, and the robot 6140 can recognize that the robot 6140 grasps the object, from the amount of the flowing current.

Figure 42C:
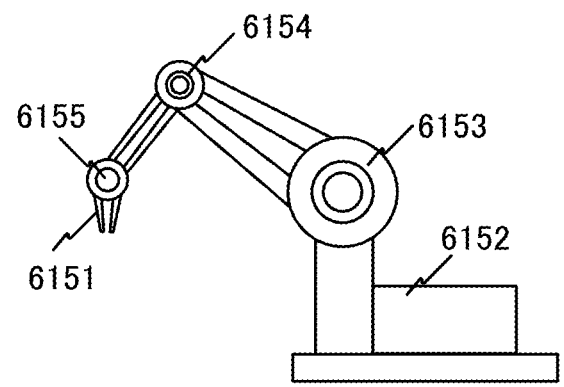

FIG. 42C illustrates an example of an industrial robot. The industrial robot preferably includes a plurality of drive shafts to control the driving range minutely. An example in which an industrial robot 6150 includes a function unit 6151, a control unit 6152, a drive shaft 6153, a drive shaft 6154, and a drive shaft 6155 is illustrated. The function unit 6151 preferably includes a sensor such as an image detection module.

The function unit 6151 preferably has one or more functions of grasping, cutting, welding, applying, and bonding an object, for example. The productivity of the industrial robot 6150 is increased as the response is improved. In order that the industrial robot 6150 can operate precisely, a sensor that detects a minute current or the like is preferably provided.

Note that this embodiment can be combined with any of the other embodiments in this specification as appropriate.

Example 1

To verify that a product-sum operation of the first data and the second data with the configuration of the arithmetic circuit MAC1, the arithmetic circuit MAC1A, the arithmetic circuit MAC2, or the arithmetic circuit MAC3 is properly performed, a circuit was actually manufactured, and the circuit was subjected to measurement.

<Multiplication Circuit>

Figure 43:
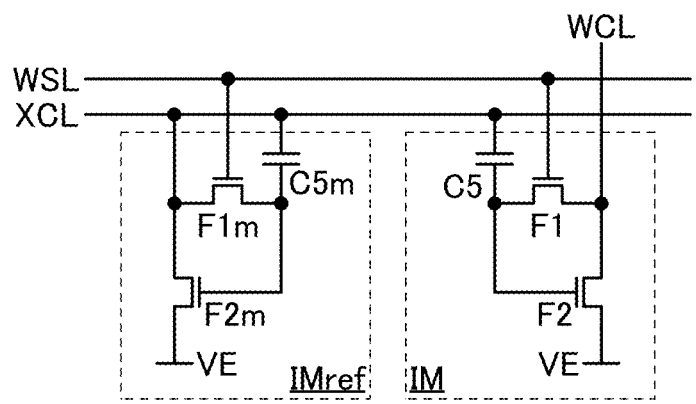
FIG. 43 is a circuit diagram showing a prototype arithmetic circuit.

FIG. 43 illustrates part of a configuration of the arithmetic circuit actually manufactured. The cell IM and the cell IMref illustrated in FIG. 43 correspond to the cell IM and the cell IMref provided in a row of the cell array CA in FIG. 1, respectively. Thus, the cell IM and the cell IMref in FIG. 43 are electrically connected to the wiring WSL in the same row, and the cell IM and the cell IMref in FIG. 43 are electrically connected to the wiring XCL in the same row. In addition, for the circuit configurations of the cell IM and the cell IMref in FIG. 43, the descriptions of the arithmetic circuit MAC1 in FIG. 1 are referred to.

As the sizes of each of the transistor F1, the transistor F2, the transistor F1*m*, and the transistor F2*m* included in the cell IM and the cell IMref, the channel length was 350 nm, and the channel width was 350 nm.

As described in Embodiment 1, an appropriate voltage is applied to the source, drain, and gate of each of transistor F2 and the transistor F2*m* in FIG. 43 so that the transistor F2 and the transistor F2*m* operate in the subthreshold region, i.e., a region in which a drain current exponentially changes with respect to a change in a gate voltage.

In addition, a potential supplied by the wiring VE was set to a ground potential of 0 V.

First, a high-level potential is input to the wiring WSL to turn on the transistor F1 and the transistor F1*m*. Then, a current $WI_{W0}$ which is W times as large as a reference current Iwo is input to the wiring WCL and a reference current $I_{X0}$ is input to the wiring XCL. At this time, the gate voltage of the transistor F1 is set in a self-determining manner at a voltage which can make the current $WI_{W0}$ flow between the source and the drain of the transistor F1, and the gate voltage of the transistor F1*m* is set in a self-determining manner at a voltage which can make the current $I_{X0}$ flow between the source and the drain of the transistor F1*m*. After the gate voltage of each of the transistor FT and the transistor F1*m* is determined, a low-level potential is input to the wiring WSL to turn off the transistor F1 and the transistor F1*m*, and the gate voltage of each of the transistor F1 and the transistor F1*m* is stored. Note that these operations correspond to the operations from Time T12 to Time T14 in the timing chart in FIG. 6, and are hereinafter referred to as the first operation.

Next, a current $I_X=XI_{X0}$ which is X times larger than the reference current $I_{X0}$ is input to the wiring XCL and a constant voltage Vd is input to the wiring WCL. At this time, the voltage of the wiring XCL changes, so that the gate voltage of the transistor F1 is changed due to the capacitive coupling of the capacitor C5. At this time, the current flowing between the source and the drain of the transistor F1 is a current $I_Y=YI_{W0}$ which is Y times larger than a reference current Iwo. In addition, since the transistor F1 and the transistor F2 operate in the subthreshold region, $YI_{W0}=WXI_{W0}$ can be achieved. That is, Y is the product of W and X. Note that these operations correspond to the operations in the period from Time T21 to Time T23 in the timing chart in FIG. 6 and are hereinafter referred to as the second operation.

<<Multiplication Characteristics>>

Figure 44A:
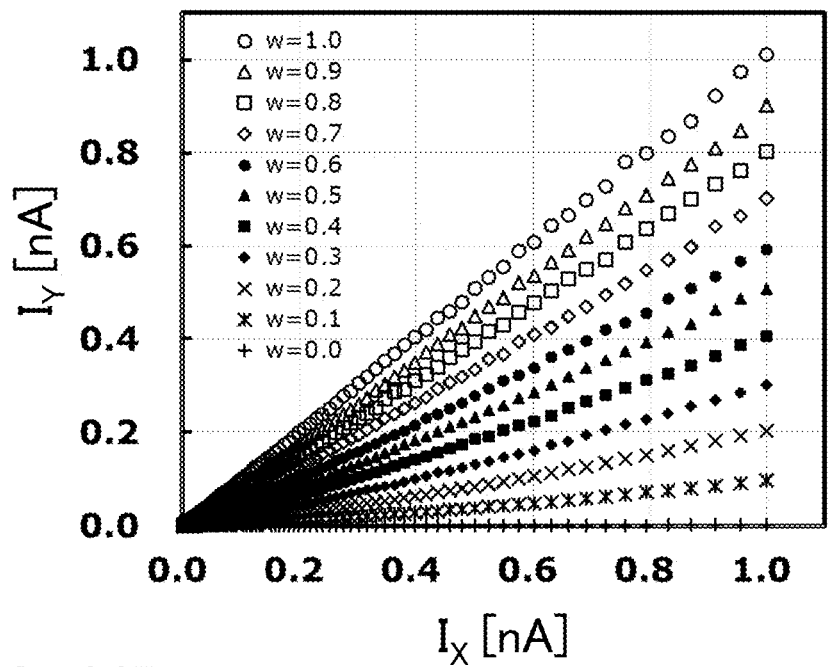
FIG. 44A is a graph showing multiplication characteristics of a prototype arithmetic circuit.

Here, $I_X$-$I_Y$ characteristics were measured with the conditions that Iwo was 1 nA, $I_{X0}$ was 1 nA, Vd was 1 V, and W and X were swept from 0.0 to 1.0 by 0.1. FIG. 44A shows $I_X$-$I_Y$ characteristics of the measurement results. In the second operation after the first operation of determining W, $I_Y$ particularly shows the median of currents flowing between the source and the drain of the transistor F1 measured 30 times. A variation σ of $I_Y$ is less than 0.1 nA.

From the $I_X$-$I_Y$ characteristics in FIG. 44A, the correlation coefficient of $I_Y$ and X with each value of W was estimated to be 0.969 or more. From this, it can be said that the multiplication characteristics of W and X (Y=WX) of the circuit in FIG. 43 are favorable.

<<Retention Characteristics>>

Figure 44B:
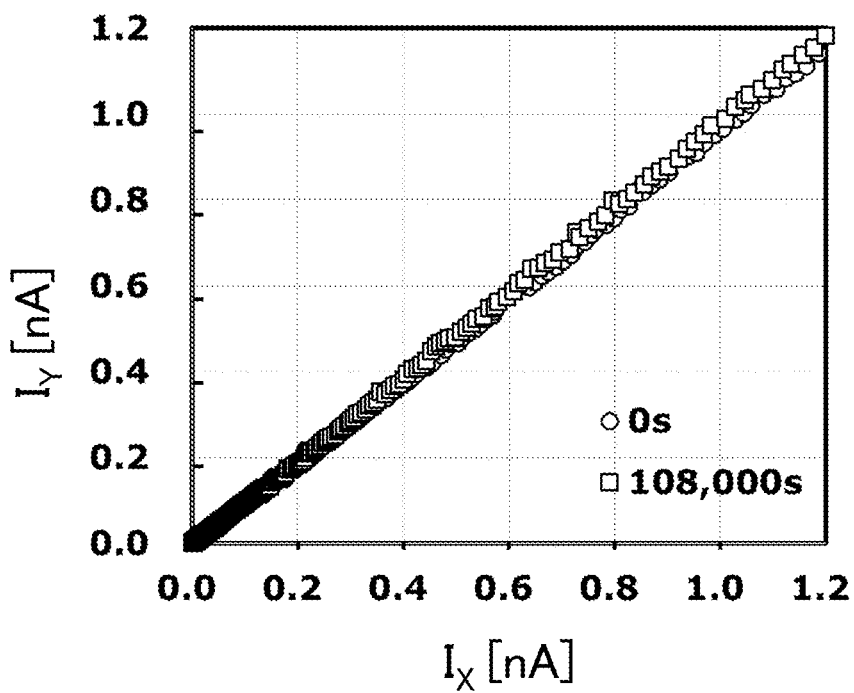
FIG. 44B is a graph showing retention characteristics of a prototype arithmetic circuit.

To examine storing characteristics of the circuit illustrated in FIG. 43, $I_X$-$I_Y$ characteristics were measured with W=1.0 just after the first operation (at 0 s) and 108000 s after the first operation. FIG. 44B shows the $I_X$-$I_Y$ characteristics of the measurement results. As illustrated in FIG. 44, the amount of change in $I_Y$ from just after the first operation (at 0 s) to 108000 s after the first operation was less than 3%. From this, it can be said that the storing characteristics of the circuit in FIG. 43 is preferable.

<<Difference in Element Variations Between Current Writing and Voltage Writing>>

The above-described first operation and second operation are operations in which a desirable current is supplied to the wiring WCL and the wiring XCL to perform multiplication of W and X (hereinafter referred to as a current-writing method and described as Current write in the diagram); an operation in which a voltage is written to each gate of the transistor F1 and the transistor F1*m* to perform multiplication of W and X (hereinafter referred to as a voltage-writing method and described as Voltage write in the diagram) can be performed in principle. Here, the degree of an element variation σ was studied in the current-writing method and the voltage writing method.

Note that to measure the element variation a, 16 circuits illustrated in FIG. 43 were prepared and multiplications with the current-writing method and multiplication operations with the voltage-writing method were performed in each circuit.

Figure 45A:
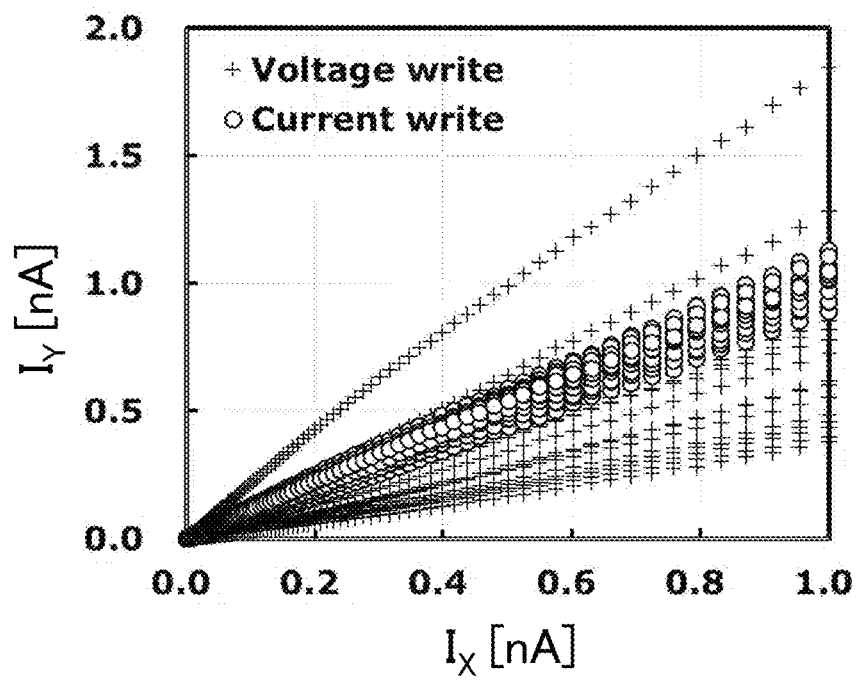
FIG. 45A is a graph showing multiplication characteristics in a voltage-writing method (Voltage write) and a current-writing method (Current write) of a prototype arithmetic circuit.

FIG. 45A illustrates the $I_X$-$I_Y$ characteristics of the 16 circuits in FIG. 43 when multiplication operations are performed with the current-writing method and the voltage-writing method. FIG. 45A illustrates that a variation σ of $I_Y$ in the elements with the voltage-writing method is 39%, and a variation σ of $I_Y$ in the elements with the current-writing method is 7%. That is, it was confirmed that variations of elements of the circuit in FIG. 43 can be decreased with a multiplication operation with the current-writing method rather than the voltage-writing operation.

Figure 45B:
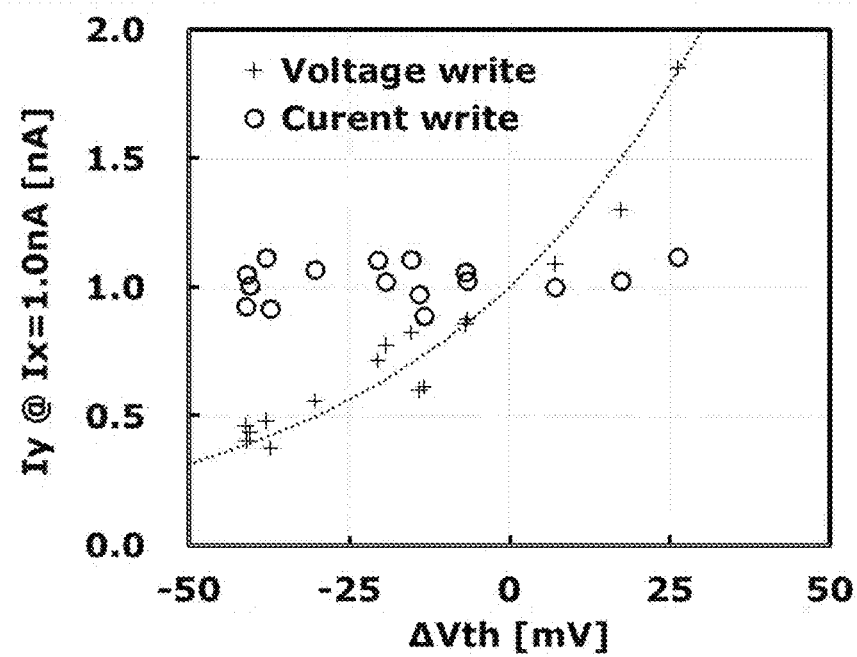
FIG. 45B is a graph showing a relation of a difference in a threshold voltage and an output current in a voltage-writing method (Voltage write) and a current-writing method (Current write) of a prototype arithmetic circuit.

Next, the dependence of the element variation σ of $I_Y$ on a difference $\Delta V_{th}$ of the threshold voltages of the transistor F1 and the transistor F1m in the elements was studied. FIG. 45B is a graph showing the relation between $\Delta V_{th}$ and $I_Y$ in the elements with $I_X$ of 1.0 nA. The threshold voltage of the transistor F1 in each element is $V_{th}$, the threshold voltage of the transistor F1m in each element is $V_{thm}$, and the difference between the threshold voltages of the transistor F1 and the transistor F1m is $\Delta V_{th} = V_{thm} - V_{th}$.

In the case of a voltage-writing method, as shown in FIG. 45B, the element variation σ can be approximated as the exponential function of $\Delta V_{th}$. Specifically, $I_Y$ in the voltage-writing method was fitted with an exponential function ($I_Y = 10^{\Delta Vth/0.100}$) with a subthreshold slope (S value) of 100 mV. An element variation of $\Delta V_{th}$ was measured and the result was $\Delta V_{th} = +21$ mV. This is substituted for the fitted exponential function; $I_Y$ becomes 0.62 A or 1.62, and the difference from $I_Y$ when $\Delta V_{th} = 0$ is $\Delta I_Y = -0.38$ or 0.62. The element variation σ in $I_Y$ with the voltage-writing method is 39%; thus, the absolute value of the amount of change $\Delta I_Y = -0.38$ from $I_Y$ when $\Delta V_{th} = 0$ was approximately close to this. That is, it can be found that a variation of $\Delta V_{th}$ in elements of 21 mV is reflected to σ. The variation σ in $I_Y$ of elements with the current-writing method is 7%; thus, the amount of change from $I_Y$ when $\Delta V_{th} = 0$ is $\Delta I_Y = 0.07$. Here, $1 - 0.07 = 10^{\Delta Vth/0.100}$ is solved for $\Delta V_{th}$, and $\Delta V_{th}$ is 3 mV. FIG. 45B shows that the variation of $I_Y$ in elements can be corrected with the current-writing method because the variation σ in elements is reduced to about ±3 mV when converted into $\Delta V_{th}$ of a fitted exponential function.

<Current Circuit>

Since the transistor F1 included in the cell IM operates in the subthreshold region, the current amount of the reference currents Iwo and $WI_{W0}$ flowing between the source and the drain of the transistor F1 is necessary to be more than or equal to $1.0 \times 10^{-12}$ A and less than or equal to $1.0 \times 10^{-8}$ A, for example. Similarly, since the transistor F1m included in the cell IMref operates in the subthreshold region, the current amount of the reference currents $I_{X0}$ and $XI_{X0}$ flowing between the source and the drain of the transistor F1m is necessary to be more than or equal to $10 \times 10^{-12}$ A and less than or equal to $1.0 \times 10^{-8}$ A, for example.

Figure 46A:
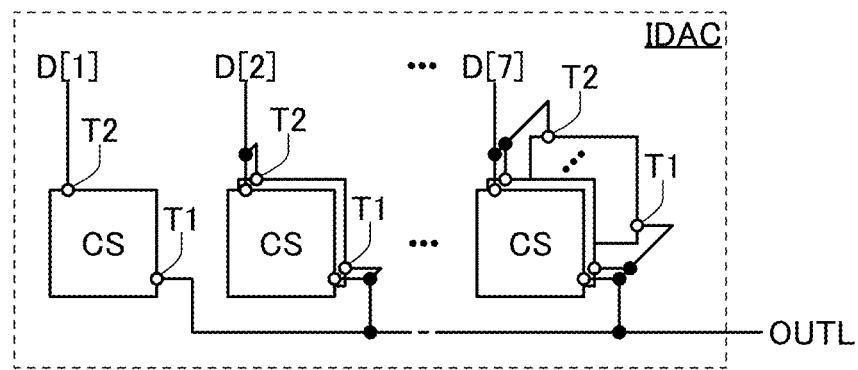
FIG. 46A and FIG. 46B are circuit diagrams showing a circuit included in a prototype arithmetic circuit.
Figure 46B:
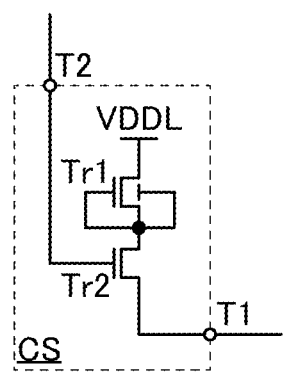

FIG. 46A and FIG. 46B illustrate the circuits that were actually manufactured capable of outputting a small current described above. A current circuit IDAC illustrated in FIG. 46A corresponds to the circuit WCS in FIG. 2A and the circuit XCS in FIG. 2C. Thus, for a circuit configuration of the current circuit IDAC in FIG. 46A, the descriptions of the circuit WCS in FIG. 2A and the circuit XCS in FIG. 2C are referred to.

The current circuit IDAC in FIG. 46A is configured to output a current to a wiring OUTL in response to 8-bit signals. Specifically, when the first-bit to eighth-bit values are input to a wiring D[1] to a wiring D[8], respectively, whereby it is decided whether the current source CS included in the current circuit IDAC outputs a current in response to the values. To a wiring D[s](s is an integer more than or equal to 1 and less than or equal to 8), $2^{s-1}$ current source(s) SC is/are electrically connected. In the case where the current source CS outputs $I_{ut}$ as a current amount, for example, the current source CS electrically connected to the wiring D[s] outputs a current of $2^{s-1} \times I_{ut}$ in total when a high-level potential is input to the wiring D[s]. Thus, the current circuit IDAC can output a current of the product of $I_{ut}$ and an integer from 1 to 256 in response to 8-bit signals.

The current source CS included in the current circuit IDAC in FIG. 46A is the current source CS illustrated in FIG. 46B, and the current source CS in FIG. 46B corresponds to the current source CS1 in FIG. 3A. Thus, for the current source CS in FIG. 46B, the descriptions of the current source CS1 in FIG. 3A can be referred to.

Each of the transistor Tr1 and the transistor Tr2 included in the current source CS in FIG. 46B has a channel length of 350 nm and a channel width of 350 nm.

As described in Embodiment 1, a current within a current range in which the transistor Tr1 operates in the subthreshold region flows between the first terminal and the second terminal of the transistor Tr1. In other words, the current $I_{ut}$ flowing from the current source CS can be a current within a current range in which the transistor Tr1 operates in the subthreshold region.

The potential applied by the wiring VDDL is 2 V. The wiring OUTL is biased to 0.5 V. To the wiring D[1] to the wiring D[7], 0 V is supplied when data of each bit is "0", and 2 V is supplied when data of each bit is "1".

Figure 47A:
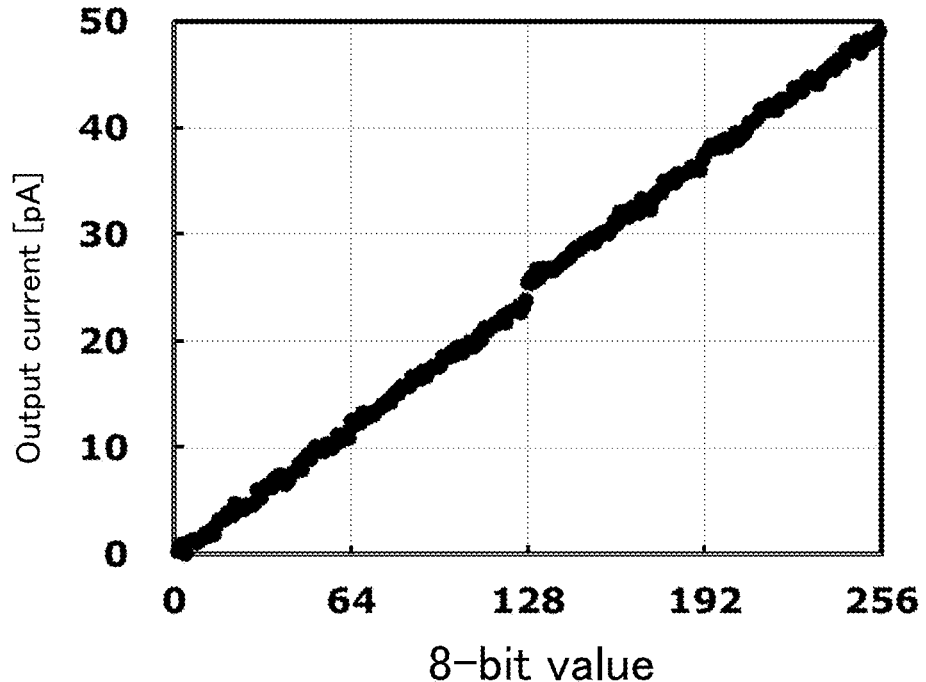
FIG. 47A is a graph showing output characteristics of a current circuit.

FIG. 47A is a graph showing output characteristics of a current output from the current circuit IDAC to the wiring OUTL when 8-bit signals are input to the current circuit IDAC. From the output characteristics in FIG. 47A, it is confirmed that the current circuit in FIG. 46A can output a current of more than or equal to $1.0 \times 10^{-12}$ and less than or equal to $5.0 \times 10^{-11}$ substantially linearly in response to 8-bit signals.

Figure 47B:
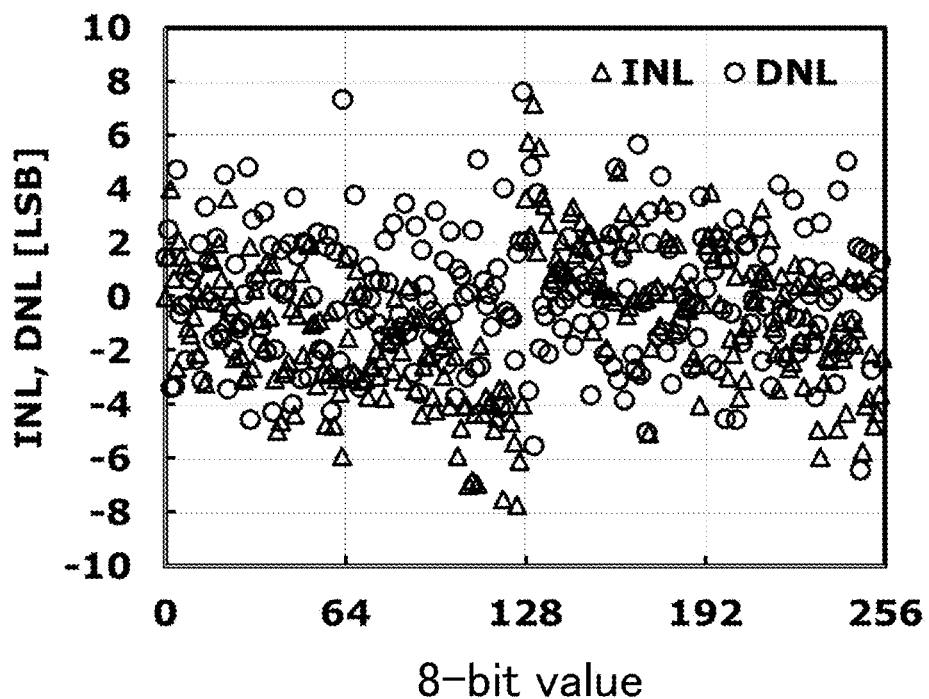
FIG. 47B is a graph showing currents INL and DNL output from a current circuit.

FIG. 47B illustrates INL (Integral Non-Linearity) and DNL (Differential Non-Linearity) of the current output from the current circuit IDAC to the wiring OUTL. From FIG. 47A and FIG. 47B, it is confirmed that ENOB (effective number of bits) of the current circuit IDAC is 5.04 bit.

Example 2

To verify the performance of a neural network including the multiplication circuit in FIG. 43 and the current circuit IDAC in FIG. 46A described in Example 1, a calculation was performed by using a circuit simulator.

Figure 48:
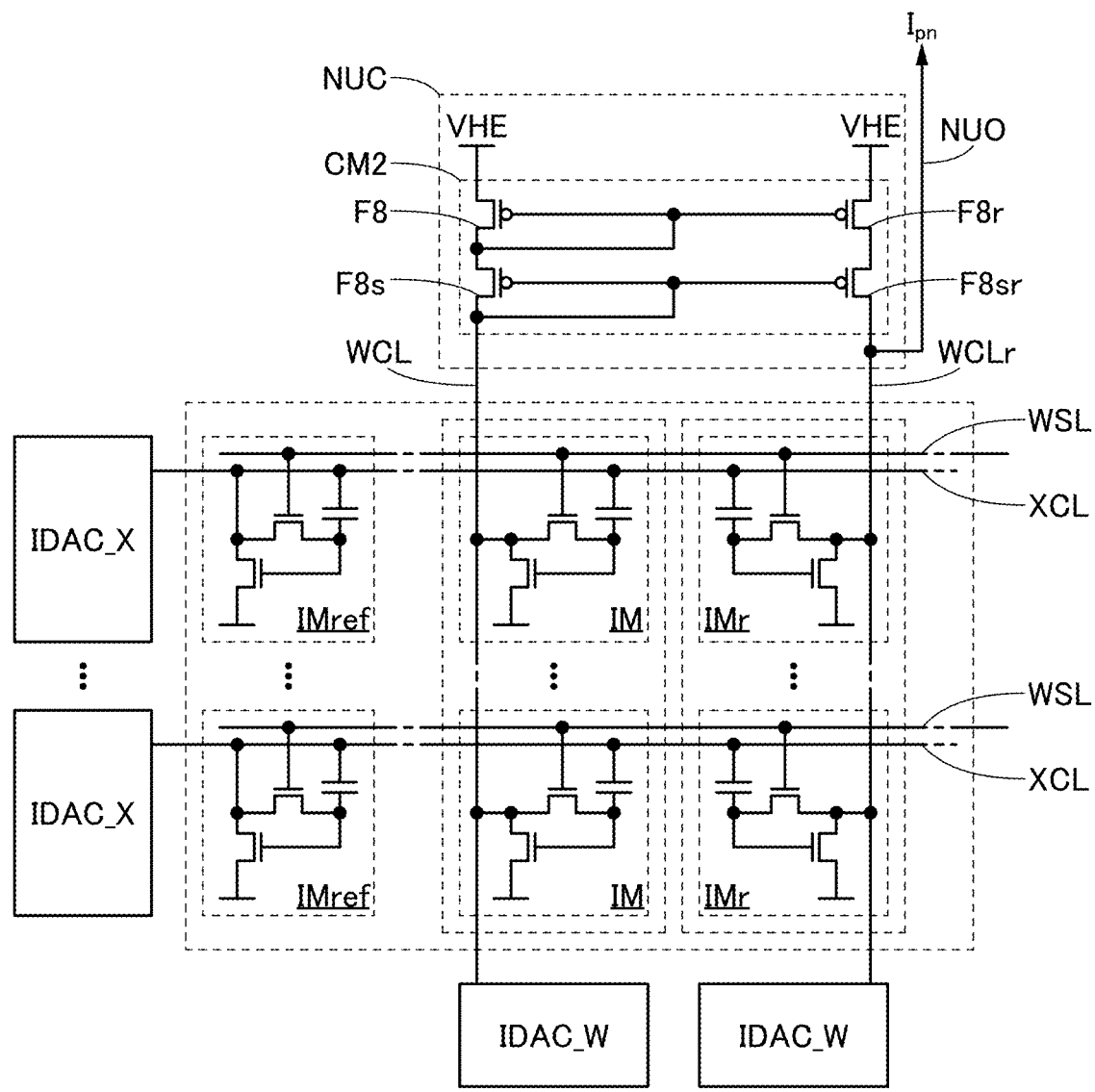
FIG. 48 is a circuit diagram showing conditions for a circuit calculation.

First, a circuit configuration is described. FIG. 48 is a circuit configuration input to a circuit simulator which is based on the arithmetic circuit MAC2 in FIG. 7 described in the above embodiment. The cell IM (cell IMr) and the cell IMref in FIG. 48 correspond to the cell IM and the cell IMref in FIG. 43, respectively, and a circuit NUC corresponds to the converter circuit ITRZD shown in FIG. 7. A plurality of current circuits IDAC_X illustrated in FIG. 48 corresponds to the circuit XCS, and a plurality of current circuits IDAC_W illustrated in FIG. 48 corresponds to the circuit WCS.

The circuit NUC includes a cascode-connected current mirror circuit CM2, and the circuit NUC corresponds to the converter circuit ITRZD4 illustrated in FIG. 11B. The current mirror circuit CM2 includes a transistor F8, a transistor F8s, a transistor F8r, and a transistor F8sr, and these transistors are p-channel transistors. Each of the transistor F8, the transistor F8s, the transistor F8r, and the transistor F8sr has a channel length of 500 nm and a channel width of 5000 nm.

Since the arithmetic circuit in FIG. 48 is manufactured based on the arithmetic circuit MAC2 in FIG. 7, a negative coefficient of weight as well as a positive coefficient of weight (first data) can be stored in the cell IM and the cell IMr. In the arithmetic circuit illustrated in FIG. 48, a current corresponding to the product-sum of a positive coefficient of weight and a neuron signal (second data) flows in the wiring WCL electrically connected to a plurality of cells IM, and a current corresponding to the product-sum of a negative coefficient of weight and the neuron signal flows in the wiring WCLr electrically connected to a plurality of cells IMr.

The circuit NUC outputs a difference current $I_{pn}$ between a current flowing in the wiring WCL and a current flowing in the wiring WCLr to a wiring NUO using the current mirror circuit CM2.

The potential applied by the wiring VHE is 2 V.

Next, configuration examples of the structured neural network are described.

The formed neural network was a three-layer fully connected neural network. The number of neurons of the input layer was 785, the number of neurons of the hidden layer was 101, and the number of neurons of the output layer was 10. One of the neurons of the input layer and one of the neurons of the hidden layer function as neurons supplying biases.

In the input layer, IDAC_X illustrated in FIG. 48 generates a current corresponding to the data input to the neural network and the current flows in the wiring XCL in each row. Then, the current $I_{pn}$ corresponding to a product-sum of the current and the coefficient of weight between neurons of the input layer and neurons of the hidden layer stored in the cell IM and the cell IMr is output to the wiring NUO. That is, the current $I_{pn}$ corresponds to a signal output from the neuron of the hidden layer.

Thus, in the arithmetic circuit performing the product-sum of the coefficient of weight between neurons of the hidden layer and neurons of the output layer and a signal output by the neuron of the hidden layer, the signal output by the neuron of the hidden layer is not generated in the current circuit IDAC_X but input to the wiring XCL directly from the wiring NUO.

Figure 49:
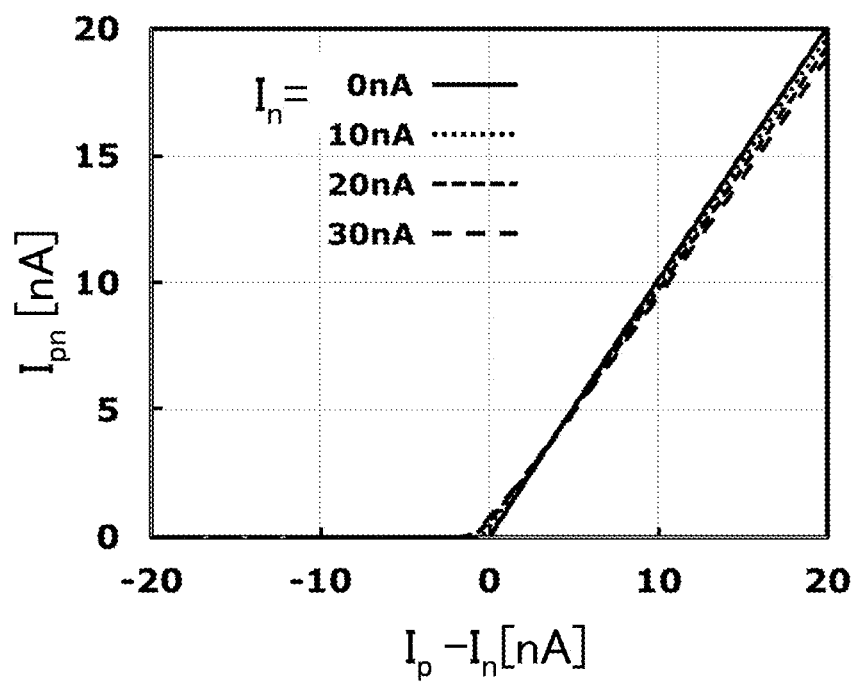
FIG. 49 is a graph showing output characteristics of an arithmetic circuit.

In addition to the structure, the threshold voltages of the transistor F2 and the transistor F2m included in the arithmetic circuit performing a product-sum of the coefficient of weight between neurons of the hidden layer and neurons of the output layer and the signal output from the hidden layer are higher than the threshold voltages of the transistor F2 and the transistor F2m included in the arithmetic circuit performing a product-sum of the coefficient of weight between neurons of the input layer and neurons of the hidden layer and the signal output from the input layer by approximately 0.2 V. Thus, it is confirmed with a calculation using a circuit simulator that the signal output from the neuron of the hidden layer (current $I_{pn}$) shows output characteristics shown in FIG. 49. In FIG. 49, the sum of currents flowing in the wiring WCL is $I_p$, and the sum of currents flowing in the wiring WCLr is In. The output characteristics shown in FIG. 49 is output characteristics corresponding to a ReLU function. In other words, the circuit NUC can be a circuit capable of performing activation function operation as well as differential operation.

Next, the result of a simulation of recognizing handwriting by using the MNIST database is described.

In the simulation, a neural network in which the multiplication characteristics in FIG. 44A were used as the multiplication operation model and the output characteristics in FIG. 49 were used as the activation function model was used. It was assumed that current writing to the cell IM and the cell IMref was performed with the current circuit IDAC in FIG. 46 (using the model of the output characteristics in FIG. 47A) as the writing of the coefficient of weight. Variations in the current-writing method in FIG. 45A and FIG. 45B were considered. With this neural network, a model calculation with 5-bit precision was performed, and the recognition accuracy of input data was 92.6%. Meanwhile, the recognition accuracy in the case where the multiplication was ideal multiplication was 97.9%. Therefore, it can be said that handwriting recognition using a neural network including the arithmetic circuit shown in FIG. 48 has a sufficient recognition accuracy.

REFERENCE NUMERALS

MAC1: arithmetic circuit, MAC1A: arithmetic circuit, MAC2: arithmetic circuit, MAC2-1: arithmetic circuit, MAC2-2: arithmetic circuit, MAC3: arithmetic circuit, WCS: circuit, XCS: circuit, IDAC: current circuit, IDAC_W: current circuit, IDAC_X: current circuit, WSD: circuit, ITRZ[1]: converter circuit, ITRZ[n]: converter circuit, ITRZ1: converter circuit, ITRZ2: converter circuit, ITRZ3: converter circuit, ITRZD[j]: converter circuit, ITRZD1: converter circuit, ITRZD2: converter circuit, ITRZD3: converter circuit, ITRZD4: converter circuit, ITRZD4[i]: converter circuit, ITRZD4[n]: converter circuit, NUC: circuit, SWS1: circuit, SWS2: circuit, CA: cell array, SCA: circuit, VINI: circuit, IM: cell, IM[1,1]: cell, IM[1,j]: cell, IM[m,j]: cell, IM[i,j]: cell, IM[m,1]: cell, IM[1,n]: cell, IM[m,n]: cell, IM[1,h]: cell, IM[n,h]: cell, IMr[1,j]: cell, IMr[i,j]: cell, IMr[m,j]: cell, IMr[1,h]: cell, IMr[n,h]: cell, IMs[i,j]: cell, IMsr[i,j]: cell, IMref: cell, IMref[1]: cell, IMref[i]: cell, IMref[m]: cell, IMref[n]: cell, IMrefs[i]: cell, CES[1,j]: circuit, CES[i,j]: circuit, CES[m,j]: circuit, CESref[i]: circuit, NN[1,1]: node, NN[m,1]: node, NN[i,j]: node, NN[m,j]: node, NN[1,n]: node, NN[m,n]: node, NNr[1,j]: node, NNr[m,j]: node, NNref[1]: node, NNref[m]: node, NNrefs[i]: node, CS: current source, CS1: current source, CS2: current source, CS3: current source, CS4: current source, CI: current source, CIr: current source, CSA: current source, CM1: current mirror circuit, CM2: current mirror circuit, ADC: analog-digital converter circuit, C5: capacitor, C5m: capacitor, C5ms: capacitor, C5r: capacitor, C5s: capacitor, C5sr: capacitor, C6: capacitor, CMP1: comparator, CMP2: comparator, F1: transistor, F1m: transistor, F1ms: transistor, F1r: transistor, F1s: transistor, F1sr: transistor, F2: transistor, F2m: transistor, F2ms: transistor, F2r: transistor, F2s: transistor, F2sr: transistor, F3: transistor, F3[1]: transistor, F3[j]: transistor, F3[n]: transistor, F3r: transistor, F3r[j]: transistor, F4: transistor, F4[1]: transistor, F4[j]: transistor, F4[n]: transistor, F4r: transistor, F4r[j]: transistor, F5: transistor, F6: transistor, F6r: transistor, F6s: transistor, F6sr: transistor, F7: transistor, F7r: transistor, F7s: transistor, F8: transistor, F8r: transistor, F8s: transistor, F8sr: transistor, Tr1: transistor, Tr1[i]: transistor, Tr1[2]: transistor, Tr1[K]: transistor, Tr2: transistor, Tr2[1]: transistor, Tr2[2]: transistor, Tr2[K]: transistor, Tr3: transistor, R5: resistor, RP: resistor, RM: resistor, SNC[i]: sensor, SNC[m]: sensor, PD[i]: photodiode, PD[m]: photodiode, OP1: operational amplifier, OP2: operational amplifier, OPP: operational amplifier, OPM: operational amplifier, SWW: switch, SWX: switch, T1: terminal, T2: terminal, U1: terminal, U2: terminal, U3: terminal, SWL1: wiring, SWL2: wiring, WCL: wiring, WCL[i]: wiring, WCL[j]: wiring, WCL[n]: wiring, WCLr: wiring, WCLr[j]: wiring, XCL: wiring, XCL[i]: wiring, XCL[i]: wiring, XCL[m]: wiring, XCLs[i]: wiring, WSL: wiring, WSL[i]: wiring, WSL[j]: wiring, WSL[m]: wiring, WSLs[j]: wiring, OL: wiring, OL[i]: wiring, OL[j]: wiring, OL[n]: wiring, DW: wiring, DW[i]: wiring, DW[2]: wiring, DW[K]: wiring, DX[1]: wiring, DX[2]: wiring, DX[L]: wiring, D[i]: wiring, D[2]: wiring, D[7]: wiring, CL[i]: wiring, CL[2]: wiring, CL[P]: wiring, VE: wiring, VDDL: wiring, VINIL1: wiring, VINIL2: wiring, VINIL3: wiring, VWL: wiring, VTL: wiring, VTHL: wiring, VRL: wiring, VRL2: wiring, VRL3: wiring, VRPL: wiring, VRML: wiring, VHE: wiring, VSE: wiring, OEL: wiring, OUTL: wiring, NUO: wiring, TM[1]: wiring, TM[n]: wiring, TH[1,h]: wiring, TH[n,h]: wiring, THr[1,h]: wiring, THr[n,h]: wiring, PLS: sensor portion, SMS: odor sensor, TRCN: path, MEMD: memory portion, ATCM: atmospheric component, NOI: odor component, NOIa: odor molecule, DT: data, SNC: sensor, KZT: structure body, ERDa1: wiring, ERDa2: wiring, ERDb1: wiring, ERDb2: wiring, DGG: strain gauge, LP: connection portion, CNDa: conductor, CNDb: conductor, KNM: sensing film, UDE: electronic device, PLSA: sensor portion, KZU: structure body, SSM: insulator, CNEa: conductor, CNEb: conductor, CNEc: conductor, CNEd: conductor, EREa1: wiring, EREa2: wiring, EREb1: wiring, EREb2: wiring, EREc1: wiring, EREc2: wiring, EREd1: wiring, EREd2: wiring, DGH: strain gauge, CIR: circuit, CNVL: wiring, SZ1: insulator, SZ2: insulator, SITA: electronic device, CHM: sensor portion, ABJ: evaluated material, SST: lipid film, KAN: buffer film, HAIS1: wiring, HAIS2: wiring, DEN: reference electrode, SIN: hydrophilic portion, SOS: hydrophobic portion, VIC: voltage-current converter circuit, KYT1: first housing, KYT2: second housing, KYT3: third housing, DAZ: base, JIK: axis, CB: cable bare, YOK: container, YEK: solution, SCL1: scribe line, SCL2: scribe line, 10: hand portion, 10A: hand portion, 11a: finger portion, 11b: finger portion, 12a: joint portion, 12b: joint portion, 13: extending portion, 14: support portion, 15: bus wiring, 16a: joint portion, 16b: joint portion, 100: neural network, 300: transistor, 311: substrate, 313: semiconductor region, 314a: low-resistance region, 314b: low-resistance region, 315: insulator, 316: conductor, 320: insulator, 322: insulator, 324: insulator, 326: insulator, 328: conductor, 330: conductor, 350: insulator, 352: insulator, 354: insulator, 356: conductor, 360: insulator, 362: insulator, 364: insulator, 366: conductor, 370: insulator, 372: insulator, 374: insulator, 376: conductor, 380: insulator, 382: insulator, 384: insulator, 386: conductor, 402: insulator, 404: insulator, 500: transistor, 503: conductor, 503a: conductor, 503b: conductor, 510: insulator, 512: insulator, 514: insulator, 516: insulator, 518: conductor, 520: insulator, 522: insulator, 524: insulator, 530: oxide, 530a: oxide, 530b: oxide, 530c: oxide, 530c1: oxide, 530c2: oxide, 540: conductor, 540a: conductor, 540b: conductor, 542: conductor, 542a: conductor, 542b: conductor, 543a: region, 543b: region, 544: insulator, 546: conductor, 548: conductor, 550: insulator, 552: insulator, 560: conductor, 560a: conductor, 560b: conductor, 574: insulator, 580: insulator, 581: insulator, 582: insulator, 586: insulator, 600: capacitor, 600A: capacitor, 600B: capacitor, 610: conductor, 611: conductor, 612: conductor, 620: conductor, 630: insulator, 631: insulator, 650: insulator, 651: insulator, 4700: electronic component, 4702: printed substrate, 4704: mounting board, 4710: semiconductor device, 4711: mold, 4712: land, 4713: electrode pad, 4714: wire, 4730: electronic component, 4731: interposer, 4732: package substrate, 4733: electrode, 4735: semiconductor device, 4800: semiconductor wafer, 4800a: chip, 4801: wafer, 4801a: wafer, 4802: circuit portion, 4803: spacing, 4803a: spacing, 5200: portable game console, 5201: housing, 5202: display portion, 5203: button, 5300: desktop information terminal, 5301: main body, 5302: display, 5303: keyboard, 5500: information terminal, 5510: housing, 5511: display portion, 5600: TV, 5650: antenna, 5670: radio wave tower, 5675A: radio wave, 5675B: radio wave, 5680: broadcast station, 5700: automobile, 5800: electric refrigerator-freezer, 5801: housing, 5802: refrigerator door, 5803: freezer door, 5900: information terminal, 5901: housing, 5902: display portion, 5903: operation button, 5904: operator, 5905: band, 6100: external device, 6101: housing, 6102: cap, 6103: USB connector, 6104: substrate, 6105: chip, 6106: controller chip, 6140: robot, 6141a: tactile sensor, 6141b: tactile sensor, 6141c: tactile sensor, 6141d: tactile sensor, 6141e: tactile sensor, 6150: industrial robot, 6151: function unit, 6152: control unit, 6153: drive shaft, 6154: drive shaft, 6155: drive shaft, 6240: digital camera, 6241: housing, 6242: display portion, 6243: operation button, 6244: shutter button, 6246: lens, 6300: video camera, 6301: first housing, 6302: second housing, 6303: display portion, 6304: operation key, 6305: lens, 6306: connection portion, 6431: housing, 6432: display portion, 6433: palm print reading portion, 6434: wiring, 6435: hand, 6900: alarm, 6901: sensor, 6902: receiver, 6903: transmitter, 6904: sensor circuit, 6905: air vent, 6906: operation key, 6907: display portion, 6908: operation key, 6909: operation key, 6910: wiring, 6911: speaker, 6912: lighting device, 7500: stationary game machine, 7520: main body, 7522: controller

The invention claimed is:

1. A semiconductor device, comprising:
a first circuit, a second circuit, a first cell, a second cell, a first wiring, and a second wiring,
wherein the first cell comprises a first transistor,
wherein the second cell comprises a second transistor,
wherein the first cell is electrically connected to the first circuit through the first wiring,
wherein the first cell is electrically connected to the second circuit through the second wiring,
wherein the second cell is electrically connected to the second circuit through the second wiring,
wherein the first circuit has a function of making a first current flow from the first circuit to the first cell through the first wiring,
wherein the second circuit has a function of making a second current flow from the second circuit to the second cell through the second wiring and a function of supplying a first potential corresponding to the second current from the second circuit to each of the first cell and the second cell through the second wiring,
wherein the first cell has a function of setting a current flowing between a first terminal and a second terminal of the first transistor to the first current,
wherein the second cell has a function of setting a current flowing between a first terminal and a second terminal of the second transistor to the second current,
wherein the second circuit has a function of changing the second current flowing in the second wiring to a third current to change the first potential supplied to each of the first cell and the second cell to a second potential,
wherein the first cell has a function of changing the first current flowing between the first terminal and the second terminal of the first transistor to a fourth current corresponding to a difference between the first potential and the second potential,
wherein an amount of each of the first current and the fourth current is an amount of current flowing when the first transistor operates in a subthreshold region, and
wherein an amount of each of the second current and the third current is an amount of current flowing when the second transistor operates in a subthreshold region.

2. The semiconductor device, according to claim 1,
wherein each of the first transistor and the second transistor comprises a metal oxide in a channel formation region.

3. A semiconductor device, comprising:
a first circuit, a second circuit, a first cell, a second cell, a first wiring, and a second wiring,
wherein the first cell comprises a first transistor, a third transistor, and a first capacitor,
wherein the second cell comprises a second transistor, a fourth transistor, and a second capacitor,
wherein the first circuit is electrically connected to the first wiring,
wherein the second circuit is electrically connected to the second wiring,
wherein a first terminal of the third transistor is electrically connected to a first terminal of the first transistor and the first wiring,
wherein a second terminal of the third transistor is electrically connected to a gate of the first transistor and a first terminal of the first capacitor,
wherein a second terminal of the first capacitor is electrically connected to the second wiring,
wherein a first terminal of the fourth transistor is electrically connected to a first terminal of the second transistor and the second wiring,
wherein a second terminal of the fourth transistor is electrically connected to a gate of the second transistor and a first terminal of the second capacitor,
wherein a second terminal of the second capacitor is electrically connected to the second wiring,
wherein the first circuit has a function of making a first current flow from the first circuit to the first terminal of the first transistor through the first wiring,
wherein the second circuit has a function of making a second current flow from the second circuit to the first terminal of the second transistor through the second wiring and a function of supplying a first potential corresponding to the second current from the second circuit to each of the second terminal of the first capacitor and the second terminal of the second capacitor through the second wiring,
wherein the first cell has a function of setting the first current flowing between the first terminal and a second terminal of the first transistor,
wherein the second cell has a function of setting the second current flowing between the first terminal and a second terminal of the second transistor,
wherein the second circuit has a function of changing the second current flowing in the second wiring to a third current to change the first potential supplied to each of the second terminal of the first capacitor and the second terminal of the second capacitor to a second potential,
wherein the first cell has a function of changing the first current flowing between the first terminal and the second terminal of the first transistor to a fourth current corresponding to a difference between the first potential and the second potential,
wherein an amount of each of the first current and the fourth current is an amount of current flowing when the first transistor operates in a subthreshold region, and
wherein an amount of each of the second current and the third current is an amount of current flowing when the second transistor operates in a subthreshold region.

4. The semiconductor device, according to claim 3,
wherein each of the first transistor to the fourth transistor comprises a metal oxide in a channel formation region.

5. The semiconductor device, according to claim 1,
wherein the first circuit comprises a fifth transistor and a sixth transistor,
wherein the sixth transistor comprises a first gate and a second gate,
wherein a first terminal of the fifth transistor is electrically connected to the first wiring, and
wherein a second terminal of the fifth transistor is electrically connected to a first terminal of the sixth transistor, the first gate of the sixth transistor, and the second gate of the sixth transistor.

6. The semiconductor device, according to claim 5,
wherein each of the fifth transistor and the sixth transistor comprises a metal oxide in a channel formation region.

7. The semiconductor device, according to claim 1,
wherein the second circuit comprises a seventh transistor and an eighth transistor,
wherein the eighth transistor comprises a third gate and a fourth gate,
wherein a first terminal of the seventh transistor is electrically connected to the second wiring, and
wherein a second terminal of the seventh transistor is electrically connected to a first terminal of the eighth transistor, the third gate of the eighth transistor, and the fourth gate of the eighth transistor.

8. The semiconductor device, according to claim 7,
wherein each of the seventh transistor and the eighth transistor comprises a metal oxide in a channel formation region.

9. The semiconductor device, according to claim 1,
wherein the second circuit comprises an optical sensor,
wherein the optical sensor is electrically connected to the second wiring,
wherein the optical sensor has:
a function of performing first sensing to make the second current flow from the optical sensor to the second wiring; and
a function of performing second sensing to change an amount of the second current to an amount of the third current.

10. The semiconductor device, according to claim 1,
wherein the second circuit comprises a sensor,
wherein the sensor is electrically connected to the second wiring,
wherein the sensor has:
a function of detecting an odor component; and
a function of making the second current flow from the sensor to the second wiring when the odor component is not detected and changing an amount of the second current to an amount of the third current when the odor component is detected.

11. The semiconductor device, according to claim 1,
wherein the second circuit comprises a sensor,
wherein the sensor is electrically connected to the second wiring,
wherein the sensor has:
a function of detecting a contact of an object; and
a function of making the second current flow from the sensor to the second wiring when the contact of the object is not detected and changing an amount of the second current to an amount of the third current when the contact of the object is detected.

12. The semiconductor device, according to claim 1,
wherein the second circuit comprises a sensor,
wherein the sensor is electrically connected to the second wiring,
wherein the sensor has:
  a function of detecting a taste component; and
  a function of making the second current flow from the sensor to the second wiring when the taste component is not detected and changing an amount of the second current to an amount of the third current when the taste component is detected.

13. An electronic device, comprising:
the semiconductor device according to claim 1, and a housing, wherein a product-sum operation is performed with the semiconductor device.

14. The semiconductor device, according to claim 3,
wherein the first circuit comprises a fifth transistor and a sixth transistor,
wherein the sixth transistor comprises a first gate and a second gate,
wherein a first terminal of the fifth transistor is electrically connected to the first wiring, and
wherein a second terminal of the fifth transistor is electrically connected to a first terminal of the sixth transistor, the first gate of the sixth transistor, and the second gate of the sixth transistor.

15. The semiconductor device, according to claim 14,
wherein each of the fifth transistor and the sixth transistor comprises a metal oxide in a channel formation region.

16. The semiconductor device, according to claim 3,
wherein the second circuit comprises a seventh transistor and an eighth transistor,
wherein the eighth transistor comprises a third gate and a fourth gate,
wherein a first terminal of the seventh transistor is electrically connected to the second wiring, and
wherein a second terminal of the seventh transistor is electrically connected to a first terminal of the eighth transistor, the third gate of the eighth transistor, and the fourth gate of the eighth transistor.

17. The semiconductor device, according to claim 16,
wherein each of the seventh transistor and the eighth transistor comprises a metal oxide in a channel formation region.

18. The semiconductor device, according to claim 3,
wherein the second circuit comprises an optical sensor,
wherein the optical sensor is electrically connected to the second wiring,
wherein the optical sensor has:
  a function of performing first sensing to make the second current flow from the optical sensor to the second wiring; and
  a function of performing second sensing to change an amount of the second current to an amount of the third current.

19. The semiconductor device, according to claim 3,
wherein the second circuit comprises a sensor,
wherein the sensor is electrically connected to the second wiring,
wherein the sensor has:
  a function of detecting an odor component; and
  a function of making the second current flow from the sensor to the second wiring when the odor component is not detected and changing an amount of the second current to an amount of the third current when the odor component is detected.

20. An electronic device, comprising:
the semiconductor device according to claim 3, and a housing,
wherein a product-sum operation is performed with the semiconductor device.

* * * * *